(12) United States Patent
Liu et al.

(10) Patent No.: US 10,273,237 B2
(45) Date of Patent: Apr. 30, 2019

(54) IMIDAZOPYRIDAZINE COMPOUNDS USEFUL AS MODULATORS OF IL-12, IL-23 AND/OR IFN-α RESPONSES

(71) Applicant: BRISTOL-MYERS SQUIBB COMPANY, Princeton, NJ (US)

(72) Inventors: Chunjian Liu, Pennington, NJ (US); James Lin, Lawrenceville, NJ (US); Ryan M. Moslin, Princeton, NJ (US); David S. Weinstein, East Windsor, NJ (US); John S. Tokarski, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/102,991

(22) PCT Filed: Dec. 10, 2014

(86) PCT No.: PCT/US2014/069476
§ 371 (c)(1),
(2) Date: Jun. 9, 2016

(87) PCT Pub. No.: WO2015/089143
PCT Pub. Date: Jun. 18, 2015

(65) Prior Publication Data
US 2016/0304524 A1 Oct. 20, 2016

Related U.S. Application Data

(60) Provisional application No. 61/914,102, filed on Dec. 10, 2013.

(51) Int. Cl.
C07D 487/04 (2006.01)
C07D 487/14 (2006.01)
C07D 498/14 (2006.01)

(52) U.S. Cl.
CPC ......... *C07D 487/04* (2013.01); *C07D 487/14* (2013.01); *C07D 498/14* (2013.01)

(58) Field of Classification Search
None
See application file for complete search history.

(56) References Cited

U.S. PATENT DOCUMENTS 9,315,494 B2 4/2016 Moslin et al.
2010/0168116 A1 7/2010 Hellberg et al.

FOREIGN PATENT DOCUMENTS

| EP | 2 518 072 | 10/2012 |
|---|---|---|
| WO | WO 2007/013673 | 2/2007 |
| WO | WO 2007/038314 | 4/2007 |
| WO | WO 2008/030579 | 3/2008 |
| WO | WO 2008/072682 | 6/2008 |
| WO | WO 2009/100375 | 8/2009 |
| WO | WO2014/074660 | 5/2014 |
| WO | WO2014/074661 | 5/2014 |
| WO | WO2014/074670 | 5/2014 |
| WO | WO2015/069310 | 5/2015 |

OTHER PUBLICATIONS

Schafer et al., Drug Discovery Today, 2008, 13 (21/22), 913-916.*
Horig et al., Journal of Translational Medicine, 2004, 2(44).*
J. G. Cannon Chapter Nineteen in Burger's Medicinal Chemistry and Drug Discovery, Fifth Edition, vol. I: Principles and Practice, Wiley-Interscience 1995, pp. 783-802, 784.*

* cited by examiner

*Primary Examiner* — Savitha M Rao
*Assistant Examiner* — Gregg Polansky
(74) *Attorney, Agent, or Firm* — Elliott Korsen

(57) ABSTRACT

Compounds having the following formula (I), or a stereoisomer or pharmaceutically-acceptable salt thereof, where $R^1$, $R^2$, $R^3$, $R^4$, and $R^5$ are as defined herein, are useful in the modulation of IL-12, IL-23 and/or IFNα, by acting on Tyk-2 to cause signal transduction inhibition.

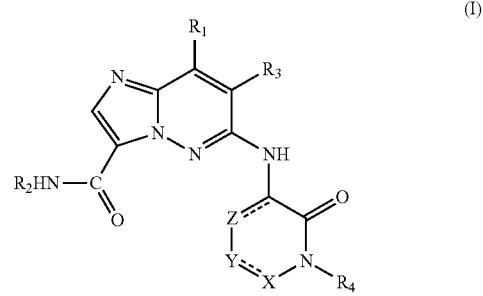

(I)

2 Claims, No Drawings

Specification includes a Sequence Listing.

SEQUENCE LISTING

<160> NUMBER OF SEQ ID NOS: 1

<210> SEQ ID NO 1
<211> LENGTH: 317
<212> TYPE: PRT
<213> ORGANISM: Homo sapiens

<400> SEQUENCE: 1

Met Gly Ser Ser His His His His His His Ser Ser Gly Glu Thr Val
1               5                   10                  15

Arg Phe Gln Gly His Met Asn Leu Ser Gln Leu Ser Phe His Arg Val
            20                  25                  30

```
Asp Gln Lys Glu Ile Thr Gln Leu Ser His Leu Gly Gln Gly Thr Arg
        35                  40                  45
Thr Asn Val Tyr Glu Gly Arg Leu Arg Val Glu Gly Ser Gly Asp Pro
        50                  55                  60
Glu Glu Gly Lys Met Asp Asp Glu Asp Pro Leu Val Pro Gly Arg Asp
65                  70                  75                  80
Arg Gly Gln Glu Leu Arg Val Val Leu Lys Val Leu Asp Pro Ser His
                85                  90                  95
His Asp Ile Ala Leu Ala Phe Tyr Glu Thr Ala Ser Leu Met Ser Gln
                100                 105                 110
Val Ser His Thr His Leu Ala Phe Val His Gly Val Cys Val Arg Gly
            115                 120                 125
Pro Glu Asn Ile Met Val Thr Glu Tyr Val Glu His Gly Pro Leu Asp
        130                 135                 140
Val Trp Leu Arg Arg Glu Arg Gly His Val Pro Met Ala Trp Lys Met
145                 150                 155                 160
Val Val Ala Gln Gln Leu Ala Ser Ala Leu Ser Tyr Leu Glu Asn Lys
                165                 170                 175
Asn Leu Val His Gly Asn Val Cys Gly Arg Asn Ile Leu Leu Ala Arg
                180                 185                 190
Leu Gly Leu Ala Glu Gly Thr Ser Pro Phe Ile Lys Leu Ser Asp Pro
            195                 200                 205
Gly Val Gly Leu Gly Ala Leu Ser Arg Glu Glu Arg Val Glu Arg Ile
        210                 215                 220
Pro Trp Leu Ala Pro Glu Cys Leu Pro Gly Gly Ala Asn Ser Leu Ser
225                 230                 235                 240
Thr Ala Met Asp Lys Trp Gly Phe Gly Ala Thr Leu Leu Glu Ile Cys
                245                 250                 255
Phe Asp Gly Glu Ala Pro Leu Gln Ser Arg Ser Pro Ser Glu Lys Glu
                260                 265                 270
His Phe Tyr Gln Arg Gln His Arg Leu Pro Glu Pro Ser Cys Pro Gln
            275                 280                 285
Leu Ala Thr Leu Thr Ser Gln Cys Leu Thr Tyr Glu Pro Thr Gln Arg
        290                 295                 300
Pro Ser Phe Arg Thr Ile Leu Arg Asp Leu Thr Arg Leu
305                 310                 315
```

IMIDAZOPYRIDAZINE COMPOUNDS USEFUL AS MODULATORS OF IL-12, IL-23 AND/OR IFN-α RESPONSES

CROSS-REFERENCE TO RELATED APPLICATIONS

This application claims the benefit of U.S. Provisional Application No. 61/914,102, filed Dec. 10, 2013, the disclosure of which is incorporated herein by reference in its entirety.

FIELD OF THE INVENTION

This invention relates to compounds useful in the modulation of IL-12, IL-23 and/or IFNα by acting on Tyk-2 to cause signal transduction inhibition. Provided herein are imidazopyradazine compounds, compositions comprising such compounds, and methods of their use. The invention further pertains to pharmaceutical compositions containing at least one compound according to the invention that are useful for the treatment of conditions related to the modulation of IL-12, IL-23 and/or IFNα in a mammal.

BACKGROUND OF THE INVENTION

The heterodimeric cytokines interleukin (IL)-12 and IL-23, which share a common p40 subunit, are produced by activated antigen-presenting cells and are critical in the differentiation and proliferation of Th1 and Th17 cells, two effector T cell lineages which play key roles in autoimmunity. IL-23 is composed of the p40 subunit along with a unique p19 subunit. IL-23, acting through a heterodimeric receptor composed of IL-23R and IL-12Rβ1, is essential for the survival and expansion of Th17 cells which produce pro-inflammatory cytokines such as IL-17A, IL-17F, IL-6 and TNF-α (McGeachy, M. J. et al., "The link between IL-23 and Th17 cell-mediated immune pathologies", Semin. Immunol., 19:372-376 (2007)). These cytokines are critical in mediating the pathobiology of a number of autoimmune diseases, including rheumatoid arthritis, multiple sclerosis, inflammatory bowel disease, and lupus. IL-12, in addition to the p40 subunit in common with IL-23, contains a p35 subunit and acts through a heterodimeric receptor composed of IL-12Rβ1 and IL-12Rβ2. IL-12 is essential for Th1 cell development and secretion of IFNγ, a cytokine which plays a critical role in immunity by stimulating MHC expression, class switching of B cells to IgG subclasses, and the activation of macrophages (Gracie, J. A. et al., "Interleukin-12 induces interferon-gamma-dependent switching of IgG alloantibody subclass", Eur. J. Immunol., 26:1217-1221 (1996); Schroder, K. et al., "Interferon-gamma: an overview of signals, mechanisms and functions", J. Leukoc. Biol., 75(2):163-189 (2004)).

The importance of the p40-containing cytokines in autoimmunity is demonstrated by the discovery that mice deficient in either p40, p19, or IL-23R are protected from disease in models of multiple sclerosis, rheumatoid arthritis, inflammatory bowel disease, lupus and psoriasis, among others (Kyttaris, V. C. et al., "Cutting edge: IL-23 receptor deficiency prevents the development of lupus nephritis in C57BL/6-lpr/lpr mice", J. Immunol., 184:4605-4609 (2010); Hong, K. et al., "IL-12, independently of IFN-gamma, plays a crucial role in the pathogenesis of a murine psoriasis like skin disorder", J. Immunol., 162:7480-7491 (1999); Hue, S. et al., "Interleukin-23 drives innate and T cell-mediated intestinal inflammation", J. Exp. Med., 203:2473-2483 (2006); Cua, D. J. et al., "Interleukin-23 rather than interleukin-12 is the critical cytokine for autoimmune inflammation of the brain", Nature, 421:744-748 (2003); Murphy, C. A. et al., "Divergent pro- and anti-inflammatory roles for IL-23 and IL-12 in joint autoimmune inflammation", J. Exp. Med., 198:1951-1957 (2003)).

In human disease, high expression of p40 and p19 has been measured in psoriatic lesions, and Th17 cells have been identified in active lesions in the brain from MS patients and in the gut mucosa of patients with active Crohn's disease (Lee, E. et al., "Increased expression of interleukin 23 p19 and p40 in lesional skin of patients with psoriasis vulgaris", J. Exp. Med., 199:125-130 (2004); Tzartos, J. S. et al., "Interleukin-17 production in central nervous system infiltrating T cells and glial cells is associated with active disease in multiple sclerosis", Am. J. Pathol., 172:146-155 (2008)). The mRNA levels of p19, p40, and p35 in active SLE patients were also shown to be significantly higher compared with those in inactive SLE patients (Huang, X. et al., "Dysregulated expression of interleukin-23 and interleukin-12 subunits in systemic lupus erythematosus patients", Mod. Rheumatol., 17:220-223 (2007)), and T cells from lupus patients have a predominant Th1 phenotype (Tucci, M. et al., "Overexpression of interleukin-12 and T helper 1 predominance in lupus nephritis", Clin. Exp. Immunol., 154:247-254 (2008)).

Moreover, genome-wide association studies have identified a number of loci associated with chronic inflammatory and autoimmune diseases that encode factors that function in the IL-23 and IL-12 pathways. These genes include IL23A, IL12A, IL12B, IL12RB1, IL12RB2, IL23R, JAK2, TYK2, STAT3, and STAT4 (Lees, C. W. et al., "New IBD genetics: common pathways with other diseases", Gut, 60:1739-1753 (2011); Tao, J. H. et al., "Meta-analysis of TYK2 gene polymorphisms association with susceptibility to autoimmune and inflammatory diseases", Mol. Biol. Rep., 38:4663-4672 (2011); Cho, J. H. et al., "Recent insights into the genetics of inflammatory bowel disease", Gastroenterology, 140:1704-1712 (2011)).

Indeed, anti-p40 treatment, which inhibits both IL-12 and IL-23, as well as IL-23-specific anti-p19 therapies have been shown to be efficacious in the treatment of autoimmunity in diseases including psoriasis, Crohn's Disease and psoriatic arthritis (Leonardi, C. L. et al., "PHOENIX 1 study investigators. Efficacy and safety of ustekinumab, a human interleukin-12/23 monoclonal antibody, in patients with psoriasis: 76-week results from a randomized, double-blind, placebo-controlled trial (PHOENIX 1)", Lancet, 371:1665-1674 (2008); Sandborn, W. J. et al., "Ustekinumab Crohn's Disease Study Group. A randomized trial of Ustekinumab, a human interleukin-12/23 monoclonal antibody, in patients with moderate-to-severe Crohn's disease", Gastroenterology, 135:1130-1141 (2008); Gottlieb, A. et al., "Ustekinumab, a human interleukin 12/23 monoclonal antibody, for psoriatic arthritis: randomized, double-blind, placebo-controlled, crossover trial", Lancet, 373:633-640 (2009)). Therefore, agents which inhibit the action of IL-12 and IL-23 may be expected to have therapeutic benefit in human autoimmune disorders.

The Type I group of interferons (IFNs), which include the IFNα members as well as IFNβ, IFNε, IFNκ and IFNω, act through a heterodimer IFNα/β receptor (IFNAR). Type I IFNs have multiple effects in both the innate and adaptive immune systems including activation of both the cellular and humoral immune responses as well as enhancing the expression and release of autoantigens (Hall, J. C. et al., "Type I interferons: crucial participants in disease amplification in autoimmunity", *Nat. Rev. Rheumatol.,* 6:40-49 (2010)).

In patients with systemic lupus erythematosus (SLE), a potentially fatal autoimmune disease, increased serum levels of interferon (IFN)-α (a type I interferon) or increased expression of type I IFN-regulated genes (a so-called IFNα signature) in peripheral blood mononuclear cells and in affected organs has been demonstrated in a majority of patients (Bennett, L. et al., "Interferon and granulopoiesis signatures in systemic lupus erythematosus blood", *J. Exp. Med.,* 197:711-723 (2003); Peterson, K. S. et al., "Characterization of heterogeneity in the molecular pathogenesis of lupus nephritis from transcriptional profiles of laser-captured glomeruli", *J. Clin. Invest.,* 113:1722-1733 (2004)), and several studies have shown that serum IFNα levels correlate with both disease activity and severity (Bengtsson, A. A. et al., "Activation of type I interferon system in systemic lupus erythematosus correlates with disease activity but not with antiretroviral antibodies", *Lupus,* 9:664-671 (2000)). A direct role for IFNα in the pathobiology of lupus is evidenced by the observation that the administration of IFNα to patients with malignant or viral diseases can induce a lupus-like syndrome. Moreover, the deletion of the IFNAR in lupus-prone mice provides high protection from autoimmunity, disease severity and mortality (Santiago-Raber, M. L. et al., "Type-I interferon receptor deficiency reduces lupus-like disease in NZB mice", *J. Exp. Med.,* 197:777-788 (2003)), and genome-wide association studies have identified loci associated with lupus that encode factors that function in the type I interferon pathway, including IRF5, IKBKE, TYK2, and STAT4 (Deng, Y. et al., "Genetic susceptibility to systemic lupus erythematosus in the genomic era", *Nat. Rev. Rheumatol.,* 6:683-692 (2010); Sandling, J. K. et al., "A candidate gene study of the type I interferon pathway implicates IKBKE and IL8 as risk loci for SLE", *Eur. J. Hum. Genet.,* 19:479-484 (2011)). In addition to lupus, there is evidence that aberrant activation of type I interferon-mediated pathways are important in the pathobiology of other autoimmune diseases such as Sjögren's syndrome and scleroderma (Båve, U. et al., "Activation of the type I interferon system in primary Sjögren's syndrome: a possible etiopathogenic mechanism", *Arthritis Rheum.,* 52:1185-1195 (2005); Kim, D. et al., "Induction of interferon-alpha by scleroderma sera containing autoantibodies to topoisomerase I: association of higher interferon-alpha activity with lung fibrosis", *Arthritis Rheum.,* 58:2163-2173 (2008)). Therefore, agents which inhibit the action of type I interferon responses may be expected to have therapeutic benefit in human autoimmune disorders.

Tyrosine kinase 2 (Tyk2) is a member of the Janus kinase (JAK) family of nonreceptor tyrosine kinases and has been shown to be critical in regulating the signal transduction cascade downstream of receptors for IL-12, IL-23 and type I interferons in both mice (Ishizaki, M. et al., "Involvement of Tyrosine Kinase-2 in Both the IL-12/Th1 and IL-23/Th17 Axes In Vivo" *J. Immunol.,* 187:181-189 (2011); Prchal-Murphy, M. et al., "TYK2 kinase activity is required for functional type I interferon responses in vivo" *PLoS One,* 7:e39141 (2012)) and humans (Minegishi, Y. et al., "Human tyrosine kinase 2 deficiency reveals its requisite roles in multiple cytokine signals involved in innate and acquired immunity" *Immunity,* 25:745-755 (2006)). Tyk2 mediates the receptor-induced phosphorylation of members of the STAT family of transcription factors, an essential signal that leads to the dimerization of STAT proteins and the transcription of STAT-dependent pro-inflammatory genes. Tyk2-deficient mice are resistant to experimental models of colitis, psoriasis and multiple sclerosis, demonstrating the importance of Tyk2-mediated signaling in autoimmunity and related disorders (Ishizaki, M. et al., "Involvement of Tyrosine Kinase-2 in Both the IL-12/Th1 and IL-23/Th17 Axes In Vivo" *J. Immunol.,* 187:181-189 (2011); Oyamada, A. et al., "Tyrosine kinase 2 plays critical roles in the pathogenic CD4 T cell responses for the development of experimental autoimmune encephalomyelitis" *J. Immunol.* 183:7539-7546 (2009)).

In humans, individuals expressing an inactive variant of Tyk2 are protected from multiple sclerosis and possibly other autoimmune disorders (Couturier, N. et al., "Tyrosine kinase 2 variant influences T lymphocyte polarization and multiple sclerosis susceptibility" *Brain* 134:693-703 (2011)). Genome-wide association studies have shown other variants of Tyk2 to be associated with autoimmune disorders such as Crohn's Disease, psoriasis, systemic lupus erythematosus, and rheumatoid arthritis, further demonstrating the importance of Tyk2 in autoimmunity (Ellinghaus, D. et al., "Combined Analysis of Genome-wide Association Studies for Crohn Disease and Psoriasis Identifies Seven Shared Susceptibility Loci" *Am. J. Hum. Genet.* 90:636-647 (2012); Graham, D. et al. "Association of polymorphisms across the tyrosine kinase gene, TYK2 in UK SLE families" *Rheumatology (Oxford)* 46:927-930 (2007); Eyre, S. et al. "High-density genetic mapping identifies new susceptibility loci for rheumatoid arthritis" *Nat. Genet.* 44:1336-1340 (2012)).

In view of the conditions that may benefit by treatment involving the modulation of cytokines and/or interferons, new compounds capable of modulating cytokines and/or interferons, such as IL-12, IL-23 and/or IFNα, and methods of using these compounds may provide substantial therapeutic benefits to a wide variety of patients in need thereof.

SUMMARY OF THE INVENTION

The invention is directed to compounds of Formula I, infra, that which are useful as modulators of IL-12, IL-23 and/or IFNα by inhibiting Tyk2-mediated signal transduction.

The present invention also provides processes and intermediates for making the compounds of the present invention.

The present invention also provides pharmaceutical compositions comprising a pharmaceutically acceptable carrier and at least one of the compounds of the present invention.

The present invention also provides a method for the modulation of IL-12, IL-23 and/or IFNα by inhibiting Tyk-2-mediated signal transduction comprising administering to a host in need of such treatment a therapeutically effective amount of at least one of the compounds of the present invention.

The present invention also provides a method for treating proliferative, metabolic, allergic, autoimmune and inflammatory diseases, comprising administering to a host in need of such treatment a therapeutically effective amount of at least one of the compounds of the present invention.

A preferred embodiment is a method for treating inflammatory and autoimmune diseases or diseases. For the purposes of this invention, an inflammatory and autoimmune disease or disorder includes any disease having an inflammatory or autoimmune component.

An alternate preferred embodiment is a method for treating metabolic diseases, including type 2 diabetes and atherosclerosis.

The present invention also provides the use of the compounds of the present invention for the manufacture of a medicament for the treatment of cancers.

The present invention also provides the compounds of the present invention for use in therapy.

These and other features of the invention will be set forth in the expanded form as the disclosure continues.

DETAILED DESCRIPTION OF THE EMBODIMENTS OF THE INVENTION

Provided herein is at least one chemical entity chosen from compounds of formula I:

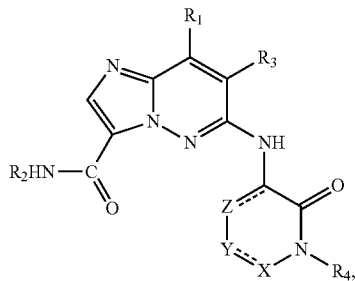

or stereoisomers, tautomers, pharmaceutically acceptable salts, solvates, or prodrugs thereof, wherein:

$R_1$ is H or —$NHR_5$;

$R_2$ is H, optionally substituted 3- to 10-membered monocyclic or bicyclic cycloalkyl, optionally substituted $C_1$-$C_6$ alkyl, optionally substituted 6- to 10-membered monocyclic or bicyclic aryl, or optionally substituted 4- to 10-membered monocyclic or bicyclic heterocyclo, each heterocyclo containing 1-3 heteroatoms selected from N, O, and S;

$R_3$ is H, halo, optionally substituted $C_1$-$C_6$ alkyl or optionally substituted $C_2$-$C_6$ alkynyl, or $R_1$ and $R_3$ can be taken together with the carbons to which they are attached to form a 4- to 8-membered ring;

$R_4$ is H, optionally substituted $C_1$-$C_6$ alkyl, optionally substituted 3- to 10-membered monocyclic or bicyclic cycloalkyl, optionally substituted 6- to 10-membered monocyclic or bicyclic aryl, optionally substituted 4- to 10-membered monocyclic or bicyclic heterocyclo, or optionally substituted 4- to 10-membered monocyclic or bicyclic heteroaryl, each heterocyclo or heteroaryl containing 1-3 heteroatoms selected from N, O, and S;

$R_5$ is optionally substituted $C_1$-$C_4$ alkyl;

X is CH or N;

Y is

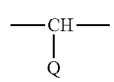

or N, where Q is H or halogen; and

Z is CH or N.

In another embodiment, there is provided a compound of formula I, wherein

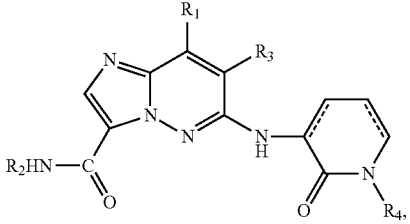

or stereoisomers, tautomers, pharmaceutically acceptable salts, solvates, or prodrugs thereof, wherein:

$R_1$ is H or $NHR_5$, wherein $R_5$ is $C_1$-$C_4$ alkyl;

$R_2$ is H, optionally substituted 3- to 10-membered monocyclic or bicyclic cycloalkyl, optionally substituted $C_1$-$C_6$ alkyl, optionally substituted 6- to 10-membered monocyclic or bicyclic aryl, or optionally substituted 4- to 10-membered monocyclic or bicyclic heterocyclo, each heterocyclo containing 1-3 heteroatoms selected from N, O, and S;

$R_3$ is H or halo; and $R_4$ is H, optionally substituted 4- to 10-membered monocyclic or bicyclic heteroaryl, $C_1$-$C_6$ alkyl, phenyl, 3- to 10-membered monocyclic or bicyclic cycloalkyl, or optionally substituted 4- to 10-membered monocyclic or bicyclic heterocyclo, each heteroaryl or heterocyclo containing 1-3 heteroatoms selected from N, O, and S.

In another embodiment, there is provided a compound of formula I having the structure:

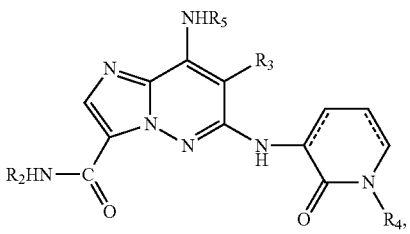

or stereoisomers, tautomers, pharmaceutically acceptable salts, solvates, or prodrugs thereof, wherein:

$R_5$ is $C_1$-$C_4$ alkyl;

$R_2$ is H, optionally substituted 3- to 10-membered monocyclic or bicyclic cycloalkyl, optionally substituted $C_1$-$C_6$ alkyl, optionally substituted 6- to 10-membered aryl, or optionally substituted 4- to 10-membered monocyclic or bicyclic heterocyclo, each heterocyclo containing 1-3 heteroatoms selected from N, O, and S;

$R_3$ is halo; and $R_4$ is optionally substituted 4- to 10-membered monocyclic or bicyclic heteroaryl, each containing 1-3 heteroatoms selected from N, O, and S.

In a more preferred embodiment, there is provided a compound of formula I, having the structure:

or stereoisomers, tautomers, pharmaceutically acceptable salts, solvates, or prodrugs thereof, wherein:
$R_2$ is H; or
$R_2$ is each of which is optionally substituted with 1, 2 or 3 substituents selected from halo, CN, $C_1$-$C_4$ alkyl and OH; or
$R_2$ is $C_1$-$C_6$ alkyl optionally substituted with 1, 2 or 3 substituents selected from $C_1$-$C_4$ alkoxy, halo, OH, CN, or 3- to 10-membered cycloalkyl optionally substituted with hydroxy-$C_1$-$C_4$-alkyl; or
$R_2$ is phenyl;
$R_2$ is $R_3$ is H or halo; and
$R_4$ is H or optionally substituted 4- to 10-membered monocyclic or bicyclic heteroaryl, each heteroaryl containing 1-3 heteroatoms selected from N, O, and S.

In an even more preferred embodiment, there is provided a compound of formula I, or stereoisomers, tautomers, pharmaceutically acceptable salts, solvates, or prodrugs thereof, wherein $R_3$ is H or halo.

In an alternate preferred embodiment, there is provided a compound of formula I, having the structure:

or stereoisomers, tautomers, pharmaceutically acceptable salts, solvates, or prodrugs thereof, wherein:
$R_1$ is H or $NHCH_3$;
$R_2$ is H, optionally substituted 3- to 10-membered monocyclic or bicyclic cycloalkyl, optionally substituted $C_1$-$C_6$ alkyl, optionally substituted 6- to 10-membered monocyclic or bicyclic aryl, or optionally substituted 4- to 10-membered monocyclic or bicyclic heterocyclo, each heterocyclo containing 1-3 heteroatoms selected from N, O, and S;
$R_3$ is H, F or Cl; and
$R_4$ is H; or
$R_4$ is each heteroaryl, optionally substituted with 1, 2 or 3 substituents selected from halo, $C_1$-$C_4$ alkyl, 3- to 10-membered monocyclic cycloalkyl, $C_1$-$C_4$ alkoxy, trihalo-$C_1$-$C_4$-alkyl, hydroxy-$C_1$-$C_4$-alkyl, 4- to 10-membered monocyclic heterocyclo, di-$C_1$-$C_4$-alkylamino, or $C_1$-$C_4$ alkylamino; or
$R_4$ is $CH_3$, i-$C_3H_7$, or each optionally substituted with 1, 2 or 3 substituents selected from halo, $C_1$-$C_4$ alkoxy, or 3- to 8-membered monocyclic cycloalkyl; or
$R_4$ is phenyl optionally substituted with halo, dihalo-$C_1$-$C_4$-alkyl, trihalo-$C_1$-$C_4$-alkyl, hydroxy-$C_1$-$C_4$-alkyl, CN, or a 4- to 10-membered monocyclic heterocyclo containing 1-3 heteroatoms selected from N, O, and S, or $C_1$-$C_4$ alkylsulfonyl; or
$R_4$ is each optionally substituted with 1, 2 or 3 substituents selected from $C_1$-$C_4$ alkyl or OH; or
$R_4$ is each optionally substituted with 1, 2 or 3 substituents selected from (trihalo-$C_1$-$C_4$-alkyl)3- to 10-membered monocyclic cycloalkylcarbonyl, dihalo 3- to 10-membered monocyclic cycloalkylcarbonyl, $C_1$-$C_4$ alkylcarbonyl, 4- to 10-membered monocyclic heteroarylcarbonyl, ($C_1$-$C_4$ alkyl) 4- to 10-membered monocyclic heteroarylcarbonyl, 4- to 10-membered monocyclic heterocyclocarbonyl, dihalo-$C_1$-$C_4$-alkyl, or $C_1$-$C_4$-alkoxy-$C_1$-$C_4$-alkylcarbonyl.

In another preferred embodiment, there is provided a compound of formula I, having the structure:

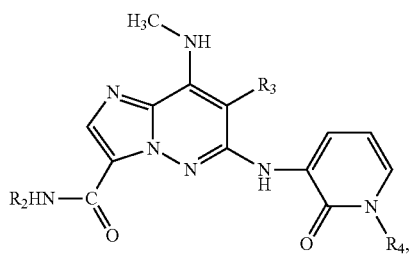

or stereoisomers, tautomers, pharmaceutically acceptable salts, solvates, or prodrugs thereof, wherein:

$R_2$ is

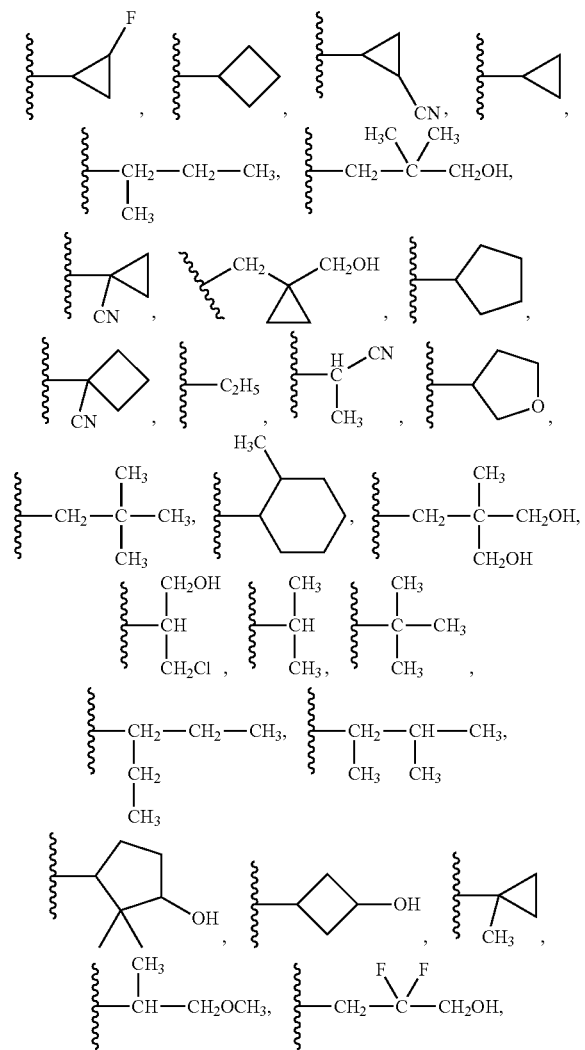

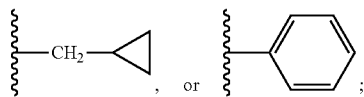

$R_3$ is

-Cl,

H or

-F;

and $R_4$ is

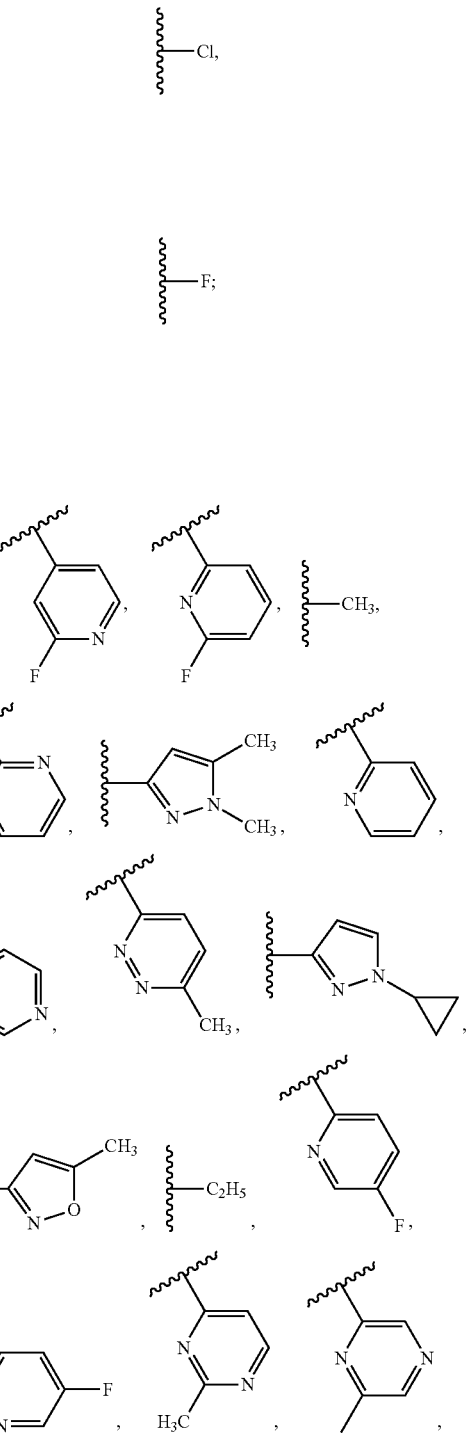

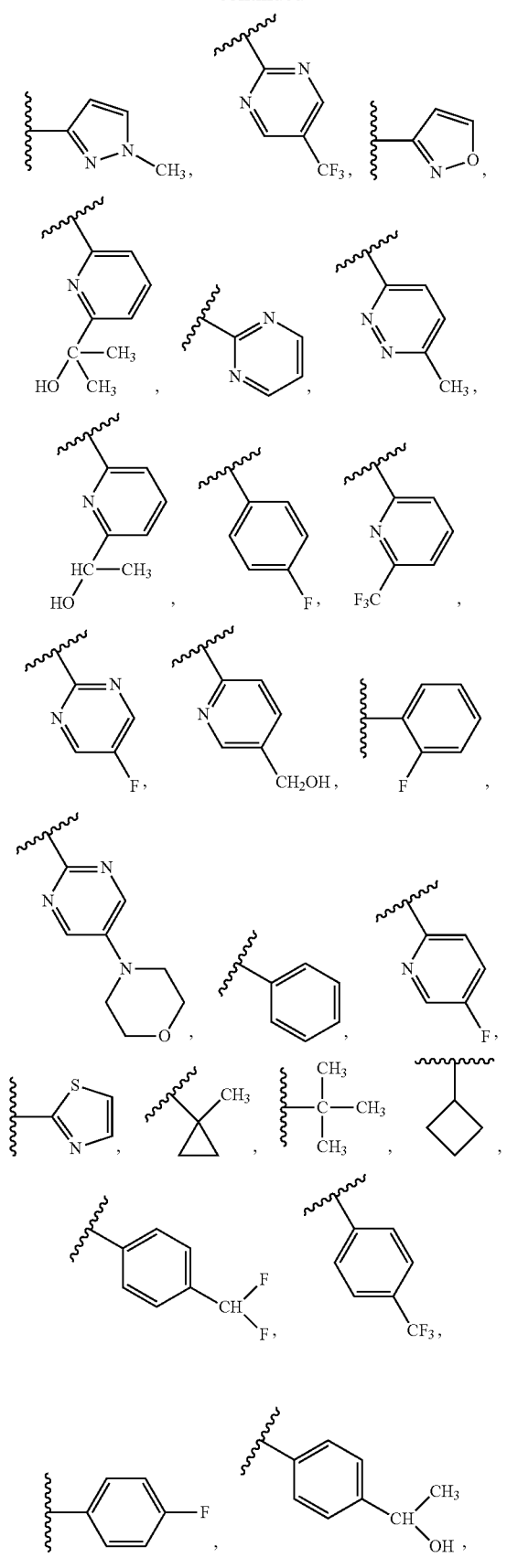
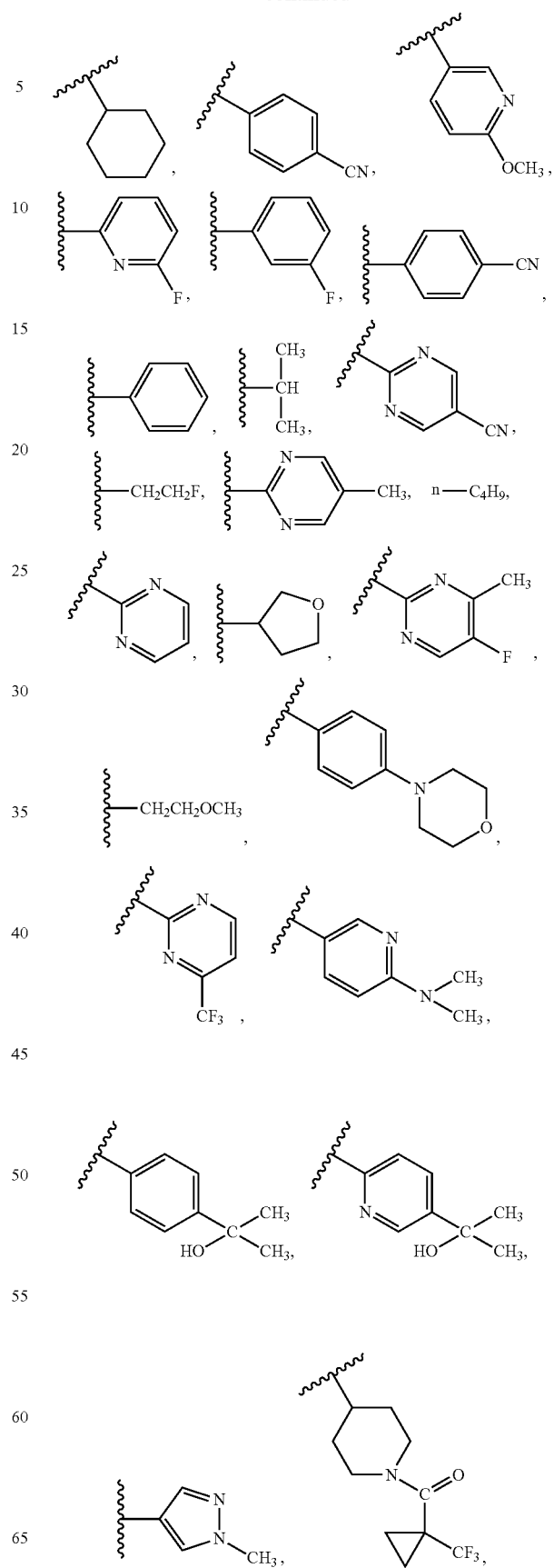

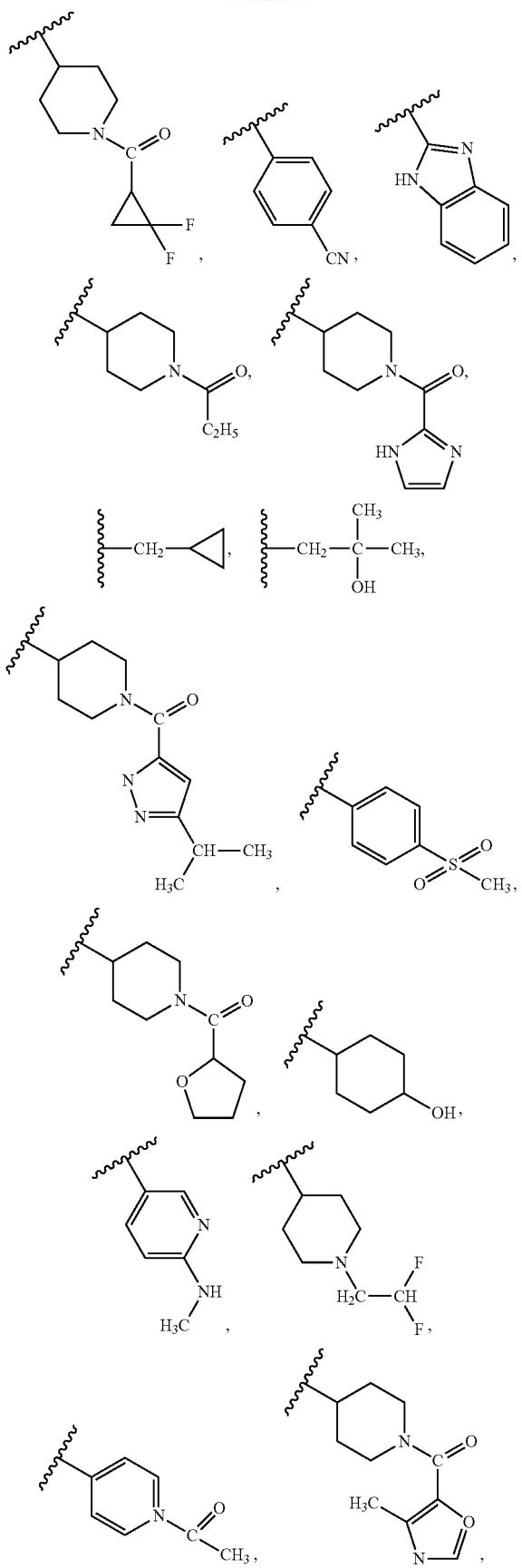

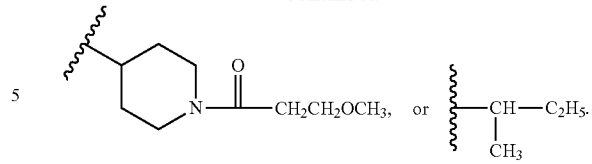

In another embodiment, there is provided a compound which is
N-((1R,2S)-2-Fluorocyclopropyl)-8-(methylamino)-6-(2-oxo-1-(pyridin-2-yl)-1,2-dihydropyridin-3-ylamino)imidazo[1,2-b]pyridazine-3-carboxamide;
6-{[5-fluoro-1-(6-methylpyridazin-3-yl)-2-oxo-1,2-dihydropyridin-3-yl]amino}-N-[(1R,2S)-2-fluorocyclopropyl]-8-(methylamino)imidazo[1,2-b]pyridazine-3-carboxamide;
N-[(1R,2S)-2-fluorocyclopropyl]-8-(methylamino)-6-{[1-(6-methylpyridin-2-yl)-2-oxo-1,2-dihydropyridin-3-yl]amino}imidazo[1,2-b]pyridazine-3-carboxamide;
N-[(1R,2S)-2-fluorocyclopropyl]-6-{[1-(6-methoxypyridazin-3-yl)-2-oxo-1,2-dihydropyridin-3-yl]amino}-8-(methylamino)imidazo[1,2-b]pyridazine-3-carboxamide; and
6-{[1-(1,5-dimethyl-1H-pyrazol-3-yl)-2-oxo-1,2-dihydropyridin-3-yl]amino}-N-[(1R,2S)-2-fluorocyclopropyl]-8-(methylamino)imidazo[1,2-b]pyridazine-3-carboxamide;
or a pharmaceutically acceptable salt, tautomer or stereoisomer thereof In another embodiment, there is provided a pharmaceutical composition comprising one or more compounds of formula (I), or stereoisomers, tautomers, pharmaceutically acceptable salts, solvates, or prodrugs thereof, and a pharmaceutically acceptable carrier or diluent.

The present invention is also directed to pharmaceutical compositions useful in treating diseases associated with the modulation of IL-12, IL-23 and/or IFNα by acting on Tyk-2 to cause signal transduction inhibition, comprising compounds of formula I, or pharmaceutically-acceptable salts thereof, and pharmaceutically-acceptable carriers or diluents.

The invention further relates to methods of treating diseases associated with the modulation of IL-12, IL-23, and/or IFNα, comprising administering to a patient in need of such treatment a therapeutically-effective amount of a compound according to formula I.

The present invention also provides processes and intermediates for making the compounds of the present invention.

The present invention also provides a method for treating proliferative, metabolic, allergic, autoimmune and inflammatory diseases (or use of the compounds of the present invention for the manufacture of a medicament for the treatment of these diseases), comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method of treating an inflammatory or autoimmune disease (or use of the compounds of the present invention for the manufacture of a medicament for the treatment of these diseases) comprising administering to a patient in need of such treatment a therapeutically-effective amount of a compound of Formula I.

The present invention also provides a method for treating a disease (or use of the compounds of the present invention for the manufacture of a medicament for the treatment of these diseases), comprising administering to a patient in need of such treatment a therapeutically-effective amount of a compound of Formula I, wherein the disease is rheumatoid arthritis, multiple sclerosis, systemic lupus erythematosus (SLE), lupus nephritis, cutaneous lupus, inflammatory bowel disease, psoriasis, Crohn's Disease, psoriatic arthritis, Sjögren's syndrome, systemic scleroderma, ulcerative colitis, Graves' disease, discoid lupus erythematosus, adult onset Stills, systemic onset juvenile idiopathic arthritis, gout, gouty arthritis, type 1 diabetes, insulin dependent diabetes mellitus, sepsis, septic shock, Shigellosis, pancreatitis (acute or chronic), glomerulonephritis, autoimmune gastritis, diabetes, autoimmune hemolytic anemia, autoimmune neutropenia, thrombocytopenia, atopic dermatitis, myasthenia gravis, pancreatitis (acute or chronic), ankylosing spondylitis, pemphigus vulgaris, Goodpasture's disease, antiphospholipid syndrome, idiopathic thrombocytopenia, ANCA-associated vasculitis, pemphigus, Kawasaki disease, Chronic Inflammatory Demyelinating Polyneuropathy (CIDP), dermatomyositis, polymyositis, uveitis, Guillain-Barre syndrome, autoimmune pulmonary inflammation, autoimmune thyroiditis, autoimmune inflammatory eye disease, and chronic demyelinating polyneuropathy.

The present invention also provides a method of treating an inflammatory or autoimmune disease (or use of the compounds of the present invention for the manufacture of a medicament for the treatment of these diseases), comprising administering to a patient in need of such treatment a therapeutically-effective amount of a compound of Formula I, wherein the disease is selected from systemic lupus erythematosus (SLE), lupus nephritis, cutaneous lupus, Crohn's Disease, ulcerative colitis, type 1 diabetes, psoriasis, rheumatoid arthritis, systemic onset juvenile idiopathic arthritis, ankylosing spondylitis, and multiple sclerosis.

The present invention also provides a method for treating rheumatoid arthritis (or use of the compounds of the present for the manufacture of a medicament for the treatment of rheumatoid arthritis, comprising administering to a patient in need of such treatment a therapeutically-effective amount of a compound of Formula I.

In addition, the present invention also provides a method of treating a condition (or use of the compounds of the present invention for the manufacture of a medicament for the treatment of these conditions) comprising administering to a patient in need of such treatment a therapeutically-effective amount of a compound of Formula I, wherein the condition is selected from acute myelogenous leukemia, chronic myelogenous leukemia, metastatic melanoma, Kaposi's sarcoma, multiple myeloma, solid tumors, ocular neovasculization, and infantile haemangiomas, B cell lymphoma, systemic lupus erythematosus (SLE), rheumatoid arthritis, psoriatic arthritis, multiple vasculitides, idiopathic thrombocytopenic purpura (ITP), myasthenia gravis, allergic rhinitis, multiple sclerosis (MS), transplant rejection, Type I diabetes, membranous nephritis, inflammatory bowel disease, autoimmune hemolytic anemia, autoimmune thyroiditis, cold and warm agglutinin diseases, Evans syndrome, hemolytic uremic syndrome/thrombotic thrombocytopenic purpura (HUS/TTP), sarcoidosis, Sjigren's syndrome, peripheral neuropathies, pemphigus vulgaris and asthma.

The present invention also provides a method of treating a IL-12, IL-23, and/or IFNα mediated disease (or use of the compounds of the present invention for the manufacture of a medicament for the treatment of said diseases), comprising administering to a patient in need of such treatment a therapeutically-effective amount of a compound of formula I The present invention also provides a method of treating a IL-12, IL-23 and/or IFNα mediated disease (or use of the compounds of the present invention for the manufacture of a medicament for the treatment of these diseases), comprising administering to a patient in need of such treatment a therapeutically-effective amount of a compound of formula I, wherein the IL-12, IL-23 and/or IFNα mediated disease is a disease modulated by IL-12, IL-23 and/or IFNα.

The present invention also provides a method of treating diseases, comprising administering to a patient in need of such treatment a therapeutically-effective amount of a compound of formula I in combination with other therapeutic agents.

The present invention also provides the compounds of the present invention use in therapy.

In another embodiment, compounds of formula I are selected from exemplified compounds or combinations of exemplified compounds or other embodiments herein.

In another embodiment are compounds having an $IC_{50}$<1000 nM in at least one of the assays described below.

The present invention may be embodied in other specific forms without departing from the spirit or essential attributes thereof. This invention encompasses all combinations of preferred aspects and/or embodiments of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DETAILED DESCRIPTION OF THE INVENTION

The following are definitions of terms used in this specification and appended claims. The initial definition provided for a group or term herein applies to that group or term throughout the specification and claims, individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art,

is used in structural formulas herein to depict the bond that is the point of attachment of the moiety or substituent to the core or backbone structure.

A dash "—" that is not between two letters or symbols is used to indicate a point of attachment for a substituent. For example, —$CONH_2$ is attached through the carbon atom.

The term "optionally substituted" in reference to a particular moiety of the compound of Formula I (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "at least one chemical entity" is interchangeable with the term "a compound."

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

One skilled in the field will understand that, when the designation "$CO_2$" is used herein, this is intended to refer to the group

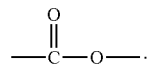

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl($C_0$)alkyl. The term "heteroarylalkyl" refers to a substituted alkyl group as defined above where at least one of the substituents is a heteroaryl.

When reference is made to a substituted alkenyl, alkynyl, alkylene, alkenylene, or alkynylene group, these groups are substituted with one to three substituents as defined above for substituted alkyl groups.

The term "alkoxy" refers to an oxygen atom substituted by alkyl or substituted alkyl, as defined herein. For example, the term "alkoxy" includes the group —O—$C_{1-6}$alkyl such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

It should be understood that the selections for all groups, including for example, alkoxy, thioalkyl, and aminoalkyl, will be made by one skilled in the field to provide stable compounds.

The term "substituted", as used herein, means that any one or more hydrogens on the designated atom or group is replaced with a selection from the indicated group, provided that the designated atom's normal valence is not exceeded. When a substituent is oxo, or keto, (i.e., =O) then 2 hydrogens on the atom are replaced. Keto substituents are not present on aromatic moieties. Unless otherwise specified, substituents are named into the core structure. For example, it is to be understood that when (cycloalkyl)alkyl is listed as a possible substituent, the point of attachment of this substituent to the core structure is in the alkyl portion. Ring double bonds, as used herein, are double bonds that are formed between two adjacent ring atoms (e.g., C=C, C=N, or N=N).

Combinations of substituents and/or variables are permissible only if such combinations result in stable compounds or useful synthetic intermediates. A stable compound or stable structure is meant to imply a compound that is sufficiently robust to survive isolation from a reaction mixture to a useful degree of purity, and subsequent formulation into an efficacious therapeutic agent. It is preferred that the presently recited compounds do not contain a N-halo, S(O)$_2$H, or S(O)H group.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3, 4, 5, 6, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, and naphthyl groups, each of which may be substituted.

Accordingly, in compounds of formula I, the term "cycloalkyl" includes cyclopropyl, cyclobutyl, cyclopentyl, cyclohexyl, cycloheptyl, bicyclooctyl, etc., as well as the following ring systems:

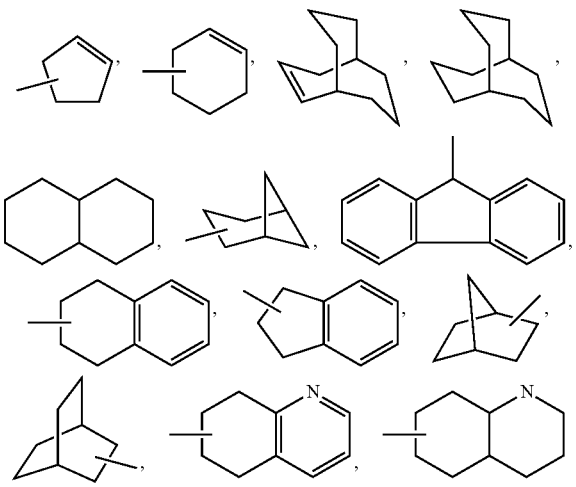

and the like, which optionally may be substituted at any available atoms of the ring(s). Preferred cycloalkyl groups include cyclopropyl, cyclopentyl, cyclohexyl, and

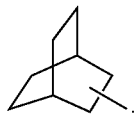

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes OCF$_3$.

Thus, examples of aryl groups include:

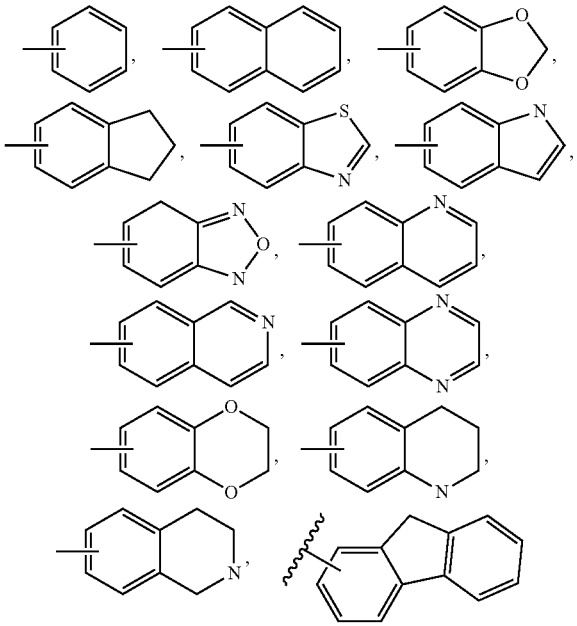

(fluorenyl) and the like, which optionally may be substituted at any available carbon or nitrogen atom. A preferred aryl group is optionally-substituted phenyl.

The terms "heterocycle", "heterocycloalkyl", "heterocyclo", "heterocyclic", or "heterocyclyl" may be used interchangeably and refer to substituted and unsubstituted 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or fully unsaturated. The heterocyclo group may be attached at any available nitrogen or carbon atom. As used herein the terms "heterocycle", "heterocycloalkyl", "heterocyclo", "heterocyclic", and "heterocyclyl" include "heteroaryl" groups, as defined below.

In addition to the heteroaryl groups described below, exemplary monocyclic heterocyclyl groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl. Additional monocyclic heterocyclyl groups include

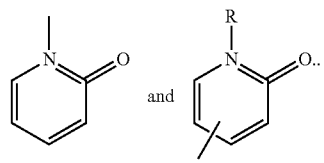

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzindolyl, phenanthrollinyl, acridinyl, phenanthridinyl, xanthenyl and the like.

In compounds of formula I, preferred heteroaryl groups include

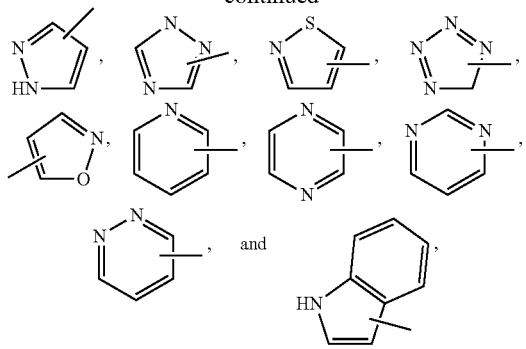

and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0 to 2, substituents selected from those recited above for the aryl, cycloalkyl, heterocyclo and/or heteroaryl groups, as appropriate.

The term "carbocyclyl" or "carbocyclic" refers to a saturated or unsaturated monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6]system, or 9 or 10 ring atoms arranged as a bicyclo [5,6] or [6,6]system. Examples of mono- and bicyclic carbocycles include cyclopropyl, cycloalkyl cyclopentyl, 1-cyclo pent-1-enyl, 1-cyclopent-2-enyl, 1-cyclopent-3-enyl, cyclohexyl 1-cyclohex-1-enyl, 1-cyclohex-2-enyl, 1-cyclohex-3-enyl, phenyl and naphthyl. The carbocyclic ring may be substituted in which case the substituents are selected from those recited above for cycloalkyl and aryl groups.

The term "heteroatoms" shall include oxygen, sulfur and nitrogen.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula I may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s) may include zwitterions (inner salts), e.g., when a compound of formula I, contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Prodrugs and solvates of the inventive compounds are also contemplated. The term "prodrug" denotes a compound which, upon administration to a subject, undergoes chemical conversion by metabolic or chemical processes to yield a compound of the formula I, and/or a salt and/or solvate thereof. Any compound that will be converted in vivo to provide the bioactive agent (i.e., the compound for formula I) is a prodrug within the scope and spirit of the invention. For example, compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$alkanoyloxy-$C_{1-6}$alkyl, e.g., acetoxymethyl, pivaloyloxymethyl or propionyloxymethyl, $C_{1-6}$alkoxycarbonyloxy-$C_{1-6}$alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:

a) Bundgaard, H., ed., *Design of Prodrugs*, Elsevier (1985), and Widder, K. et al., eds., Methods in Enzymology, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991); and c) Bundgaard, H., *Adv. Drug Deliv. Rev.*, 8:1-38 (1992), each of which is incorporated herein by reference.

Compounds of the formula I and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers.

It should further be understood that solvates (e.g., hydrates) of the compounds of Formula I are also with the scope of the present invention. Methods of solvation are generally known in the art.

Utility

The compounds of the invention modulate IL-23-stimulated and IFNα-stimulated cellular functions, including gene transcription. Other types of cellular functions that may be modulated by the compounds of the instant invention include, but are not limited to, IL-12-stimulated responses.

Accordingly, compounds of formula I have utility in treating conditions associated with the modulation of the function of IL-23 or IFNα, and particularly the selective inhibition of function of IL-23, IL-12 and/or IFNα, by acting onTyk2 to mediate signal transduction. Such conditions include IL-23-, IL-12-, or IFNα-associated diseases in which pathogenic mechanisms are mediated by these cytokines.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as modulators of IL-23-, IL-12 and IFNα-stimulated cellular responses, compounds of Formula I are useful in treating IL-23-, IL-12- or IFNα-associated diseases including, but not limited to, inflammatory diseases such as Crohn's disease, asthma, graft versus host disease, allograft rejection, chronic obstructive pulmonary disease; autoimmune diseases such as Graves' disease, rheumatoid arthritis, systemic lupus erythematosis, cutaneous lupus, lupus nephritis, discoid lupus erythematosus, psoriasis; auto-inflammatory diseases including CAPS, TRAPS, FMF, adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, cutaneous lupus, lupus nephritis, discoid lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hyposia [should this be hypoxia], vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's disease, ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

When the terms "IL-23-, IL-12- and/or IFNα-associated condition" or "IL-23-, IL-12- and/or IFNα-associated disease or disorder" are used herein, each is intended to encompass all of the conditions identified above as if repeated at length, as well as any other condition that is affected by IL-23, IL-12 and/or IFNα.

The present invention thus provides methods for treating such conditions, comprising administering to a subject in need thereof a therapeutically-effective amount of at least one compound of Formula I or a salt thereof. "Therapeutically effective amount" is intended to include an amount of a compound of the present invention that is effective when administered alone or in combination to inhibit IL-23, IL-12 and/or IFNα function and/or treat diseases.

The methods of treating IL-23-, IL-12 and/or IFNα-associated conditions may comprise administering compounds of Formula I alone or in combination with each other and/or other suitable therapeutic agents useful in treating such conditions. Accordingly, "therapeutically effective amount" is also intended to include an amount of the combination of compounds claimed that is effective to inhibit IL-23, IL-12 and/or IFNα function and/or treat diseases associated with IL-23, IL-12 and/or IFNα.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating IL-23-, IL-12- or IFNα-associated conditions by inhibiting Tyk2-mediated signal transduction, including IL-23-, IL-12- and/or IFNα-mediated diseases, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula I and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Remington's Pharmaceutical Sciences, 17th Edition (1985), which is incorporated herein by reference in its entirety.

The compounds of Formula I may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5 250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species that are affected by modulation of IL-23, IL-12 and/or IFNα-mediated functions.

Biological Assays

Probe Displacement Assay

The probe displacement assay is conducted as follows: In a 385 well plate, test compounds along with recombinantly expressed His-tagged protein corresponding to amino acids 575-869 of human Tyk2 (sequence shown below) at 2.5 nM, 40 nM ((R)—N-(1-(3-(8-methyl-5-(methylamino)-8H-imidazo[4,5-d]thiazolo[5,4-b]pyridin-2-yl)phenyl)ethyl)-2-([$^3$H]methylsulfonyl)benzamide) (preparation described below) and 80 µg/mL Copper His-Tag scintillation proximity assay beads (Perkin Elmer, Catalog #RPNQ0095) in 50 mM HEPES, pH 7.5, containing 100 µg/mL bovine serum albumin and 5% DMSO were incubated for 30 minutes at room temperature. The amount of radiolabeled probe (preparation described below) bound to Tyk2 was then quantified by scintillation counting, and the inhibition by the test compound calculated by comparison to wells either with no inhibitor (0% inhibition) or without Tyk2 (100% inhibition). The IC50 value is defined as the concentration of test compound required to inhibit radiolabeled probe binding by 50%.

Protein Sequence of recombinant Hig-tagged Tyk2 (575-869):

```
MGSSHHHHHH SSGETVRFQG HMNLSQLSFH RVDQKEITQL

SHLGQGTRTN VYEGRLRVEG SGDPEEGKMDDEDPLVPGRD

RGQELRVVLK VLDPSHHDIA LAFYETASLM SQVSHTHLAF

VHGVCVRGPE NIMVTEYVEHGPLDVWLRRE RGHVPMAWKM

VVAQQLASAL SYLENKNLVH GNVCGRNILL ARLGLAEGTS

PFIKLSDPGVGLGALSREER VERIPWLAPE CLPGGANSLS

TAMDKWGFGA TLLEICFDGE APLQSRSPSE

KEHFYQRQHRLPEPSCPQLA TLTSQCLTYE PTQRPSFRTI

LRDLTRL
```

The preparation of radiolabeled probe, (R)—N-(1-(3-(8-methyl-5-(methylamino)-8H-imidazo[4,5-d]thiazolo[5,4-b]pyridin-2-yl)phenyl)ethyl)-2-([$^3$H]methylsulfonyl)benzamide, was performed as described below:

2-([$^3$H]methylsulfonyl)benzoic acid: 2-Mercaptobenzoic acid (2.3 mg, 0.015 mmol) and cesium carbonate (2 mg, 0.006 mmol) were added to a 5 mL round-bottomed flask. The flask was attached to a ported glass vacuum line and anhydrous DMF (0.5 mL) was introduced with magnetic stirring. An ampoule of tritiated methyl iodide (200 mCi, Perkin-Elmer lot 3643419) was added to the reaction flask and stirring was maintained at rt for 3 h. In-process HPLC analysis with radiometric detection indicated 80% conversion to the desired product by comparison with authentic standard. Without purification, the crude product was reacted with mCPBA (10 mg, 0.058 mmol) pre-dissolved in $CH_2Cl_2$ (1 mL) at room temperature with stirring. The reaction was stirred for 7 h and additional mCPBA (10 mg, 0.058 mmol) was added. The reaction was stirred for approximately 24 h and HPLC analysis indicated 35-40% conversion to the desired sulfonate product. The crude product was purified by semi-preparative HPLC (Luna 5 um C18 (10×250 cm); A: MeOH/$H_2O$=15/85(0.1% TFA); B: MeOH; 270 nm; 0-8 min 0% B 1 ml/min; 8-10 min 0% B 1-3 ml/min; 10-55 min 0% B 3 ml/min; 55-65 min 0-10% B 3 ml/min; 65-75 min 10-50% B 3 ml/min; 75-80 min 50-100% B 3 ml/min) to give 81 mCi (40% radiochemical yield) of 2-([$^3$H]methylsulfonyl)benzoic acid product identified by its HPLC co-elution with an authentic standard. The radiochemical purity was measured by HPLC to be 99% (Luna 5u C18 (4.6×150 cm); A: $H_2O$(0.1% TFA); B: MeOH; 1.2 ml/min; 270 nm; 0-10 min 20% B; 10-15 min 20-100% B; 15-25 min 100% B. The product was dissolved in anhydrous acetonitrile to give a final solution activity of 5.8 mCi/mL. (R)—N-(1-(3-(8-methyl-5-(methylamino)-8H-imidazo[4,5-d]thiazolo[5,4-b]pyridin-2-yl)phenyl)ethyl)-2-([$^3$H]methylsulfonyl)benzamide: A solution of 2-([$^3$H]methylsulfonyl)benzoic acid (23.2 mCi) in acetonitrile was added to a 5 mL round-bottomed flask which was then attached to a vacuum line and carefully evaporated to dryness. (R)-2-(3-(1-aminoethyl)phenyl)-N,8-dimethyl-8H-imidazo[4,5-d]thiazolo[5,4-b]pyridin-5-amine (prepared as described in WO 2004/106293 and Dyckman et al., *Bioorganic and Medicinal Chemistry Letters*, 383-386 (2011)) (1.1 mg, 0.0033 mmol) and PyBOP (2 mg, 0.0053 mmol) dissolved in anhydrous DMF (1.5 mL) were added to the flask followed by N,N-diisopropylethylamine (0.010 mL). The resulting clear solution was stirred at room temperature for 18 h. HPLC analysis (Luna 5u C18 (4.6×150 cm); A: $H_2O$(0.1% TFA); B: MeOH; 1.2 ml/min; 335 nm; 0-20 min 50% B; 20-25 min 50-100% B; 25-30 min 100% B) indicated approximately a 20% conversion to the desired product by retention time comparison to a sample of non-radiolabeled (R)—N-(1-(3-(8-methyl-5-(methylamino)-8H-imidazo[4,5-d]thiazolo[5,4-b]pyridin-2-yl)phenyl)ethyl)-2-(methylsulfonyl)benzamide. The crude reaction mixture was purified by semi-preparative HPLC (Luna 5u C18 (10×250 cm); A: MeOH/$H_2O$=50/50(0.1% TFA); B: MeOH; 335 nm; 0-40 min 0% B 3 ml/min; 40-45 min 0-100% B 3 ml/min). The purification routine was performed a second time to yield a total of 1.7 mCi (7% radiochemical yield) of the desired product in 99.9% radiochemical purity. Mass spectral analysis of the tritiated product (m/z M+H 527.33) was used to establish the specific activity at 80.6 Ci/mmol.

| Probe Displacement Data | |
|---|---|
| Example | Probe Displacement (EC50, uM) |
| 3 | 0.005 |
| 6 | 0.015 |
| 25 | 0.016 |
| 32 | 0.027 |
| 35 | 0.005 |
| 61 | 0.020 |
| 63 | 0.007 |
| 74 | 0.009 |
| 79 | 0.006 |
| 83 | 0.002 |
| 85 | 0.005 |
| 86 | 0.006 |
| 93 | 0.012 |
| 101 | 0.012 |
| 106 | 0.013 |
| 109 | 0.004 |
| 118 | 0.018 |
| 124 | 0.004 |
| 126 | 0.008 |
| 132 | 0.014 |
| 133 | 0.019 |
| 136 | 0.011 |
| 140 | 0.014 |
| 145 | 0.005 |
| 155 | 0.007 |
| 163 | 0.008 |
| 180 | 0.017 |
| 187 | 0.029 |
| 188 | 0.021 |
| 190 | 0.023 |
| 197 | 0.016 |
| 202 | 0.008 |
| 207 | 0.015 |
| 207 | 0.022 |
| 211 | 0.057 |
| 214 | 0.073 |
| 245 | 0.007 |

Kit225 T Cell Assay

Kit225 T cells with a stably-integrated STAT-dependent luciferase reporter were plated in RPMI (GIBCO) containing 10% heat-inactivated FBS (GIBCO) and 100 U/mL PenStrep (GIBCO). The cells were then stimulated with either 20 ng/mL human recombinant IL-23 or 200 U/mL human recombinant IFNα (PBL InterferonSource) for 5-6 hours. Luciferase expression was measured using the STEADY-GLO® Luciferase Assay System (PROMEGA®) according to the manufacturer's instructions. Inhibition data were calculated by comparison to no inhibitor control wells for 0% inhibition and non-stimulated control wells for 100% inhibition. Dose response curves were generated to determine the concentration required to inhibit 50% of cellular response (IC50) as derived by non-linear regression analysis.

| Kit225 T Cell Inhibition Data | | |
|---|---|---|
| Ex # | IL-23 Kit225 Reporter, LE (IC50, uM) | IFNa Kit225 Reporter, LE (IC50, uM) |
| 1 | 0.48 | 0.31 |
| 2 | 0.16 | 0.09 |
| 3 | 0.05 | 0.03 |
| 4 | 0.52 | 0.32 |
| 5 | 0.15 | 0.15 |
| 6 | 0.07 | 0.14 |
| 7 | 0.27 | 0.30 |
| 8 | 0.67 | 0.38 |
| 9 | 0.12 | 0.04 |
| 10 | 0.15 | 0.12 |
| 11 | 0.31 | 0.26 |
| 12 | 0.17 | 0.10 |
| 13 | 0.15 | 0.23 |
| 14 | 0.57 | 0.46 |
| 15 | 0.19 | 0.27 |
| 16 | 0.40 | 0.36 |
| 17 | 0.24 | 0.18 |
| 18 | 0.48 | 0.15 |
| 19 | 0.33 | 0.40 |
| 20 | 0.13 | 0.08 |
| 21 | 0.61 | 0.11 |
| 22 | 0.15 | 0.05 |
| 23 | 0.07 | 0.02 |
| 24 | 0.15 | 0.04 |
| 25 | 0.20 | 0.10 |
| 26 | 0.27 | 0.11 |
| 27 | 0.66 | 0.45 |
| 28 | 0.60 | 0.30 |
| 29 | 0.34 | 0.20 |
| 30 | 0.39 | 0.20 |
| 31 | 0.21 | 0.11 |
| 32 | 0.22 | 0.08 |
| 33 | 0.28 | 0.26 |
| 34 | 0.06 | 0.05 |
| 35 | 0.02 | 0.05 |
| 36 | 0.10 | 0.10 |
| 37 | 0.02 | 0.03 |
| 38 | 0.16 | 0.06 |
| 39 | 0.19 | 0.06 |
| 40 | 0.16 | 0.05 |
| 41 | 0.08 | 0.06 |
| 42 | 0.05 | 0.02 |
| 43 | 0.59 | 0.11 |
| 44 | 0.38 | 0.13 |
| 45 | 0.37 | 0.20 |
| 46 | 0.36 | 0.16 |
| 47 | 0.11 | 0.04 |
| 48 | 0.18 | 0.18 |
| 49 | 0.02 | 0.05 |
| 50 | 1.16 | 0.45 |
| 51 | 0.16 | 0.22 |
| 52 | 0.21 | 0.13 |
| 53 | 0.17 | 0.08 |
| 54 | 0.21 | 0.10 |
| 55 | 0.18 | 0.23 |
| 56 | 0.06 | 0.03 |
| 57 | 0.30 | 0.52 |
| 58 | 0.09 | 0.97 |
| 59 | 0.18 | 0.18 |
| 60 | 0.24 | 0.47 |
| 61 | 0.21 | 0.18 |
| 62 | 0.64 | 0.27 |
| 63 | 0.14 | 0.11 |

| Ex # | IL-23 Kit225 Reporter, LE (IC50, uM) | IFNa Kit225 Reporter, LE (IC50, uM) |
|---|---|---|
| 64 | 0.04 | 0.03 |
| 65 | 0.06 | 0.04 |
| 66 | 0.09 | 0.18 |
| 67 | 0.07 | 0.14 |
| 68 | 0.03 | 0.01 |
| 69 | 0.11 | 0.04 |
| 70 | 0.13 | 0.14 |
| 71 | 0.21 | 0.12 |
| 72 | 0.46 | 0.44 |
| 73 | 0.19 | 0.12 |
| 74 | 0.17 | 0.11 |
| 75 | 0.19 | 0.13 |
| 76 | 0.41 | 0.56 |
| 77 | 0.02 | 0.03 |
| 78 | 0.23 | 0.18 |
| 79 | 0.14 | 0.03 |
| 80 | 1.74 | 0.33 |
| 81 | 0.18 | 0.12 |
| 82 | 0.04 | 0.04 |
| 83 | 0.20 | 0.12 |
| 84 | 3.86 | 4.27 |
| 85 | 0.34 | 0.11 |
| 86 | 0.03 | 0.03 |
| 87 | 0.22 | 0.16 |
| 88 | 0.04 | 0.02 |
| 89 | 0.04 | 0.03 |
| 90 | 0.11 | 0.07 |
| 91 | 0.23 | 0.15 |
| 92 | 0.42 | 0.62 |
| 93 | 0.09 | 0.03 |
| 94 | 0.04 | 0.05 |
| 95 | 0.16 | 0.15 |
| 96 | 0.47 | 0.30 |
| 97 | 0.19 | 0.11 |
| 98 | 0.04 | 0.02 |
| 99 | 0.11 | 0.23 |
| 100 | 0.04 | 0.03 |
| 101 | 0.14 | 0.17 |
| 102 | 0.26 | 0.26 |
| 103 | 0.06 | 0.02 |
| 104 | 0.20 | 0.08 |
| 105 | 0.32 | 0.09 |
| 106 | 0.18 | 0.16 |
| 107 | 0.23 | 0.27 |
| 108 | 0.21 | 0.08 |
| 109 | | |
| 110 | 0.30 | 0.21 |
| 111 | 0.24 | 0.13 |
| 112 | 0.28 | 0.52 |
| 113 | | |
| 114 | | |
| 115 | | |
| 116 | 0.08 | 0.05 |
| 117 | 0.24 | 0.15 |
| 118 | 0.27 | 0.15 |
| 119 | 0.08 | 0.12 |
| 120 | 0.20 | 0.07 |
| 121 | 0.59 | 0.29 |
| 122 | 0.15 | 0.04 |
| 123 | 1.49 | 0.47 |
| 124 | 0.15 | 0.08 |
| 125 | 0.24 | 0.16 |
| 126 | 0.30 | 0.19 |
| 127 | 0.12 | 0.04 |
| 128 | 0.44 | 0.24 |
| 129 | 0.44 | 0.16 |
| 130 | 0.64 | 0.31 |
| 131 | 0.17 | 0.13 |
| 132 | 0.40 | 0.32 |
| 133 | 0.43 | 0.20 |
| 134 | 0.22 | 0.14 |
| 135 | 0.28 | 0.24 |
| 136 | 0.17 | 0.08 |
| 137 | 0.29 | 0.14 |
| 138 | 0.33 | 0.26 |
| 139 | 0.25 | 0.19 |
| 140 | 0.19 | 0.15 |
| 141 | 0.16 | 0.18 |
| 142 | 0.07 | 0.09 |
| 143 | 0.12 | 0.50 |
| 144 | 0.14 | 0.08 |
| 145 | 0.03 | 0.01 |
| 146 | 0.13 | 0.16 |
| 147 | 0.03 | 0.02 |
| 148 | 0.12 | 0.28 |
| 149 | 0.07 | 0.06 |
| 150 | 0.06 | 0.02 |
| 151 | 0.03 | 0.02 |
| 152 | 0.36 | 0.12 |
| 153 | 0.06 | 0.03 |
| 154 | 0.04 | 0.03 |
| 155 | 0.03 | 0.02 |
| 156 | 0.08 | 0.06 |
| 157 | 0.03 | 0.02 |
| 158 | 0.13 | 0.10 |
| 159 | 0.03 | 0.04 |
| 160 | 0.05 | 0.03 |
| 161 | 0.71 | 0.34 |
| 162 | 0.65 | 0.25 |
| 163 | 0.24 | 0.07 |
| 164 | 0.05 | 0.02 |
| 165 | 0.43 | 0.13 |
| 166 | 0.29 | 0.05 |
| 167 | 0.10 | 0.13 |
| 168 | 0.87 | 0.46 |
| 169 | 0.08 | 0.04 |
| 170 | 0.19 | 0.37 |
| 171 | 0.21 | 0.14 |
| 172 | 0.26 | 0.18 |
| 173 | 0.05 | 0.05 |
| 174 | 0.05 | 0.04 |
| 175 | 0.31 | 0.11 |
| 176 | 0.05 | 0.03 |
| 177 | 0.01 | 0.03 |
| 178 | 0.05 | 0.03 |
| 179 | 0.48 | 0.57 |
| 180 | 0.05 | 0.02 |
| 181 | 0.29 | 0.35 |
| 182 | 0.22 | 0.27 |
| 183 | 0.22 | 0.27 |
| 184 | 0.30 | 1.44 |
| 185 | 0.30 | 0.35 |
| 186 | 0.43 | 0.26 |
| 187 | 0.22 | 0.38 |
| 188 | 0.07 | 0.23 |
| 189 | 0.23 | 0.19 |
| 190 | 0.26 | 0.29 |
| 191 | 0.04 | 0.02 |
| 192 | 0.23 | 0.18 |
| 193 | 0.14 | 0.33 |
| 194 | 0.89 | 0.30 |
| 195 | 0.11 | 0.06 |
| 196 | 0.16 | 0.04 |
| 197 | 0.06 | 0.06 |
| 198 | 0.19 | 0.04 |
| 199 | 0.33 | 0.09 |
| 200 | 0.11 | 0.26 |
| 201 | 0.15 | 0.10 |
| 202 | 0.35 | 0.33 |
| 203 | 0.19 | 0.20 |
| 204 | 0.07 | 0.10 |
| 207 | 0.12 | 0.18 |

-continued

| Kit225 T Cell Inhibition Data | | |
|---|---|---|
| Ex # | IL-23 Kit225 Reporter, LE (IC50, uM) | IFNa Kit225 Reporter, LE (IC50, uM) |
| 206 | 0.49 | 0.38 |
| 207 | 0.29 | 0.26 |
| 208 | 0.08 | 0.06 |
| 209 | 0.18 | 0.33 |
| 210 | 0.22 | 0.39 |
| 211 | 0.36 | 0.49 |
| 212 | 0.11 | 2.48 |
| 213 | 0.23 | 0.42 |
| 214 | 0.36 | 0.81 |
| 215 | 0.19 | 0.30 |
| 216 | 0.90 | 0.44 |
| 217 | 0.09 | 0.10 |
| 218 | 0.19 | 0.13 |
| 219 | 0.25 | 0.07 |
| 220 | 0.17 | 0.28 |
| 221 | 0.50 | 0.14 |
| 222 | 0.29 | 0.13 |
| 223 | 1.18 | 0.24 |
| 224 | 0.68 | 0.47 |
| 225 | 0.10 | 0.03 |
| 226 | 0.24 | 0.09 |
| 227 | 0.62 | 0.37 |
| 228 | 0.21 | 0.10 |
| 229 | 0.24 | 0.18 |
| 230 | 0.12 | 0.07 |
| 231 | 0.20 | 0.14 |
| 232 | 0.48 | 0.27 |
| 233 | 0.72 | 0.28 |
| 234 | 0.29 | 0.14 |
| 235 | 0.56 | 0.91 |
| 236 | 0.85 | 0.35 |
| 237 | 0.44 | 0.40 |
| 238 | 0.06 | 0.53 |
| 239 | 0.21 | 0.10 |
| 240 | 0.06 | 0.21 |
| 241 | 0.14 | 0.09 |
| 242 | 0.17 | 0.36 |
| 243 | 0.05 | 0.02 |
| 244 | 0.29 | 0.12 |
| 245 | 0.29 | 0.26 |
| 246 | 0.20 | 0.22 |
| 247 | 0.42 | 0.35 |
| 248 | 0.28 | 0.23 |
| 249 | 0.50 | 0.25 |
| 250 | 0.10 | 0.39 |
| 251 | 0.35 | 0.40 |
| 252 | 0.45 | 0.19 |
| 253 | 0.18 | 0.45 |
| 254 | 0.23 | 0.26 |
| 255 | 0.0308 | 0.0280 |

-continued

| Kit225 T Cell Inhibition Data | | |
|---|---|---|
| Ex # | IL-23 Kit225 Reporter, LE (IC50, uM) | IFNa Kit225 Reporter, LE (IC50, uM) |
| 256 | 0.0130 | 0.0098 |
| 257 | 0.18 | 0.07 |
| 258 | 1.22 | 0.59 |
| 259 | 0.61 | 0.42 |
| 260 | 0.01 | 0.01 |
| 261 | 0.01 | 0.02 |
| 262 | 0.09 | 0.11 |
| 263 | 0.16 | 0.05 |
| 264 | 0.09 | 0.04 |
| 265 | 0.04 | 0.06 |
| 266 | 0.12 | 0.11 |
| 267 | 0.36 | 0.29 |

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the preparations and examples section set out hereinafter. Several of the compounds described were chiral, some were prepared as racemic mixtures, while others were prepared as a single enantiomer. In each case the preparation of the homochiral examples, or the preparation of the opposite enantiomer, may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diaststereoselectivity of transformations, providing enantioenriched products upon cleavage of the chiral auxiliary.

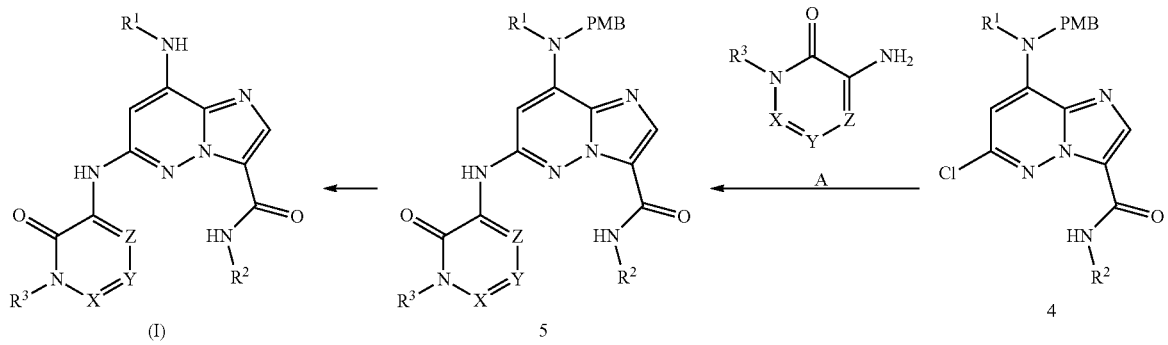

Scheme 1

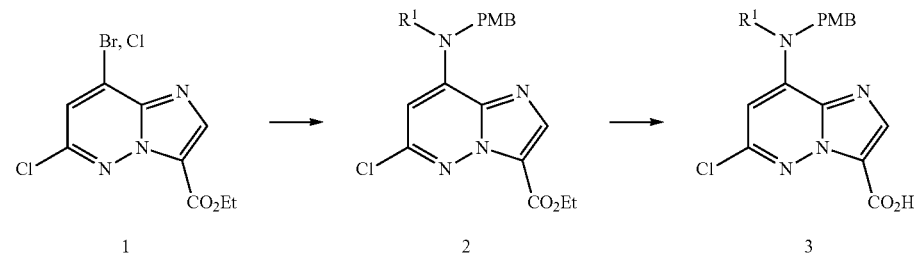

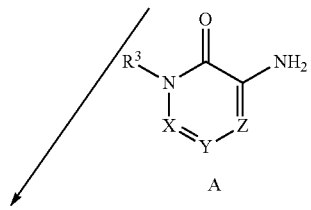

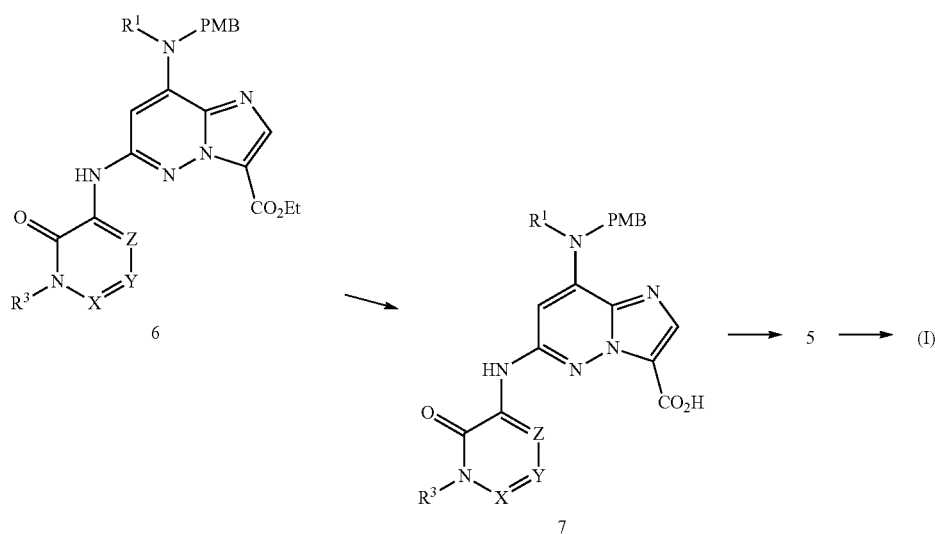

The compounds of Formula (I) can be prepared according to Scheme 1. Treatment of imidazopyridazine derivative (1) (WO 2009/100375) with p-methoxybenzyl protected amine (R¹NHPMB) provides ester 2. The latter is hydrolyzed to acid 3, which is subsquently converted to amide 4 by standard coupling reaction. Buchwald reaction of 4 with A, promoted by catalysts such as tris(dibenzylideneacetone) dipalladium(0)/Xant Phos and palladium(II) acetate/BrettPhos, affords 5. Removal of the PMB protection group from 5 lead to the formation of compound (I). Alternatively, Buchwald reaction can be performed with 2 and A to give rise to intermediate 6, which is then transformed to compound (I) by hydrolysis, followed by amide formation and deprotection.

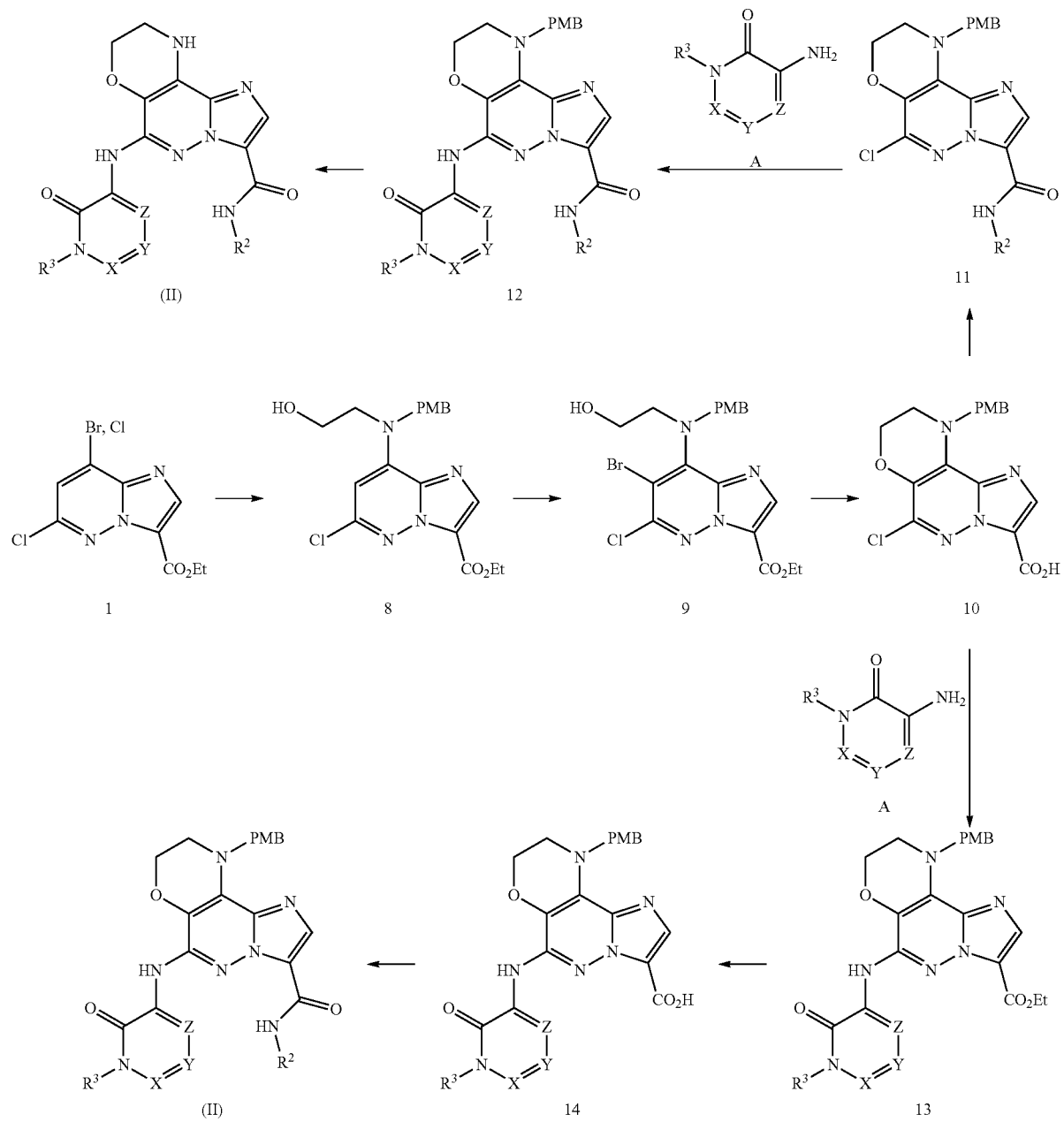

The compounds of Formula (II) can be prepared according to Scheme 2. Reaction of imidazopyridazine derivative (1) (WO 2009/100375) with p-methoxybenzyl protected hydroxylethylamine (HOCH$_2$CH$_2$NHPMB) supplies intermediate 8. Treatment of 8 with NBS give bromoimidazopyridazine 9, which is then cyclized to form tricyclic compound 10 with catalyst such as [1,1'-binaphthalen]-2-yldi-tert-butylphosphine/palladium (II) acetate. Compound 10 can be converted to amide 11 by hydrolysis and subsquent amide formation coupling reaction. Buchwald reaction of 11 with A promoted by catalysts such as tris(dibenzylideneacetone)dipalladium(0)/XantPhos and palladium (II) acetate/BrettPhos, followed by a deprotection step, provides compound (II). Alternatively, Buchwald reaction is conducted with 10 and A to give rise to 13, which is then transformed to compound (II) by a sequence of hydrolysis, amide formation coupling, and deprotection.

Scheme 3

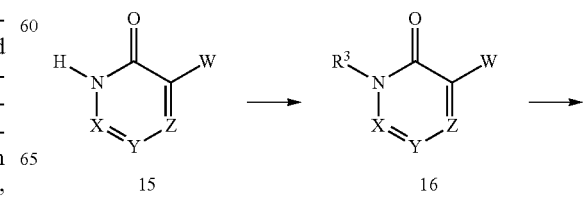

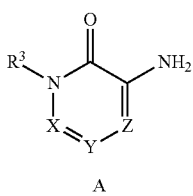

Intermediate A can be prepared from 15 (Scheme 3). Compound 15 can be N-(cyclo)alkylated or (hetero)arylated in a variety of ways to provide 16. It can be N-(cyclo) alkylated or (hetero)arylated with (cyclo)alkyl halides, (cyclo)alkyl tosylates, (cyclo)alkyl mesylates, or (hetero)aryl halides in the presence of base such as potassium carbonate, cesium carbonate, and sodium hydride. It can be N-(cyclo) alkylated or (hetero)arylated with boronic acid or boronic ester in the presence of copper (II) acetae and pyridine or 2,2'-dipyridyl. The N-(hetero)arylation can also be realized with (hetero)aryl halides, copper (I) iodide, and N1,N2-dimethylethane-1,2-diamine. Then, 16 can be converted to A using methods that are determined by the functionality of W. W can be $NH_2$, (which requires no transformation to A), protected amine such as NHBoc and NHCbz, $NO_2$, $CO_2R$, and halide (Cl, Br, and I).

Scheme 4

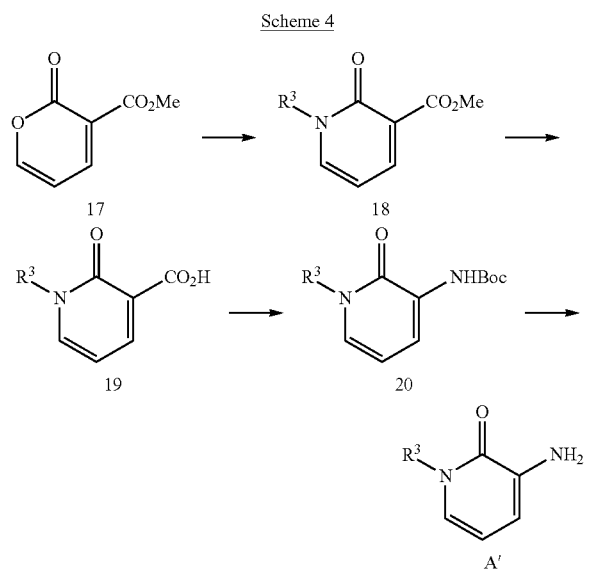

When X, Y, Z in structure A are all equal to CH, 3-amino-1-substituted pyridin-2(1H)-one (A') can also be prepared from commercially available methyl 2-oxo-2H-pyran-3-carboxylate (17) by a route shown in Scheme 4. Treatment of 17 with primary amine ($R^3NH_2$) yields pyridone carboxylate 18, which is hydrolyzed to acid 19. A' is then obtained from 19 via Curtius rearrangement, followed by removal of the Boc group.

EXAMPLES

Preparation of compounds of Formula (I), and intermediates used in the preparation of compounds of Formula (I), can be prepared using procedures shown in the following Examples and related procedures. The methods and conditions used in these examples, and the actual compounds prepared in these Examples, are not meant to be limiting, but are meant to demonstrate how the compounds of Formula (I) can be prepared. Starting materials and reagents used in these examples, when not prepared by a procedure described herein, are generally either commercially available, or are reported in the chemical literature, or may be prepared by using procedures described in the chemical literature.

In the Examples given, the phrase "dried and concentrated" generally refers to drying of a solution in an organic solvent over either sodium sulfate or magnesium sulfate, followed by filtration and removal of the solvent from the filtrate (generally under reduced pressure and at a temperature suitable to the stability of the material being prepared). Column chromatography was performed with pre-packed silica gel cartridges using an Isco medium pressure chromatography apparatus (Teledyne Corporation), eluting with the solvent or solvent mixture indicated. Preparative high performance liquid chromatography (HPLC) was performed using a reverse phase column (Waters Sunfire $C_{18}$, Waters Xbridge $C_{18}$, PHENOMENEX® Axia $C_{18}$, YMC S5 ODS or the like) of a size appropriate to the quantity of material being separated, generally eluting with a gradient of increasing concentration of methanol or acetonitrile in water, also containing 0.05% or 0.1% trifluoroacetic acid or 10 mM ammonium acetate, at a rate of elution suitable to the column size and separation to be achieved. Chemical names were determined using ChemDraw Ultra, version 9.0.5 (CambridgeSoft). The following abbreviations are used:

$NaHCO_3$ (aq)=saturated aqueous sodium bicarbonate
brine=saturated aqueous sodium chloride
DCM=dichloromethane
DIEA=N,N-diisopropylethylamine
DMAP=4-(N,N-dimethylamino)pyridine
DMF=N,N-dimethylformamide
DMSO=dimethyl sulfoxide
EDC=N-(3-dimethylaminopropyl)-N'-ethylcarbodiimide hydrochloride
EtOAc=ethyl acetate
HOAT=1-hydroxy-7-azabenzotriazole
HOBT=1-hydroxybenzotriazole hydrate
rt=ambient room temperature (generally about 20-25° C.)
TEA=triethylamine
TFA=trifluoroacetic acid
THF=tetrahydrofuran Intermediate 4a 6-Chloro-N-(1-cyanocyclopropyl)-8-((4-methoxybenzyl)(methyl)amino)imidazo[1,2-b]pyridazine-3-carboxamide

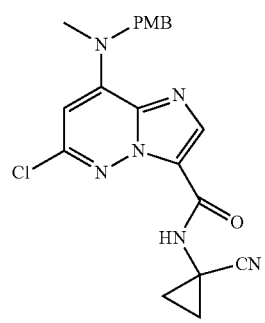

Step 1: Ethyl 6-chloro-8-((4-methoxybenzyl)(methyl)amino)imidazo[1,2-b]pyridazine-3-carboxylate

Step 3: 6-Chloro-N-(1-cyanocyclopropyl)-8-((4-methoxybenzyl)(methyl)amino)imidazo[1,2-b]pyridazine-3-carboxamide (4a)

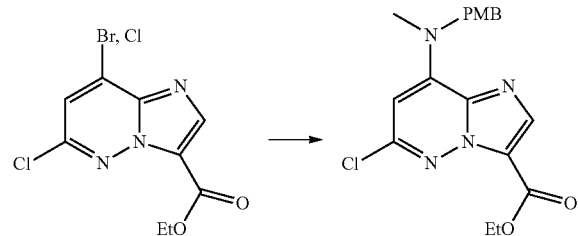

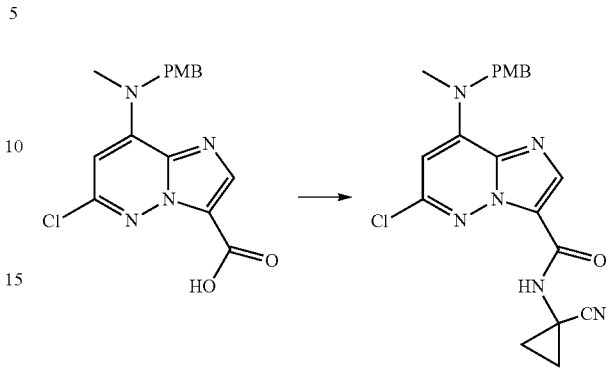

A mixture of ethyl 8-bromo-6-chloroimidazo[1,2-b]pyridazine-3-carboxylate (WO 2009/100375) (5 g, 16.42 mmol), 1-(4-methoxyphenyl)-N-methylmethanamine (3.23 g, 21.34 mmol), and N,N-diisopropylethylamine (5.74 ml, 32.8 mmol) in 1,4-dioxane (30 ml) was heated at 90° C. for 5 h. The volatiles were removed under vacuum. The residue was diluted with ethyl acetate (200 mL), washed with water (2×50 mL) and brine (50 mL), and dried over anhydrous MgSO₄. The desired product, ethyl 6-chloro-8-((4-methoxybenzyl)(methyl)amino)imidazo[1,2-b]pyridazine-3-carboxylate (6.10 g, 16.27 mmol, 99% yield), was isolated as a pale yellow solid by ISCO (330 g silica gel, solid loading, 20-40% ethyl acetate/hexane).

Step 2: 6-Chloro-8-((4-methoxybenzyl)(methyl)amino)imidazo[1,2-b]pyridazine-3-carboxylic acid A mixture of 6-chloro-8-((4-methoxybenzyl)(methyl)amino)imidazo[1,2-b]pyridazine-3-carboxylic acid (1.00 g, 2.88 mmol), 1-aminocyclopropanecarbonitrile, HCl (0.462 g, 3.89 mmol), BOP (1.658 g, 3.75 mmol), and N,N-diisopropylethylamine (2.015 mL, 11.54 mmol) in DMF (15 mL) was stirred at 50° C. for 3 h. The mixture was diluted with ethyl acetate (160 mL), washed with water (3×30 mL) and brine (30 mL), and dried over anhydrous MgSO₄. The desired product, 6-chloro-N-(1-cyanocyclopropyl)-8-((4-methoxybenzyl)(methyl)amino)imidazo[1,2-b]pyridazine-3-carboxamide (1.08 g, 2.63 mmol, 91% yield), was isolated as a white solid by ISCO (80 g silica gel, solid loading, 1-3% MeOH/dichloromethane).

The following intermediates (4b-t) (Figure 1) were prepared according to the precedure described for the preparation of 4a.

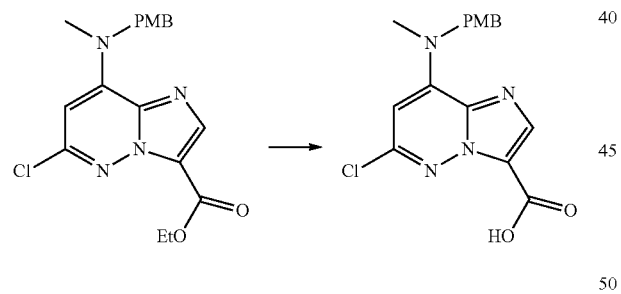

FIG. 1

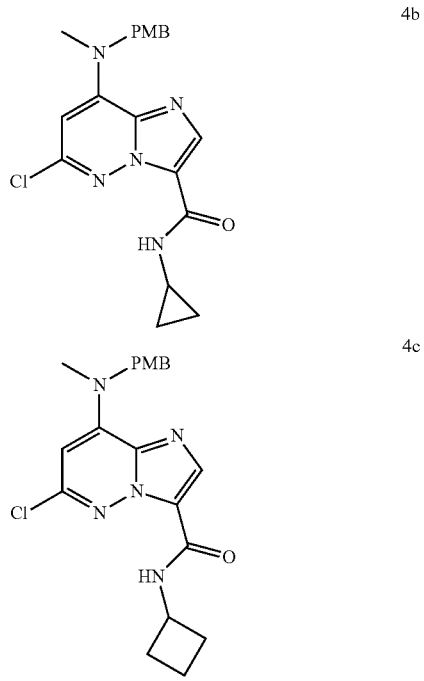

To a solution of ethyl 6-chloro-8-((4-methoxybenzyl)(methyl)amino)imidazo[1,2-b]pyridazine-3-carboxylate (4.0 g, 10.67 mmol) in tetrahydrofuran (66 mL) and methanol (22 mL) at rt was added a solution of lithium hydroxide hydrate (1.791 g, 42.7 mmol) in water (20 mL). The mixture was stirred at rt for 2 h, then concentrated under vacuum to a volume of about 20 mL. The residue was acidified with saturated 1 N HCl solution to pH 4-5. The precipitating product, 6-chloro-8-((4-methoxybenzyl)(methyl)amino)imidazo[1,2-b]pyridazine-3-carboxylic acid (3.59 g, 10.35 mmol, 97% yield), was collected as a white solid by suction filtration and dried over Drierite® under vacuum.

| | |
|---|---|
| 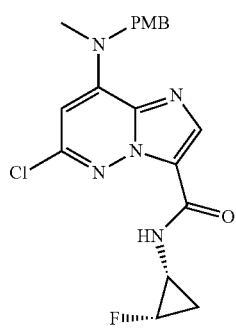 4d | 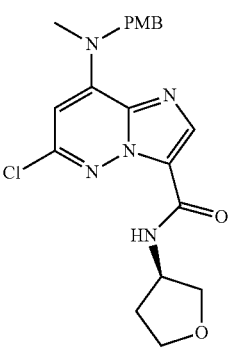 4h |
| 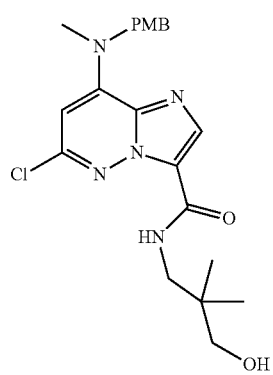 4e | 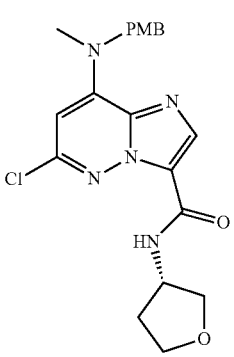 4i |
| 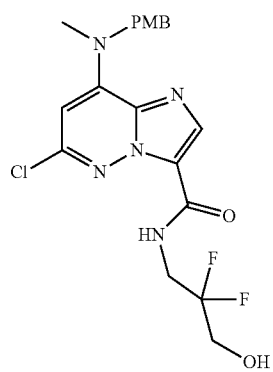 4f | 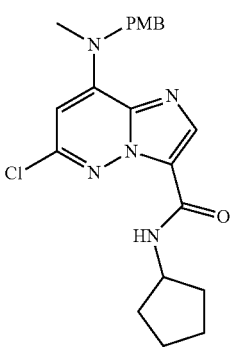 4j |
| 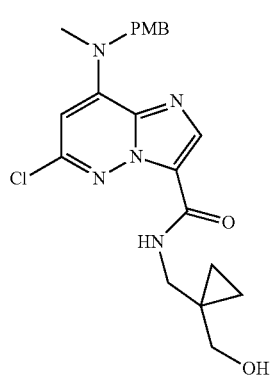 4g | 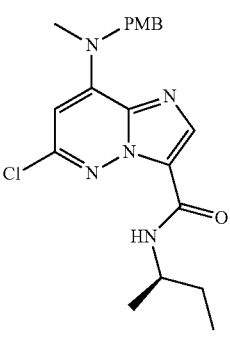 4k |

| | |
|---|---|
| 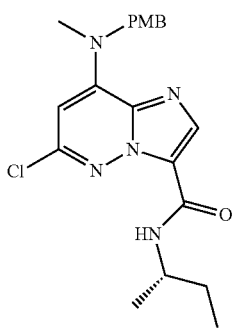 4l | 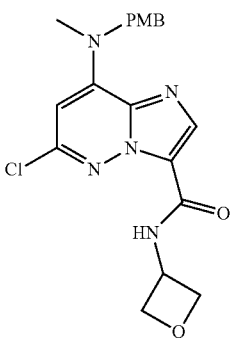 4p |
| 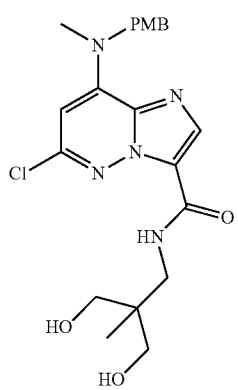 4m | 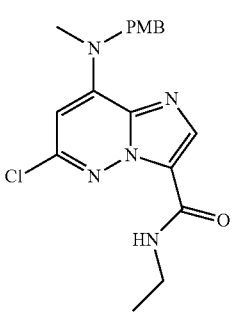 4q |
| 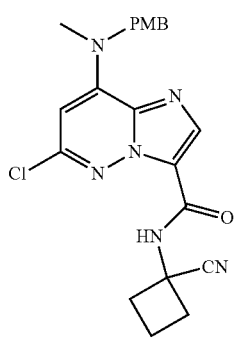 4n | 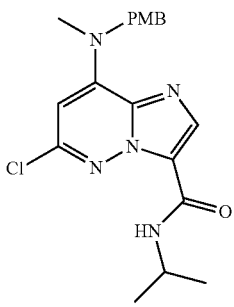 4r |
| 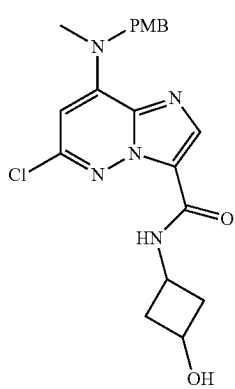 4o | 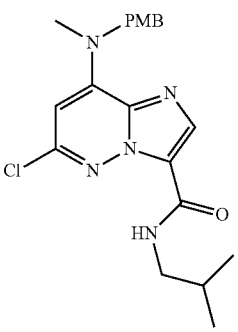 4s |

49

-continued

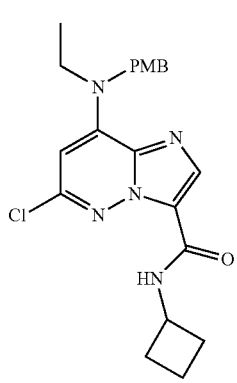

Intermediate 4u

6-Chloro-N-(trans-2-fluorocyclopropyl)-8-((4-methoxybenzyl)(methyl)amino)imidazo[1,2-b]pyridazine-3-carboxamide

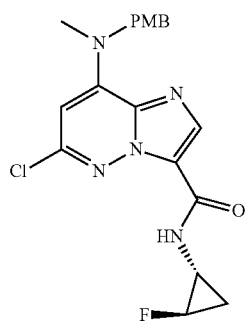

Step 1: tert-Butyl (trans-2-fluorocyclopropyl)carbamate

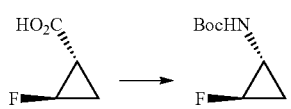

To a solution of trans-2-fluorocyclopropanecarboxylic acid (0.150 g, 1.441 mmol) in anhydrous t-BuOH (7 mL) at rt was added diphenyl phosphorazidate (0.342 ml, 1.585 mmol), followed by triethylamine (0.261 ml, 1.873 mmol). The mixture was heated at reflux for 16 h. The volatiles were removed under vacuum. The residue was diluted with dichloromethane (60 mL), washed with saturated NaHCO₃ solution, and dried over anhydrous MgSO₄. After the solvent was removed under vacuum, the residue was subjected to ISCO (24 g silica gel, 0-20% ethyl acetate/hexane) to afford the desired product, tert-butyl (trans-2-fluorocyclopropyl)carbamate (0.123 g, 0.702 mmol, 48.7% yield), as a white solid.

Step 2: trans-2-Fluorocyclopropanamine, TFA

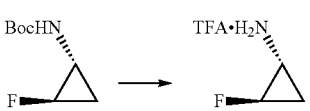

To a solution of tert-butyl (trans-2-fluorocyclopropyl)carbamate (0.123 g, 0.702 mmol) in dichloromethane (2 mL) at 0° C. was added TFA (2 mL, 26.0 mmol). The mixture was stirred at rt for 1 h. The volatile were removed under vacuum to give the desired product, trans-2-fluorocyclopropanamine, TFA (0.132 g, 0.698 mmol, 99% yield), as a waxy solid.

Step 3: 6-Chloro-N-(trans-2-fluorocyclopropyl)-8-((4-methoxybenzyl)(methyl)amino)imidazo[1,2-b]pyridazine-3-carboxamide (4u)

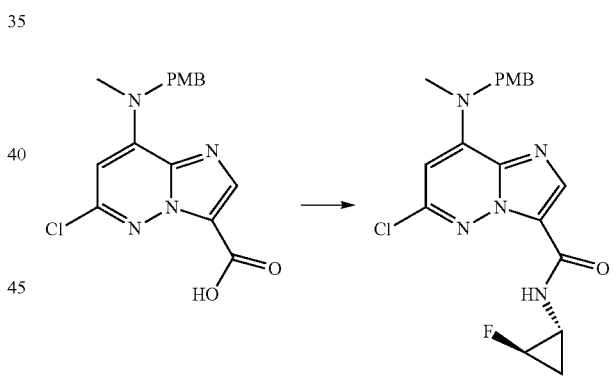

A mixture of 6-chloro-8-((4-methoxybenzyl)(methyl)amino)imidazo[1,2-b]pyridazine-3-carboxylic acid (0.210 g, 0.606 mmol), BOP (0.268 g, 0.606 mmol), and N,N-diisopropylethylamine (0.370 mL, 2.120 mmol) in DMF (4 mL) was stirred at rt for 16 h. Then, trans-2-fluorocyclopropanamine, TFA (0.132 g, 0.696 mmol) in DMF (1 mL) was added. The resulting mixture was stirred at rt for 2 h, diluted with ethyl acetate (60 mL), washed with water (2×20 mL) and brine (20 mL), and dried over anhydrous MgSO₄. The desired product, rac-6-chloro-N-trans-2-fluorocyclopropyl)-8-((4-methoxybenzyl)(methyl)amino)imidazo[1,2-b]pyridazine-3-carboxamide (0.137 g, 0.339 mmol, 56.0% yield), was isolated as white solid by ISCO (24 g silica gel, solid loading, 35-70% ethyl acetate/hexane).

Intermediate 4v

6-Chloro-N-(3-hydroxy-2-(hydroxymethyl)-2-methylpropyl)-8-((4-methoxybenzyl)(methyl)amino)imidazo[1,2-b]pyridazine-3-carboxamide

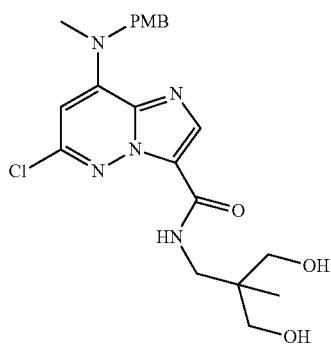

Step 1: 6-Chloro-8-((4-methoxybenzyl)(methyl)amino)-N-((3-methyloxetan-3-yl)methyl)imidazo[1,2-b]pyridazine-3-carboxamide

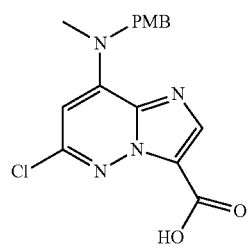

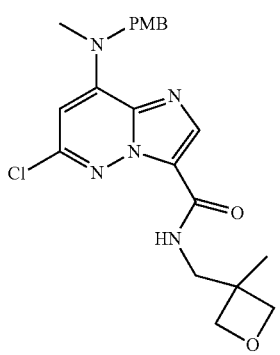

A solution of 6-chloro-8-((4-methoxybenzyl)(methyl)amino)imidazo[1,2-b]pyridazine-3-carboxylic acid (0.8219 g, 2.370 mmol), (3-methyloxetan-3-yl)methanamine, HCl (0.479 g, 4.74 mmol), BOP (1.363 g, 3.08 mmol) and DIPEA (1.076 ml, 6.16 mmol) in DMF (11.85 ml) was stirred overnight. Water (70 mL) was added, and the precipitate was filtered and washed with water to give 6-chloro-8-((4-methoxybenzyl)(methyl)amino)-N-((3-methyloxetan-3-yl)methyl)imidazo[1,2-b]pyridazine-3-carboxamide (0.9264 g, 2.112 mmol, 89% yield) as an off-white solid.

Step 2: 6-Chloro-N-(3-hydroxy-2-(hydroxymethyl)-2-methylpropyl)-8-((4-methoxybenzyl)(methyl)amino)imidazo[1,2-b]pyridazine-3-carboxamide (4v)

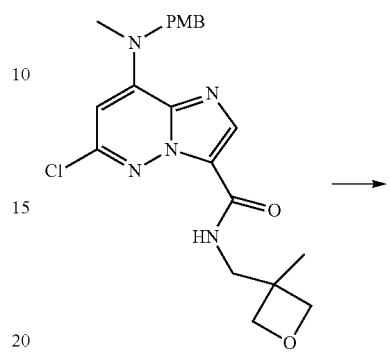

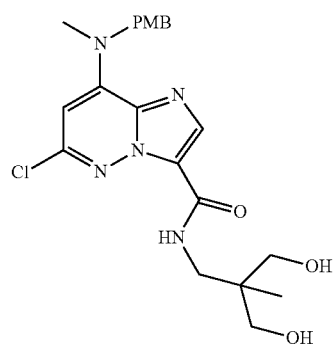

A heterogeneous, colorless solution of 6-chloro-8-((4-methoxybenzyl)(methyl)amino)-N-((3-methyloxetan-3-yl)methyl)imidazo[1,2-b]pyridazine-3-carboxamide (0.5445 g, 1.267 mmol) in water (15.83 ml) and methanol (15.83 ml), and trifluoroacetic acid (0.6 ml, 7.79 mmol) in a sealed pressure tube was heated at 50° C. After 1.75 h, the reaction was cooled to room temperature. Saturated aqueous Na$_2$CO$_3$ (2 mL) was added, the pressure tube was sealed and the reaction was heated to 75° C. After stirring overnight, the reaction was cooled to room temperature, concentrated in vacuo not to dryness and diluted with CH$_2$Cl$_2$ (40 mL). After separation of the layers, the aqueous layer was extracted with CH$_2$Cl$_2$ (40 mL). The organic layers were combined, dried over Na$_2$SO$_4$, filtered and concentrated in vacuo. The residue was purified by flash chromatography using an ISCO 24 g column eluting with 0-20% MeOH/CH$_2$Cl$_2$. Appropriate fractions were collected and concentrated in vacuo to give 6-chloro-N-(3-hydroxy-2-(hydroxymethyl)-2-methylpropyl)-8-((4-methoxybenzyl)(methyl)amino)imidazo[1,2-b]pyridazine-3-carboxamide (0.397 g, 0.753 mmol, 59.5% yield) as a white foam.

Intermediate A1

3-Amino-5-fluoro-1-methylpyridin-2(1H)-one

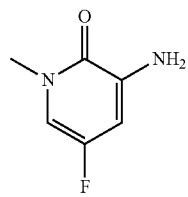

Step 1: 5-fluoro-1-methyl-3-nitropyridin-2(1H)-one

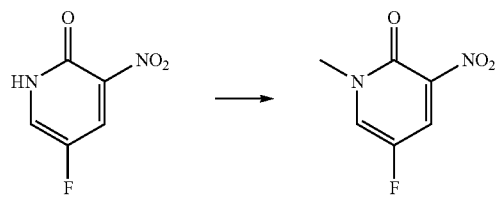

A suspension of 5-fluoro-3-nitropyridin-2-ol (0.416 g, 2.63 mmol) and potassium carbonate (0.800 g, 5.79 mmol) in DMF (6 mL) was stirred at rt for 15 min, and iodomethane (0.246 mL, 3.95 mmol) was then added. The mixture was stirred at rt for 24 h, diluted with ethyl acetate (20 mL) and filtered through Celite®. The filtrate was concentrated under vacuum to dryness. The residue was dissolved in ethyl acetate (80 mL), washed with brine (20 mL), and dried over anhydrous MgSO$_4$. The desired product, 5-fluoro-1-methyl-3-nitropyridin-2(1H)-one (0.261 g, 1.516 mmol, 57.6% yield), was isolated as a yellow solid by ISCO (40 g solica gel, 50-100% ethyl acetate/hexane).

Step 2: 3-Amino-5-fluoro-1-methylpyridin-2(1H)-one (A1)

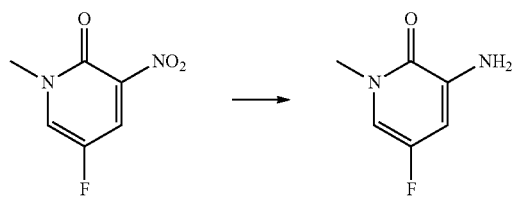

To a mixture of 5-fluoro-1-methyl-3-nitropyridin-2(1H)-one (260 mg, 1.511 mmol) and ammonium chloride (1131 mg, 21.15 mmol) in methanol (12 mL) and tetrahydrofuran (4 mL) at rt was added zinc dust (1383 mg, 21.15 mmol) in one portion. The mixture was stirred at rt for 30 min, diluted with ethyl acetate (20 mL), and filtrated through Celite®. The filtrate was concentrated under vacuum to dryness. To the residue was added water (20 mL) and the mixture was extracted with dichloromethane (3×40 mL). The combined extract was dried over anhydrous MgSO$_4$. Removal of solvent under vacuum provided the desired product, 3-amino-5-fluoro-1-methylpyridin-2(1H)-one (202 mg, 1.421 mmol, 94% yield), as a tan solid.

Intermediate A2

3-Amino-5-fluoro-1-(2-fluoroethyl)pyridin-2(1H)-one

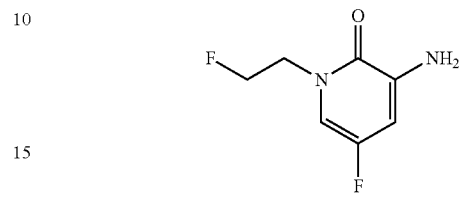

Step 1: 5-Fluoro-1-(2-fluoroethyl)-3-nitropyridin-2(1H)-one

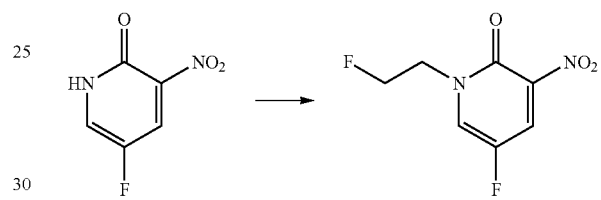

A suspension of 5-fluoro-3-nitropyridin-2-ol (500 mg, 3.16 mmol) and cesium carbonate (2061 mg, 6.33 mmol) in DMF (8 mL) was stirred at rt for 10 min, and 1-bromo-2-fluoroethane (723 mg, 5.69 mmol) was then added. The mixture was stirred at 75° C. for 4 h. Two products with the desired MS were detected. The mixture was diluted with ethyl acetate (15 mL) and filtered through Celite®. The filtrate was concentrated under vacuum to dryness. The residue was dissolved in ethyl acetate (100 mL), washed with water (20 mL) and brine (20 mL), and dried over anhydrous MgSO$_4$. The desired product, 5-fluoro-1-(2-fluoroethyl)-3-nitropyridin-2(1H)-one (146 mg, 0.715 mmol, 22.61% yield), was isolated as a yellow solid by ISCO (40 g solica gel, 30-50% ethyl acetate/hexane).

Step 2: 3-Amino-5-fluoro-1-(2-fluoroethyl)pyridin-2(1H)-one (A2)

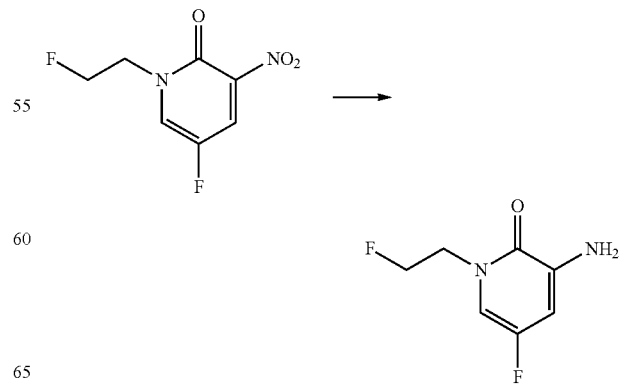

To a mixture of 5-fluoro-1-(2-fluoroethyl)-3-nitropyridin-2(1H)-one (146 mg, 0.715 mmol) and ammonium chloride (536 mg, 10.01 mmol) in methanol (6 mL) and tetrahydrofuran (2 mL) at rt was added zinc dust (655 mg, 10.01 mmol) in one portion. The mixture was stirred at rt for 30 min, diluted with ethyl acetate (20 mL), and filtrated through Celite®. The filtrate was concentrated under vacuum to dryness. To the residue was added water (20 mL) and the mixture was extracted with dichloromethane (3×40 mL). The combined extract was dried over anhydrous MgSO$_4$. Removal of solvent under vacuum provided the desired product, 3-amino-5-fluoro-1-(2-fluoroethyl)pyridin-2(1H)-one (109 mg, 0.626 mmol, 88% yield), as a tan solid.

Intermediate A3

3-Amino-5-fluoro-1-(2-hydroxy-2-methylpropyl)pyridin-2(1H)-one

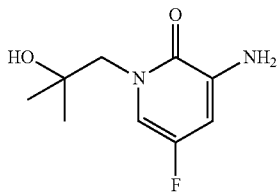

Step 1: 5-Fluoro-1-(2-hydroxy-2-methylpropyl)-3-nitropyridin-2(1H)-one

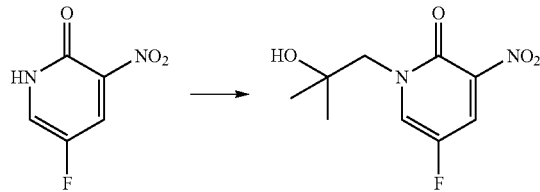 [SMILES: O=c1[nH]cc(F)cc1[N+](=O)[O-] ; CC(C)(O)Cn1cc(F)cc([N+](=O)[O-])c1=O]

A solution of 5-fluoro-3-nitropyridin-2(1H)-one (0.7058 g, 4.46 mmol), 1-chloro-2-methylpropan-2-ol (1.454 g, 13.39 mmol), potassium carbonate (1.234 g, 8.93 mmol) and sodium iodide (2.008 g, 13.39 mmol) in DMF (22.32 ml) in a pressure tube was heated to 125° C. and stirred overnight. LCMS showed ~1:1 starting material:desired product. The reaction was cooled to room temperature. EtOAc (150 mL) was added, and the solution was filtered through Celite®. The filtrate was washed with brine (40 mL), and the organic layer was dried over Na$_2$SO$_4$, filtered and concentrated in vacuo to give a residue which was purified by flash chromatography using an ISCO 80 g column (solid loading) eluting with 20-100% EtOAc/hexane. Appropriate fractions were collected and concentrated in vacuo to give 5-fluoro-1-(2-hydroxy-2-methylpropyl)-3-nitropyridin-2(1H)-one (0.127 g, 0.497 mmol, 11.12% yield).

Step 2: 3-Amino-5-fluoro-1-(2-hydroxy-2-methylpropyl)pyridin-2(1H)-one (A3)

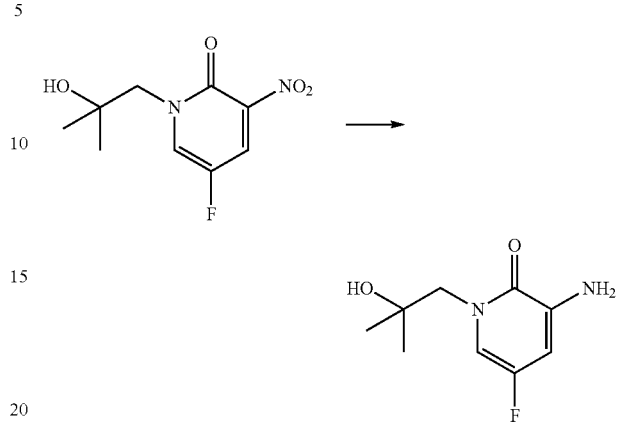

To a homogeneous, yellow solution of 5-fluoro-1-(2-hydroxy-2-methylpropyl)-3-nitropyridin-2(1H)-one (0.127 g, 0.552 mmol) in methanol (5.17 ml) and tetrahydrofuran (1.724 ml) under nitrogen were added ammonium chloride (0.413 g, 7.72 mmol) and zinc (0.505 g, 7.72 mmol). After 30 min, the reaction mixture was diluted with EtOAc (25 mL) and filtered through Celite®. The filtrate was concentrated in vacuo. Water (3 mL) was added to the residue, and the aqueous layer was extracted with CH$_2$Cl$_2$ (4×30 mL). The organic layers were combined, dried over Na$_2$SO$_4$, filtered and concentrated in vacuo to give 3-amino-5-fluoro-1-(2-hydroxy-2-methylpropyl)pyridin-2(1H)-one (0.098 g, 0.489 mmol, 89% yield) as a brown solid.

The following intermediates (A4-10) (Figure 2) were prepared according to the precedures described for the preparation of A1-3.

FIG. 2

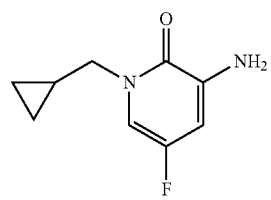

A4

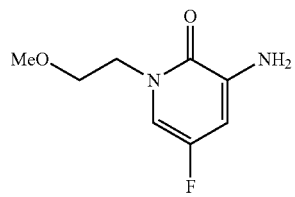

A5

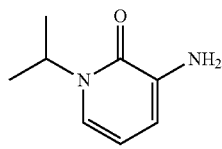

A6

-continued

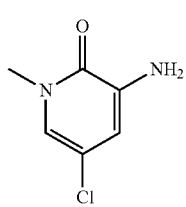

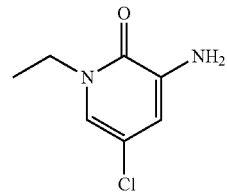

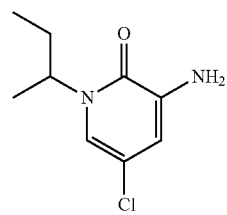

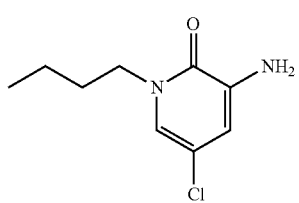

Intermediate A11

3-Amino-1-cyclohexylpyridin-2(1H)-one

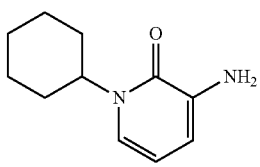 [SMILES: Nc1cccn(C2CCCCC2)c1=O]

Step 1: Cyclohexyl 4-methyl benzene sulfonate

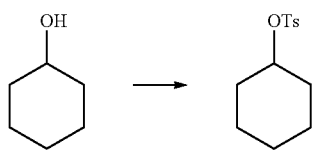 [SMILES: OC1CCCCC1 ; Cc1ccc(S(=O)(=O)OC2CCCCC2)cc1]

A solution of cyclohexanol (5 g, 49.9 mmol), in DCM (10 mL), was treated with TEA (13.92 mL, 100 mmol), DMAP (6.10 g, 49.9 mmol), followed by 4-methylbenzene-1-sulfonyl chloride (9.52 g, 49.9 mmol) slowly at 0° C. The reaction was warmed to room temperature over 2 h. The solution was partitioned between DCM and water. The organic layer was washed with brine (2×50 mL) and dried over anhydrous Na$_2$SO$_4$. The desired product, cyclohexyl 4-methylbenzenesulfonate (6.0 g, 23.59 mmol, 47.3% yield) was isolated as a white solid by ISCO (24 g silica gel, solid loading, 5-10% Ethyl acetate/Pet ether).

Step 2: 1-Cyclohexyl-3-nitropyridin-2(1H)-one

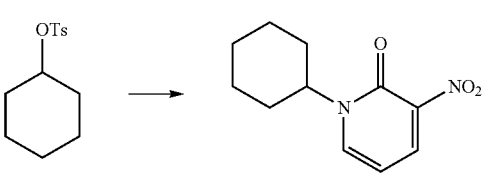 [SMILES: Cc1ccc(S(=O)(=O)OC2CCCCC2)cc1 ; O=c1c([N+](=O)[O-])cccn1C1CCCCC1]

A mixture of cyclohexyl 4-methylbenzenesulfonate (1.815 g, 7.14 mmol) and 3-nitropyridin-2-ol (1 g, 7.14 mmol) in DMF (10 mL) was heated at 80° C. in the presence of cesium carbonate (2.326 g, 7.14 mmol) for 15 h. The reaction mixture was cooled to rt. The solid was filtered off and then solvent was removed under vacuum. The residue was diluted with ethyl acetate (50 mL), washed with water (2×50 mL) and brine (50 mL), dried over anhydrous Na$_2$SO$_4$. The desired product, 1-cyclohexyl-3-nitropyridin-2(1H)-one (75 mg, 0.317 mmol, 4.44% yield) was isolated as a yellow solid through ISCO (12 g silica gel, solid loading 10-50% ethyl acetate/hexane).

Step 3: 3-Amino-1-cyclohexylpyridin-2(1H)-one (A11)

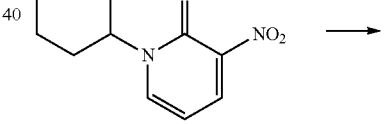

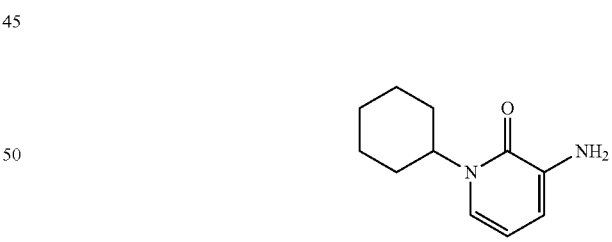

A mixture of 1-cyclohexyl-3-nitropyridin-2(1H)-one (95 mg, 0.427 mmol) and ammonium chloride (320 mg, 5.98 mmol) was dissolved in methanol (3 mL) and tetrahydrofuran (1 mL). To the reaction mixture zinc dust (391 mg, 5.98 mmol) was added in one portion. The reaction mixture was stirred at rt for 2 h. Then reaction mixture was diluted with ethyl acetate (93 mL) and filtered through celite. The filtrate was concentrated under vacuum to dryness. The desired product, 3-amino-1-cyclohexylpyridin-2(1H)-one (47 mg, 0.244 mmol, 57.2% yield) was isolated as a brown solid by ISCO (12 g silica gel, solid loading, 50-70% ethyl acetate/hexane).

Intermediate A12

3-Amino-1-(4-fluorophenyl)pyridin-2(1H)-one

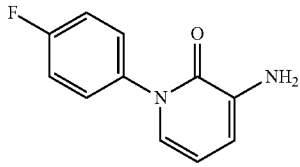 [SMILES: Nc1cccn(-c2ccc(F)cc2)c1=O]

Step 1:
1-(4-Fluorophenyl)-3-nitropyridin-2(1H)-one

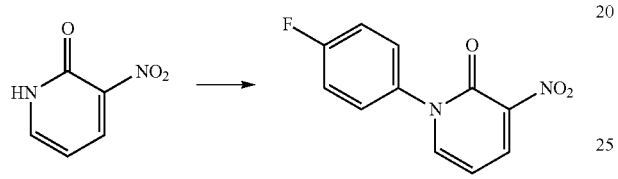

A mixture of 3-nitropyridin-2-ol (0.80 g, 5.71 mmol), (4-fluorophenyl)boronic acid (1.198 g, 8.57 mmol), diacetoxycopper (1.556 g, 8.57 mmol), and pyridine (7 mL, 87 mmol) in 1,4-dioxane (24 mL) was heated at 80° C. for 18 h. The insoluble material was removed by suction filtration through Celite. The filtrate was concentrated under vacuum to dryness. To the residue was added 1 N NaOH (20 mL) and water (10 mL), and the resulting mixture was extracted with ethyl acetate (3×50 mL). The combined extract was washed with brine (30 mL) and dried over anhydrous $MgSO_4$. The product was isolated by ISCO (80 g silica gel, 35-55% ethyl acetate/hexane). However, the product thus obtained was contaminated with pyridine. Therefore, the impure material was dissolved in ethyl acetate (150 mL), washed with water (2×30 mL) and brine (30 mL), and dried over anhydrous $MgSO_4$. Removal of solvent under vacuum provided the desired product, 1-(4-fluorophenyl)-3-nitropyridin-2(1H)-one (0.508 g, 2.169 mmol, 38.0% yield), as a yellow solid.

Step 2: 3-Amino-1-(4-fluorophenyl)pyridin-2(1H)-one (A12)

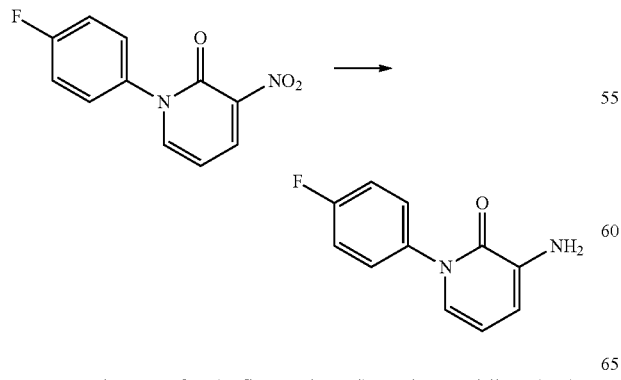

To a mixture of 1-(4-fluorophenyl)-3-nitropyridin-2(1H)-one (0.508 g, 2.169 mmol) and ammonium chloride (1.625 g, 30.4 mmol) in methanol (21 mL) and tetrahydrofuran (7 mL) at rt was added zinc dust (1.986 g, 30.4 mmol) in one portion. The mixture was stirred at rt for 30 min. It was diluted with ethyl acetate (20 mL) and filtrated through Celite®. The filtrate was concentrated under vacuum to dryness. To the residue was added water (20 mL) and the mixture was extracted with dichloromethane (3×40 mL). The combined extract was dried over anhydrous $MgSO_4$. Removal of solvent under vacuum provided the desired product, 3-amino-1-(4-fluorophenyl)pyridin-2(1H)-one (0.439 g, 2.150 mmol, 99% yield), as a tan solid.

The following intermediates (A13-28) (Figure 3) were prepared according to the precedure described for the preparation of A12.

FIG. 3

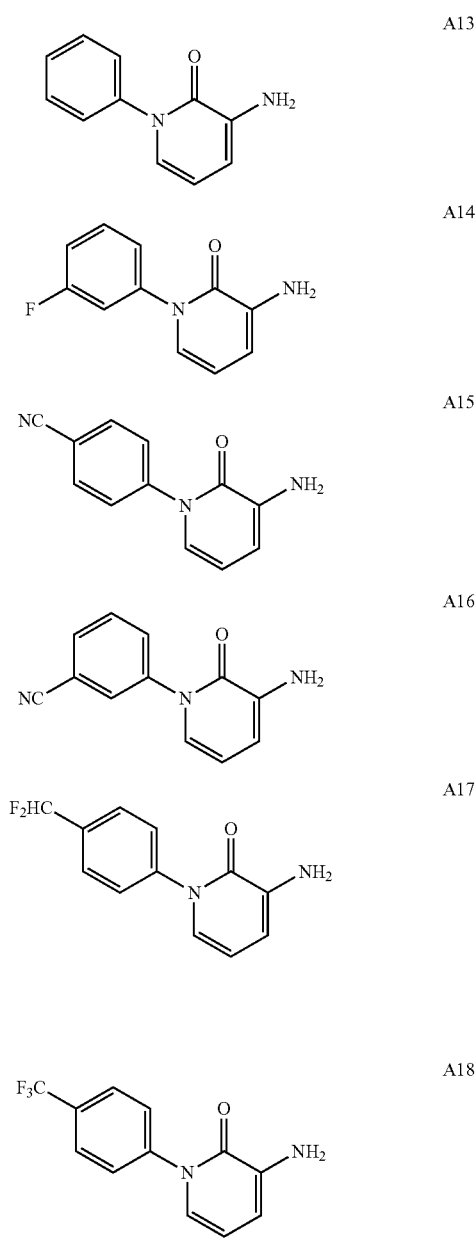

-continued

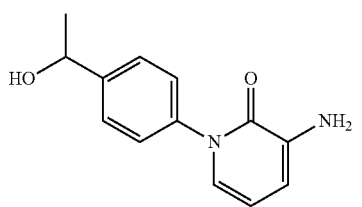
A19

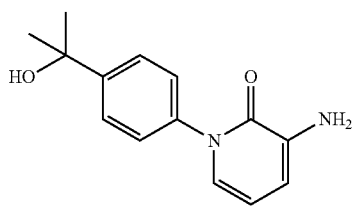
A20

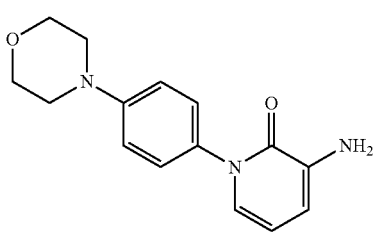
A21

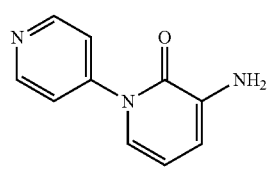
A22

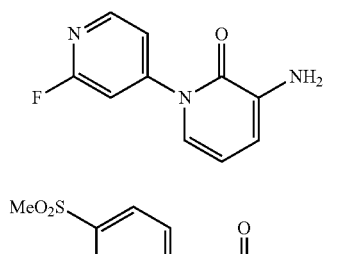
A23

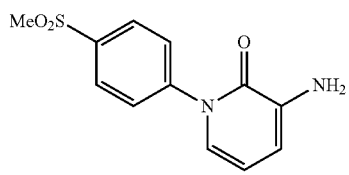
A24

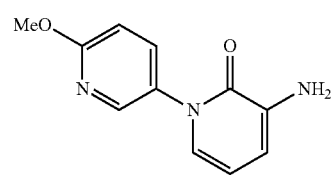
A25

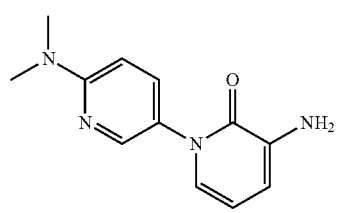
A26

-continued

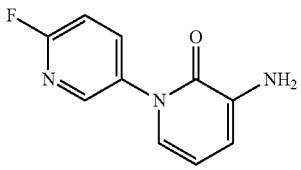
A27

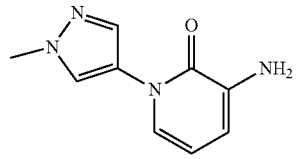
A28

Intermediate A29

3-amino-1-cyclopropylpyridin-2(1H)-one

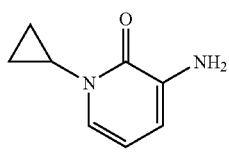 [SMILES: Nc1cccn(C2CC2)c1=O]

Step 1: Benzyl (2-oxo-1,2-dihydropyridin-3-yl)carbamate

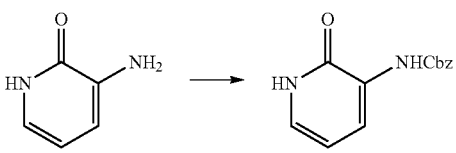 [SMILES: Nc1ccc[nH]c1=O ; O=C(Nc1ccc[nH]c1=O)OCc1ccccc1]

To a mixture of 3-aminopyridin-2(1H)-one (3.25 g, 29.5 mmol) and sodium carbonate (6.26 g, 59.0 mmol) in tetrahydrofuran (100 mL) at rt was added benzyl carbonochloridate (5.27 mL, 36.9 mmol) over 5 min. The mixture was stirred at rt for 24 h, diluted with ethyl acetate (150 mL), and filtered through Celite®. The filtrate was concentrated under vacuum to a volume of approximate 200 mL, washed with water (40 mL), and dried over anhydrous MgSO$_4$. The solution was concentrated under vacuum to a volume of approximate 50 mL. The precipitating material (the first crop of product) was collected as a white solid by suction. The filtrate was concentrated under vacuum to almost dryness. The residue was stirred with diethyl ether (50 mL). The insoluble material (the second crop of product) was collected as a white solid by suction. The two crops of product was combined and dried at 50° C. under vacuum to give the desired product, benzyl (2-oxo-1,2-dihydropyridin-3-yl)carbamate (5.77 g, 23.62 mmol, 80% yield), as a white solid.

Step 2: Benzyl (1-cyclopropyl-2-oxo-1,2-dihydropyridin-3-yl)carbamate

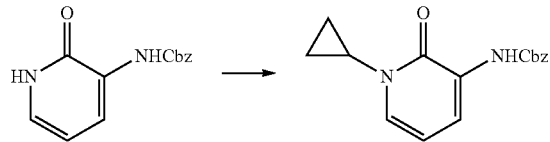 [SMILES: O=C(Nc1ccc[nH]c1=O)OCc1ccccc1 ; O=C(Nc1cccn(C2CC2)c1=O)OCc1ccccc1]

A mixture of benzyl (2-oxo-1,2-dihydropyridin-3-yl)carbamate (0.800 g, 3.28 mmol), potassium cyclopropyltrifluoroborate (0.969 g, 6.55 mmol), copper (II) acetate (0.625 g, 3.44 mmol), 2,2'-dipyridyl (0.537 g, 3.44 mmol), and sodium carbonate (0.764 g, 7.21 mmol) in 1,2-dichloroethane (20 mL) was heated at 70° C. under air for 15 h. The reaction mixture was diluted with ethyl acetate (20 mL) and filtered through Celite. The filtrate was further diluted with ethyl acetate (100 mL), washed with water (40 mL), 0.5 N HCl solution (40 ml), water (40 mL), and brine (40 mL). The organic solution was dried over anhydrous MgSO$_4$. The desired product, benzyl (1-cyclopropyl-2-oxo-1,2-dihydropyridin-3-yl)carbamate (0.251 g, 0.883 mmol, 27.0% yield), was isolated as a white solid by ISCO (80 g silica gel, solid loading, 20-50% ethyl acetate/hexane.

Step 3: 3-Amino-1-cyclopropylpyridin-2(1H)-one (A29)

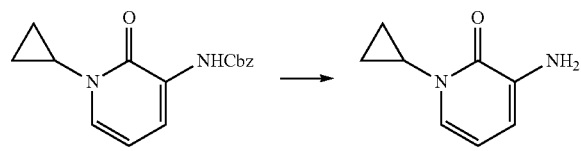 [SMILES: O=C(Nc1cccn(C2CC2)c1=O)OCc1ccccc1 ; Nc1cccn(C2CC2)c1=O]

A mixture of benzyl (1-cyclopropyl-2-oxo-1,2-dihydropyridin-3-yl)carbamate (251 mg, 0.883 mmol) and 10% Pd/C (65 mg, 0.061 mmol) in MeOH (18 mL) and THF (6 mL) was stirred at rt under H$_2$, provided with a H$_2$ balloon, for 1 h. The solid phase was removed by suction filtration through Celite®. The filtrate was concentrated under vacuum to dryness to provide the desired product, 3-amino-1-cyclopropylpyridin-2(1H)-one (133 mg, 0.886 mmol, 100% yield) as a white solid.

Intermediate A30

3-Amino-1-cyclopropyl-5-fluoropyridin-2(1H)-one

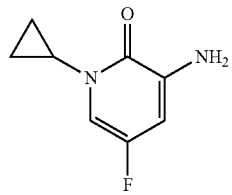 [SMILES: Nc1cc(F)cn(C2CC2)c1=O]

This intermediate was prepared in the same way as A29.

Intermediate A30

3-Amino-3'-fluoro-2H-[1,2'-bipyridin]-2-one

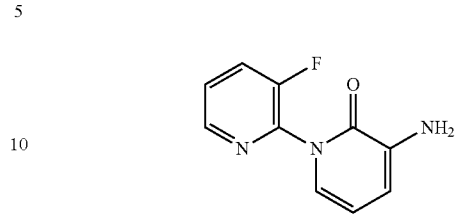

Step 1: 3-Bromo-3'-fluoro-2H-[1,2'-bipyridin]-2-one

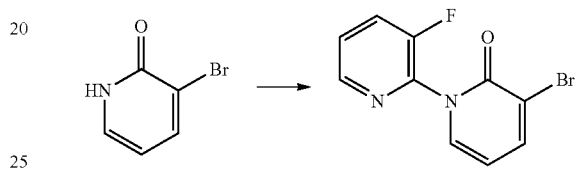

A mixture of 2,3-difluoropyridine (0.827 g, 7.18 mmol), 3-bromopyridin-2-ol (1.00 g, 5.75 mmol), and cesium carbonate (5.62 g, 17.24 mmol) in NMP (20 mL) was stirred at 110° C. for 15 h. The reaction mixture was poured into a stirring mixture of ethyl acetate (200 mL) and water (40 mL). After the aqueous layer was separated, the organic layer was washed with water (2×40 mL) and brine (30 mL), and dried over anhydrous MgSO$_4$. The desired product, 3-bromo-3'-fluoro-2H-[1,2'-bipyridin]-2-one (0.332 g, 1.234 mmol, 21.47% yield), was isolated as a white solid by ISCO (120 g silica gel, 30-70% ethyl acetate/hexane).

Step 2: 3-Amino-3'-fluoro-2H-[1,2'-bipyridin]-2-one (A30)

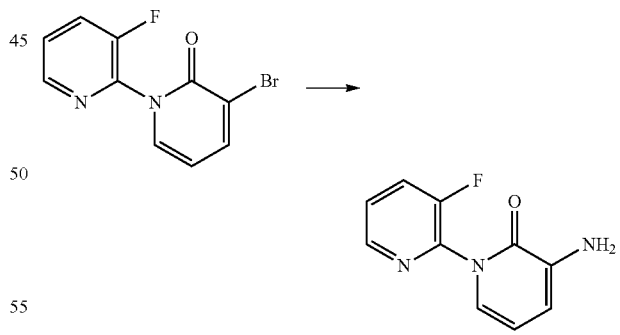

A mixture of 3-bromo-3'-fluoro-2H-[1,2'-bipyridin]-2-one (150 mg, 0.557 mmol), copper powder (0.477 μl, 0.067 mmol), L-ascorbic acid (19.64 mg, 0.111 mmol), (D,L)-pipecolic acid (21.60 mg, 0.167 mmol), and sodium azide (72.5 mg, 1.115 mmol) in ethanol (2 mL) was flushed with nitrogen, and then heated at 100° C. in a closed vial for 16 h. Additional sodium azide (60 mg) was added, and the mixture continued to be heated for anothe 8 h. It was diluted with ethyl acetate (30 mL) and filtered through Celite®. The filtrate was concentrated under vacuum. The residue was subjected to ISCO (12 g silica gel, solid loading, 60-85% ethyl acetate/hexane) to provide the desired product, 3-amino-3'-fluoro-2H-[1,2'-bipyridin]-2-one (63 mg, 0.307 mmol, 55.1% yield), as a dark brown solid.

Intermediate A31

3-Amino-2H-[1,2'-bipyridin]-2-one

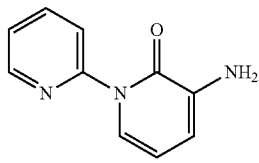 [SMILES: Nc1cccn(-c2ccccn2)c1=O]

Step 1: Benzyl (2-oxo-2H-[1,2'-bipyridin]-3-yl)carbamate

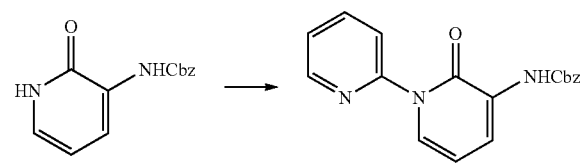 [SMILES: O=C(Nc1ccc[nH]c1=O)OCc1ccccc1 ; O=C(Nc1cccn(-c2ccccn2)c1=O)OCc1ccccc1]

A mixture of benzyl (2-hydroxypyridin-3-yl)carbamate (1.500 g, 6.14 mmol), 2-bromopyridine (1.261 g, 7.98 mmol), N1,N2-dimethylethane-1,2-diamine (0.262 mL, 2.457 mmol), copper I) iodide (0.234 g, 1.228 mmol), and potassium carbonate (1.698 g, 12.28 mmol) in 1,4-dioxane (30 mL) in a pressure tube was heated at 115° C. for 12 h. The reaction mixture was diluted with ethyl acetate (10 mL) and filtered through Celite®. The filtrate was further diluted with ethyl acetate (125 mL), washed with water (2×25 mL) and brine (25 mL), and dried over anhydrous MgSO₄. The desired product, benzyl (2-oxo-2H-[1,2'-bipyridin]-3-yl)carbamate (1.20 g, 3.73 mmol, 60.8% yield), was isolated as a white solid by ISCO (80 g silica gel, solid loading, 25-45% ethyl acetate).

Step 2: 3-Amino-2H-[1,2'-bipyridin]-2-one (A31)

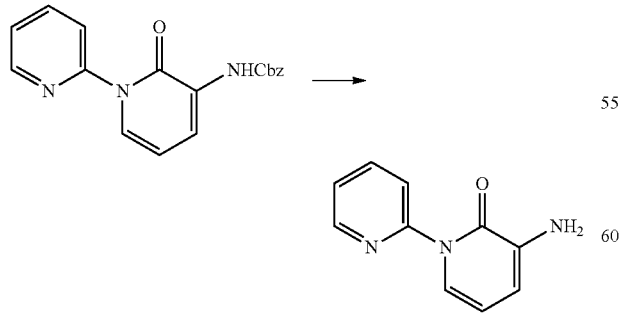

A mixture of benzyl (2-oxo-2H-[1,2'-bipyridin]-3-yl)carbamate (1.19 g, 3.70 mmol) and 10% Pd/C (0.30 g, 0.282 mmol) in MeOH (54 mL) and THF (18 mL) was stirred at rt under $H_2$, provided with a $H_2$ balloon, for 1 h. The solid phase was removed by suction filtration through Celite®. The filtrate was concentrated under vacuum to dryness to provide the desired product, 3-amino-2H-[1,2'-bipyridin]-2-one (0.672 g, 3.59 mmol, 97% yield) as a white solid.

Intermediate A32

3-Amino-6'-(methylamino)-2H-[1,3'-bipyridin]-2-one

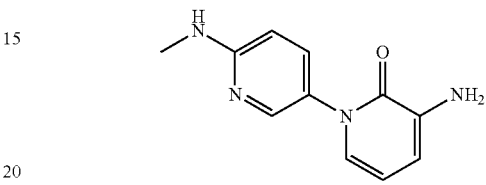

Step 1: 5-Bromo-N-methylpyridin-2-amine

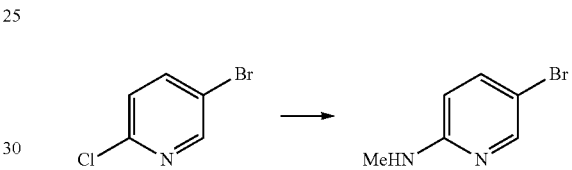

A mixture of 5-bromo-2-chloropyridine (3 g, 15.5 mmol), methylamine hydrochloride (3.16 g, 46.8 mmol), and DIPEA (8.17 mL, 46.8 mmol) was heated at 170° C. under microwave for 4 h. The mixture was diluted with water and extracted with EtOAc. The organic layers was separated and washed with brine. Organic layer was dried over anhydrous Na₂SO₄ and concentrated. The residue was applied to ISCO (24 g silica gel, solid loading, 70-80% ethyl acetate/hexane) to afford 5-bromo-N-methylpyridin-2-amine (800 mg, 4.28 mmol, 27.4% yield) as a brown solid.

Step 2: Benzyl (6'-(methylamino)-2-oxo-2H-[1,3'-bipyridin]-3-yl)carbamate

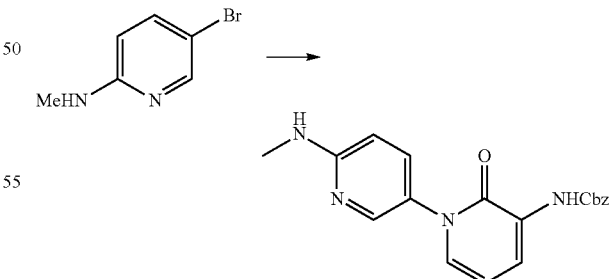

A mixture of 5-bromo-N-methylpyridin-2-amine (199 mg, 1.065 mmol), benzyl (2-oxo-1,2-dihydropyridin-3-yl)carbamate (200 mg, 0.819 mmol), K₂CO₃ (226 mg, 1.638 mmol), N,N'-dimethyl-1,2-ethanediamine (0.035 mL, 0.328 mmol) and copper (I) iodide (31.2 mg, 0.164 mmol) in dioxane (8 mL) was heated at 115° C. for 12 h. The reaction mixture was diluted with ethyl acetate (10 mL) and filtered through Celite. The filtrate was diluted with ethyl acetate (60 mL), washed with water (3×20 mL) and brine (20 mL), dried over anhydrous Na₂SO₄ and concentrated under vaccum. The residue was purified by ISCO (24 g silica gel, solid loading, 50-60% ethyl acetate/hexane) to give benzyl (6'-(methylamino)-2-oxo-2H-[1,3'-bipyridin]-3-yl)carbamate (100 mg, 0.280 mmol, 34.2% yield) as a beige solid.

Step 3: 3-Amino-6'-(methylamino)-2H-[1,3'-bipyridin]-2-one (A32)

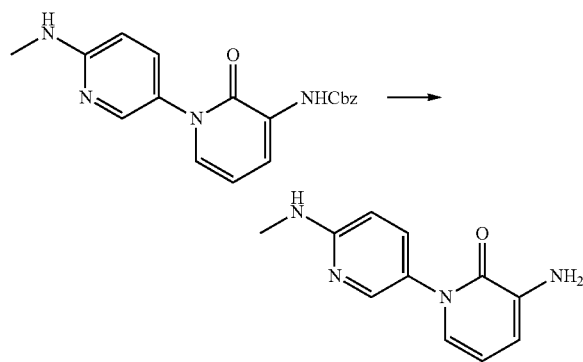

A mixture of benzyl (6'-(methylamino)-2-oxo-2H-[1,3'-bipyridin]-3-yl)carbamate (80 mg, 0.228 mmol) in MeOH (15 mL) was added Pd/C (24.30 mg, 0.228 mmol). The reaction mixture was stirred at rt for 2 h under hydrogen atmosphere (1 atmospheric pressure). The reaction mixture was filtered through celite and filtrate was concentrated under vacuum to get 3-amino-6'-(methylamino)-2H-[1,3'-bipyridin]-2-one (42 mg, 0.226 mmol, 98% yield).

Intermediate A33

3-Amino-1-(6-methylpyridazin-3-yl)pyridin-2(1H)-one

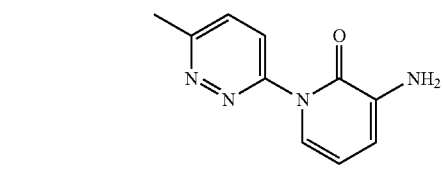

Step 1: Benzyl (1-(6-methylpyridazin-3-yl)-2-oxo-1,2-dihydropyridin-3-yl)carbamate

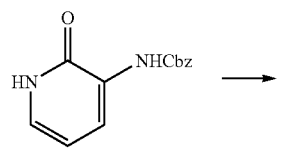

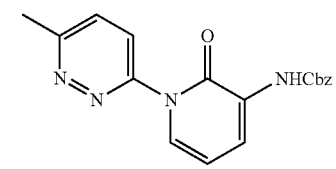

A mixture of benzyl (2-hydroxypyridin-3-yl)carbamate (2.45 g, 10.03 mmol), 3-chloro-6-methylpyridazine (2.58 g, 20.06 mmol), N1,N2-dimethylethane-1,2-diamine (0.320 mL, 3.01 mmol), copper(I) iodide (0.573 g, 3.01 mmol), and potassium carbonate (2.77 g, 20.06 mmol) in 1,4-dioxane (50 mL) in a pressure tube was heated at 110° C. for 20 h. Additional 3-chloro-6-methylpyridazine (1.29 g, 10.03 mmol), N1,N2-dimethylethane-1,2-diamine (0.16 mL, 1.50 mmol), copper(I) iodide (0.282 g, 1.50 mmol), and potassium carbonate (1.38 g, 10.03 mmol) were added. The mixture was heated at 110° C. for another 36 h. The reaction was complete, giving the desired product as the major. The reaction mixture was diluted with ethyl acetate (50 mL) and filtered through Celite. The filtrate was further diluted with ethyl acetate (300 mL), washed with water (3×60 mL) and brine (60 mL), and dried over anhydrous MgSO₄. An impure product was obtained by ISCO (220 g silica gel, solid loading, 1-6% MeOH/dichloromethane). This impure product was further purified by another ISCO run (80 g silica gel, solid loading, 20-50% ethyl acetate/dichloromethane) to provide the desired product, benzyl (1-(6-methylpyridazin-3-yl)-2-oxo-1,2-dihydropyridin-3-yl)carbamate (0.734 g, 2.182 mmol, 21.76% yield), as a white solid.

Step 2: 3-Amino-1-(6-methylpyridazin-3-yl)pyridin-2(1H)-one (A33)

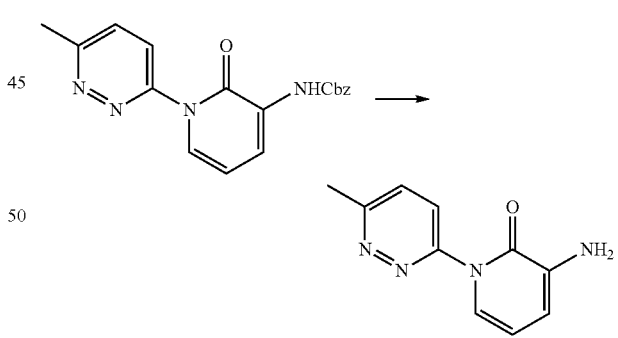

A mixture of benzyl (1-(6-methylpyridazin-3-yl)-2-oxo-1,2-dihydropyridin-3-yl)carbamate (0.734 g, 2.182 mmol) and 10% Pd/C (0.200 g, 0.188 mmol) in MeOH (45 mL) and THF (15 mL) was stirred at rt under H₂, provided with a H₂ balloon, for 1 h. The solid phase was removed by suction filtration through Celite®. The filtrate was concentrated under vacuum to dryness to provide the desired product, 3-amino-1-(6-methylpyridazin-3-yl)pyridin-2(1H)-one (0.436 g, 2.156 mmol, 99% yield), as a white solid.

Intermediate A34

3-Amino-1-(thiazol-2-yl)pyridin-2(1H)-one

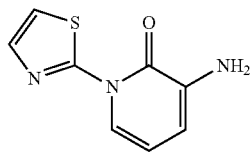 [SMILES: Nc1cccn(-c2nccs2)c1=O]

Step 1: Benzyl (2-oxo-1-(thiazol-2-yl)-1,2-dihydropyridin-3-yl)carbamate

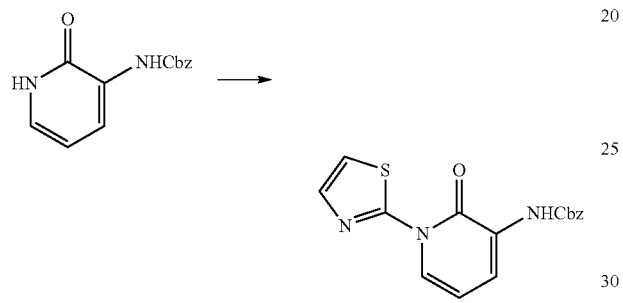

A mixture of benzyl (2-hydroxypyridin-3-yl)carbamate (650 mg, 2.66 mmol), 2-bromothiazole (567 mg, 3.46 mmol), N1,N2-dimethylethane-1,2-diamine (0.113 mL, 1.065 mmol), copper(I) iodide (101 mg, 0.532 mmol), and potassium carbonate (736 mg, 5.32 mmol) in 1,4-dioxane (12 mL) in a pressure tube was heated at 115° C. for 12 h. The reaction mixture was diluted with ethyl acetate (10 mL) and filtered through Celite®. The filtrate was further diluted with ethyl acetate (125 mL), washed with water (2×25 mL) and brine (25 mL), and dried over anhydrous MgSO₄. The desired product, benzyl (2-oxo-1-(thiazol-2-yl)-1,2-dihydropyridin-3-yl)carbamate (374 mg, 1.142 mmol, 42.9% yield), was isolated as a white solid by ISCO (80 g silica gel, solid loading, 25-45% ethyl acetate).

Step 2: 3-Amino-1-(thiazol-2-yl)pyridin-2(1H)-one (A34)

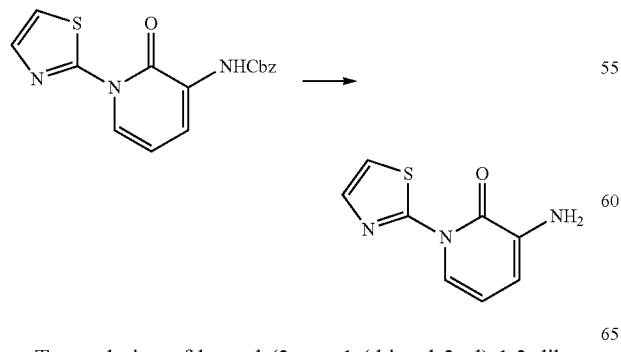

To a solution of benzyl (2-oxo-1-(thiazol-2-yl)-1,2-dihydropyridin-3-yl)carbamate (0.374 g, 1.142 mmol) in acetonitrile (20 mL) at 0° C. was added iodotrimethylsilane (0.778 mL, 5.71 mmol) over 3 min. The mixture was stirred at rt for 4 h before diethylamine (0.955 mL, 9.14 mmol) was added. The mixture was stirred at rt for 10 min and then concentrated under vacuum to dryness. To the residue was added water (15 mL), and the resulting mixture was extracted with CH₂Cl₂ (3×40 mL). The combined sxtract was dried over anhydrous MgSO₄. The desired product, 3-amino-1-(thiazol-2-yl)pyridin-2(1H)-one (0.161 g, 0.833 mmol, 72.9% yield), was isolated as a white solid by ISCO (40 g silica gel, 20-40% ethyl acetate/hexane).

The following intermediates (A35-53) (Figure 4) were prepared according to the precedures described for the preparation of A31-34.

FIG. 4

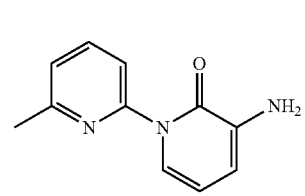
A35

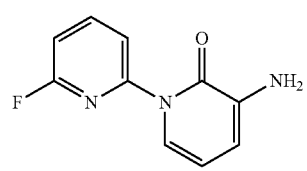
A36

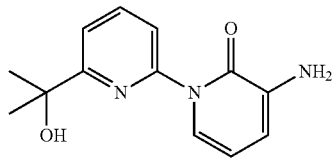
A37

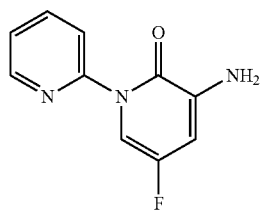
A38

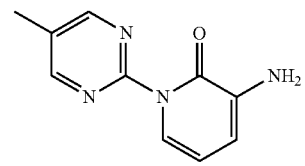
A39

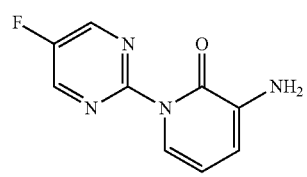
A40

-continued

A41 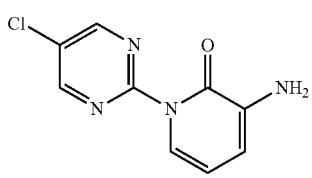

A42 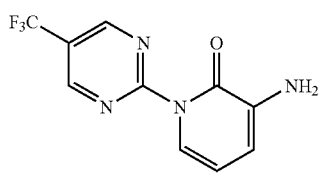

A43 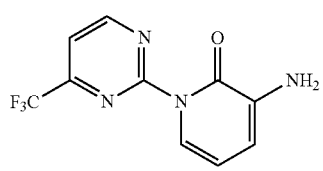

A45 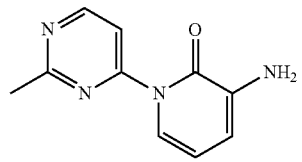

A46 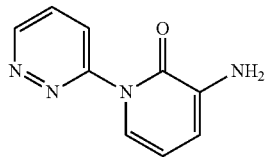

A47 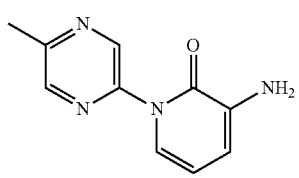

A48 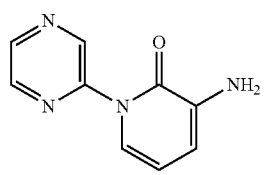

A49 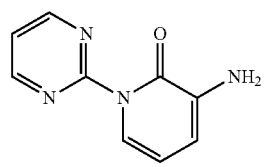

A50 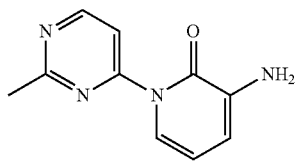

-continued

A51 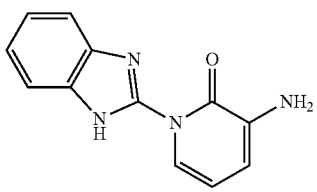

A52 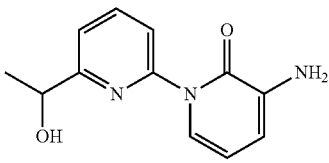

A53 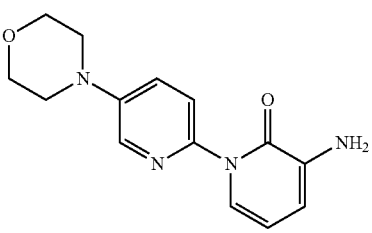

Intermediate A54

3-Amino-5-fluoro-1-(6-methylpyridazin-3-yl)pyridin-2(1H)-one

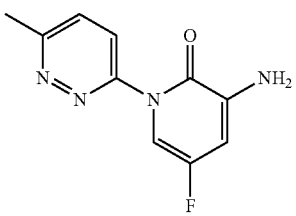 [SMILES: Cc1ccc(-n2cc(F)cc(N)c2=O)nn1]

Step 1: 3-Amino-5-fluoropyridin-2(1H)-one

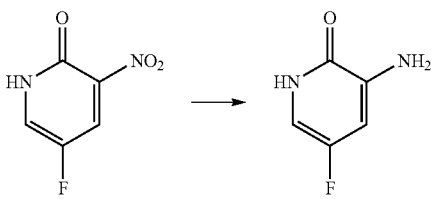 [SMILES: O=c1[nH]cc(F)cc1[N+](=O)[O-] ; Nc1cc(F)c[nH]c1=O]

A mixture of 5-fluoro-3-nitropyridin-2(1H)-one (1.10 g, 6.96 mmol) and 10% Pd/C (0.330 g, 0.031 mmol) in methanol (36 mL) and tetrahydrofuran (12 mL) was stirred under hydrogen, provided by a hydrogen balloon, at rt for 2 h. The catalyst was removed by filtration. The filtrate was concentrated under vacuum to almost drynee. The residue was dissolved in ethyl acetate (150 mL), dried over anhydrous MgSO$_4$, and concentrated under vacuum to provide the desired product, 3-amino-5-fluoropyridin-2(1H)-one (0.459 g, 3.58 mmol, 51.5% yield), as a beige solid.

Step 2: 3-Amino-5-fluoro-1-(6-methylpyridazin-3-yl)pyridin-2(1H)-one (A54)

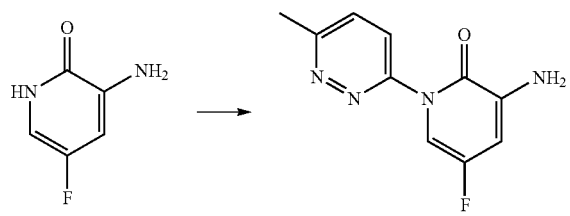 [SMILES: Nc1cc(F)c[nH]c1=O ; Cc1ccc(-n2cc(F)cc(N)c2=O)nn1]

A mixture of 3-amino-5-fluoropyridin-2-ol (0.660 g, 5.15 mmol), 3-chloro-6-methylpyridazine (1.325 g, 10.30 mmol), N1,N2-dimethylethane-1,2-diamine (0.165 mL, 1.546 mmol), copper(I) iodide (0.294 g, 1.546 mmol), and potassium carbonate (1.424 g, 10.30 mmol) in 1,4-dioxane (25 mL) in a pressure tube was heated at 110° C. for 20 h. Additional 3-chloro-6-methylpyridazine (0.662 g, 5.15 mmol), copper(I) iodide (0.197 g, 0.773 mmol), and potassium carbonate (0.712 g, 5.15 mmol) were added. The mixture was heated at 110° C. for another 20 h. The reaction mixture was diluted with ethyl acetate (15 mL) and filtered through Celite. The filtrate was concentrated under vacuum. The residue was subjected to ISCO (80 g silica gel, solid loading, 1-5% MeOH/CH$_2$Cl$_2$) to provide the desire product, 3-amino-5-fluoro-1-(6-methylpyridazin-3-yl)pyridin-2(1H)-one (0.167 g, 0.758 mmol, 14.72% yield), as a white solid.

The following intermediates (A55-56) (Figure 5) were prepared according to the procedure described for the preparation of A54.

FIG. 5

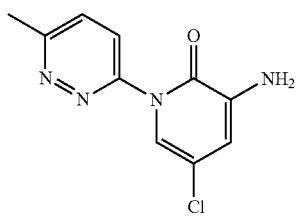

A55

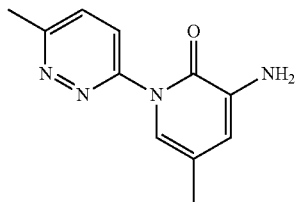

A56

Intermediate A57

5-Amino-3-(pyridin-2-yl)pyrimidin-4(3H)-one

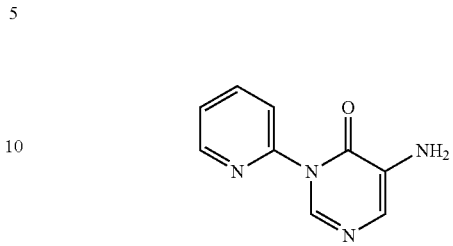

A mixture of 5-aminopyrimidin-4-ol (300 mg, 2.70 mmol), 2-bromopyridine (640 mg, 4.05 mmol), N1,N2-dimethylethane-1,2-diamine (0.115 mL, 1.080 mmol), copper (I) iodide (103 mg, 0.540 mmol), and potassium carbonate (746 mg, 5.40 mmol) in 1,4-dioxane (12 mL) in a pressure tube was heated at 110° C. for 16 h. The reaction mixture was diluted with ethyl acetate (30 mL) and filtered through Celite. The filtrate was concentrated under vacuum. The residue was subjected to ISCO (80 g silica gel, solid loading, 2-7% MeOH/CH2Cl2) to provide the desire product, 5-amino-3-(pyridin-2-yl)pyrimidin-4(3H)-one (0.380 g, 2.019 mmol, 74.8% yield), as a white solid. The following intermediates (A58-59) (Figure 6) were prepared according to the procedures described for the preparation of A57.

FIG. 6

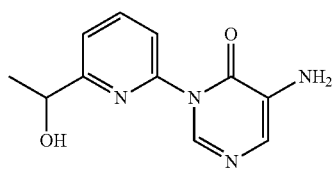

A58

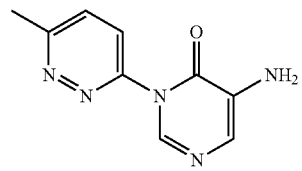

A59

Intermediate A60

3-Amino-1-(5-fluoro-4-methylpyrimidin-2-yl)pyridin-2(1H)-one

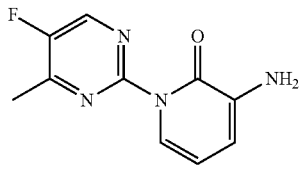 [SMILES: Cc1nc(-n2cccc(N)c2=O)ncc1F]

Step 1: 2-Chloro-5-fluoro-4-methylpyrimidine

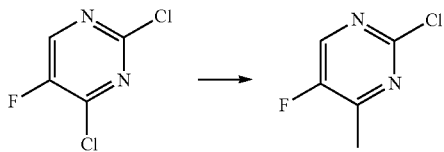

To a solution of 2,4-dichloro-5-fluoropyrimidine (5 g, 29.9 mmol) in THF (200 mL) was added acetylacetone iron (III) salt (1.058 g, 2.99 mmol) and the reaction mixture was cooled to 0° C. Methylmagnesium bromide in Et$_2$O (14.97 mL, 44.9 mmol) was added dropwise at the same temperature. After 30 min, the reaction was completed and quenched with saturated aqueous NH$_4$Cl solution. Diethyl ether was added and the layers were separated and the aqueous layer was further extracted with several portions of Et$_2$O. The combined organic phases were dried over sodium sulfate, filtered and the solvent was removed under vacuum. The desired product, 2-chloro-5-fluoro-4-methylpyrimidine (1.9 g, 12.70 mmol, 42.4% yield) was isolated as a white solid by ISCO (40 g silica gel, liquid loading, 0-5% ethylacetate/pet ether).

Step 2: Benzyl (1-(5-fluoro-4-methylpyrimidin-2-yl)-2-oxo-1,2-dihydropyridin-3-yl)carbamate

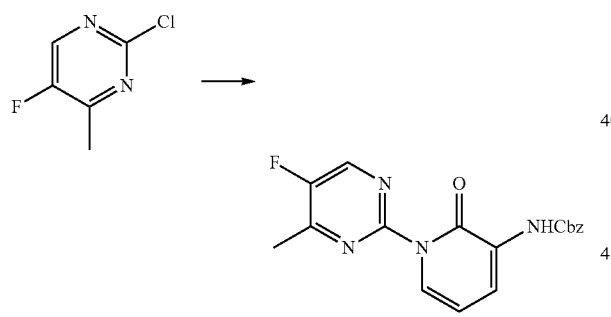

To a stirred solution of benzyl (2-oxo-1,2-dihydropyridin-3-yl)carbamate (3.17 g, 12.96 mmol) in 1,4-dioxane (150 mL) under nitrogen atmosphere, NaH (0.519 g, 12.96 mmol) was added and kept stir at rt for 10 min. 2-chloro-5-fluoro-4-methylpyrimidine (1.9 g, 12.96 mmol) was added and heated in a pressure tube at 110° C. for 24 h. The reaction mixture was concentrated under vacuum to remove the solvent. To the crude residue was extracted with EtOAc (50 mL) and water (50 mL). The aq. layer was further extracted with EtOAc (3×50 mL) and the combined organic layer was washed with brine (50 mL), dried over sodium sulfate. The desired product benzyl (1-(5-fluoro-4-methylpyrimidin-2-yl)-2-oxo-1,2-dihydropyridin-3-yl)carbamate (300 mg, 0.820 mmol, 6.32% yield) was isolated as a brown solid by ISCO (24 g silica gel, solid loading, 40-100% ethyl acetate/pet ether).

Step 3: 3-Amino-1-(5-fluoro-4-methylpyrimidin-2-yl)pyridin-2(1H)-one (A60)

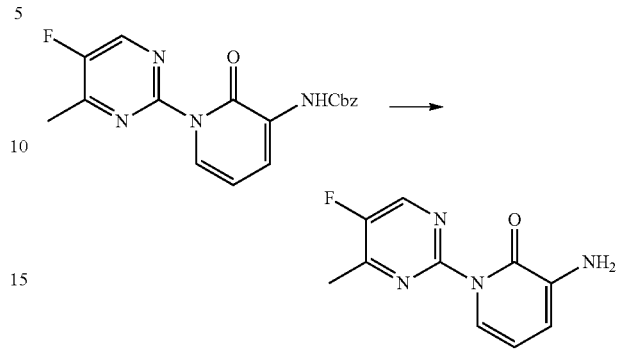

To a stirred solution of benzyl (1-(5-fluoro-4-methylpyrimidin-2-yl)-2-oxo-1,2-dihydropyridin-3-yl)carbamate (300 mg, 0.847 mmol) in methanol (10 mL) and tetrahydrofuran (10 mL), 10% Pd/C (70 mg, 0.066 mmol) was added and kept under hydrogen atmosphere of 10 psi at rt for 2 h. The solvent was filtered through celite bed and removed under vacuum to dryness. The desired product 3-amino-1-(5-fluoro-4-methylpyrimidin-2-yl)pyridin-2(1H)-one (100 mg, 0.407 mmol, 48.0% yield) was isolated as a brown solid by ISCO (12 g silica gel, solid loading, 90-100% ethylacetate/pet ether).

Intermediate A61

3-Amino-1-(1,5-dimethyl-1H-pyrazol-3-yl)pyridin-2(1H)-one

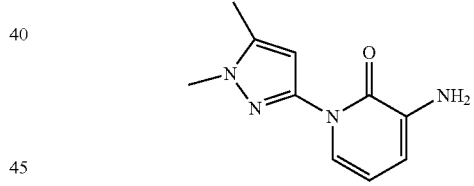

Step 1: Methyl 1-(1,5-dimethyl-1H-pyrazol-3-yl)-2-oxo-1,2-dihydropyridine-3-carboxylate

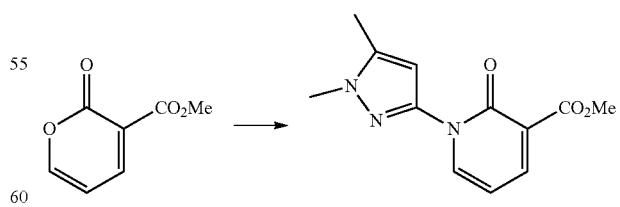

To an orange, homogeneous solution of methyl 2-oxo-2H-pyran-3-carboxylate (1.9201 g, 12.46 mmol) in DMF (12.44 ml) under nitrogen at 0° C. was added 1,5-dimethyl-1H-pyrazol-3-amine (1.3822 g, 12.44 mmol). After 6 h, the cold bath was removed, and the reaction was stirred to room temperature for 15 min EDCI (1-(3-dimethylaminopropyl)

ethyl carbodiimide) (3.10 g, 16.17 mmol) and DMAP (0.380 g, 3.11 mmol) were added. After stirring overnight, the reaction was diluted with EtOAc (200 mL) and water (50 mL). The layers were separated, and the organic layer was washed with water (50 mL) and brine (50 mL), dried over Na2SO4, filtered and concentrated in vacuo to give a residue which was purified by flash chromatography using an ISCO 330 g column (solid loading) eluting with 10-100% EtOAc/hex. Appropriate fractions were collected and concentrated in vacuo to give methyl 1-(1,5-dimethyl-1H-pyrazol-3-yl)-2-oxo-1,2-dihydropyridine-3-carboxylate (0.8397 g, 3.40 mmol, 27.3% yield) as a light orange solid.

Step 2: 1-(1,5-Dimethyl-1H-pyrazol-3-yl)-2-oxo-1,2-dihydropyridine-3-carboxylic acid

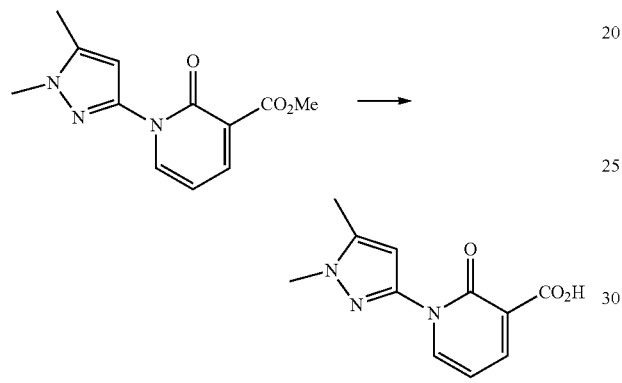

To a light orange, homogeneous solution of methyl 1-(1,5-dimethyl-1H-pyrazol-3-yl)-2-oxo-1,2-dihydropyridine-3-carboxylate (0.8397 g, 3.40 mmol) in tetrahydrofuran (25.5 ml) and methanol (8.49 ml) was added lithium hydroxide hydrate (0.5796 g, 13.81 mmol) in water (9 mL). After 1 h, the reaction was concentrated in vacuo not to dryness. Aqueous 1 N HCl was added until pH 5; the precipitate was filtered, washed with water and dried over Drierite at 50° C. to give 1-(1,5-dimethyl-1H-pyrazol-3-yl)-2-oxo-1,2-dihydropyridine-3-carboxylic acid (0.741 g, 3.18 mmol, 94% yield) as a white solid.

Step 3: tert-Butyl (1-(1,5-dimethyl-1H-pyrazol-3-yl)-2-oxo-1,2-dihydropyridin-3-yl)carbamate

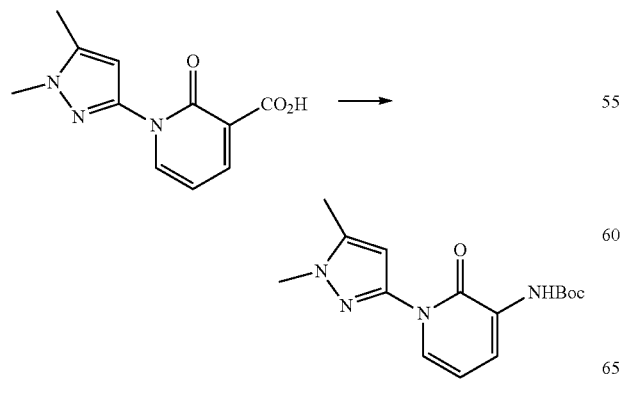

To a colorless, heterogeneous solution 1-(1,5-dimethyl-1H-pyrazol-3-yl)-2-oxo-1,2-dihydropyridine-3-carboxylic acid (0.7407 g, 3.18 mmol) and TEA (0.75 ml, 5.38 mmol) in t-BuOH (10.99 ml) under nitrogen was added diphenyl phosphorazidate (0.888 ml, 4.12 mmol). The reaction was heated to 75° C. After 2 days, the reaction was cooled to room temperature and concentrated in vacuo to give a residue which was purified by flash chromatography using an ISCO 40 g column (solid loading) eluting with 0-75% EtOAc/hexane. Appropriate fractions were collected and concentrated in vacuo to give tert-butyl (1-(1,5-dimethyl-1H-pyrazol-3-yl)-2-oxo-1,2-dihydropyridin-3-yl)carbamate (0.5827 g, 1.915 mmol, 60% yield) as a white solid.

Step 4: 3-Amino-1-(1,5-dimethyl-1H-pyrazol-3-yl)pyridin-2(1H)-one (A61)

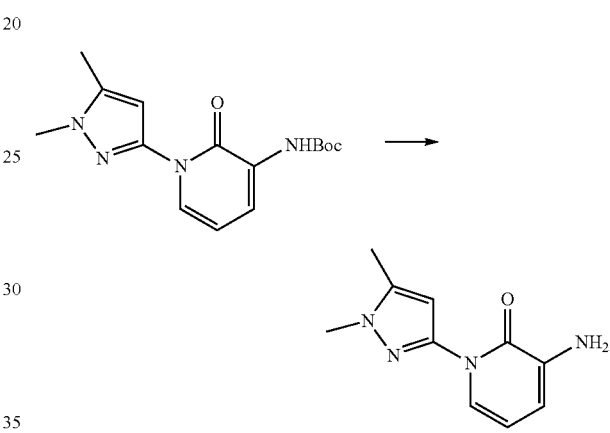

To a colorless, homogeneous solution of tert-butyl (1-(1,5-dimethyl-1H-pyrazol-3-yl)-2-oxo-1,2-dihydropyridin-3-yl)carbamate (0.5827 g, 1.915 mmol) in Dichloromethane (12.76 ml) under nitrogen was added 4 N hydrogen chloride/dioxane (10 ml, 40.0 mmol); precipitation ensued. After stirring overnight, the precipitate was filtered and washed with CH2Cl2. Water (4 mL) was added to the precipitate, followed by saturated aqueous NaHCO3 until the solution was pH 11 by litmus paper. EtOAc (30 mL) was added, and the layers were separated. The aqueous layer was extracted with EtOAc (4×30 mL), and the organic layers were combined, dried over Na2SO4, filtered and concentrated in vacuo to give 3-amino-1-(1,5-dimethyl-1H-pyrazol-3-yl)pyridin-2(1H)-one (0.3120 g, 1.528 mmol, 80% yield) as an off-white solid.

The following intermediates (A62-71) (Figure 7) were prepared according to the following procedure described for the preparation of A61.

FIG. 7

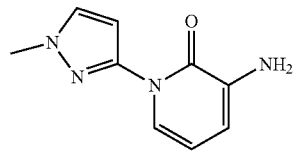

A62

| | |
|---|---|
| A63 | 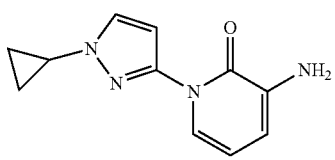 |
| A64 | 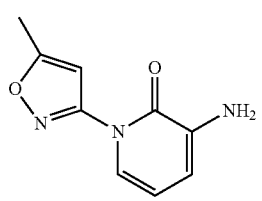 |
| A65 | 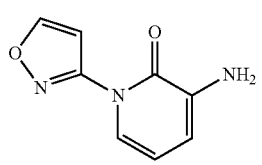 |
| A66 | 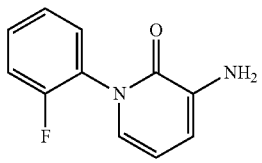 |
| A67 | 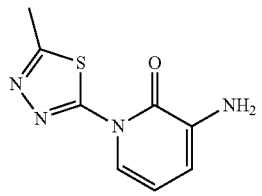 |
| A68 | 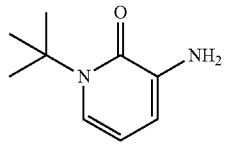 |
| A69 | 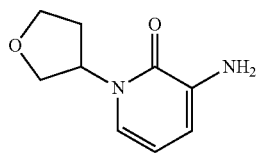 |
| A70 | 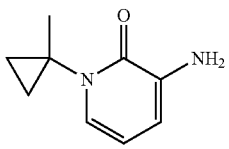 |
| A71 | 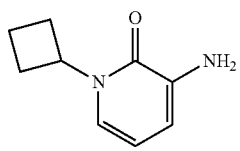 |

Example A72

3-Amino-1-(4-hydroxycyclohexyl)pyridin-2(1H)-one

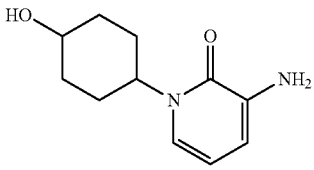 [SMILES: Nc1cccn(C2CCC(O)CC2)c1=O]

Step 1: 4-((tert-Butyldimethylsilyl)oxy)cyclohexanamine

To a solution of 4-aminocyclohexanol (10 g, 87 mmol) in DCM (150 mL), imidazole (29.6 g, 434 mmol) and TBDMS-Cl (19.63 g, 130 mmol) was added and the reaction mixture was stirred at room temperature for 24 h. The reaction mixture was concentrated under reduced pressure and the crude residue was diluted with water (150 mL) and extracted with ethyl acetate (3×75 mL). The organic layer was washed with 10% NaOH solution (50 mL), water (50 mL), followed by brine (50 mL). The organic phases were dried over $Na_2SO_4$. The desired product, 4-((tert-butyldimethylsilyl)oxy)cyclohexanamine (12 g, 52.3 mmol, 60.2% yield) was obtained as crude material. The crude sample forwarded to next step.

Step 2: Methyl 1-(4-((tert-butyldimethylsilyl)oxy)cyclohexyl)-2-oxo-1,2-dihydropyridine-3-carboxylate

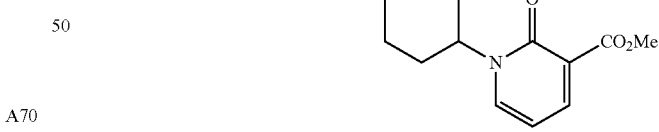

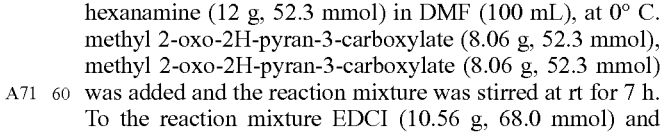

To a solution of 4-((tert-butyldimethylsilyl)oxy)cyclohexanamine (12 g, 52.3 mmol) in DMF (100 mL), at 0° C. methyl 2-oxo-2H-pyran-3-carboxylate (8.06 g, 52.3 mmol), methyl 2-oxo-2H-pyran-3-carboxylate (8.06 g, 52.3 mmol) was added and the reaction mixture was stirred at rt for 7 h. To the reaction mixture EDCI (10.56 g, 68.0 mmol) and DMAP (1.597 g, 13.08 mmol) was added and the reaction mixture was further stirred overnight at rt. The reaction mixture was diluted with water (100 mL) and extracted with ethyl acetate (3×100 mL). The organic layer was given brine wash (75 mL) and dried over $Na_2SO_4$. The desired product methyl 1-(4-((tert-butyldimethylsilyl) oxy) cyclohexyl)-2- oxo-1, 2-dihydropyridine-3-carboxylate (4.6 g, 12.58 mmol, 24.06% yield) was isolated as a brown gummy compound by ISCO (120 g silica gel, solid loading, 38-43% ethyl acetate/hexane).

Step 3: 1-(4-((tert-Butyldimethylsilyl)oxy)cyclohexyl)-2-oxo-1,2-dihydropyridine-3-carboxylic acid

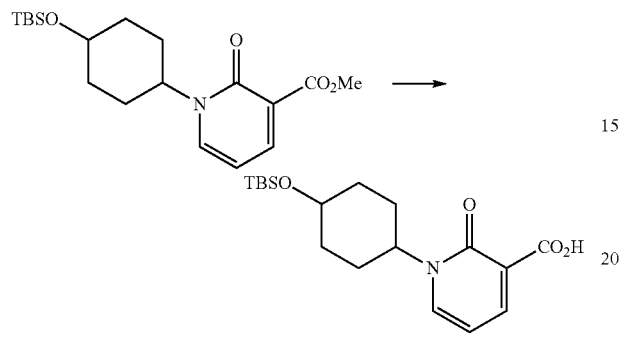

To a solution of methyl 1-(4-((tert-butyldimethylsilyl) oxy)cyclohexyl)-2-oxo-1,2-dihydro pyridine-3-carboxylate (4.6 g, 12.58 mmol) in THF (8 mL), MeOH (8 mL) and water (8 mL), and then LiOH (1.205 g, 50.3 mmol) was added. The reaction mixture was stirred at rt for 3 h. The reaction mixture was concentrated to remove the solvent, the sample was diluted with 3 mL water, then 1.5N HCl was added drop wise at cooling, (pH~5). The compound was precipitating, the precipitate was filter and dried over under vacuum to afford 1-(4-((tert-butyldimethylsilyl) oxy) cyclohexyl)-2-oxo-1, 2-dihydropyridine-3-carboxylic acid (4.0 g, 11.38 mmol, 90% yield).

Step 4: 2-(Trimethylsilyl)ethyl(1-(4-((tert-butyldimethylsilyl)oxy)cyclohexyl)-2-oxo-1,2-dihydro pyridin-3-yl)carbamate

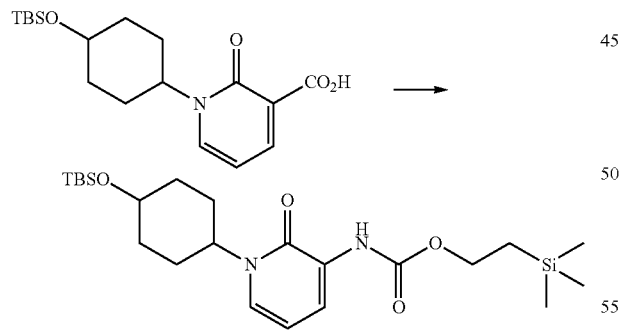

To a solution of 1-(4-((tert-butyldimethylsilyl)oxy)cyclohexyl)-2-oxo-1,2-dihydropyridine-3-carboxylic acid (4.0 g, 11.38 mmol) in toluene (4 mL) was added Et$_3$N (6.34 mL, 45.5 mmol) followed by diphenylphosphoryl azide (2.94 mL, 13.66 mmol) at rt dropwise. The reaction mixture was heated to 45° C. for 2 h. Temperature was then raised to 70° C. and 2-(trimethylsilyl) ethanol (13.05 mL, 91 mmol) was added dropwise. The reaction mixture was heated at same temperature for another 8 h, then concentrated under vacuum. The desired product, 2-(trimethylsilyl) ethyl (1-(4-((tert-butyldimethylsilyl)oxy)cyclohexyl)-2-oxo-1,2-dihydropyridin-3-yl)carbamate (2.1 g, 4.50 mmol, 39.5% yield) was isolated as a white solid by ISCO (120 g silica gel, solid loading, 10-20% ethylacetate/hexane).

Step 5: 3-Amino-1-(4-hydroxycyclohexyl) pyridin-2 (1H)-one (A72)

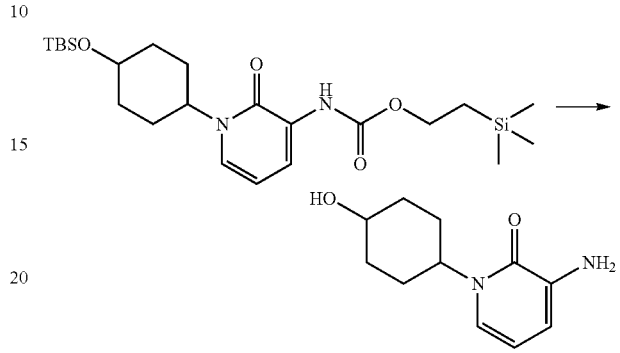

The solution of 2-(trimethylsilyl)ethyl (1-(4-((tert-butyldimethylsilyl)oxy)cyclohexyl)-2-oxo-1,2-dihydropyridin-3-yl)carbamate (2.0 g, 4.28 mmol) in DCM (8 mL) was cooled to 0° C. Then 4M HCl in dioxane (0.651 mL, 21.42 mmol) was added slowly and reaction mixture was stirred at rt for overnight. The reaction mixture was concentrated completely to remove excess solvent. The reaction mixture was taken in Pet ether/diethyl ether and the compound was stirred for some time (20-30 mins) and then filtered The organic phase were removed under vaccum and afforded 3-amino-1-(4-hydroxycyclohexyl)pyridin-2(1H)-one (540 mg, 2.59 mmol, 60.5% yield) as off white solid.

Intermediate A73

3-Amino-1-(4-(1-hydroxyethyl)phenyl)pyridin-2 (1H)-one

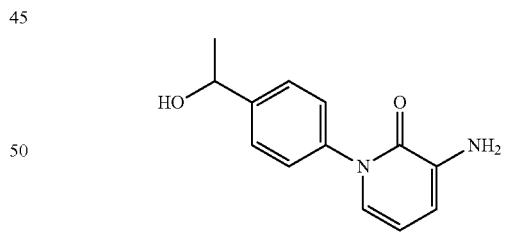

Step 1:
1-(4-Acetylphenyl)-3-nitropyridin-2(1H)-one

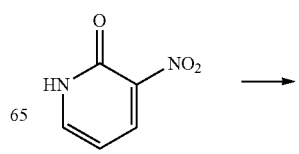

-continued

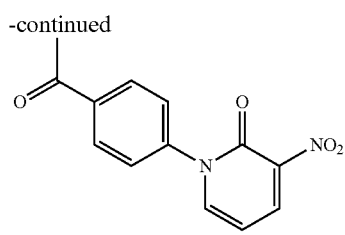

A solution of 3-nitropyridin-2(1H)-one (2.5466 g, 18.18 mmol), (4-acetylphenyl)boronic acid (3.58 g, 21.81 mmol), diacetoxycopper (4.95 g, 27.3 mmol) and pyridine (20 ml, 247 mmol) in Dioxane (72.7 ml) in a sealed tube was heated at 80° C. and stirred overnight. After cooling to room temperature, (4-acetylphenyl)boronic acid (0.8831 g) and diacetoxycopper (1.21 g) were added, and heating was resumed. The reaction was stirred overnight, cooled to room temperature, diluted with EtOAc (50 mL) and filtered through Celite. The filtrate was concentrated in vacuo. Water (20 mL) and EtOAc (50 mL) were added, and the layers were separated. The organic layer was washed with brine (20 mL), dried over Na2SO4, filtered and concentrated in vacuo to give a residue which was purified by flash chromatography using an ISCO 120 g column (solid loading) eluting with 30-100% EtOAc/hexane. Appropriate fractions were collected and concentrated in vacuo to give 1-(4-acetylphenyl)-3-nitropyridin-2(1H)-one (1.2024 g, 4.66 mmol, 25.6% yield) as a yellow solid.

Step 2:
1-(4-Acetylphenyl)-3-aminopyridin-2(1H)-one

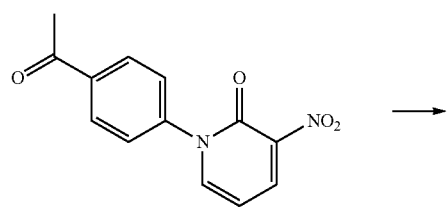

To a heterogeneous solution of 1-(4-acetylphenyl)-3-nitropyridin-2(1H)-one (0.4 g, 1.549 mmol) in methanol (16.60 ml) and tetrahydrofuran (5.53 ml) under nitrogen were added ammonium chloride (1.160 g, 21.69 mmol) and zinc (1.418 g, 21.69 mmol). After 30 min, the reaction was concentrated in vacuo. The residue was dissolved in water (5 mL) and CH2Cl2 (20 mL). After separation, the aqueous layer was extracted with CH2CL2 (2×20 mL). The organic layers were combined, dried over Na2SO4, filtered and concentrated in vacuo to give a residue which was purified by flash chromatography using an ISCO 24 g column (solid loading) eluting with 0-5% MeOH/CH2CL2. Appropriate fractions were collected and concentrated in vacuo to give 1-(4-acetylphenyl)-3-aminopyridin-2(1H)-one (0.1661 g, 0.728 mmol, 47.0% yield) as a tan solid.

Step 3: 3-Amino-1-(4-(1-hydroxyethyl)phenyl)pyridin-2(1H)-one (A73)

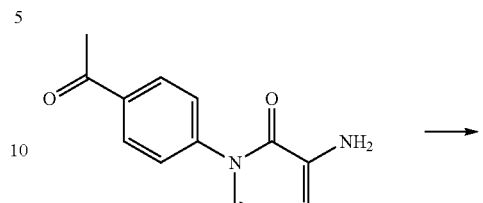

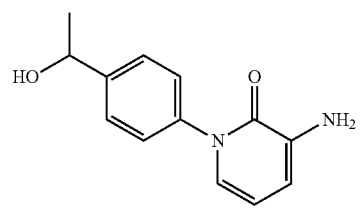 [SMILES: CC(O)c1ccc(-n2cccc(N)c2=O)cc1]

To a heterogeneous, colorless solution of 1-(4-acetylphenyl)-3-aminopyridin-2(1H)-one (0.142 g, 0.622 mmol) in EtOH (6.22 ml) under nitrogen at 0° C. was added sodium borohydride (0.118 g, 3.11 mmol). After 30 min, this was combined with another similarly run reaction and concentrated in vacuo. The residue was mostly dissolved in water (3 mL) followed by extraction with CH2Cl2 (3×20 mL). The organic layers were combined, dried over Na2SO4, filtered and concentrated in vacuo to give 3-amino-1-(4-(1-hydroxyethyl)phenyl)pyridin-2(1H)-one (0.1415 g, 0.615 mmol, 85.2% yield) as a white solid.

Intermediate A74

4-Amino-2-phenylpyridazin-3 (2H)-one

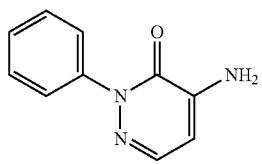 [SMILES: Nc1ccnn(-c2ccccc2)c1=O]

A colorless, heterogeneous solution of 4,5-dichloro-2-phenylpyridazin-3(2H)-one (0.2504 g, 1.039 mmol) and hydrazine, H2O (0.505 ml, 10.39 mmol) in Ethanol (3.0 ml) was microwaved at 85° C. for 20 min. This was combined with two other reactions of comparable scale, concentrated in vacuo to give a residue which was purified by flash chromatography using an ISCO 80 g column (solid loading) eluting with 0-20% MeOH/CH2Cl2. Appropriate fractions were collected and concentrated in vacuo to give 4-amino-2-phenylpyridazin-3(2H)-one as an orange foam (0.3051 g, 53.0% yield).

Intermediate 7a 6-((1-Methyl-2-oxo-1,2-dihydropyridin-3-yl)amino)-8-(methylamino)imidazo[1,2-b]pyridazine-3-carboxylic acid, 2 HCl

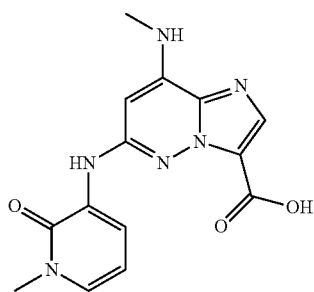 [SMILES: CNc1cc(Nc2cccn(C)c2=O)nn2c(C(=O)O)cnc12]

Step 1: Ethyl 8-((4-methoxybenzyl)(methyl)amino)-6-((1-methyl-2-oxo-1,2-dihydropyridin-3-yl)amino)imidazo[1,2-b]pyridazine-3-carboxylate

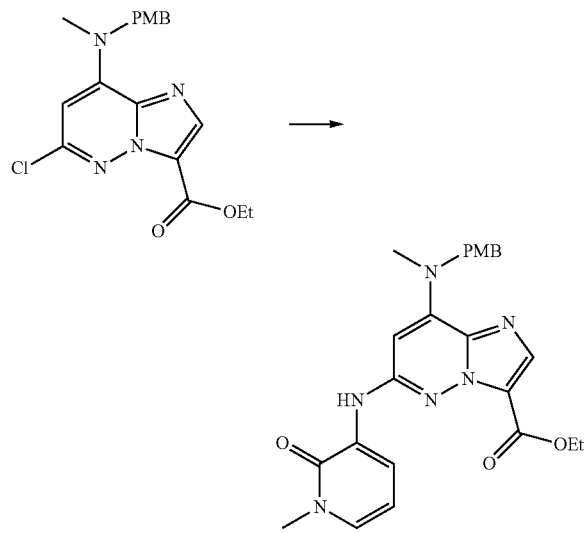

A solution of ethyl 6-chloro-8-((4-methoxybenzyl)(methyl)amino)imidazo[1,2-b]pyridazine-3-carboxylate (1.35 g, 3.60 mmol), 3-amino-1-methylpyridin-2(1H)-one (0.537 g, 4.32 mmol), xantphos (0.250 g, 0.432 mmol), cesium carbonate (4.46 g, 13.69 mmol) and tris(dibenzylideneacetone)dipalladium(0) (0.396 g, 0.432 mmol) in N-methyl-2-pyrrolidinone (18.01 ml) in a sealed pressure tube was heated at 125° C. After 2 h, the reaction was cooled to room temperature, diluted with EtOAc (200 mL) and filtered through Celite. The filtrate was washed with water (40 mL). The aqueous layer was extracted with EtOAc (2×125 mL). The organic layers were combined and washed with water (3×40 mL) and brine (40 mL), dried over Na$_2$SO$_4$, filtered and concentrated in vacuo to give a residue which was purified by flash chromatography using an ISCO 120 g column (solid loading) eluting with 0-100% EtOAc/hexane. Appropriate fractions were collected and concentrated in vacuo to give ethyl 8-((4-methoxybenzyl)(methyl)amino)-6-((1-methyl-2-oxo-1,2-dihydropyridin-3-yl)amino)imidazo[1,2-b]pyridazine-3-carboxylate (1.25 g, 2.70 mmol, 75% yield) as a tan solid.

Step 2: 8-((4-Methoxybenzyl)(methyl)amino)-6-((1-methyl-2-oxo-1,2-dihydropyridin-3-yl)amino)imidazo[1,2-b]pyridazine-3-carboxylic acid

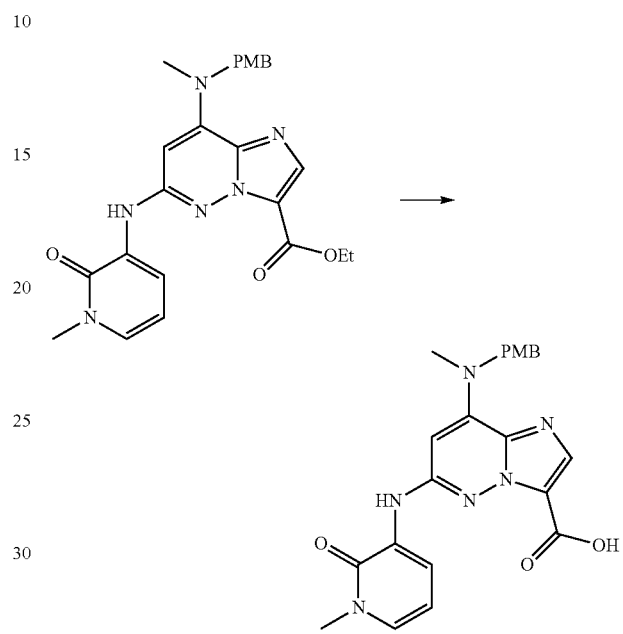

To a homogeneous solution of ethyl 8-((4-methoxybenzyl)(methyl)amino)-6-((1-methyl-2-oxo-1,2-dihydropyridin-3-yl)amino)imidazo[1,2-b]pyridazine-3-carboxylate (1.25 g, 2.70 mmol) in tetrahydrofuran (20.27 ml) and methanol (6.76 ml) was added lithium hydroxide, H2O (0.4601 g, 10.96 mmol) in water (7 mL). After 1 h, the reaction was concentrated in vacuo not to dryness. 1 N aqueous HCl was added until pH 5 by litmus paper. The precipitate was filtered and washed with water, dried over Drierite to give 8-((4-methoxybenzyl)(methyl)amino)-6-((1-methyl-2-oxo-1,2-dihydropyridin-3-yl)amino)imidazo[1,2-b]pyridazine-3-carboxylic acid (1.0071 g, 2.318 mmol, 86% yield) as a white solid.

Step 3: 6-((1-Methyl-2-oxo-1,2-dihydropyridin-3-yl)amino)-8-(methylamino)imidazo[1,2-b]pyridazine-3-carboxylic acid, 2 HCl (7a)

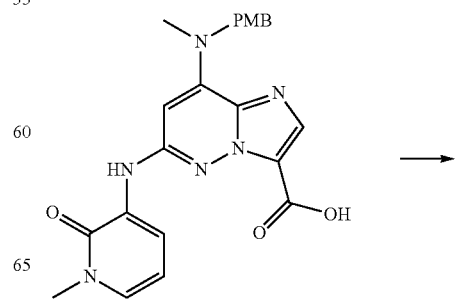

87
-continued

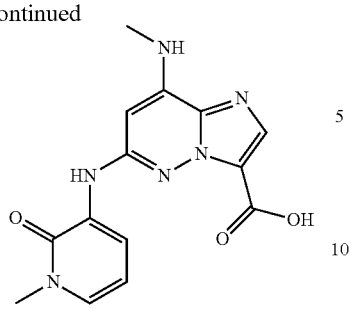

To a heterogeneous solution of 8-((4-methoxybenzyl)(methyl)amino)-6-((1-methyl-2-oxo-1,2-dihydropyridin-3-yl)amino)imidazo[1,2-b]pyridazine-3-carboxylic acid (1.0041 g, 2.311 mmol) in dichloromethane (46.2 ml) under nitrogen was added 4N hydrogen chloride/dioxane (30 ml, 120 mmol). After 30 min, the precipitate was filtered and rinsed with CH2Cl2 to give 6-((1-methyl-2-oxo-1,2-dihydropyridin-3-yl)amino)-8-(methylamino)imidazo[1,2-b]pyridazine-3-carboxylic acid, 2 HCl (0.7684 g, 1.984 mmol, 86% yield) as a white solid.

The following intermediate 7b-c was prepared according to the procedure described for the preparation of 7a.

7b

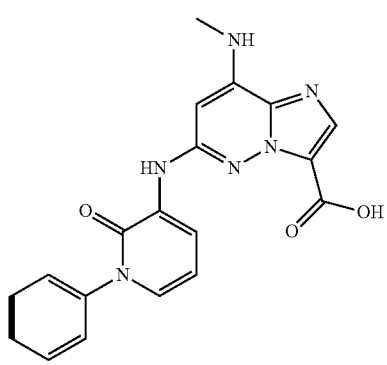

7c

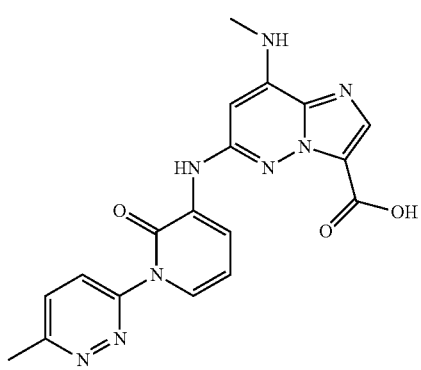

88
Example 1

N-(1-Cyanocyclopropyl)-6-(1-methyl-2-oxo-1,2-dihydropyridin-3-ylamino)-8-(methylamino)imidazo[1,2-b]pyridazine-3-carboxamide

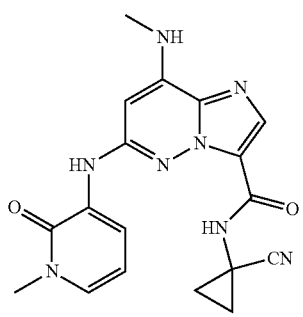 [SMILES: CNc1cc(Nc2cccn(C)c2=O)nn2c(C(=O)NC3(C#N)CC3)cnc12]

A mixture of 6-chloro-N-(1-cyanocyclopropyl)-8-((4-methoxybenzyl)(methyl)amino)imidazo[1,2-b]pyridazine-3-carboxamide (4a) (80 mg, 0.195 mmol), 3-amino-1-methylpyridin-2(1H)-one (29.0 mg, 0.234 mmol), tris(dibenzylideneacetone)dipalladium(0) (21.40 mg, 0.023 mmol), xantphos (13.52 mg, 0.023 mmol), and cesium carbonate (178 mg, 0.545 mmol) in N-methyl-2-pyrrolidinone (1.4 mL) was heated at 120° C. for 2.5 h. The reaction mixture was diluted with ethyl acetate (10 mL) and filtered through Celite®. The filtrate was diluted with ethyl acetate (60 mL), washed with water (3×20 mL) and brine (20 mL), and dried over anhydrous MgSO4. The solvent was removed under vacuum. The residue was dissolved in dichloromethane (3.5 mL). To this solution at rt was added hydrocloride acid in 1,4-dioxane (3.5 mL, 14.00 mmol). The mixture was stirred at rt for 30 min, then concentrated under vacuum. The residue was purified by prep. HPLC to provide the desired product, N-(1-cyanocyclopropyl)-6-((1-methyl-2-oxo-1,2-dihydropyridin-3-yl)amino)-8-(methylamino)imidazo[1,2-b]pyridazine-3-carboxamide (17.9 mg, 0.046 mmol, 23.81% yield), as a white solid. LCMS (M+H)=$^1$H NMR (400 MHz, DMSO-$d_6$): δ 9.21 (s, 1H), 8.55 (s, 1H), 8.03 (dd, J=7.5, 1.8 Hz, 1H), 7.92 (s, 1H), 7.45 (q, J=4.5 Hz, 1H), 7.36 (dd, J=6.8, 1.8 Hz, 1H), 6.36 (s, 1H), 6.31 (t, J=7.0 Hz, 1H), 3.56 (s, 3H), 2.86 (d, J=4.8 Hz, 3H), 1.66-1.60 (m, 2H), 1.34-1.29 (m, 2H).

Example 2

6-((1-(4-Cyanophenyl)-2-oxo-1,2-dihydropyridin-3-yl)amino)-N-cyclopropyl-8-(methylamino)imidazo[1,2-b]pyridazine-3-carboxamide

Example 3

N-((1R,2S)-2-Fluorocyclopropyl)-8-(methylamino)-6-(2-oxo-1-(pyridin-2-yl)-1,2-dihydropyridin-3-ylamino)imidazo[1,2-b]pyridazine-3-carboxamide

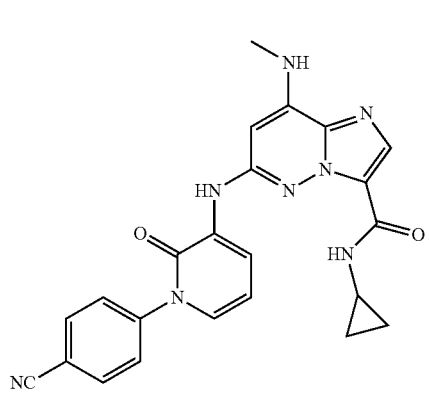 [SMILES: CNc1cc(Nc2cccn(-c3ccc(C#N)cc3)c2=O)nn2c(C(=O)NC3CC3)cnc12]

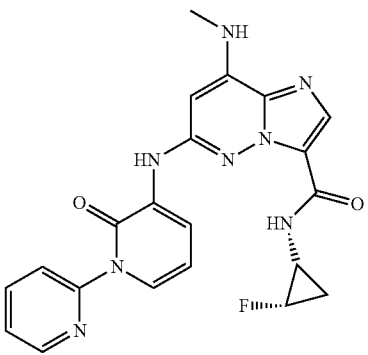

A mixture of 6-chloro-N-cyclopropyl-8-((4-methoxybenzyl)(methyl)amino)imidazo[1,2-b]pyridazine-3-carboxamide (4b) (70 mg, 0.181 mmol), 4-(3-amino-2-oxopyridin-1(2H)-yl)benzonitrile (A15) (47.9 mg, 0.227 mmol), tris(dibenzylideneacetone)dipalladium(0) (19.94 mg, 0.022 mmol), xantphos (12.60 mg, 0.022 mmol), and cesium carbonate (166 mg, 0.508 mmol) in N-methyl-2-pyrrolidinone (1.5 mL) was heated at 125° C. for 2 h. The reaction mixture was diluted with ethyl acetate (10 mL) and filtered through Celite®. The filtrate was diluted with ethyl acetate (60 mL), washed with water (2×20 mL) and brine (20 mL), and dried over anhydrous MgSO$_4$. The solvent was removed under vacuum. The residue was dissolved in dichloromethane (3.5 mL). To this solution at rt was added hydrchloride acid in 1,4-dioxane (3.5 mL, 14.00 mmol). The mixture was stirred at rt for 30 min, then concentrated under vacuum. The residue was purified by prep. HPLC to provide the desired product, 6-((1-(4-cyanophenyl)-2-oxo-1,2-dihydropyridin-3-yl)amino)-N-cyclopropyl-8-(methylamino)imidazo[1,2-b]pyridazine-3-carboxamide (4.5 mg, 10.01 mol, 5.52% yield), as a white solid. LCMS (M+H)$^+$=441.1. $^1$H NMR (400 MHz, DMSO-d$_6$): δ 8.63 (s, 1H), 8.58 (d, J=4.2 Hz, 1H), 8.08-8.03 (m, 2H), 8.01 (dd, J=7.3, 1.5 Hz, 1H), 7.86 (s, 1H), 7.80-7.72 (m, 2H), 7.46 (d, J=5.1 Hz, 1H), 7.36 (dd, J=7.0, 1.8 Hz, 1H), 6.43 (t, J=7.3 Hz, 1H), 6.37 (s, 1H), 2.92 (td, J=7.3, 3.9 Hz, 1H), 2.86 (d, J=4.8 Hz, 3H), 0.85-0.76 (m, 2H), 0.61-0.54 (m, 2H).

A mixture of 6-chloro-N-((1R,2S)-2-fluorocyclopropyl)-8-((4-methoxybenzyl)(methyl)amino)imidazo[1,2-b]pyridazine-3-carboxamide (4d) (55 mg, 0.136 mmol), 3-amino-2H-[1,2'-bipyridin]-2-one (A31) (31.9 mg, 0.170 mmol), palladium(II) acetate (6.12 mg, 0.027 mmol), BrettPhos (14.62 mg, 0.027 mmol), and potassium carbonate (28.2 mg, 0.204 mmol) in 1,4-dioxane (1.0 mL) was heated at 80° C. for 2.5 h. The reaction mixture was diluted with DMSO (3 mL), followed by ethyl acetate (60 mL). To this mixture was added water (15 mL) and the mixture was stirred at rt for 5 min. The aqueous layer was removed. The organic layer was washed with water (15 mL) and brine (15 mL), and dried over anhydrous MgSO$_4$. The solvent was removed under vacuum. The residue was dissolved in dichloromethane (4 mL). To this solution at rt was added hydrochloric acid in 1,4-dioxane (3.0 mL, 12.00 mmol). The mixture was stirred at rt for 30 min, then concentrated under vacuum. The residue was purified by prep. HPLC to provide the desired product, N-((1R,2S)-2-fluorocyclopropyl)-8-(methylamino)-6-((2-oxo-2H-[1,2'-bipyridin]-3-yl)amino)imidazo[1,2-b]pyridazine-3-carboxamide (27.4 mg, 0.062 mmol, 45.4% yield), as a beige solid. LCMS (M+H)$^+$=435.3. $^1$H NMR (400 MHz, DMSO-d$_6$): δ 8.72-8.57 (m, 3H), 8.08-8.01 (m, 1H), 7.99 (dd, J=7.4, 1.7 Hz, 1H), 7.91 (s, 1H), 7.84 (dt, J=8.1, 0.9 Hz, 1H), 7.56-7.46 (m, 3H), 6.43-6.38 (m, 2H), 4.99-4.77 (m, 1H), 3.04-2.96 (m, 1H), 2.87 (d, J=4.8 Hz, 3H), 1.25 (dtd, J=15.2, 8.5, 6.1 Hz, 1H), 1.06-0.93 (m, 1H).

Example 4

N-(1-Chloro-3-hydroxypropan-2-yl)-8-(methylamino)-6-(2-oxo-1-phenyl-1,2-dihydropyridin-3-ylamino)imidazo[1,2-b]pyridazine-3-carboxamide

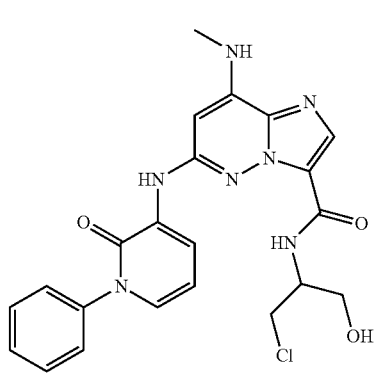 [SMILES: CNc1cc(Nc2cccn(-c3ccccc3)c2=O)nn2c(C(=O)NC(CO)CCl)cnc12]

A mixture of 6-chloro-8-((4-methoxybenzyl)(methyl)amino)-N-(oxetan-3-yl)imidazo[1,2-b]pyridazine-3-carboxamide (4p) (65 mg, 0.162 mmol), 3-amino-1-phenylpyridin-2(1H)-one (A13) (37.7 mg, 0.202 mmol), palladium(II) acetate (7.26 mg, 0.032 mmol), BrettPhos (17.36 mg, 0.032 mmol), and potassium carbonate (33.5 mg, 0.243 mmol) in 1,4-Dioxane (1.2 mL) was heated at 80° C. for 2.5 h. The reaction mixture was diluted with ethyl acetate (10 mL) and filtered through Celite®. The filtrate was diluted with ethyl acetate (60 mL), washed with water (2×25 mL) and brine (25 mL), and dried over anhydrous $MgSO_4$. The solvent was removed under vacuum. The residue was dissolved in dichloromethane (4 mL). To this solution at rt was added hydrochloric acid in 1,4-dioxane (3.0 mL, 32.00 mmol). The mixture was stirred at rt for 30 min, and then concentrated under vacuum. The residue was purified by prep. HPLC to provide the titled compound, N-(1-chloro-3-hydroxypropan-2-yl)-8-(methylamino)-6-((2-oxo-1-phenyl-1,2-dihydropyridin-3-yl)amino)imidazo[1,2-b]pyridazine-3-carboxamide (45.8 mg, 0.097 mmol, 59.9% yield), as a white solid. LCMS (M+H)$^+$=468.3. $^1$H NMR (500 MHz, DMSO-$d_6$): δ 8.61-8.53 (m, 2H), 8.02 (dd, J=7.5, 1.7 Hz, 1H), 7.92 (s, 1H), 7.60-7.52 (m, 2H), 7.52-7.44 (m, 4H), 7.30 (dd, J=6.8, 1.8 Hz, 1H), 6.46-6.36 (m, 2H), 5.18 (t, J=5.4 Hz, 1H), 4.37 (dt, J=8.3, 5.4 Hz, 1H), 3.94-3.86 (m, 1H), 3.81 (dd, J=11.0, 6.0 Hz, 1H), 3.71-3.60 (m, 2H), 2.87 (d, J=4.7 Hz, 3H).

Example 5

N-Cyclobutyl-8-(methylamino)-6-((2-oxo-1-(4-(trifluoromethyl)pyrimidin-2-yl)-1,2-dihydropyridin-3-yl)amino)imidazo[1,2-b]pyridazine-3-carboxamide

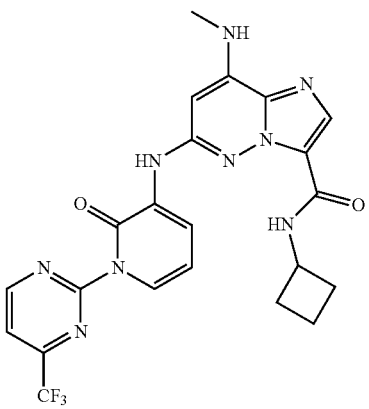 [SMILES: CNc1cc(Nc2cccn(-c3nccc(C(F)(F)F)n3)c2=O)nn2c(C(=O)NC3CCC3)cnc12]

A mixture of 6-chloro-N-cyclobutyl-8-((4-methoxybenzyl)(methyl)amino)imidazo[1,2-b]pyridazine-3-carboxamide (65 mg, 0.163 mmol) (4c), 3-amino-1-(4-(trifluoromethyl)pyrimidin-2-yl)pyridin-2(1H)-one (A43) (52.1 mg, 0.203 mmol), palladium(II) acetate (7.30 mg, 0.033 mmol), BrettPhose (17.45 mg, 0.033 mmol), and potassium carbonate (33.7 mg, 0.244 mmol) in 1,4-dioxane (1.0 mL) was heated at 80° C. for 2.5 h. The reaction mixture was diluted with ethyl acetate (6 mL) and filtered through Celite®. The filtrate was diluted with ethyl acetate (80 mL), washed with water (3×25 mL) and brine (25 mL), and dried over anhydrous $MgSO_4$. The solvent was removed under vacuum. The residue was dissolved in dichloromethane (4 mL). To this solution at rt was added hydrochloric acid in 1,4-dioxane (3.0 mL, 12.00 mmol). The mixture was stirred at rt for 30 min, and then concentrated under vacuum. The residue was purified by prep. HPLC to provide the titled compound, N-cyclobutyl-8-(methylamino)-6-((2-oxo-1-(4-(trifluoromethyl)pyrimidin-2-yl)-1,2-dihydropyridin-3-yl)amino)imidazo[1,2-b]pyridazine-3-carboxamide (36.6 mg, 0.072 mmol, 44.2% yield) as a pale solid. LCMS (M+H)+=500.4. $^1$H NMR (400 MHz, DMSO-$d_6$): δ 9.44 (d, J=5.0 Hz, 1H), 8.77-8.68 (m, 2H), 8.27 (d, J=5.1 Hz, 1H), 8.13 (dd, J=7.3, 1.6 Hz, 1H), 7.85 (s, 1H), 7.54 (dd, J=7.0, 1.6 Hz, 1H), 7.49 (q, J=4.6 Hz, 1H), 6.47 (t, J=7.2 Hz, 1H), 6.35 (s, 1H), 4.51 (sxt, J=8.2 Hz, 1H), 2.86 (d, J=4.9 Hz, 3H), 2.39-2.26 (m, 2H), 2.06-1.92 (m, 2H), 1.80-1.67 (m, 2H).

Example 6

N-(3-Hydroxy-2,2-dimethylpropyl)-8-(methylamino)-6-((1-(5-methylpyrazin-2-yl)-2-oxo-1,2-dihydropyridin-3-yl)amino)imidazo[1,2-b]pyridazine-3-carboxamide

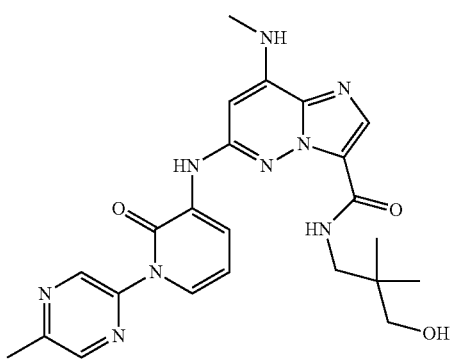 [SMILES: CNc1cc(Nc2cccn(-c3cnc(C)cn3)c2=O)nn2c(C(=O)NCC(C)(C)CO)cnc12]

A mixture of 6-chloro-N-(3-hydroxy-2,2-dimethylpropyl)-8-((4-methoxybenzyl)(methyl)amino)imidazo[1,2-b]pyridazine-3-carboxamide (4e) (65 mg, 0.150 mmol), 3-amino-1-(5-methylpyrazin-2-yl)pyridin-2(1H)-one (A47) (39.6 mg, 0.196 mmol), palladium(II) acetate (10.14 mg, 0.045 mmol), BrettPhose (24.23 mg, 0.045 mmol), and potassium carbonate (31.2 mg, 0.226 mmol) in 1,4-dioxane (1.5 mL) was heated at 80° C. for 2.5 h. The reaction mixture was diluted with ethyl acetate (6 mL) and filtered through Celite®. The filtrate was diluted with ethyl acetate (80 mL), washed with water (3×25 mL) and brine (25 mL), and dried over anhydrous $MgSO_4$. The solvent was removed under vacuum. The residue was dissolved in dichloromethane (4 mL). To this solution at rt was added hydrochloric acid in 1,4-dioxane (3.0 mL, 12.00 mmol). The mixture was stirred at rt for 30 min, and then concentrated under vacuum. To the residue was added DMSO (1.5 mL), followed by water (15 mL). The resulting mixture was basified with saturated $NaHCO_3$ solution. The insoluble material was collected by suction filtration, which was further purified by ISCO (24 g silica gel, solid loading, 0-10% MeOH/dichloromethane) to provide the desired product, N-(3-hydroxy-2,2-dimethylpropyl)-8-(methylamino)-6-((1-(5-methylpyrazin-2-yl)-2-oxo-1,2-dihydropyridin-3-yl)amino)imidazo[1,2-b]pyridazine-3-carboxamide (28.0 mg, 0.056 mmol, 37.0% yield), as a pale yellow solid solid. LCMS (M+H)$^+$=478.5. $^1$H NMR (400 MHz, DMSO-$d_6$) δ 9.02 (d, J=1.3 Hz, 1H), 8.73-8.65 (m, 2H), 8.62 (d, J=0.5 Hz, 1H), 8.02 (dd, J=7.4, 1.7 Hz, 1H), 7.88 (s, 1H), 7.55-7.47 (m, 2H), 6.53 (t, J=7.2 Hz, 1H), 6.39 (s, 1H), 4.59 (t, J=5.9 Hz, 1H), 3.34-3.30 (m, 2H), 3.12 (d, J=5.9 Hz, 2H), 2.87 (d, J=4.9 Hz, 3H), 2.60 (s, 3H), 0.81 (s, 6H).

Example 7

(R)-8-(Methylamino)-6-((2-oxo-1-phenyl-1,2-dihydropyridin-3-yl)amino)-N-(tetrahydrofuran-3-yl)imidazo[1,2-b]pyridazine-3-carboxamide

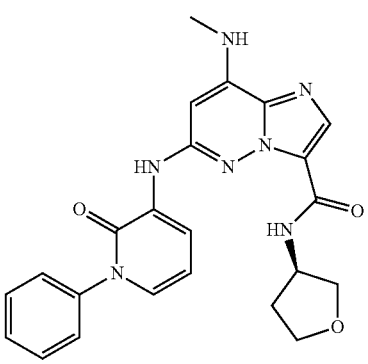 [SMILES: CNc1cc(Nc2cccn(-c3ccccc3)c2=O)nn2c(C(=O)N[C@@H]3CCOC3)cnc12]

A mixture of (R)-6-chloro-8-((4-methoxybenzyl)(methyl)amino)-N-(tetrahydrofuran-3-yl)imidazo[1,2-b]pyridazine-3-carboxamide (4h) (65 mg, 0.156 mmol), 3-amino-1-phenylpyridin-2(1H)-one (A13) (36.4 mg, 0.195 mmol), tris(dibenzylideneacetone)dipalladium(0) (17.17 mg, 0.019 mmol), xantphos 10.85 mg, 0.019 mmol), and cesium carbonate (143 mg, 0.438 mmol) in N-methyl-2-pyrrolidinone (1.5 mL) was heated at 125° C. for 2 h. The reaction mixture was diluted with ethyl acetate (20 mL) and filtered through Celite®. The filtrate was diluted with ethyl acetate (80 mL), washed with water (3×25 mL) and brine (25 mL), and dried over anhydrous $MgSO_4$. The solvent was removed under vacuum. The residue was dissolved in dichloromethane (4 mL). To this solution at rt was added hydrochloric acid in 1,4-dioxane (3 mL, 12.00 mmol). The mixture was stirred at rt for 30 min, and then concentrated under vacuum. The residue was purified by prep. HPLC to provide the titled compound, (R)-8-(methylamino)-6-((2-oxo-1-phenyl-1,2-dihydropyridin-3-yl)amino)-N-(tetrahydrofuran-3-yl)imidazo[1,2-b]pyridazine-3-carboxamide (29.3 mg, 0.065 mmol, 41.7% yield) as a white solid. LCMS (M+H)$^+$=423.2. $^1$H NMR (400 MHz, DMSO-$d_6$) δ 8.57 (s, 1H), 8.54 (d, J=6.8 Hz, 1H), 8.01 (dd, J=7.4, 1.7 Hz, 1H), 7.88 (s, 1H), 7.59-7.52 (m, 2H), 7.51-7.42 (m, 4H), 7.29 (dd, J=6.9, 1.7 Hz, 1H), 6.42 (t, J=7.2 Hz, 1H), 6.38 (s, 1H), 4.66-4.54 (m, 1H), 3.95-3.82 (m, 2H), 3.73 (td, J=8.2, 6.3 Hz, 1H), 3.65 (dd, J=9.1, 3.9 Hz, 1H), 2.86 (d, J=4.8 Hz, 3H), 2.35-2.23 (m, 1H), 1.93-1.81 (m, 1H).

Example 8

N-Cyclobutyl-8-(methylamino)-6-((3-oxo-2-phenyl-2,3-dihydropyridazin-4-yl)amino)imidazo[1,2-b]pyridazine-3-carboxamide

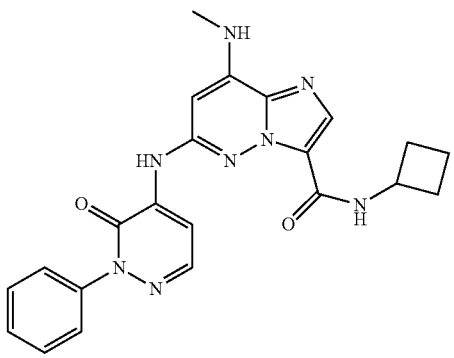 [SMILES: CNc1cc(Nc2ccnn(-c3ccccc3)c2=O)nn2c(C(=O)NC3CCC3)cnc12]

A solution of 6-chloro-N-cyclobutyl-8-((4-methoxybenzyl)(methyl)amino)imidazo[1,2-b]pyridazine-3-carboxamide (4c) (0.0558 g, 0.140 mmol), 4-amino-2-phenylpyridazin-3(2H)-one (A73) (0.033 g, 0.174 mmol), palladium acetate (6.27 mg, 0.028 mmol), brettphos (0.015 g, 0.028 mmol) and potassium carbonate (0.029 g, 0.209 mmol) in dioxane (1.073 ml) in a sealed vial was heated to 100° C. After 2 h, the reaction was cooled to room temperature, diluted with EtOAc (10 mL) and filtered through Celite. The filtrate was diluted with EtOAc (50 mL) and washed with water (2×20 mL) and brine (20 mL), dried over $Na_2SO_4$, filtered and concentrated in vacuo to give crude product. This was dissolved in dichloromethane (4.0 mL) upon which was added 4 N hydrogen chloride/dioxane (3.0 mL, 12.00 mmol) under nitrogen; precipitation ensued. After 1 h, the reaction was concentrated in vacuo, diluted with DMSO (lmL) followed by water (10 mL). Saturated aqueous $NaHCO_3$ was added until pH 11 by litmus paper. The solution was stirred for 20 min, filtered and washed with water to give crude product which was diluted with DMSO (lmL) and MeOH (2.5 mL), and subjected to autoprep HPLC. The appropriate fractions were collected and concentrated in vacuo not to dryness. Saturated aqueous NaHCO3 was added until pH 11 by litmus paper, and the solution was stirred for 20 min. The precipitate was filtered and dried at 50° C. under vacuum to give N-cyclobutyl-8-(methylamino)-6-((3-oxo-2-phenyl-2,3-dihydropyridazin-4-yl)amino)imidazo[1,2-b]pyridazine-3-carboxamide (0.00786 g, 0.018 mmol, 13.04% yield) as an off-white solid. LCMS (M+H)$^+$=431.4. $^1$H NMR (500 MHz, DMSO-$d_6$) δ ppm 9.41 (1 H, s), 8.57 (1 H, d, J=7.77 Hz), 7.94-8.03 (2 H, m), 7.93 (1 H, s), 7.61-7.68 (3 H, m), 7.50-7.57 (2 H, m), 7.40-7.48 (1 H, m), 6.57 (1 H, s), 4.51 (1 H, sxt, J=8.27 Hz), 2.88 (3 H, d, J=4.99 Hz), 2.27-2.40 (2 H, m), 1.94-2.11 (2 H, m), 1.64-1.81 (2 H, m).

Example 9

N-(3-Hydroxy-2,2-dimethylpropyl)-6-((1-methyl-2-oxo-1,2-dihydropyridin-3-yl)amino)-8-(methylamino)imidazo[1,2-b]pyridazine-3-carboxamide

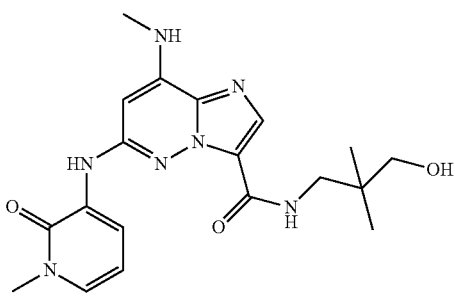 [SMILES: CNc1cc(Nc2cccn(C)c2=O)nn2c(C(=O)NCC(C)(C)CO)cnc12]

A homogeneous solution of 6-((1-methyl-2-oxo-1,2-dihydropyridin-3-yl)amino)-8-(methylamino)imidazo[1,2-b]pyridazine-3-carboxylic acid, 2 HCl (7a) (0.0333 g, 0.086 mmol), 3-amino-2,2-dimethylpropan-1-ol (0.018 g, 0.172 mmol), BOP (0.049 g, 0.112 mmol) and DIPEA (0.120 ml, 0.688 mmol) was stirred overnight. Water (4 mL) was added, and the precipitate was filtered, washed with water (2 mL) and dried. MeOH (1 mL) was added to the precipitate, and the solution was stirred for an hour. This was filtered and washed with MeOH to give N-(3-hydroxy-2,2-dimethylpropyl)-6-((1-methyl-2-oxo-1,2-dihydropyridin-3-yl)amino)-8-(methylamino)imidazo[1,2-b]pyridazine-3-carboxamide (0.0143 g, 0.036 mmol, 41.6% yield) as a white solid. LCMS (M+H)$^+$=400.2. $^1$H NMR (500 MHz, DMSO-$d_6$) δ 8.70 (t, J=6.7 Hz, 1H), 8.47 (s, 1H), 7.87 (d, J=1.7 Hz, 1H), 7.86 (s, 1H), 7.44 (d, J=5.0 Hz, 1H), 7.35-7.30 (m, 1H), 6.35 (s, 1H), 6.31 (t, J=7.2 Hz, 1H), 4.55 (t, J=6.0 Hz, 1H), 3.54 (s, 3H), 3.10 (d, J=5.8 Hz, 2H), 2.87 (d, J=5.0 Hz, 3H), 0.78 (s, 6H).

The following examples (ex. 10-238) (Table 1) were prepared according to the procedures described for the preparation of example 1-9.

TABLE 1
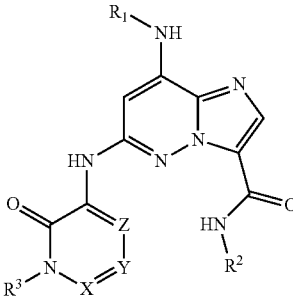
| Ex # | R¹ | R² | R³ | X | Y | Z | (M + H)+ |
|---|---|---|---|---|---|---|---|
| 10 | Me | c-Pr | 4-F—Ph | CH | CH | CH | 434.1 |
| 11 | Me | 1-CN-c-Pr | Me | CH | CF | CH | 397.1 |
| 12 | Me | 1-CN-c-Pr | 4-F—Ph | CH | CH | CH | 459.1 |
| 13 | Me | 1-CN-c-Pr | 4-CN—Ph | CH | CH | CH | 466.1 |
| 14 | Me | 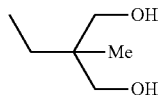 | 4-F—Ph | CH | CH | CH | 496.3 |
| 15 | Me | c-Pr | cPrCH$_2$ | CH | CF | CH | 412.2 |
| 16 | Me | 1-CN-cPr | cPrCH$_2$ | CH | CF | CH | 437.2 |
| 17 | Me | c-Pr | 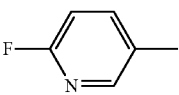 | CH | CH | CH | 435.1 |
| 18 | Me | c-Pr | 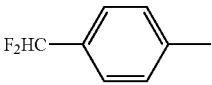 | CH | CH | CH | 466.0 |
| 19 | Me | 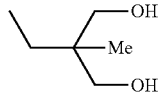 | 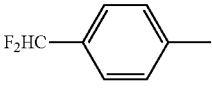 | CH | CH | CH | 528.0 |
| 20 | Me | 1-CN-c-Pr | 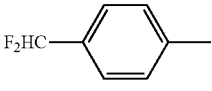 | CH | CH | CH | 491.2 |
| 21 | Me | c-Pr | FCH$_2$CH$_2$ | CH | CF | CH | 404.2 |
| 22 | Me | c-Pr | Me | CH | CCl | CH | 388.3 |
| 23 | Me | 1-CN-cPr | Me | CH | CCl | CH | 413.2 |
| 24 | Me | 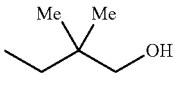 | Me | CH | CF | CH | 418.4 |
| 25 | Me | 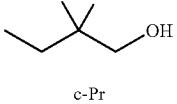 | 4-CN—Ph | CH | CH | CH | 487.3 |
| 26 | Me | c-Pr | 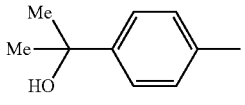 | CH | CH | CH | 474.4 |
| 27 | Me | 1-CN-c-Pr | 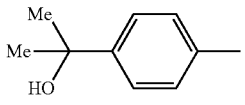 | CH | CH | CH | 499.4 |

TABLE 1-continued

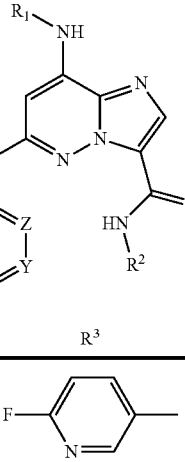

| Ex # | R¹ | R² | R³ | X | Y | Z | (M + H)⁺ |
|---|---|---|---|---|---|---|---|
| 28 | Me | 1-CN-c-Pr |  6-F-pyridin-3-yl | CH | CH | CH | 460.3 |
| 29 | Me |  1-ethylcyclopropyl-CH₂OH | 4-F—Ph | CH | CH | CH | 478.3 |
| 30 | Me |  1-ethylcyclopropyl-CH₂OH | Me | CH | CF | CH | 416.3 |
| 31 | Me | 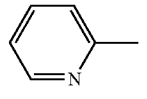 1-ethylcyclopropyl-CH₂OH | Me | CH | CCl | CH | 4322.2 |
| 32 | Me | c-Pr |  pyridin-2-yl | CH | CH | CH | 417.2 |
| 33 | Me |  2,2-dimethyl-butan-1-ol | 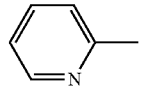 5-F-6-methylpyridin-2-yl | CH | CH | CH | 481.3 |
| 34 | Me | c-Bu | 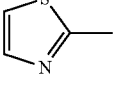 pyridin-2-yl | CH | CH | CH | 431.3 |
| 35 | Me | c-Pr | 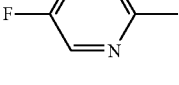 thiazol-2-yl | CH | CH | CH | 423.2 |
| 36 | Me | c-Pr |  5-F-pyridin-2-yl | CH | CH | CH | 435.3 |
| 37 | Me | 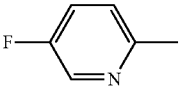 2-F-cyclopropyl | 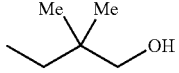 5-F-pyridin-2-yl | CH | CH | CH | 453.3 |
| 38 | Me | 2,2-dimethyl-butan-1-ol | 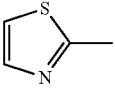 thiazol-2-yl | CH | CH | CH | 469.3 |

TABLE 1-continued
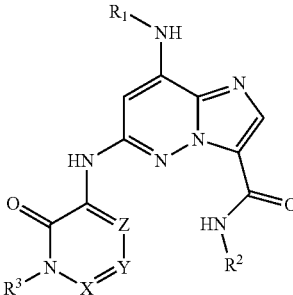
| Ex # | R¹ | R² | R³ | X | Y | Z | (M + H)⁺ |
|---|---|---|---|---|---|---|---|
| 39 | Me |  | 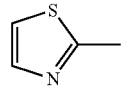 | CH | CH | CH | 467.3 |
| 40 | Me | 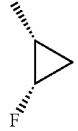 | 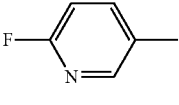 | CH | CH | CH | 453.3 |
| 41 | Me | c-Pr | 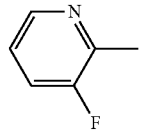 | CH | CH | CH | 435.3 |
| 42 | Me | 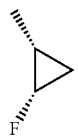 | 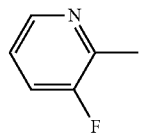 | CH | CH | CH | 453.3 |
| 43 | Me | 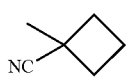 | Me | CH | CHCl | CH | 427.1 |
| 44 | Me | c-Pr | cPr | CH | CH | CH | 380.4 |
| 45 | Me | 1-CN-cPr | cPr | CH | CH | CH | 405.4 |
| 46 | Me | c-Pr | 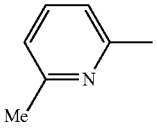 | CH | CH | CH | 431.4 |
| 47 | Me | c-Bu | 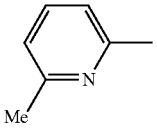 | CH | CH | CH | 445 |
| 48 | Me | 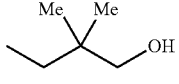 | cPr | CH | CH | CH | 426.4 |

TABLE 1-continued
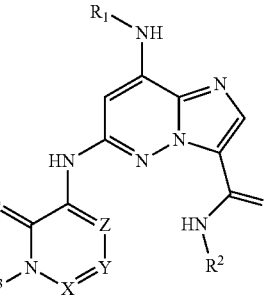
| Ex # | R¹ | R² | R³ | X | Y | Z | (M + H)⁺ |
|---|---|---|---|---|---|---|---|
| 49 | Me | 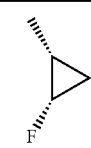 | 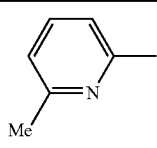 2,6-dimethylpyridine | CH | CH | CH | 449.3 |
| 50 | Me |  | Ph | CH | CH | CH | 446.4 |
| 51 | Me | 1-CN-c-Pr | cPr | CH | CF | CH | 423.3 |
| 52 | Me | c-Bu | 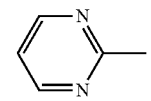 2-pyrimidinyl | CH | CH | CH | 432.4 |
| 53 | Me | 1-CN-c-Pr | 3-F—Ph | CH | CH | CH | 459.3 |
| 54 | Me | 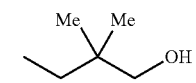 | 3-F—Ph | CH | CH | CH | 480.3 |
| 55 | Me | 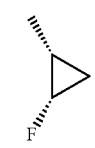 | 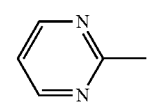 2-pyrimidinyl | CH | CH | CH | 436.3 |
| 56 | Me | c-Bu | 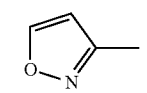 3-methylisoxazole | CH | CH | CH | 421.3 |
| 57 | Me | 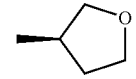 | Me | CH | CH | CH | 384.3 |
| 58 | Me |  | Me | CH | CH | CH | 384.3 |
| 59 | Me | 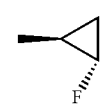 | 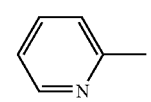 2-pyridinyl | CH | CH | CH | 435.3 |
| 60 | Me | 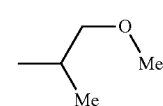 | Me | CH | CH | CH | 386.2 |

TABLE 1-continued
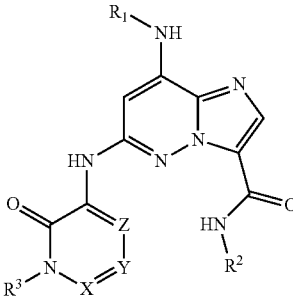
| Ex # | R¹ | R² | R³ | X | Y | Z | (M + H)⁺ |
|---|---|---|---|---|---|---|---|
| 61 | Me | 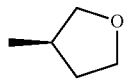 | 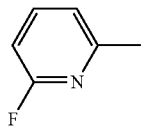 | CH | CH | CH | 465.3 |
| 62 | Me | 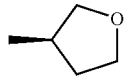 | 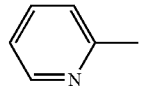 | CH | CH | CH | 447.4 |
| 63 | Me | c-Pr | 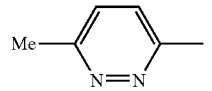 | CH | CH | CH | 432.4 |
| 64 | Me | c-Bu | 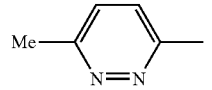 | CH | CH | CH | 446.4 |
| 65 | Me | 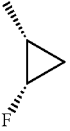 | 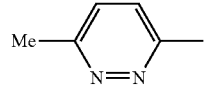 | CH | CH | CH | 450.4 |
| 66 | Me | Et | 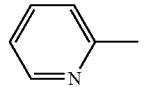 | CH | CH | CH | 405.3 |
| 67 | Me | Et | 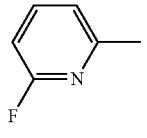 | CH | CH | CH | 423.2 |
| 68 | Me | c-Bu | Me | CH | CH | CH | 368.3 |
| 69 | Me | c-Bu | 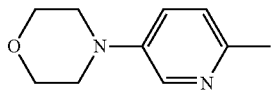 | CH | CH | CH | 516.4 |
| 70 | Me | 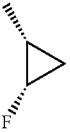 | 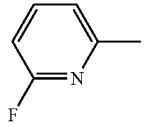 | CH | CH | CH | 504.4 |

TABLE 1-continued
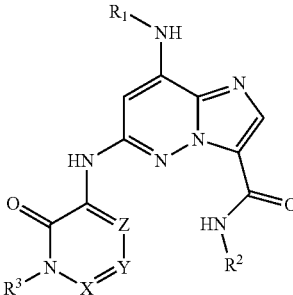
| Ex # | R¹ | R² | R³ | X | Y | Z | (M + H)⁺ |
|---|---|---|---|---|---|---|---|
| 71 | Me | c-Bu | 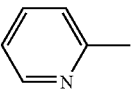 | CN | N | CH | 432.1 |
| 72 | Me | 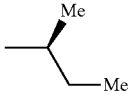 | Me | CH | CH | CH | 370.1 |
| 73 | Me | 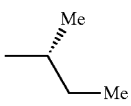 | Me | CH | CH | CH | 370.1 |
| 74 | Me | 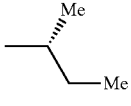 | 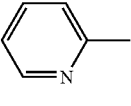 | CH | CH | CH | 433.1 |
| 75 | Me | 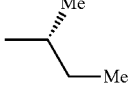 | 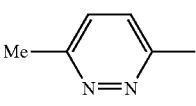 | CH | CH | CH | 448.1 |
| 76 | Me | 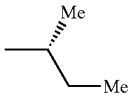 | 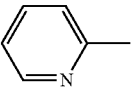 | CH | N | CH | 434.1 |
| 77 | Me | c-Bu | 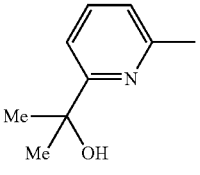 | CH | CH | CH | 489.1 |
| 78 | Me | c-Bu | 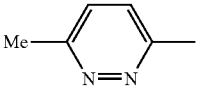 | CH | N | CH | 447.1 |
| 79 | Me | 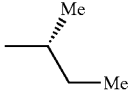 | 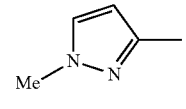 | CH | CH | CH | 436.3 |

TABLE 1-continued
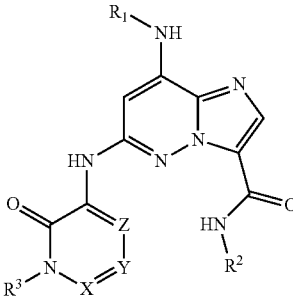
| Ex # | R¹ | R² | R³ | X | Y | Z | (M + H)⁺ |
|---|---|---|---|---|---|---|---|
| 80 | Me |  | 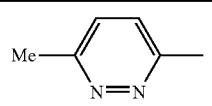 | CH | N | CH | 451.1 |
| 81 | Me | c-Pr | 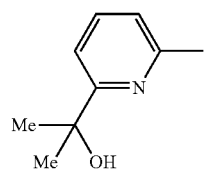 | CH | CH | CH | 475.1 |
| 82 | Me |  | 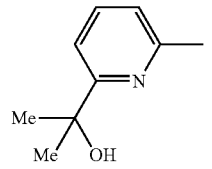 | CH | CH | CH | 493.1 |
| 83 | Me | 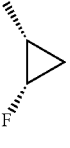 | 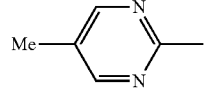 | CH | CH | CH | 450.2 |
| 84 | Me | c-Bu | Me | CH | CH | N | 369.2 |
| 85 | Me | c-Pr | 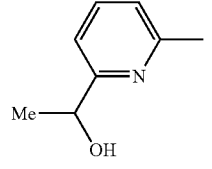 | CH | CH | CH | 461.1 |
| 86 | Me | c-Bu | 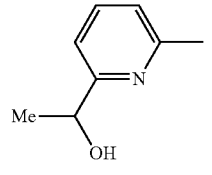 | CH | CH | CH | 475.1 |
| 87 | Me | c-Bu | 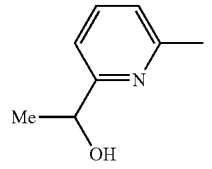 | CH | N | CH | 476.1 |

TABLE 1-continued
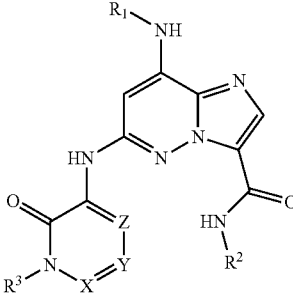
| Ex # | R¹ | R² | R³ | X | Y | Z | (M + H)⁺ |
|---|---|---|---|---|---|---|---|
| 88 | Me | 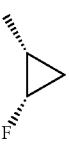 | 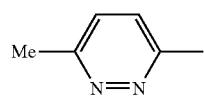 | CH | CCl | CH | 484.0 |
| 89 | Me |  | 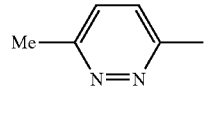 | CH | CF | CH | 468.0 |
| 90 | Me | 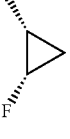 | 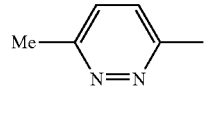 | CH | CMe | CH | 464.0 |
| 91 | Me | c-Pr | 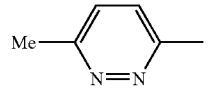 | CH | CMe | CH | 446.1 |
| 92 | Me | c-Bu | 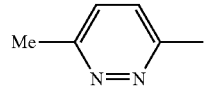 | CH | CMe | CH | 460.1 |
| 93 | Me | c-Bu | 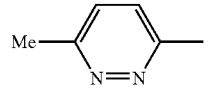 | CH | CF | CH | 464.1 |
| 94 | Me | c-Pr | 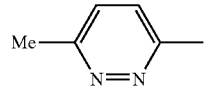 | CH | CF | CH | 450.3 |
| 95 | Me | c-Pentyl | 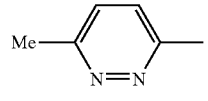 | CH | CH | CH | 460.1 |
| 96 | Me | 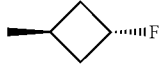 | 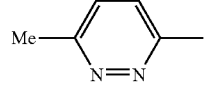 | CH | CH | CH | 464.3 |

TABLE 1-continued
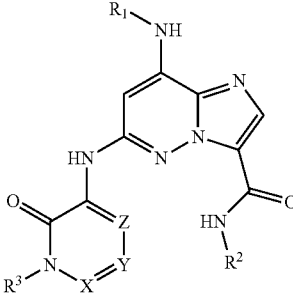
| Ex # | R¹ | R² | R³ | X | Y | Z | (M + H)⁺ |
|---|---|---|---|---|---|---|---|
| 97 | Me | i-Pr | 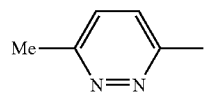 | CH | CH | CH | 434.3 |
| 98 | Me | 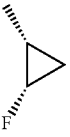 | 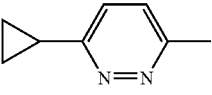 | CH | CH | CH | 476.3 |
| 99 | Me | Et | 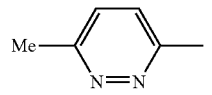 | CH | CH | CH | 420.3 |
| 100 | Me |  | 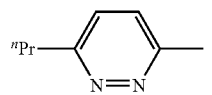 | CH | CH | CH | 478.4 |
| 101 | Me | CH₂CH₂F | 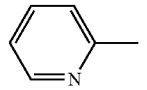 | CH | CH | CH | 423.4 |
| 102 | Me | CH₂CH₂F | 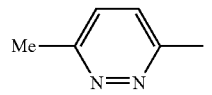 | CH | CH | CH | 438.4 |
| 103 | Me | 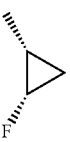 | 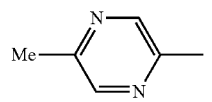 | CH | CH | CH | 450.4 |
| 104 | Me | c-Bu | 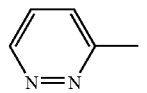 | CH | CH | CH | 432.3 |
| 105 | Me | 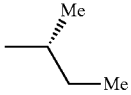 | 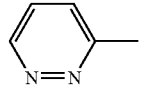 | CH | CH | CH | 434.4 |

TABLE 1-continued
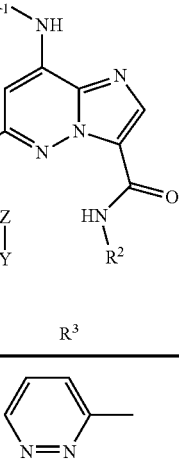
| Ex # | R¹ | R² | R³ | X | Y | Z | (M + H)⁺ |
|---|---|---|---|---|---|---|---|
| 106 | Me | i-Pr | 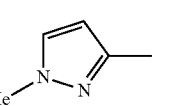 | CH | CH | CH | 420.4 |
| 107 | Me | Et | 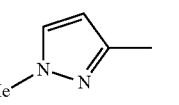 | CH | CH | CH | 408.3 |
| 108 | Me | i-Pr | 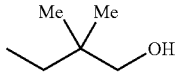 | CH | CH | CH | 422.4 |
| 109 | Me | 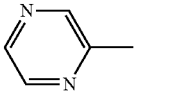 | 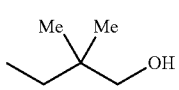 | CH | CH | CH | 464.3 |
| 110 | Me | 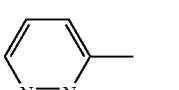 |  | CH | CH | CH | 448.4 |
| 111 | Me | 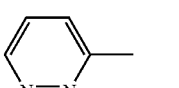 | 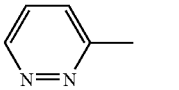 | CH | CH | CH | 446.4 |
| 112 | Me | i-Bu | 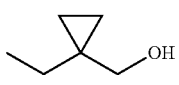 | CH | CH | CH | 434.3 |
| 113 | Me | 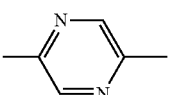 | 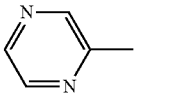 | CH | CH | CH | 476.5 |
| 114 | Me | 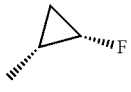 |  | CH | CH | CH | 462.4 |
| 115 | Me | H | Me | CH | CH | CH | 314.2 |
| 116 | Me |  | Me | CH | CH | CH | 372.1 |

TABLE 1-continued

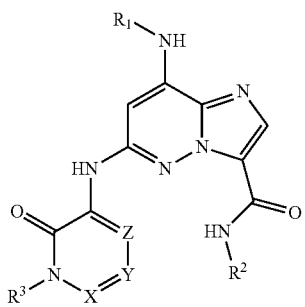

| Ex # | R¹ | R² | R³ | X | Y | Z | (M + H)⁺ |
|---|---|---|---|---|---|---|---|
| 117 | Me | 2,2-dimethyl-1-butanol (CH₂CH₃, CH₃, CH₂OH) | Me | CH | CH | CH | 400.2 |
| 118 | Me | c-Pr | MeO-propyl | CH | CF | CH | 416.1 |
| 119 | Me | c-Pr | Ph | CH | CH | CH | 416.1 |
| 120 | Me | 1-CN-cPr | Ph | CH | CH | CH | 441.1 |
| 121 | Me | c-Pr | 2-methyl-2-butanol (Me, HO, Me) | CH | CF | CH | 430.3 |
| 122 | Me | 2,2-dimethyl-1-butanol | 4-F—Ph | CH | CH | CH | 480.2 |
| 123 | Me | 1-CN-c-Pr | MeO-propyl | CH | CF | CH | 441.2 |
| 124 | Me | 2,2-dimethyl-1-butanol | F₂HC—C₆H₄— | CH | CH | CH | 512.2 |
| 125 | Me | 2,2-dimethyl-1-butanol | 3-CN—Ph | CH | CH | CH | 487.1 |
| 126 | Me | c-Pr | 3-CN—Ph | CH | CH | CH | 441.1 |
| 127 | Me | 2,2-dimethyl-1-butanol | Ph | CH | CH | CH | 462.2 |
| 128 | Me | c-Pr | 4-pyridyl | CH | CH | CH | 417.1 |
| 129 | Me | CH(Me)CN (isopropyl nitrile) | Me | CH | CH | CH | 367.1 |

TABLE 1-continued

| Ex # | R¹ | R² | R³ | X | Y | Z | (M + H)⁺ |
|---|---|---|---|---|---|---|---|
| 130 | Me | C(Me)₂CN | Me | CH | CH | CH | 381.1 |
| 131 | Me | 1-ethyl-1-(hydroxymethyl)cyclopropyl | Ph | CH | CH | CH | 460.4 |
| 132 | Me | 2-ethyl-2-methyl-1,3-propanediol-yl | 4-(CF₃)C₆H₄ | CH | CH | CH | 546.1 |
| 133 | Me | 1-ethyl-1-(hydroxymethyl)cyclopropyl | 4-(CF₃)C₆H₄ | CH | CH | CH | 528.2 |
| 134 | Me | c-Pr | 2-fluoro-4-pyridyl | CH | CH | CH | 435.1 |
| 135 | Me | c-Pr | 4-(1-hydroxyethyl)phenyl | CH | CH | CH | 460.2 |
| 136 | Me | 2,2-dimethyl-1-butanol-yl | 4-(CF₃)C₆H₄ | CH | CH | CH | 530.2 |
| 137 | Me | 1-CN-c-Pr | 4-(CF₃)C₆H₄ | CH | CH | CH | 509.2 |
| 138 | Me | 2,2-dimethyl-1-butanol-yl | 2-fluoro-4-pyridyl | CH | CH | CH | 481.2 |
| 139 | Me | c-Pr | 4-morpholinophenyl | CH | CH | CH | 501.2 |

TABLE 1-continued
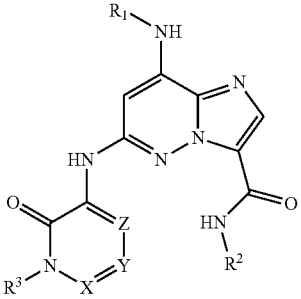
| Ex # | R¹ | R² | R³ | X | Y | Z | (M + H)⁺ |
|------|----|----|----|----|----|----|----------|
| 140 | Me | 1-CN-c-Pr | 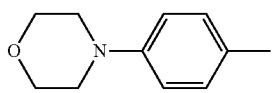 | CH | CH | CH | 526.1 |
| 141 | Me |  | 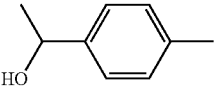 | CH | CH | CH | 478.3 |
| 142 | Me | c-Bu | 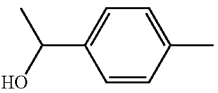 | CH | CH | CH | 474.3 |
| 143 | Me | 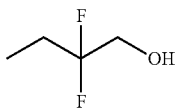 | Ph | CH | CH | CH | 470.3 |
| 144 | Me | c-Pr | 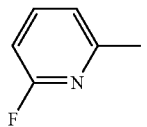 | CH | CH | CH | 435.2 |
| 145 | Me | 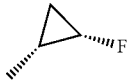 | 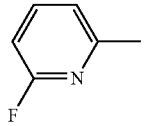 | CH | CH | CH | 453.2 |
| 146 | Me | 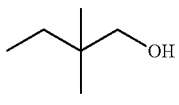 | 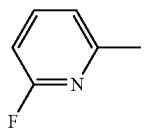 | CH | CH | CH | 481.2 |
| 147 | Me |  | 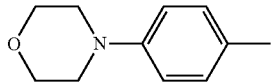 | CH | CH | CH | 519.4 |
| 148 | Me | 1-CN-c-Bu | Ph | CH | CH | CH | 455.2 |
| 149 | Me | c-Pr | 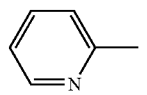 | CH | CF | CH | 435.2 |

TABLE 1-continued
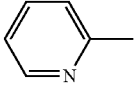
| Ex # | R¹ | R² | R³ | X | Y | Z | (M + H)⁺ |
|---|---|---|---|---|---|---|---|
| 150 | Me | c-Bu | 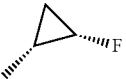 | CH | CF | CH | 449.2 |
| 151 | Me | 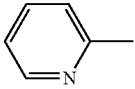 | 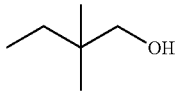 | CH | CF | CH | 453.1 |
| 152 | Me | c-Pr | 2-F—Ph | CH | CH | CH | 434.2 |
| 153 | Me | 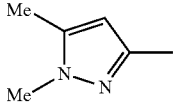 | 2-F—Ph | CH | CH | CH | 480.2 |
| 154 | Me | c-Pr | 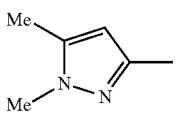 | CH | CH | CH | 434.2 |
| 155 | Me | c-Bu | 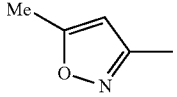 | CH | CH | CH | 448.2 |
| 156 | Me | 1-CN-cPr | 2-F—Ph | CH | CH | CH | 459.2 |
| 157 | Me | c-Bu | 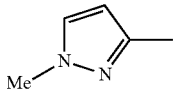 | CH | CH | CH | 435.2 |
| 158 | Me | c-Pr | 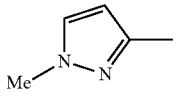 | CH | CH | CH | 420.2 |
| 159 | Me | c-Bu |  | CH | CH | CH | 434.2 |
| 160 | Me | 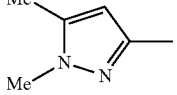 |  | CH | CH | CH | 452.2 |
| 161 | Me | c-Pr | 1-methylcyclopropyl | CH | CH | CH | 394.4 |
| 162 | Me | 1-CN-cPr | 1-methyylcyclopropyl | CH | CH | CH | 419.2 |

TABLE 1-continued
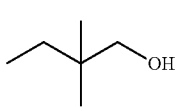
| Ex # | R¹ | R² | R³ | X | Y | Z | (M + H)⁺ |
|---|---|---|---|---|---|---|---|
| 163 | Me | 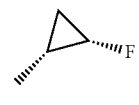 | 1-methylcyclopropyl | CH | CH | CH | 440.2 |
| 164 | Me | 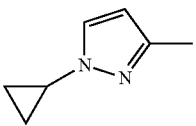 | 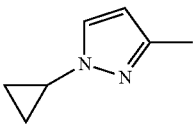 | CH | CH | CH | 464.2 |
| 165 | Me | c-Pr | 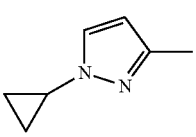 | CH | CH | CH | 446.2 |
| 166 | Me | c-Bu |  | CH | CH | CH | 460.2 |
| 167 | Me | 1-CN-cPr | 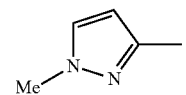 | CH | CH | CH | 460.2 |
| 168 | Me | 1-Me-cPr | Me | CH | CH | CH | 468.2 |
| 169 | Me | 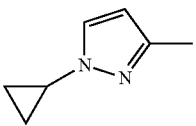 | 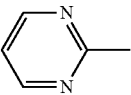 | CH | CH | CH | 438.2 |
| 170 | Me | c-Pentyl | 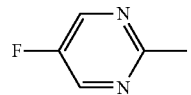 | CH | CH | CH | 446.2 |
| 171 | Me | c-Pr | 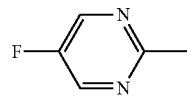 | CH | CH | CH | 436.2 |
| 172 | Me | c-Pentyl | 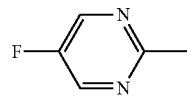 | CH | CH | CH | 464.2 |

TABLE 1-continued

| Ex # | R¹ | R² | R³ | X | Y | Z | (M + H)⁺ |
|---|---|---|---|---|---|---|---|
| 173 | Me | c-Bu | 5-F-pyrimidin-2-yl | CH | CH | CH | 450.3 |
| 174 | Me | trans-2-F-cyclopropyl | 5-F-pyrimidin-2-yl | CH | CH | CH | 454.2 |
| 175 | Me | c-Pr | 5-CF₃-pyrimidin-2-yl | CH | CH | CH | 486.1 |
| 176 | Me | c-Bu | 5-CF₃-pyrimidin-2-yl | CH | CH | CH | 418.1 |
| 177 | Me | c-Bu | 4-Me-pyrimidin-2-yl | CH | CH | CH | 446.1 |
| 178 | Me | trans-2-F-cyclopropyl | 4-Me-pyrimidin-2-yl | CH | CH | CH | 450.1 |
| 179 | Me | c-Pr | Ph | N | CH | CH | 417.2 |
| 180 | Me | trans-2-F-cyclopropyl | Ph | N | CH | CH | 435.2 |
| 181 | Me | trans-2-F-cyclopropyl | 3-Et-6-Me-pyridazinyl | CH | CH | CH | 464.3 |
| 182 | Me | 2-ethylthiazolyl | Ph | CH | CH | CH | 473.1 |
| 183 | Me | 3-fluoropropyl | Ph | CH | CH | CH | 422.3 |

TABLE 1-continued
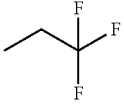
| Ex # | R¹ | R² | R³ | X | Y | Z | (M + H)⁺ |
|---|---|---|---|---|---|---|---|
| 184 | Me | 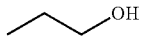 | Ph | CH | CH | CH | 458.3 |
| 185 | Me | 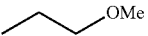 | Ph | CH | CH | CH | 420.2 |
| 186 | Me | 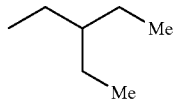 | Ph | CH | CH | CH | 434.2 |
| 187 | Me | 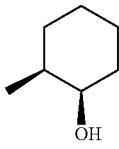 | Ph | CH | CH | CH | 460.2 |
| 188 | Me | 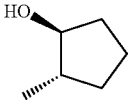 | Ph | CH | CH | CH | 474.1 |
| 189 | Me | 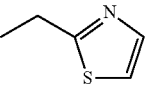 | Ph | CH | CH | CH | 460.1 |
| 190 | Me | 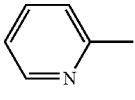 | 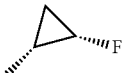 | CH | CH | CH | 474.2 |
| 191 | Me | 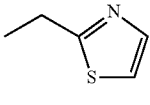 | Ph | CH | CH | CH | 434.2 |
| 192 | Me | 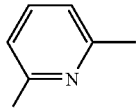 | 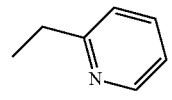 | CH | CH | CH | 492.2 |
| 193 | Me | 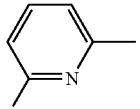 | 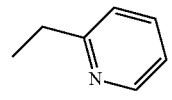 | CH | CH | CH | 486.3 |
| 194 | Me | 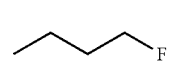 | Ph | CH | CH | CH | 436.2 |

TABLE 1-continued
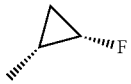
| Ex # | R¹ | R² | R³ | X | Y | Z | (M + H)⁺ |
|---|---|---|---|---|---|---|---|
| 195 | Me | 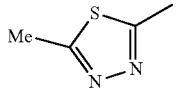 | 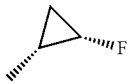 | CH | CH | CH | 456.3 |
| 196 | Me | 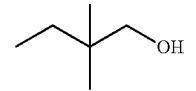 | 3-CN—Ph | N | CH | CH | 459.3 |
| 197 | Me | 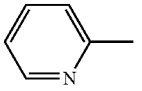 | 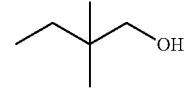 | CH | CH | CH | 463.4 |
| 198 | Me | 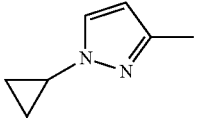 | 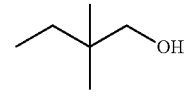 | CH | CH | CH | 492.5 |
| 199 | Me | 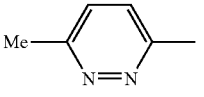 | 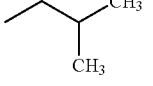 | CH | CH | CH | 478.4 |
| 200 | Me | 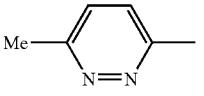 |  | CH | CH | CH | 448.4 |
| 201 | Me | 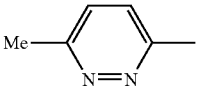 | 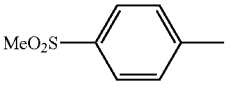 | CH | CH | CH | 460.4 |
| 202 | Me | c-Pr | 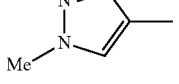 | CH | CH | CH | 492.0 (M − H)⁺ |
| 203 | Me | c-Pr | 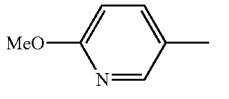 | CH | CH | CH | 420.2 |
| 204 | Me | c-Pr |  | CH | CH | CH | 447.2 |

TABLE 1-continued
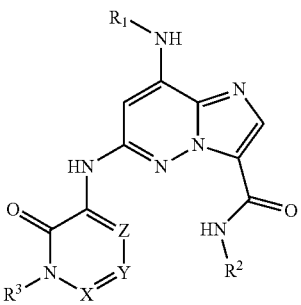
| Ex # | R¹ | R² | R³ | X | Y | Z | (M + H)⁺ |
|---|---|---|---|---|---|---|---|
| 205 | Me | c-Pr | 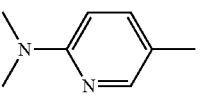 | CH | CH | CH | 460.2 |
| 206 | Me | c-Pr | 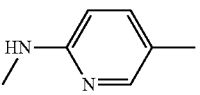 | CH | CH | CH | 445.4 |
| 207 | Me | neopentyl | Me | CH | CH | CH | 384.0 |
| 208 | Me | c-Pentyl | Me | CH | CH | CH | 382.0 |
| 209 | Me | i-Pr | Me | CH | CH | CH | 356.0 |
| 210 | Me | Et | Me | CH | CH | CH | 342.0 |
| 211 | Me | t-Bu | Me | CH | CH | CH | 370.0 |
| 212 | Me | Ph | Me | CH | CH | CH | 390.0 |
| 213 | Me | c-Pr | i-Pr | CH | CH | CH | 381.6 |
| 214 | Me | 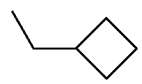 | Me | CH | CH | CH | 382.0 |
| 215 | Me | 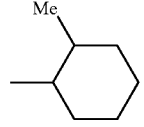 | Me | CH | CH | CH | 410.2 |
| 216 | Me | 1-CN-c-Pr | i-Pr | CH | CH | CH | 407.2 |
| 217 | Me | 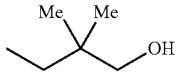 | i-Pr | CH | CH | CH | 428.2 |
| 218 | Me | c-Pr | t-Bu | CH | CH | CH | 395.4 |
| 219 | Me | 1-CN-c-Pr | t-Bu | CH | CH | CH | 421.2 |
| 220 | Me | c-Pr | 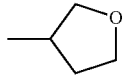 | CH | CH | CH | 410.0 |
| 221 | Me | c-Bu | 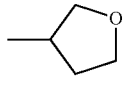 | CH | CH | CH | 424.0 |
| 222 | Me | c-Pentyl | 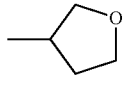 | CH | CH | CH | 438.2 |

TABLE 1-continued
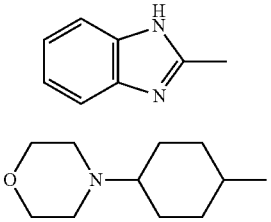
| Ex # | R¹ | R² | R³ | X | Y | Z | (M + H)⁺ |
|---|---|---|---|---|---|---|---|
| 223 | Me | c-Pr | 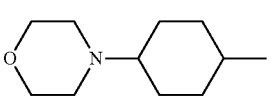 | CH | CH | CH | 456.2 |
| 224 | Me | c-Pr | 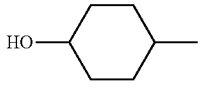 | CH | CH | CH | 507.0 |
| 225 | Me | c-Bu | 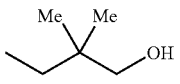 | CH | CH | CH | 521.4 |
| 226 | Me | c-Pr | c-Hexyl | CH | CH | CH | 422.2 |
| 227 | Me | c-Pr | 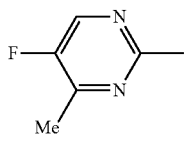 | CH | CH | CH | 436.2 |
| 228 | Me | c-Pr | c-Bu | CH | CH | CH | 394.2 |
| 229 | Me | 1-CN-c-Pr | c-Bu | CH | CH | CH | 419.4 |
| 230 | Me | 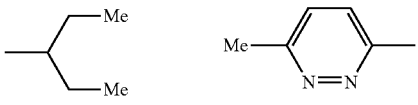 | c-Bu | CH | CH | CH | 440.2 |
| 231 | Me | 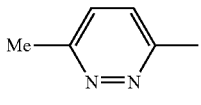 | c-Bu | CH | CH | CH | 464.0 |
| 232 | Et | c-Bu | Me | CH | CH | CH | 382.2 |
| 233 | Me | 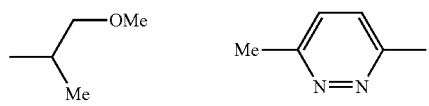 | 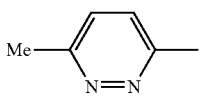 | CH | CH | CH | 462.0 |
| 234 | Me | 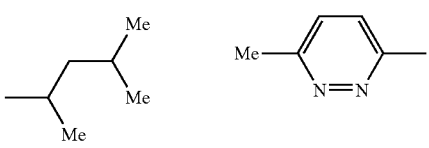 | 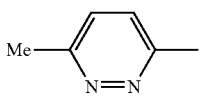 | CH | CH | CH | 464.2 |
| 235 | Me | 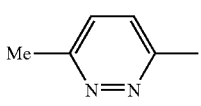 | 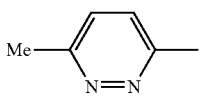 | CH | CH | CH | 476.2 |

TABLE 1-continued

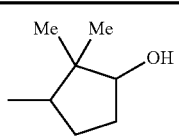

| Ex # | R¹ | R² | R³ | X | Y | Z | (M + H)⁺ |
|---|---|---|---|---|---|---|---|
| 236 | Me | 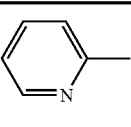 | 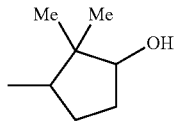 | CH | CH | CH | 489.2 |
| 237 | Me | 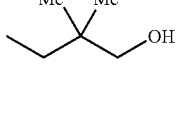 | Ph | CH | CH | CH | 488.2 |
| 238 | Me | 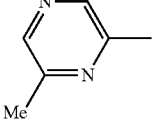 | | CH | CH | CH | 477.6 |

TABLE 2

¹H NMR data

| Example # | ¹H NMR data |
|---|---|
| 10 | ¹H NMR (400 MHz, DMSO-$d_6$) δ 8.61 (s, 2H), 8.00 (dd, J = 7.4, 1.7 Hz, 1H), 7.87 (s, 1H), 7.61-7.55 (m, 2H), 7.48 (q, J = 4.6 Hz, 1H), 7.44-7.37 (m, 2H), 7.33 (dd, J = 6.9, 1.7 Hz, 1H), 6.41 (t, J = 7.2 Hz, 1H), 6.38 (s, 1H), 2.98-2.90 (m, 1H), 2.87 (d, J = 4.8 Hz, 3H), 0.86-0.80 (m, 2H), 0.63-0.57 (m, 2H) |
| 11 | ¹H NMR (400 MHz, DMSO-$d_6$) δ 9.08 (s, 1H), 8.77 (s, 1H), 8.35 (dd, J = 10.1, 3.1 Hz, 1H), 7.96 (s, 1H), 7.52 (dd, J = 4.7, 3.2 Hz, 1H), 7.48 (q, J = 4.6 Hz, 1H), 6.47 (s, 1H), 3.53 (s, 3H), 2.86 (d, J = 4.8 Hz, 3H), 1.61-1.54 (m, 2H), 1.36-1.29 (m, 2H) |
| 12 | ¹H NMR (500 MHz, DMSO-$d_6$) δ 9.21 (s, 1H), 8.62 (s, 1H), 8.14 (dd, J = 7.5, 1.7 Hz, 1H), 7.94 (s, 1H), 7.59-7.52 (m, 2H), 7.47 (d, J = 4.7 Hz, 1H), 7.42-7.35 (m, 2H), 7.31 (dd, J = 6.9, 1.7 Hz, 1H), 6.42 (t, J = 7.1 Hz, 1H), 6.38 (s, 1H), 2.86 (d, J = 4.7 Hz, 3H), 1.68-1.60 (m, 2H), 1.40-1.31 (m, 2H) |
| 13 | ¹H NMR (400 MHz, DMSO-$d_6$) δ 9.20 (s, 1H), 8.67 (s, 1H), 8.18 (dd, J = 7.5, 1.8 Hz, 1H), 8.08-8.02 (m, 2H), 7.94 (s, 1H), 7.80-7.73 (m, 2H), 7.49 (q, J = 4.8 Hz, 1H), 7.36 (dd, J = 6.9, 1.7 Hz, 1H), 6.46 (t, J = 7.2 Hz, 1H), 6.39 (s, 1H), 2.86 (d, J = 4.8 Hz, 3H), 1.69-1.60 (m, 2H), 1.40-1.31 (m, 2H) |
| 14 | ¹H NMR (500 MHz, DMSO-$d_6$) δ 8.73 (t, J = 6.7 Hz, 1H), 8.58 (s, 1H), 8.01 (dd, J = 7.4, 1.5 Hz, 1H), 7.90 (s, 1H), 7.60-7.49 (m, 3H), 7.44-7.36 (m, 2H), 7.30 (dd, J = 6.9, 1.5 Hz, 1H), 6.44 (t, J = 7.2 Hz, 1H), 6.39 (s, 1H), 4.55 (t, J = 5.9 Hz, 2H), 3.41-3.22 (m, 6H), 2.87 (d, J = 4.5 Hz, 3H), 0.79 (s, 3H) |
| 15 | ¹H NMR (400 MHz, DMSO-$d_6$) δ 8.78 (s, 1H), 8.42 (d, J = 3.7 Hz, 1H), 8.15 (dd, J = 9.9, 3.1 Hz, 1H), 7.88 (s, 1H), 7.58 (dd, J = 4.8, 3.1 Hz, 1H), 7.49 (d, J = 5.1 Hz, 1H), 6.45 (s, 1H), 3.85 (d, J = 7.0 Hz, 2H), 2.94-2.84 (m, 4H), 1.35-1.23 (m, 1H), 0.80-0.72 (m, 2H), 0.62-0.49 (m, 4H), 0.49-0.42 (m, 2H) |
| 16 | ¹H NMR (400 MHz, DMSO-$d_6$) δ 9.10 (s, 1H), 8.82 (s, 1H), 8.35 (dd, J = 10.1, 3.1 Hz, 1H), 7.98 (s, 1H), 7.58 (dd, J = 4.6, 3.1 Hz, 1H), 7.50 (d, J = 4.6 Hz, 1H), 6.49 (s, 1H), 3.86 (d, J = 7.3 Hz, 2H), 2.88 (d, J = 4.4 Hz, 3H), 1.66-1.55 (m, 2H), 1.41-1.23 (m, 3H), 0.59-0.41 (m, 4H) |
| 17 | ¹H NMR (400 MHz, DMSO-$d_6$) δ 8.66 (s, 1H), 8.60 (d, J = 4.0 Hz, 1H), 8.47 (d, J = 2.6 Hz, 1H), 8.25 (ddd, J = 8.7, 7.0, 2.8 Hz, 1H), 8.04 (dd, J = 7.5, 1.5 |

TABLE 2-continued

¹H NMR data

| Example # | ¹H NMR data |
| --- | --- |
| | Hz, 1H), 7.88 (s, 1H), 7.52-7.38 (m, 3H), 6.45 (t, J = 7.2 Hz, 1H), 6.40 (s, 1H), 2.93 (tt, J = 7.3, 3.9 Hz, 1H), 2.87 (d, J = 4.8 Hz, 3H), 0.88-0.78 (m, 2H), 0.64-0.57 (m, 2H) |
| 18 | ¹H NMR (400 MHz, DMSO-$d_6$) δ 8.63 (s, 1H), 8.61 (d, J = 4.0 Hz, 1H), 8.02 (dd, J = 7.4, 1.7 Hz, 1H), 7.88 (s, 1H), 7.78 (d, J = 8.4 Hz, 2H), 7.68 (d, J = 8.1 Hz, 2H), 7.48 (q, J = 4.5 Hz, 1H), 7.37 (dd, J = 6.8, 1.8 Hz, 1H), 7.32-7.01 (m, 1H), 6.44 (t, J = 7.2 Hz, 1H), 6.39 (s, 1H), 2.94 (tt, J = 7.3, 3.8 Hz, 1H), 2.87 (d, J = 4.8 Hz, 3H), 0.86-0.79 (m, 2H), 0.64-0.57 (m, 2H) |
| 19 | ¹H NMR (500 MHz, DMSO-$d_6$) δ 8.70 (t, J = 6.5 Hz, 1H), 8.57 (s, 1H), 8.02 (dd, J = 7.4, 1.5 Hz, 1H), 7.89 (s, 1H), 7.76 (d, J = 8.3 Hz, 1H), 7.65 (d, J = 8.3 Hz, 1H), 7.48 (d, J = 5.0 Hz, 1H), 7.33 (dd, J = 6.9, 1.4 Hz, 1H), 7.28-7.01 (m, 1H), 6.46 (t, J = 7.2 Hz, 1H), 6.38 (s, 1H), 3.40-3.21 (m, 6H), 2.87 (d, J = 4.7 Hz, 2H), 0.79 (s, 2H) |
| 20 | ¹H NMR (400 MHz, DMSO-$d_6$) δ 9.21 (s, 1H), 8.64 (br. s., 1H), 8.16 (d, J = 7.5 Hz, 1H), 7.94 (s, 1H), 7.81-7.72 (m, 2H), 7.67 (d, J = 8.4 Hz, 2H), 7.46 (d, J = 4.6 Hz, 1H), 7.35 (dd, J = 6.9, 1.4 Hz, 1H), 7.31-6.97 (m, 1H), 6.45 (t, J = 7.2 Hz, 1H), 6.38 (s, 1H), 2.86 (d, J = 4.6 Hz, 3H), 1.70-1.59 (m, 2H), 1.41-1.32 (m, 2H) |
| 21 | ¹H NMR (500 MHz, DMSO-$d_6$) δ 8.80 (s, 1H), 8.42 (d, J = 4.0 Hz, 1H), 8.20 (dd, J = 9.9, 3.0 Hz, 1H), 7.88 (s, 1H), 7.55-7.48 (m, 2H), 6.45 (s, 1H), 4.81 (t, J = 4.7 Hz, 1H), 4.72 (t, J = 5.0 Hz, 1H), 4.35 (t, J = 4.7 Hz, 1H), 4.30 (t, J = 4.7 Hz, 1H), 2.95-2.83 (m, 1H), 2.86 (d, J = 5.0 Hz, 3H), 0.79-0.71 (m, 2H), 0.60-0.52 (m, 2H) |
| 22 | ¹H NMR (400 MHz, DMSO-$d_6$) δ 8.70 (s, 1H), 8.46 (d, J = 3.7 Hz, 1H), 8.09 (d, J = 2.6 Hz, 1H), 7.87 (s, 1H), 7.60 (d, J = 2.6 Hz, 1H), 7.49 (q, J = 4.6 Hz, 1H), 6.42 (s, 1H), 3.56 (s, 3H), 2.91-2.83 (m, 4H), 0.81-0.73 (m, 2H), 0.60-0.52 (m, 2H) |
| 23 | ¹H NMR (400 MHz, DMSO-$d_6$) δ 9.05 (s, 1H), 8.73 (s, 1H), 8.22 (d, J = 2.6 Hz, 1H), 7.94 (s, 1H), 7.59 (d, J = 2.6 Hz, 1H), 7.49 (q, J = 4.9 Hz, 1H), 6.45 (s, 1H), 3.54 (s, 3H), 2.86 (d, J = 4.8 Hz, 3H), 1.61-1.55 (m, 2H), 1.36-1.29 (m, 2H) |
| 24 | ¹H NMR (400 MHz, DMSO-$d_6$) δ 8.76 (s, 1H), 8.59 (t, J = 6.6 Hz, 1H), 8.09 (dd, J = 10.1, 3.1 Hz, 1H), 7.89 (s, 1H), 7.51 (dd, J = 4.6, 3.1 Hz, 2H), 6.45 (s, 1H), 3.52 (s, 3H), 3.34-3.28 (m, 3H), 3.11 (s, 2H), 2.87 (d, J = 4.8 Hz, 3H), 0.78 (s, 6H) |
| 25 | ¹H NMR (400 MHz, DMSO-$d_6$) δ 8.71 (t, J = 6.3 Hz, 1H), 8.62 (s, 1H), 8.07 (d, J = 8.6 Hz, 2H), 8.02 (d, J = 6.6 Hz, 1H), 7.90 (s, 1H), 7.76 (d, J = 8.4 Hz, 2H), 7.51 (d, J = 4.8 Hz, 1H), 7.36 (d, J = 6.2 Hz, 1H), 6.50 (t, J = 7.2 Hz, 1H), 6.39 (s, 1H), 3.39-3.33 (m, 3H), 3.15 (s, 2H), 2.89 (d, J = 4.4 Hz, 3H), 0.83 (s, 6H) |
| 26 | ¹H NMR (400 MHz, DMSO-$d_6$) δ 8.62 (d, J = 4.0 Hz, 1H), 8.58 (s, 1H), 7.99 (dd, J = 7.4, 1.7 Hz, 1H), 7.87 (s, 1H), 7.64 (d, J = 8.6 Hz, 2H), 7.46 (d, J = 4.8 Hz, 1H), 7.42 (d, J = 8.6 Hz, 2H), 7.33 (dd, J = 6.9, 1.7 Hz, 1H), 6.40 (t, J = 7.2 Hz, 1H), 6.37 (s, 1H), 5.17 (s, 1H), 2.94 (m, 1H), 2.88 (d, J = 4.8 Hz, 3H), 1.50 (s, 6H), 0.86-0.80 (m, 2H), 0.63-0.57 (m, 2H) |
| 27 | ¹H NMR (400 MHz, DMSO-$d_6$) δ 9.24 (s, 1H), 8.62 (s, 1H), 8.15 (dd, J = 7.3, 1.8 Hz, 1H), 7.96 (s, 1H), 7.64 (d, J = 8.6 Hz, 2H), 7.49 (d, J = 4.8 Hz, 1H), 7.43 (d, J = 8.6 Hz, 2H), 7.33 (dd, J = 6.8, 1.8 Hz, 1H), 6.43 (t, J = 7.2 Hz, 1H), 6.39 (s, 1H), 5.17 (s, 1H), 2.88 (d, J = 4.8 Hz, 3H), 1.70-1.62 (m, 2H), 1.50 (s, 6H), 1.41-1.34 (m, 2H) |
| 28 | ¹H NMR (400 MHz, DMSO-$d_6$) δ 9.20 (s, 1H), 8.67 (s, 1H), 8.44 (s, 1H), 8.27-8.16 (m, 2H), 7.94 (s, 1H), 7.49 (d, J = 4.6 Hz, 1H), 7.44-7.37 (m, 2H), 6.46 (t, J = 7.2 Hz, 1H), 6.39 (s, 1H), 2.86 (d, J = 4.8 Hz, 3H), 1.70-1.59 (m, 2H), 1.41-1.32 (m, 2H) |
| 29 | ¹H NMR (400 MHz, DMSO-$d_6$) δ 8.70 (t, J = 6.2 Hz, 1H), 8.57 (s, 1H), 8.03 (dd, J = 7.4, 1.7 Hz, 1H), 7.89 (s, 1H), 7.60-7.52 (m, 2H), 7.49 (q, J = 4.8 Hz, 1H), 7.45-7.36 (m, 2H), 7.31 (dd, J = 6.9, 1.7 Hz, 1H), 6.49 (t, J = 7.2 Hz, 1H), 6.38 (s, 1H), 4.59 (t, J = 5.7 Hz, 1H), 3.49 (d, J = 6.2 Hz, 2H), 3.33 (d, J = 5.7 Hz, 2H), 2.89 (d, J = 4.8 Hz, 3H), 0.50-0.45 (m, 2H), 0.44-0.38 (m, 2H) |
| 30 | ¹H NMR (400 MHz, DMSO-$d_6$) δ 8.76 (s, 1H), 8.57 (t, J = 6.1 Hz, 1H), 8.20 (dd, J = 10.1, 3.1 Hz, 1H), 7.90 (s, 1H), 7.56-7.46 (m, 2H), 6.46 (s, 1H), 4.51 (t, J = 5.6 Hz, 1H), 3.55 (s, 3H), 3.44 (d, J = 6.2 Hz, 2H), 3.29 (d, J = 5.5 Hz, 2H), 2.89 (d, J = 4.8 Hz, 3H), 0.45-0.41 (m, 2H), 0.39-0.35 (m, 2H) |
| 31 | ¹H NMR (400 MHz, DMSO-$d_6$) δ 8.71 (s, 1H), 8.58 (t, J = 6.3 Hz, 1H), 8.08 (d, J = 2.6 Hz, 1H), 7.88 (s, 1H), 7.58 (d, J = 2.4 Hz, 1H), 7.50 (q, J = 4.6 Hz, 1H), 6.44 (s, 1H), 4.46 (br. s., 1H), 3.54 (s, 3H), 3.52 (d, J = 6.2 Hz, 2H), 3.32 (br. s., 2H), 2.87 (d, J = 4.8 Hz, 3H), 0.42-0.37 (m, 2H), 0.37-0.32 (m, 2H) |
| 32 | ¹H NMR (500 MHz, DMSO-$d_6$) δ 8.67-8.62 (m, 2H), 8.59 (d, J = 4.2 Hz, 1H), 8.04 (td, J = 7.8, 1.7 Hz, 1H), 8.00 (dd, J = 7.4, 1.5 Hz, 1H), 7.87-7.82 (m, 2H), 7.57-7.51 (m, 2H), 7.46 (q, J = 4.7 Hz, 1H), 6.44 (t, J = 7.1 Hz, 1H), 6.37 (s, 1H), 2.92 (td, J = 7.4, 3.9 Hz, 1H), 2.86 (d, J = 5.0 Hz, 3H), 0.83-0.77 (m, 2H), 0.60-0.54 (m, 2H) |
| 33 | ¹H NMR (400 MHz, DMSO-$d_6$) δ 8.68 (t, J = 6.6 Hz, 1H), 8.61 (s, 1H), 8.42 (d, J = 2.0 Hz, 1H), 8.21 (ddd, J = 8.7, 7.2, 2.9 Hz, 1H), 8.01 (dd, J = 7.5, 1.5 Hz, 1H), 7.88 (s, 1H), 7.49 (q, J = 4.8 Hz, 1H), 7.41 (dd, J = 8.7, 3.0 Hz, 1H), |

TABLE 2-continued

¹H NMR data

| Example # | ¹H NMR data |
|---|---|
| | 7.38 (dd, J = 6.8, 1.8 Hz, 1H), 6.48 (t, J = 7.3 Hz, 1H), 6.38 (s, 1H), 4.60 (br. s., 1H), 3.35 (s, 2H), 3.13 (s, 2H), 2.87 (d, J = 4.8 Hz, 3H), 0.82 (s, 6H) |
| 34 | ¹H NMR (500 MHz, DMSO-d₆) δ 8.72 (d, J = 8.0 Hz, 1H), 8.67-8.62 (m, 2H), 8.10 (dd, J = 7.2, 1.7 Hz, 1H), 8.05 (td, J = 7.8, 1.9 Hz, 1H), 7.88-7.86 (m, 2H), 7.56 (dd, J = 7.2, 1.7 Hz, 1H), 7.53 (ddd, J = 7.4, 4.9, 1.0 Hz, 1H), 7.46 (q, J = 4.7 Hz, 1H), 6.44 (t, J = 7.2 Hz, 1H), 6.39 (s, 1H), 4.52 (sxt, J = 8.2 Hz, 1H), 2.87 (d, J = 5.0 Hz, 3H), 2.39-2.27 (m, 2H), 2.04-1.92 (m, 2H), 1.78-1.68 (m, 2H) |
| 35 | ¹H NMR (400 MHz, DMSO-d₆) δ 8.96 (s, 1H), 8.54 (d, J = 4.0 Hz, 1H), 8.48 (dd, J = 7.4, 1.7 Hz, 1H), 8.08 (dd, J = 7.3, 1.5 Hz, 1H), 7.86 (s, 1H), 7.84 (d, J = 3.5 Hz, 1H), 7.71 (d, J = 3.5 Hz, 1H), 7.50 (q, J = 4.6 Hz, 1H), 6.65 (t, J = 7.4 Hz, 1H), 6.41 (s, 1H), 2.93-2.88 (m, 1H), 2.87 (d, J = 4.8 Hz, 3H), 0.82-0.74 (m, 2H), 0.57-0.51 (m, 2H) |
| 36 | ¹H NMR (500 MHz, DMSO-d₆) δ 8.65 (d, J = 2.8 Hz, 1H), 8.63 (s, 1H), 8.59 (d, J = 3.9 Hz, 1H), 8.03-7.97 (m, 2H), 7.95-7.90 (m, 1H), 7.86 (s, 1H), 7.52 (dd, J = 7.1, 1.8 Hz, 1H), 7.45 (q, J = 4.9 Hz, 1H), 6.45 (t, J = 7.2 Hz, 1H), 6.36 (s, 1H), 2.91 (td, J = 7.3, 3.7 Hz, 1H), 2.86 (d, J = 5.0 Hz, 3H), 0.82-0.77 (m, 2H), 0.59-0.54 (m, 2H) |
| 37 | ¹H NMR (400 MHz, DMSO-d₆) δ 8.67-8.60 (m, 3H), 8.04-7.96 (m, 2H), 7.95-7.89 (m, 2H), 7.53-7.46 (m, 2H), 6.44-6.37 (m, 2H), 4.99-4.76 (m, 1H), 2.99 (dq, J = 9.1, 4.5 Hz, 1H), 2.87 (d, J = 4.8 Hz, 3H), 1.30-1.18 (m, 1H), 1.05-0.92 (m, 1H) |
| 38 | ¹H NMR (400 MHz, DMSO-d₆) δ 8.93 (s, 1H), 8.65 (t, J = 6.5 Hz, 1H), 8.45 (dd, J = 7.4, 1.7 Hz, 1H), 8.06 (dd, J = 7.5, 1.5 Hz, 1H), 7.88 (s, 1H), 7.83 (d, J = 3.5 Hz, 1H), 7.71 (d, J = 3.5 Hz, 1H), 7.53 (q, J = 4.6 Hz, 1H), 6.69 (t, J = 7.4 Hz, 1H), 6.41 (s, 1H), 4.56 (t, J = 5.6 Hz, 1H), 3.28 (d, J = 6.6 Hz, 2H), 3.10 (d, J = 5.3 Hz, 2H), 2.88 (d, J = 4.8 Hz, 3H), 0.77 (s, 6H) |
| 39 | ¹H NMR (500 MHz, DMSO-d₆) δ 8.92 (s, 1H), 8.63 (t, J = 6.1 Hz, 1H), 8.44 (dd, J = 7.2, 1.7 Hz, 1H), 8.11 (dd, J = 7.4, 1.5 Hz, 1H), 7.88 (s, 1H), 7.83 (d, J = 3.6 Hz, 1H), 7.71 (d, J = 3.3 Hz, 1H), 7.50 (q, J = 4.7 Hz, 1H), 6.72 (t, J = 7.4 Hz, 1H), 6.43 (s, 1H), 4.54 (br. s., 1H), 3.44 (d, J = 6.1 Hz, 2H), 3.29 (d, J = 11.9 Hz, 2H), 2.88 (d, J = 5.0 Hz, 3H), 0.45-0.40 (m, 2H), 0.38-0.33 (m, 2H) |
| 40 | ¹H NMR (400 MHz, DMSO-d₆) δ 8.66-8.58 (m, 2H), 8.44 (d, J = 2.0 Hz, 1H), 8.22 (ddd, J = 8.7, 7.2, 2.9 Hz, 1H), 8.00 (dd, J = 7.5, 1.5 Hz, 1H), 7.91 (s, 1H), 7.52-7.46 (m, 1H), 7.41 (dd, J = 8.7, 3.0 Hz, 1H), 7.38 (dd, J = 6.9, 1.7 Hz, 1H), 6.44-6.34 (m, 2H), 5.01-4.76 (m, 1H), 2.99 (dq, J = 9.1, 4.5 Hz, 1H), 2.86 (d, J = 4.8 Hz, 3H), 1.32-1.18 (m, 1H), 1.08-0.92 (m, 1H) |
| 41 | ¹H NMR (400 MHz, DMSO-d₆) δ 8.67 (s, 1H), 8.58 (d, J = 4.0 Hz, 1H), 8.51 (dt, J = 4.7, 1.2 Hz, 1H), 8.11-8.01 (m, 2H), 7.86 (s, 1H), 7.76-7.68 (m, 1H), 7.47 (d, J = 4.8 Hz, 1H), 7.41 (dd, J = 6.9, 1.7 Hz, 1H), 6.47 (t, J = 7.3 Hz, 1H), 6.36 (s, 1H), 2.92 (td, J = 7.3, 3.9 Hz, 1H), 2.86 (d, J = 4.4 Hz, 3H), 0.85-0.76 (m, 2H), 0.61-0.54 (m, 2H) |
| 42 | ¹H NMR (400 MHz, DMSO-d₆) δ 8.65 (s, 1H), 8.63 (d, J = 4.2 Hz, 1H), 8.50 (dt, J = 4.7, 1.2 Hz, 1H), 8.09-8.01 (m, 2H), 7.91 (s, 1H), 7.75-7.69 (m, 1H), 7.50 (q, J = 4.7 Hz, 1H), 7.38 (dd, J = 6.9, 1.7 Hz, 1H), 6.43 (t, J = 7.2 Hz, 1H), 6.39 (s, 1H), 4.99-4.77 (m, 1H), 3.04-2.96 (m, 1H), 2.86 (d, J = 4.8 Hz, 3H), 1.25 (dtd, J = 15.1, 8.6, 6.1 Hz, 1H), 1.06-0.93 (m, 1H) |
| 43 | ¹H NMR (500 MHz, DMSO-d₆) δ 9.07 (br. s., 1H), 8.77 (br. s., 1H), 8.33-8.26 (m, 1H), 7.95 (d, J = 3.0 Hz, 1H), 7.59-7.55 (m, 1H), 7.53 (br. s., 1H), 6.45 (d, J = 2.5 Hz, 1H), 3.53 (d, J = 3.0 Hz, 3H), 2.86 (br. s., 3H), 2.71 (d, J = 2.0 Hz, 2H), 2.46-2.38 (m, 2H), 2.12-1.98 (m, 2H) |
| 44 | ¹H NMR (400 MHz, DMSO-d₆) δ 8.56 (d, J = 3.5 Hz, 1H), 8.52 (s, 1H), 7.88-7.79 (m, 2H), 7.43 (d, J = 4.6 Hz, 1H), 7.21 (d, J = 6.2 Hz, 1H), 6.34 (s, 1H), 6.24 (t, J = 7.2 Hz, 1H), 3.46 (td, J = 7.4, 3.7 Hz, 1H), 2.94-2.81 (m, 4H), 1.08-1.00 (m, 2H), 0.95-0.85 (m, 2H), 0.83-0.73 (m, 2H), 0.59-0.47 (m, 2H) |
| 45 | ¹H NMR (500 MHz, DMSO-d₆) δ 9.19 (s, 1H), 8.55 (s, 1H), 8.00 (dd, J = 7.2, 1.7 Hz, 1H), 7.92 (s, 1H), 7.45 (q, J = 4.7 Hz, 1H), 7.21 (dd, J = 6.9, 1.7 Hz, 1H), 6.35 (s, 1H), 6.27 (t, J = 7.1 Hz, 1H), 3.51-3.43 (m, 1H), 2.86 (d, J = 4.7 Hz, 3H), 1.66-1.59 (m, 2H), 1.35-1.28 (m, 2H), 1.08-1.01 (m, 2H), 0.94-0.86 (m, 2H) |
| 46 | ¹H NMR (400 MHz, DMSO-d₆) δ 8.62 (s, 1H), 8.60 (d, J = 4.0 Hz, 1H), 7.99 (dd, J = 7.3, 1.5 Hz, 1H), 7.92 (t, J = 7.8 Hz, 1H), 7.86 (s, 1H), 7.62 (d, J = 8.1 Hz, 1H), 7.52 (dd, J = 7.0, 1.8 Hz, 1H), 7.45 (d, J = 4.6 Hz, 1H), 7.39 (d, J = 7.5 Hz, 1H), 6.43 (t, J = 7.2 Hz, 1H), 6.36 (s, 1H), 2.92 (td, J = 7.3, 3.7 Hz, 1H), 2.86 (d, J = 4.8 Hz, 3H), 2.55 (s, 3H), 0.84-0.76 (m, 2H), 0.60-0.54 (m, 2H) |
| 47 | ¹H NMR (400 MHz, DMSO-d₆) δ 8.73 (d, J = 7.9 Hz, 1H), 8.64 (s, 1H), 8.09 (dd, J = 7.4, 1.7 Hz, 1H), 7.92 (t, J = 7.7 Hz, 1H), 7.85 (s, 1H), 7.63 (d, J = 7.9 Hz, 1H), 7.53 (dd, J = 7.2, 1.7 Hz, 1H), 7.46 (d, J = 4.8 Hz, 1H), 7.39 (d, J = 7.7 Hz, 1H), 6.43 (t, J = 7.2 Hz, 1H), 6.38 (s, 1H), 4.52 (sxt, J = 8.1 Hz, 1H), 2.87 (d, J = 4.8 Hz, 3H), 2.54 (s, 3H), 2.39-2.27 (m, 2H), 2.06-1.92 (m, 2H), 1.80-1.67 (m, 2H) |
| 48 | ¹H NMR (400 MHz, DMSO-d₆) δ 8.69 (t, J = 6.6 Hz, 1H), 8.49 (s, 1H), 7.86 (s, 1H), 7.83 (dd, J = 7.3, 1.5 Hz, 1H), 7.45 (d, J = 4.6 Hz, 1H), 7.18 (dd, |

TABLE 2-continued

¹H NMR data

| Example # | ¹H NMR data |
|---|---|
| | J = 7.0, 1.5 Hz, 1H), 6.34 (s, 1H), 6.28 (t, J = 7.2 Hz, 1H), 4.56 (t, J = 5.7 Hz, 1H), 3.51-3.42 (m, 1H), 3.28 (d, J = 6.8 Hz, 2H), 3.10 (d, J = 5.9 Hz, 2H), 2.87 (d, J = 4.8 Hz, 3H), 1.07-1.00 (m, 2H), 0.91-0.85 (m, 2H), 0.77 (s, 6H) |
| 49 | ¹H NMR (400 MHz, DMSO-d₆) δ 8.64 (d, J = 4.2 Hz, 1H), 8.61 (s, 1H), 7.98 (dd, J = 7.4, 1.7 Hz, 1H), 7.95-7.88 (m, 2H), 7.62 (d, J = 7.9 Hz, 1H), 7.53-7.44 (m, 2H), 7.39 (d, J = 7.5 Hz, 1H), 6.43-6.35 (m, 2H), 5.00-4.75 (m, 1H), 3.04-2.95 (m, 1H), 2.87 (d, J = 4.8 Hz, 3H), 2.54 (s, 3H), 1.25 (dtd, J = 15.1, 8.5, 6.2 Hz, 1H), 1.06-0.91 (m, 1H) |
| 50 | ¹H NMR (400 MHz, DMSO-d₆) δ 8.61 (s, 1H), 8.58 (d, J = 7.5 Hz, 1H), 8.08 (dd, J = 7.3, 1.8 Hz, 1H), 7.85 (s, 1H), 7.59-7.52 (m, 2H), 7.52-7.42 (m, 4H), 7.31 (dd, J = 6.9, 1.7 Hz, 1H), 6.58 (t, J = 7.2 Hz, 1H), 6.41 (s, 1H), 5.21 (d, J = 5.1 Hz, 1H), 4.09-3.99 (m, 1H), 3.98-3.88 (m, 1H), 2.87 (d, J = 4.8 Hz, 3H), 2.74-2.64 (m, 2H), 1.90-1.80 (m, 2H) |
| 51 | ¹H NMR (400 MHz, DMSO-d₆) δ 9.07 (s, 1H), 8.78 (s, 1H), 8.30 (dd, J = 10.1, 2.9 Hz, 1H), 7.95 (s, 1H), 7.48 (d, J = 5.1 Hz, 1H), 7.31 (dd, J = 5.1, 3.1 Hz, 1H), 6.47 (s, 1H), 3.56-3.45 (m, 1H), 2.86 (d, J = 4.8 Hz, 3H), 1.61-1.53 (m, 2H), 1.36-1.29 (m, 2H), 1.06-0.99 (m, 2H), 0.98-0.91 (m, 2H) |
| 52 | ¹H NMR (400 MHz, DMSO-d₆) δ 9.05 (d, J = 4.8 Hz, 2H), 8.73 (d, J = 7.9 Hz, 1H), 8.63 (s, 1H), 8.11 (dd, J = 7.3, 1.8 Hz, 1H), 7.85 (s, 1H), 7.72 (t, J = 5.0 Hz, 1H), 7.51-7.43 (m, 2H), 6.42 (t, J = 7.2 Hz, 1H), 6.36 (s, 1H), 4.52 (sxt, J = 8.2 Hz, 1H), 2.87 (d, J = 4.8 Hz, 3H), 2.38-2.26 (m, 2H), 2.06-1.92 (m, 2H), 1.79-1.66 (m, 2H) |
| 53 | ¹H NMR (500 MHz, DMSO-d₆) δ 9.21 (s, 1H), 8.64 (s, 1H), 8.15 (dd, J = 7.4, 1.8 Hz, 1H), 7.94 (s, 1H), 7.60 (td, J = 8.1, 6.5 Hz, 1H), 7.51-7.45 (m, 2H), 7.39-7.32 (m, 3H), 6.43 (t, J = 7.2 Hz, 1H), 6.38 (s, 1H), 2.86 (d, J = 4.7 Hz, 3H), 1.68-1.61 (m, 2H), 1.39-1.33 (m, 2H) |
| 54 | ¹H NMR (400 MHz, DMSO-d₆) δ 8.70 (t, J = 6.6 Hz, 1H), 8.57 (s, 1H), 7.98 (dd, J = 7.4, 1.7 Hz, 1H), 7.88 (s, 1H), 7.60 (td, J = 8.1, 6.7 Hz, 1H), 7.52-7.41 (m, 2H), 7.39-7.29 (m, 3H), 6.44 (t, J = 7.2 Hz, 1H), 6.37 (s, 1H), 4.59 (br. s., 1H), 3.33 (br. s., 2H), 3.13 (s, 2H), 2.87 (d, J = 4.8 Hz, 3H), 0.82 (s, 6H) |
| 55 | ¹H NMR (400 MHz, DMSO-d₆) δ 9.04 (d, J = 4.8 Hz, 2H), 8.64 (d, J = 4.2 Hz, 1H), 8.61 (s, 1H), 8.00 (dd, J = 7.4, 1.7 Hz, 1H), 7.91 (s, 1H), 7.72 (t, J = 5.0 Hz, 1H), 7.49 (d, J = 4.6 Hz, 1H), 7.43 (dd, J = 6.9, 1.7 Hz, 1H), 6.42-6.33 (m, 2H), 5.00-4.76 (m, 1H), 3.05-2.95 (m, 1H), 2.87 (d, J = 4.8 Hz, 3H), 1.25 (dtd, J = 15.1, 8.5, 6.2 Hz, 1H), 1.08-0.91 (m, 1H) |
| 56 | ¹H NMR (400 MHz, DMSO-d₆) δ 9.13 (d, J = 1.3 Hz, 1H), 8.76 (s, 1H), 8.67 (d, J = 7.7 Hz, 1H), 8.12 (dd, J = 7.4, 1.4 Hz, 1H), 7.85 (s, 1H), 7.60 (dd, J = 7.0, 1.5 Hz, 1H), 7.49 (br. s., 1H), 7.21 (d, J = 1.8 Hz, 1H), 6.48 (t, J = 7.3 Hz, 1H), 6.40 (s, 1H), 4.50 (sxt, J = 8.4 Hz, 1H), 2.87 (d, J = 4.6 Hz, 3H), 2.37-2.25 (m, 2H), 2.03-1.89 (m, 2H), 1.78-1.65 (m, 2H) |
| 57 | ¹H NMR (400 MHz, DMSO-d₆) δ 8.52 (d, J = 6.8 Hz, 1H), 8.49 (s, 1H), 7.90 (dd, J = 7.4, 1.7 Hz, 1H), 7.86 (s, 1H), 7.43 (d, J = 4.8 Hz, 1H), 7.33 (dd, J = 6.8, 1.5 Hz, 1H), 6.36 (s, 1H), 6.29 (t, J = 7.2 Hz, 1H), 4.63-4.52 (m, 1H), 3.89 (dd, J = 9.0, 6.2 Hz, 1H), 3.85-3.77 (m, 1H), 3.70 (td, J = 8.2, 6.3 Hz, 1H), 3.59 (dd, J = 9.0, 4.0 Hz, 1H), 3.55 (s, 3H), 2.86 (d, J = 4.8 Hz, 3H), 2.32-2.20 (m, 1H), 1.86-1.75 (m, 1H) |
| 58 | ¹H NMR (500 MHz, DMSO-d₆) δ 8.52 (d, J = 6.9 Hz, 1H), 8.48 (s, 1H), 7.90 (dd, J = 7.4, 1.8 Hz, 1H), 7.86 (s, 1H), 7.42 (q, J = 4.7 Hz, 1H), 7.33 (dd, J = 6.9, 1.7 Hz, 1H), 6.36 (s, 1H), 6.29 (t, J = 7.1 Hz, 1H), 4.62-4.52 (m, 1H), 3.89 (dd, J = 9.2, 6.4 Hz, 1H), 3.85-3.78 (m, 1H), 3.70 (td, J = 8.2, 6.1 Hz, 1H), 3.59 (dd, J = 9.2, 3.9 Hz, 1H), 3.55 (s, 3H), 2.86 (d, J = 5.0 Hz, 3H), 2.26 (dtd, J = 12.8, 7.8, 6.4 Hz, 1H), 1.85-1.76 (m, 1H) |
| 59 | ¹H NMR (400 MHz, DMSO-d₆) δ 8.67-8.62 (m, 2H), 8.57 (br. s., 1H), 8.08-8.01 (m, 2H), 7.88 (s, 1H), 7.84 (d, J = 8.1 Hz, 1H), 7.58-7.50 (m, 2H), 7.47 (d, J = 4.8 Hz, 1H), 6.46 (t, J = 7.2 Hz, 1H), 6.37 (s, 1H), 4.95-4.72 (m, 1H), 3.29-3.19 (m, 1H), 2.86 (d, J = 4.8 Hz, 3H), 1.55-1.40 (m, 1H), 1.11-1.00 (m, 1H) |
| 60 | ¹H NMR (500 MHz, METHANOL-d₄) δ 8.84 (d, J = 8.4 Hz, 1H), 8.03 (dd, J = 7.4, 1.5 Hz, 1H), 8.00 (br. s., 1H), 7.61 (s, 1H), 7.15 (dd, J = 6.9, 1.5 Hz, 1H), 6.43 (t, J = 6.9 Hz, 1H), 5.97 (s, 1H), 4.52-4.43 (m, 1H), 3.68 (s, 3H), 3.51 (d, J = 4.5 Hz, 2H), 3.34 (s, 3H), 3.04 (s, 3H), 1.34 (d, J = 6.9 Hz, 3H) |
| 61 | ¹H NMR (400 MHz, DMSO-d₆) δ 8.64 (s, 1H), 8.53 (d, J = 7.0 Hz, 1H), 8.25 (q, J = 8.1 Hz, 1H), 8.03 (dd, J = 7.3, 1.5 Hz, 1H), 7.89 (s, 1H), 7.84 (dd, J = 7.7, 1.8 Hz, 1H), 7.52 (dd, J = 7.2, 1.7 Hz, 1H), 7.48 (d, J = 4.6 Hz, 1H), 7.35 (dd, J = 8.1, 2.2 Hz, 1H), 6.47 (t, J = 7.2 Hz, 1H), 6.39 (s, 1H), 4.63-4.54 (m, 1H), 3.90 (dd, J = 9.1, 6.1 Hz, 1H), 3.87-3.81 (m, 1H), 3.72 (td, J = 8.1, 6.2 Hz, 1H), 3.63 (dd, J = 9.1, 3.9 Hz, 1H), 2.87 (d, J = 4.8 Hz, 3H), 2.34-2.22 (m, 1H), 1.90-1.80 (m, 1H) |
| 62 | ¹H NMR (400 MHz, DMSO-d₆) δ 8.66-8.63 (m, 1H), 8.62 (s, 1H), 8.54 (d, J = 7.0 Hz, 1H), 8.08-8.00 (m, 2H), 7.88 (s, 1H), 7.84 (d, J = 8.1 Hz, 1H), 7.56-7.50 (m, 2H), 7.47 (d, J = 4.6 Hz, 1H), 6.46 (t, J = 7.2 Hz, 1H), 6.39 (s, 1H), 4.64-4.55 (m, 1H), 3.90 (dd, J = 9.2, 6.2 Hz, 1H), 3.87-3.82 (m, 1H), 3.72 (td, J = 8.1, 6.2 Hz, 1H), 3.64 (dd, J = 9.1, 3.9 Hz, 1H), 2.87 (d, J = 5.1 Hz, 3H), 2.34-2.23 (m, 1H), 1.91-1.80 (m, 1H) |

TABLE 2-continued

¹H NMR data

| Example # | ¹H NMR data |
|---|---|
| 63 | ¹H NMR (400 MHz, DMSO-$d_6$) δ 8.67 (s, 1H), 8.59 (d, J = 4.0 Hz, 1H), 8.09-8.02 (m, 2H), 7.86 (s, 1H), 7.82 (d, J = 9.0 Hz, 1H), 7.59 (dd, J = 7.0, 1.8 Hz, 1H), 7.47 (d, J = 4.8 Hz, 1H), 6.49 (t, J = 7.2 Hz, 1H), 6.37 (s, 1H), 2.92 (td, J = 7.3, 3.9 Hz, 1H), 2.86 (d, J = 4.8 Hz, 3H), 2.72 (s, 3H), 0.85-0.76 (m, 2H), 0.61-0.54 (m, 2H) |
| 64 | ¹H NMR (400 MHz, DMSO-$d_6$) δ 8.71 (d, J = 7.9 Hz, 1H), 8.69 (s, 1H), 8.16 (dd, J = 7.4, 1.7 Hz, 1H), 8.06 (d, J = 8.8 Hz, 1H), 7.85 (s, 1H), 7.82 (d, J = 8.8 Hz, 1H), 7.60 (dd, J = 7.0, 1.8 Hz, 1H), 7.48 (d, J = 4.8 Hz, 1H), 6.49 (t, J = 7.2 Hz, 1H), 6.40 (s, 1H), 4.52 (sxt, J = 8.2 Hz, 1H), 2.87 (d, J = 4.8 Hz, 3H), 2.72 (s, 3H), 2.38-2.28 (m, 2H), 2.06-1.93 (m, 2H), 1.80-1.68 (m, 2H) |
| 65 | ¹H NMR (400 MHz, DMSO-$d_6$) δ 8.66 (s, 1H), 8.63 (d, J = 4.0 Hz, 1H), 8.08-8.01 (m, 2H), 7.91 (s, 1H), 7.82 (d, J = 9.0 Hz, 1H), 7.57 (dd, J = 7.0, 1.8 Hz, 1H), 7.50 (d, J = 3.7 Hz, 1H), 6.46 (t, J = 7.3 Hz, 1H), 6.40 (s, 1H), 5.00-4.76 (m, 1H), 2.99 (dq, J = 9.2, 4.6 Hz, 1H), 2.87 (d, J = 4.8 Hz, 3H), 2.72 (s, 3H), 1.31-1.19 (m, 1H), 1.06-0.92 (m, 1H) |
| 66 | ¹H NMR (400 MHz, DMSO-$d_6$) δ 8.67-8.62 (m, 2H), 8.59 (t, J = 5.6 Hz, 1H), 8.09-8.01 (m, 2H), 7.88-7.81 (m, 2H), 7.57-7.50 (m, 2H), 7.47 (d, J = 4.8 Hz, 1H), 6.45 (t, J = 7.3 Hz, 1H), 6.37 (s, 1H), 3.47-3.36 (m, 2H), 2.87 (d, J = 4.8 Hz, 3H), 1.20 (t, J = 7.3 Hz, 3H) |
| 67 | ¹H NMR (400 MHz, DMSO-$d_6$) δ 8.66 (s, 1H), 8.57 (t, J = 5.5 Hz, 1H), 8.25 (q, J = 8.1 Hz, 1H), 8.05 (dd, J = 7.3, 1.8 Hz, 1H), 7.87-7.81 (m, 2H), 7.53 (dd, J = 7.0, 1.8 Hz, 1H), 7.47 (d, J = 4.8 Hz, 1H), 7.35 (dd, J = 8.1, 2.2 Hz, 1H), 6.46 (t, J = 7.3 Hz, 1H), 6.37 (s, 1H), 3.45-3.37 (m, 2H), 2.87 (d, J = 4.8 Hz, 3H), 1.19 (t, J = 7.3 Hz, 3H) |
| 68 | ¹H NMR (400 MHz, DMSO-$d_6$) δ 8.71 (d, J = 7.9 Hz, 1H), 8.52 (s, 1H), 7.98 (dd, J = 7.3, 1.8 Hz, 1H), 7.82 (s, 1H), 7.43 (d, J = 4.8 Hz, 1H), 7.36 (dd, J = 6.8, 1.8 Hz, 1H), 6.36 (s, 1H), 6.27 (t, J = 7.0 Hz, 1H), 4.50 (sxt, J = 8.3 Hz, 1H), 3.56 (s, 3H), 2.86 (d, J = 4.8 Hz, 3H), 2.36-2.24 (m, 2H), 2.01-1.86 (m, 2H), 1.77-1.67 (m, 2H) |
| 69 | ¹H NMR (400 MHz, DMSO-$d_6$) δ 8.73 (d, J = 7.9 Hz, 1H), 8.62 (s, 1H), 8.26 (d, J = 2.9 Hz, 1H), 8.07 (dd, J = 7.3, 1.8 Hz, 1H), 7.84 (s, 1H), 7.69-7.63 (m, 1H), 7.55 (dd, J = 9.0, 2.9 Hz, 1H), 7.51-7.42 (m, 2H), 6.40 (t, J = 7.3 Hz, 1H), 6.38 (s, 1H), 4.52 (sxt, J = 8.2 Hz, 1H), 3.82-3.73 (m, 4H), 3.29-3.25 (m, 4H), 2.87 (d, J = 4.8 Hz, 3H), 2.38-2.26 (m, 2H), 2.05-1.92 (m, 2H), 1.79-1.67 (m, 2H) |
| 70 | ¹H NMR (400 MHz, DMSO-$d_6$) δ 9.44 (d, J = 5.1 Hz, 1H), 8.71 (s, 1H), 8.64 (d, J = 4.2 Hz, 1H), 8.26 (d, J = 5.0 Hz, 1H), 8.03 (dd, J = 7.4, 1.5 Hz, 1H), 7.92 (s, 1H), 7.51 (dd, J = 7.0, 1.6 Hz, 2H), 6.43 (t, J = 7.2 Hz, 1H), 6.37 (s, 1H), 5.00-4.76 (m, 1H), 3.05-2.95 (m, 1H), 2.86 (d, J = 4.8 Hz, 3H), 1.25 (dtd, J = 15.1, 8.5, 6.1 Hz, 1H), 1.07-0.93 (m, 1H) |
| 71 | ¹H NMR (400 MHz, DMSO-$d_6$) δ 8.78 (s, 1H), 8.74 (s, 1H), 8.71-8.65 (m, 2H), 8.36 (s, 1H), 8.10 (td, J = 7.8, 1.9 Hz, 1H), 7.88-7.82 (m, 2H), 7.61 (ddd, J = 7.5, 4.8, 1.1 Hz, 1H), 7.51 (d, J = 4.8 Hz, 1H), 6.41 (s, 1H), 4.53 (sxt, J = 8.3 Hz, 1H), 2.87 (d, J = 4.8 Hz, 3H), 2.35-2.24 (m, 2H), 2.16-2.02 (m, 2H), 1.80-1.63 (m, 2H) |
| 72 | ¹H NMR (500 MHz, METHANOL-$d_4$) δ 7.99 (s, 1H), 7.93 (dd, J = 7.4, 1.5 Hz, 1H), 7.62-7.62 (m, 2H), 7.18 (dd, J = 6.9, 1.5 Hz, 1H), 6.35 (t, J = 6.9 Hz, 1H), 5.98 (s, 1H), 4.22-4.12 (m, 1H), 3.68 (s, 3H), 3.05 (s, 3H), 1.67-1.56 (m, 2H), 1.29 (d, J = 6.9 Hz, 3H), 0.98 (t, J = 7.4 Hz, 3H) |
| 73 | ¹H NMR (500 MHz, DMSO-$d_6$) δ 8.52 (s, 1H), 8.33 (d, J = 8.4 Hz, 1H), 7.86 (d, J = 7.4 Hz, 1H), 7.84 (s, 1H), 7.47 (br. s., 1H), 7.36 (d, J = 6.9 Hz, 1H), 6.37 (s, 1H), 6.27-6.20 (m, 1H), 4.04-3.99 (m, 1H), 3.55 (s, 3H), 2.86 (d, J = 5.0 Hz, 3H), 1.54-1.48 (m, 2H), 1.17 (d, J = 6.9 Hz, 3H), 0.87 (t, J = 7.4 Hz, 3H) |
| 74 | ¹H NMR (400 MHz, DMSO-$d_6$) δ 8.67-8.59 (m, 2H), 8.33 (d, J = 8.4 Hz, 1H), 8.04 (td, J = 7.8, 1.8 Hz, 1H), 7.98 (dd, J = 7.3, 1.5 Hz, 1H), 7.89-7.82 (m, 2H), 7.59-7.50 (m, 2H), 7.47 (br. s., 1H), 6.44-6.35 (m, 2H), 4.10-3.98 (m, 1H), 2.87 (d, J = 4.6 Hz, 3H), 1.55 (quin, J = 7.2 Hz, 2H), 1.20 (d, J = 6.6 Hz, 3H), 0.90 (t, J = 7.4 Hz, 3H) |
| 75 | ¹H NMR (400 MHz, DMSO-$d_6$) δ 8.66 (s, 1H), 8.32 (d, J = 8.4 Hz, 1H), 8.09-8.01 (m, 2H), 7.86 (s, 1H), 7.82 (d, J = 9.0 Hz, 1H), 7.59 (dd, J = 7.0, 1.8 Hz, 1H), 7.48 (br. s., 1H), 6.45 (t, J = 7.3 Hz, 1H), 6.39 (s, 1H), 4.09-3.98 (m, 1H), 2.87 (d, J = 4.8 Hz, 3H), 2.72 (s, 3H), 1.55 (quin, J = 7.2 Hz, 2H), 1.21 (d, J = 6.6 Hz, 3H), 0.90 (t, J = 7.4 Hz, 3H) |
| 76 | ¹H NMR (400 MHz, DMSO-$d_6$) δ 8.72 (s, 1H), 8.67 (dd, J = 4.8, 1.1 Hz, 1H), 8.64 (s, 1H), 8.36 (s, 1H), 8.32 (d, J = 8.4 Hz, 1H), 8.10 (td, J = 7.8, 1.9 Hz, 1H), 7.87 (s, 1H), 7.84 (d, J = 8.1 Hz, 1H), 7.64-7.58 (m, 1H), 7.51 (br. s., 1H), 6.42 (s, 1H), 4.10-4.00 (m, 1H), 2.87 (d, J = 4.8 Hz, 3H), 1.66-1.52 (m, 2H), 1.24 (d, J = 6.6 Hz, 3H), 0.89 (t, J = 7.4 Hz, 3H) |
| 77 | ¹H NMR (400 MHz, DMSO-$d_6$) δ 8.71 (d, J = 7.9 Hz, 1H), 8.65 (s, 1H), 8.10 (dd, J = 7.3, 1.5 Hz, 1H), 8.04-7.96 (m, 1H), 7.85 (s, 1H), 7.75 (d, J = 7.5 Hz, 1H), 7.71 (d, J = 7.9 Hz, 1H), 7.60 (dd, J = 7.0, 1.5 Hz, 1H), 7.46 (br. s., 1H), 6.46 (t, J = 7.3 Hz, 1H), 6.39 (s, 1H), 5.33 (br. s., 1H), 4.52 (sxt, J = 8.2 Hz, 1H), 2.87 (d, J = 4.8 Hz, 3H), 2.38-2.27 (m, 2H), 2.06-1.92 (m, 2H), 1.80-1.67 (m, 2H), 1.48 (s, 6H) |

TABLE 2-continued

| Example # | $^1$H NMR data |
|---|---|
| 78 | $^1$H NMR (400 MHz, DMSO-$d_6$) δ 8.82 (s, 1H), 8.79 (s, 1H), 8.67 (d, J = 8.1 Hz, 1H), 8.40 (s, 1H), 8.07 (d, J = 8.8 Hz, 1H), 7.89 (d, J = 8.8 Hz, 1H), 7.86 (s, 1H), 7.51 (br. s., 1H), 6.42 (s, 1H), 4.53 (sxt, J = 8.3 Hz, 1H), 2.87 (d, J = 4.8 Hz, 3H), 2.74 (s, 3H), 2.36-2.23 (m, 2H), 2.17-2.04 (m, 2H), 1.79-1.64 (m, 2H) |
| 79 | $^1$H NMR (400 MHz, DMSO-$d_6$) δ 8.64 (s, 1H), 8.32 (d, J = 8.4 Hz, 1H), 7.91 (dd, J = 7.3, 1.8 Hz, 1H), 7.85 (s, 1H), 7.82 (d, J = 2.2 Hz, 1H), 7.64 (dd, J = 7.0, 1.8 Hz, 1H), 7.46 (d, J = 4.2 Hz, 1H), 6.75 (d, J = 2.4 Hz, 1H), 6.40-6.31 (m, 2H), 4.09-3.97 (m, 1H), 3.89 (s, 3H), 2.87 (d, J = 4.8 Hz, 3H), 1.59-1.48 (m, 2H), 1.19 (d, J = 6.8 Hz, 3H), 0.89 (t, J = 7.4 Hz, 3H) |
| 80 | $^1$H NMR (400 MHz, DMSO-$d_6$) δ 8.76 (d, J = 5.1 Hz, 1H), 8.70 (s, 1H), 8.57 (d, J = 4.0 Hz, 1H), 8.39 (s, 1H), 8.05 (d, J = 9.0 Hz, 1H), 7.93 (s, 1H), 7.88 (d, J = 8.8 Hz, 1H), 7.53 (br. s., 1H), 6.40 (s, 1H), 4.93-4.70 (m, 1H), 3.05-2.96 (m, 1H), 2.87 (d, J = 4.8 Hz, 3H), 2.74 (s, 3H), 1.30-1.14 (m, 2H) |
| 81 | $^1$H NMR (400 MHz, DMSO-$d_6$) δ 8.63 (s, 1H), 8.59 (d, J = 4.0 Hz, 1H), 8.00 (ddd, J = 7.5, 4.7, 3.4 Hz, 2H), 7.86 (s, 1H), 7.77-7.72 (m, 1H), 7.70 (d, J = 7.5 Hz, 1H), 7.58 (dd, J = 7.0, 1.5 Hz, 1H), 7.45 (br. s., 1H), 6.46 (t, J = 7.2 Hz, 1H), 6.37 (s, 1H), 5.33 (d, J = 3.1 Hz, 1H), 2.91 (td, J = 7.3, 3.7 Hz, 1H), 2.86 (d, J = 4.8 Hz, 3H), 1.48 (s, 6H), 0.84-0.77 (m, 2H), 0.60-0.55 (m, 2H) |
| 82 | $^1$H NMR (400 MHz, DMSO-$d_6$) δ 8.67-8.60 (m, 2H), 8.03-7.95 (m, 2H), 7.91 (s, 1H), 7.75 (dd, J = 7.7, 0.7 Hz, 1H), 7.69 (d, J = 7.9 Hz, 1H), 7.56 (dd, J = 7.0, 1.8 Hz, 1H), 7.48 (br. s., 1H), 6.42 (t, J = 7.3 Hz, 1H), 6.39 (s, 1H), 5.33 (d, J = 2.9 Hz, 1H), 4.99-4.76 (m, 1H), 2.99 (dq, J = 9.1, 4.5 Hz, 1H), 2.87 (d, J = 4.8 Hz, 3H), 1.48 (s, 6H), 1.25 (dtd, J = 15.1, 8.5, 6.2 Hz, 1H), 1.06-0.93 (m, 1H) |
| 83 | $^1$H NMR (400 MHz, DMSO-$d_6$) δ 8.87 (s, 2H), 8.64 (d, J = 4.0 Hz, 1H), 8.59 (s, 1H), 7.99 (dd, J = 7.3, 1.5 Hz, 1H), 7.91 (s, 1H), 7.48 (br. s., 1H), 7.38 (dd, J = 6.9, 1.7 Hz, 1H), 6.42-6.32 (m, 2H), 4.99-4.76 (m, 1H), 3.00 (dq, J = 9.1, 4.5 Hz, 1H), 2.87 (d, J = 4.8 Hz, 3H), 2.40 (s, 3H), 1.31-1.17 (m, 1H), 1.07-0.92 (m, 1H) |
| 84 | $^1$H NMR (400 MHz, DMSO-$d_6$) δ 9.60-9.50 (m, 2H), 7.88 (s, 1H), 7.60 (br. s., 1H), 7.25 (d, J = 4.6 Hz, 1H), 7.02 (d, J = 4.4 Hz, 1H), 6.78 (s, 1H), 4.59 (sxt, J = 8.3 Hz, 1H), 3.53 (s, 3H), 2.89 (d, J = 4.8 Hz, 3H), 2.37-2.24 (m, 2H), 2.20-2.04 (m, 2H), 1.84-1.68 (m, 2H) |
| 85 | $^1$H NMR (400 MHz, DMSO-$d_6$) δ 8.63 (s, 1H), 8.59 (d, J = 4.0 Hz, 1H), 8.05-7.97 (m, 2H), 7.86 (s, 1H), 7.70 (d, J = 7.7 Hz, 1H), 7.62 (d, J = 7.5 Hz, 1H), 7.56 (dd, J = 7.2, 1.7 Hz, 1H), 7.45 (br. s., 1H), 6.44 (t, J = 7.2 Hz, 1H), 6.36 (s, 1H), 5.49 (dd, J = 4.6, 3.1 Hz, 1H), 4.82-4.73 (m, 1H), 2.92 (td, J = 7.3, 3.7 Hz, 1H), 2.86 (d, J = 4.8 Hz, 3H), 1.42 (d, J = 6.6 Hz, 3H), 0.84-0.77 (m, 2H), 0.61-0.54 (m, 2H) |
| 86 | $^1$H NMR (400 MHz, DMSO-$d_6$) δ 8.72 (d, J = 7.9 Hz, 1H), 8.65 (s, 1H), 8.10 (dd, J = 7.3, 1.5 Hz, 1H), 8.02 (t, J = 7.8 Hz, 1H), 7.85 (s, 1H), 7.70 (d, J = 7.9 Hz, 1H), 7.62 (d, J = 7.7 Hz, 1H), 7.57 (dd, J = 7.0, 1.5 Hz, 1H), 7.46 (br. s., 1H), 6.44 (t, J = 7.2 Hz, 1H), 6.38 (s, 1H), 5.51 (br. s., 1H), 4.78 (q, J = 6.4 Hz, 1H), 4.52 (sxt, J = 8.3 Hz, 1H), 2.87 (d, J = 4.8 Hz, 3H), 2.38-2.27 (m, 2H), 2.06-1.92 (m, 2H), 1.80-1.68 (m, 2H), 1.41 (d, J = 6.6 Hz, 3H) |
| 87 | $^1$H NMR (400 MHz, DMSO-$d_6$) δ 8.77 (s, 1H), 8.73 (br. s., 1H), 8.68 (d, J = 8.1 Hz, 1H), 8.38 (s, 1H), 8.07 (t, J = 7.9 Hz, 1H), 7.86 (s, 1H), 7.73-7.65 (m, 2H), 7.50 (br. s., 1H), 6.41 (s, 1H), 5.53 (br. s., 1H), 4.79 (q, J = 6.5 Hz, 1H), 4.53 (sxt, J = 8.3 Hz, 1H), 2.87 (d, J = 4.6 Hz, 3H), 2.30 (q, J = 7.9 Hz, 2H), 2.18-2.02 (m, 2H), 1.81-1.63 (m, 2H), 1.42 (d, J = 6.6 Hz, 3H) |
| 88 | $^1$H NMR (400 MHz, DMSO-$d_6$) δ 8.87 (d, J = 4.6 Hz, 1H), 8.57 (br. s., 1H), 8.25 (s, 1H), 8.06 (d, J = 8.8 Hz, 1H), 7.94 (s, 1H), 7.84 (d, J = 8.8 Hz, 1H), 7.75 (d, J = 2.6 Hz, 1H), 7.55 (br. s., 1H), 6.46 (s, 1H), 4.96-4.73 (m, 1H), 2.93 (dt, J = 9.1, 4.8 Hz, 1H), 2.87 (d, J = 4.6 Hz, 3H), 2.72 (s, 3H), 1.26-1.15 (m, 1H), 1.11-0.97 (m, 1H) |
| 89 | $^1$H NMR (400 MHz, DMSO-$d_6$) δ 8.92 (d, J = 4.0 Hz, 1H), 8.52 (d, J = 2.4 Hz, 1H), 8.33 (d, J = 9.9 Hz, 1H), 8.09 (d, J = 9.0 Hz, 1H), 7.96 (s, 1H), 7.83 (d, J = 9.0 Hz, 1H), 7.77-7.72 (m, 1H), 7.53 (d, J = 4.8 Hz, 1H), 6.48 (s, 1H), 4.95-4.72 (m, 1H), 2.97 (dq, J = 9.2, 4.6 Hz, 1H), 2.87 (d, J = 4.8 Hz, 3H), 2.72 (s, 3H), 1.26-1.12 (m, 1H), 1.11-0.97 (m, 1H) |
| 90 | $^1$H NMR (400 MHz, DMSO-$d_6$) δ 8.69 (d, J = 2.6 Hz, 1H), 8.59 (br. s., 1H), 8.07-7.99 (m, 2H), 7.91 (s, 1H), 7.80 (d, J = 9.0 Hz, 1H), 7.48 (br. s., 1H), 7.39 (s, 1H), 6.37 (s, 1H), 4.97-4.72 (m, 1H), 2.98-2.90 (m, 1H), 2.87 (d, J = 4.6 Hz, 3H), 2.71 (s, 3H), 2.19 (s, 3H), 1.27-1.13 (m, 1H), 1.02-0.87 (m, 1H) |
| 91 | $^1$H NMR (400 MHz, DMSO-$d_6$) δ 8.64-8.56 (m, 2H), 8.05 (s, 1H), 8.03 (d, J = 9.0 Hz, 1H), 7.85 (s, 1H), 7.80 (d, J = 8.8 Hz, 1H), 7.44 (br. s., 1H), 7.41 (s, 1H), 6.34 (s, 1H), 2.88-2.84 (m, 4H), 2.71 (s, 3H), 2.21 (s, 3H), 0.81-0.73 (m, 2H), 0.56-0.49 (m, 2H) |
| 92 | $^1$H NMR (500 MHz, DMSO-$d_6$) δ 8.68 (d, J = 7.2 Hz, 1H), 8.57 (s, 1H), 8.12 (d, J = 1.9 Hz, 1H), 8.03 (d, J = 8.9 Hz, 1H), 7.86 (s, 1H), 7.80 (d, J = 8.9 Hz, 1H), 7.47-7.40 (m, 2H), 6.31 (s, 1H), 4.43 (sxt, J = 8.0 Hz, 1H), 2.86 (d, J = 5.0 Hz, 3H), 2.71 (s, 3H), 2.33-2.24 (m, 2H), 2.18 (d, J = 0.8 Hz, 3H), 1.97 (quind, J = 9.4, 2.5 Hz, 2H), 1.76-1.65 (m, 2H) |

TABLE 2-continued

¹H NMR data

| Example # | ¹H NMR data |
|---|---|
| 93 | ¹H NMR (500 MHz, DMSO-$d_6$) δ 8.96 (s, 1H), 8.57 (d, J = 7.9 Hz, 1H), 8.42-8.36 (m, 1H), 8.09 (d, J = 9.2 Hz, 1H), 7.90 (s, 1H), 7.83 (d, J = 9.2 Hz, 1H), 7.79-7.75 (m, 1H), 7.55 (d, J = 4.9 Hz, 1H), 6.48 (s, 1H), 4.56-4.46 (m, 1H), 2.86 (d, J = 4.9 Hz, 3H), 2.72 (br. s., 3H), 2.29 (br. s., 2H), 2.09-1.98 (m, 2H), 1.74-1.65 (m, 2H) |
| 94 | ¹H NMR (400 MHz, DMSO-$d_6$) δ 8.93 (s, 1H), 8.42 (d, J = 3.9 Hz, 1H), 8.36 (dd, J = 10.0, 3.1 Hz, 1H), 8.09 (d, J = 8.9 Hz, 1H), 7.89 (s, 1H), 7.83 (d, J = 8.9 Hz, 1H), 7.76 (dd, J = 4.8, 3.1 Hz, 1H), 7.51 (d, J = 4.9 Hz, 1H), 6.47 (s, 1H), 2.90 (td, J = 7.3, 3.7 Hz, 1H), 2.86 (d, J = 4.8 Hz, 3H), 2.72 (s, 3H), 0.80-0.73 (m, 2H), 0.63-0.57 (m, 2H) |
| 95 | ¹H NMR (500 MHz, DMSO-$d_6$) δ 8.66 (s, 1H), 8.45 (d, J = 7.4 Hz, 1H), 8.07 (d, J = 7.4 Hz, 1H), 8.05 (d, J = 8.8 Hz, 1H), 7.87 (s, 1H), 7.82 (d, J = 9.1 Hz, 1H), 7.58 (d, J = 5.7 Hz, 1H), 7.49 (d, J = 4.7 Hz, 1H), 6.44 (t, J = 7.2 Hz, 1H), 6.37 (s, 1H), 4.34-4.24 (m, 1H), 2.86 (d, J = 4.7 Hz, 3H), 2.71 (br. s., 3H), 2.01 (br. s., 2H), 1.69 (br. s., 2H), 1.57 (d, J = 4.7 Hz, 2H), 1.51-1.38 (m, 2H) |
| 96 | ¹H NMR (400 MHz, DMSO-$d_6$) δ 8.71 (d, J = 6.7 Hz, 1H), 8.68 (s, 1H), 8.19 (dd, J = 7.3, 1.7 Hz, 1H), 8.05 (d, J = 8.8 Hz, 1H), 7.87 (s, 1H), 7.82 (d, J = 8.9 Hz, 1H), 7.58 (dd, J = 7.0, 1.7 Hz, 1H), 7.48 (q, J = 4.6 Hz, 1H), 6.49 (t, J = 7.2 Hz, 1H), 6.39 (s, 1H), 5.43-5.20 (m, 1H), 4.72-4.60 (m, 1H), 2.86 (d, J = 4.9 Hz, 3H), 2.72 (s, 3H), 2.68-2.54 (m, 2H), 2.48-2.35 (m, 2H) |
| 97 | ¹H NMR (400 MHz, DMSO-$d_6$) δ 8.67 (s, 1H), 8.36 (d, J = 7.8 Hz, 1H), 8.10-8.04 (m, 2H), 7.86 (s, 1H), 7.82 (d, J = 8.9 Hz, 1H), 7.59 (dd, J = 7.1, 1.7 Hz, 1H), 7.48 (q, J = 4.7 Hz, 1H), 6.47 (t, J = 7.2 Hz, 1H), 6.40 (s, 1H), 4.24-4.14 (m, 1H), 2.87 (d, J = 4.9 Hz, 3H), 2.72 (s, 3H), 1.24 (d, J = 6.6 Hz, 6H) |
| 98 | ¹H NMR (400 MHz, DMSO-$d_6$) δ 8.65 (s, 1H), 8.63 (d, J = 4.2 Hz, 1H), 8.03 (dd, J = 7.3, 1.5 Hz, 1H), 7.99 (d, J = 8.9 Hz, 1H), 7.91 (s, 1H), 7.75 (d, J = 9.0 Hz, 1H), 7.56 (dd, J = 7.0, 1.7 Hz, 1H), 7.50 (d, J = 4.9 Hz, 1H), 6.44 (t, J = 7.2 Hz, 1H), 6.40 (s, 1H), 4.99-4.77 (m, 1H), 2.99 (dq, J = 9.1, 4.5 Hz, 1H), 2.87 (d, J = 4.8 Hz, 3H), 2.42-2.32 (m, 1H), 1.31-1.10 (m, 5H), 1.06-0.92 (m, 1H) |
| 99 | ¹H NMR (400 MHz, DMSO-$d_6$) δ 8.68 (s, 1H), 8.58 (t, J = 5.5 Hz, 1H), 8.11 (dd, J = 7.5, 1.6 Hz, 1H), 8.05 (d, J = 8.8 Hz, 1H), 7.85 (s, 1H), 7.82 (d, J = 8.9 Hz, 1H), 7.58 (dd, J = 7.0, 1.6 Hz, 1H), 7.48 (q, J = 4.8 Hz, 1H), 6.50 (t, J = 7.2 Hz, 1H), 6.38 (s, 1H), 3.47-3.37 (m, 2H), 2.87 (d, J = 4.8 Hz, 3H), 2.72 (s, 3H), 1.20 (t, J = 7.2 Hz, 3H) |
| 100 | ¹H NMR (400 MHz, DMSO-$d_6$) δ 8.66 (s, 1H), 8.64 (d, J = 4.2 Hz, 1H), 8.08 (d, J = 8.9 Hz, 1H), 8.04 (dd, J = 7.4, 1.5 Hz, 1H), 7.92 (s, 1H), 7.84 (d, J = 8.9 Hz, 1H), 7.60 (dd, J = 7.0, 1.7 Hz, 1H), 7.50 (q, J = 4.7 Hz, 1H), 6.45 (t, J = 7.2 Hz, 1H), 6.40 (s, 1H), 5.00-4.77 (m, 1H), 3.03-2.94 (m, 3H), 2.87 (d, J = 4.9 Hz, 3H), 1.80 (sxt, J = 7.5 Hz, 2H), 1.25 (dtd, J = 15.1, 8.5, 6.1 Hz, 1H), 1.06-0.93 (m, 4H) |
| 101 | ¹H NMR (400 MHz, DMSO-$d_6$) δ 8.82 (t, J = 5.8 Hz, 1H), 8.67-8.62 (m, 2H), 8.08-8.00 (m, 2H), 7.90 (s, 1H), 7.84 (d, J = 8.1 Hz, 1H), 7.56-7.46 (m, 3H), 6.43 (t, J = 7.2 Hz, 1H), 6.40 (s, 1H), 4.70-4.52 (m, 2H), 3.80-3.65 (m, 2H), 2.87 (d, J = 4.9 Hz, 3H) |
| 102 | ¹H NMR (400 MHz, DMSO-$d_6$) δ 8.82 (t, J = 5.9 Hz, 1H), 8.68 (s, 1H), 8.10 (dd, J = 7.4, 1.7 Hz, 1H), 8.05 (d, J = 8.8 Hz, 1H), 7.90 (s, 1H), 7.82 (d, J = 8.9 Hz, 1H), 7.56 (dd, J = 7.0, 1.6 Hz, 1H), 7.51 (d, J = 4.9 Hz, 1H), 6.48 (t, J = 7.2 Hz, 1H), 6.41 (s, 1H), 4.70-4.52 (m, 2H), 3.80-3.65 (m, 2H), 2.87 (d, J = 4.6 Hz, 3H), 2.72 (s, 3H) |
| 103 | ¹H NMR (400 MHz, DMSO-$d_6$) δ 9.03 (d, J = 1.3 Hz, 1H), 8.69 (s, 1H), 8.65-8.60 (m, 2H), 8.02 (dd, J = 7.4, 1.5 Hz, 1H), 7.91 (s, 1H), 7.53 (dd, J = 7.0, 1.7 Hz, 1H), 7.50 (d, J = 4.9 Hz, 1H), 6.45 (t, J = 7.2 Hz, 1H), 6.41 (s, 1H), 4.99-4.76 (m, 1H), 2.99 (dq, J = 9.1, 4.5 Hz, 1H), 2.87 (d, J = 4.9 Hz, 3H), 2.60 (s, 3H), 1.31-1.18 (m, 1H), 1.06-0.92 (m, 1H) |
| 104 | ¹H NMR (400 MHz, DMSO-$d_6$) δ 9.35 (dd, J = 4.8, 1.4 Hz, 1H), 8.75-8.68 (m, 2H), 8.21 (dd, J = 8.8, 1.5 Hz, 1H), 8.17 (dd, J = 7.3, 1.7 Hz, 1H), 7.97 (dd, J = 8.8, 4.8 Hz, 1H), 7.86 (s, 1H), 7.65 (dd, J = 7.0, 1.7 Hz, 1H), 7.49 (d, J = 4.9 Hz, 1H), 6.51 (t, J = 7.2 Hz, 1H), 6.40 (s, 1H), 4.52 (sxt, J = 8.2 Hz, 1H), 2.87 (d, J = 4.8 Hz, 3H), 2.39-2.27 (m, 2H), 2.06-1.93 (m, 2H), 1.80-1.67 (m, 2H) |
| 105 | ¹H NMR (400 MHz, DMSO-$d_6$) δ 9.35 (dd, J = 4.8, 1.3 Hz, 1H), 8.68 (s, 1H), 8.32 (d, J = 8.4 Hz, 1H), 8.20 (dd, J = 8.8, 1.3 Hz, 1H), 8.04 (dd, J = 7.3, 1.6 Hz, 1H), 7.96 (dd, J = 8.7, 4.8 Hz, 1H), 7.86 (s, 1H), 7.64 (dd, J = 7.0, 1.6 Hz, 1H), 7.49 (d, J = 4.9 Hz, 1H), 6.47 (t, J = 7.2 Hz, 1H), 6.39 (s, 1H), 4.09-3.98 (m, 1H), 2.87 (d, J = 4.8 Hz, 3H), 1.55 (quin, J = 7.2 Hz, 2H), 1.21 (d, J = 6.7 Hz, 3H), 0.90 (t, J = 7.4 Hz, 3H) |
| 106 | ¹H NMR (400 MHz, DMSO-$d_6$) δ 9.35 (dd, J = 4.8, 1.4 Hz, 1H), 8.69 (s, 1H), 8.37 (d, J = 7.8 Hz, 1H), 8.20 (dd, J = 8.7, 1.4 Hz, 1H), 8.09 (dd, J = 7.3, 1.7 Hz, 1H), 7.97 (dd, J = 8.7, 4.8 Hz, 1H), 7.86 (s, 1H), 7.64 (dd, J = 7.0, 1.7 Hz, 1H), 7.49 (q, J = 4.7 Hz, 1H), 6.49 (t, J = 7.2 Hz, 1H), 6.40 (s, 1H), 4.25-4.13 (m, 1H), 2.87 (d, J = 4.8 Hz, 3H), 1.24 (d, J = 6.6 Hz, 6H) |
| 107 | ¹H NMR (400 MHz, DMSO-$d_6$) δ 8.66 (s, 1H), 8.56 (t, J = 5.6 Hz, 1H), 7.99 (dd, J = 7.3, 1.7 Hz, 1H), 7.84 (s, 1H), 7.82 (d, J = 2.2 Hz, 1H), 7.62 (dd, J = 7.1, 1.7 Hz, 1H), 7.46 (q, J = 4.7 Hz, 1H), 6.74 (d, J = 2.3 Hz, 1H), 6.41 (t, |

TABLE 2-continued

¹H NMR data

| Example # | ¹H NMR data |
|---|---|
| | J = 7.2 Hz, 1H), 6.37 (s, 1H), 3.89 (s, 3H), 3.45-3.35 (m, 2H), 2.87 (d, J = 4.9 Hz, 3H), 1.18 (t, J = 7.3 Hz, 3H) |
| 108 | ¹H NMR (400 MHz, DMSO-d₆) δ 8.65 (s, 1H), 8.36 (d, J = 7.9 Hz, 1H), 7.96 (dd, J = 7.3, 1.7 Hz, 1H), 7.85 (s, 1H), 7.82 (d, J = 2.3 Hz, 1H), 7.63 (dd, J = 7.1, 1.7 Hz, 1H), 7.47 (q, J = 4.6 Hz, 1H), 6.75 (d, J = 2.3 Hz, 1H), 6.41-6.35 (m, 2H), 4.23-4.13 (m, 1H), 3.89 (s, 3H), 2.87 (d, J = 4.9 Hz, 3H), 1.21 (d, J = 6.5 Hz, 6H) |
| 109 | ¹H NMR (400 MHz, DMSO-d₆) δ 9.19 (d, J = 0.9 Hz, 1H), 8.78-8.74 (m, 2H), 8.72-8.65 (m, 2H), 8.04 (dd, J = 7.3, 1.7 Hz, 1H), 7.88 (s, 1H), 7.57 (dd, J = 7.1, 1.7 Hz, 1H), 7.51 (q, J = 4.8 Hz, 1H), 6.55 (t, J = 7.2 Hz, 1H), 6.39 (s, 1H), 4.59 (t, J = 5.9 Hz, 1H), 3.34-3.29 (m, 2H), 3.13 (d, J = 5.9 Hz, 2H), 2.87 (d, J = 4.9 Hz, 3H), 0.81 (s, 6H) |
| 110 | ¹H NMR (400 MHz, DMSO-d₆) δ 9.35 (dd, J = 4.8, 1.4 Hz, 1H), 8.71 (t, J = 6.7 Hz, 1H), 8.67 (s, 1H), 8.18 (dd, J = 8.7, 1.4 Hz, 1H), 8.02 (dd, J = 7.3, 1.7 Hz, 1H), 7.96 (dd, J = 8.7, 4.8 Hz, 1H), 7.88 (s, 1H), 7.62 (dd, J = 7.0, 1.7 Hz, 1H), 7.51 (q, J = 4.7 Hz, 1H), 6.55 (t, J = 7.2 Hz, 1H), 6.37 (s, 1H), 3.27 (d, J = 6.7 Hz, 2H), 2.87 (d, J = 4.9 Hz, 3H), 0.87 (s, 9H) |
| 111 | ¹H NMR (400 MHz, DMSO-d₆) δ 9.35 (dd, J = 4.8, 1.5 Hz, 1H), 8.73-8.66 (m, 2H), 8.19 (dd, J = 8.7, 1.5 Hz, 1H), 8.06 (dd, J = 7.3, 1.7 Hz, 1H), 7.96 (dd, J = 8.7, 4.8 Hz, 1H), 7.88 (s, 1H), 7.63 (dd, J = 7.0, 1.7 Hz, 1H), 7.51 (q, J = 4.8 Hz, 1H), 6.54 (t, J = 7.2 Hz, 1H), 6.38 (s, 1H), 3.34 (d, J = 6.2 Hz, 2H), 2.87 (d, J = 4.9 Hz, 3H), 1.05 (s, 3H), 0.49-0.43 (m, 2H), 0.28-0.22 (m, 2H) |
| 112 | ¹H NMR (500 MHz, DMSO-d₆) δ 9.35 (d, J = 4.0 Hz, 1H), 8.69 (br. s., 2H), 8.18 (d, J = 8.8 Hz, 1H), 8.04 (d, J = 7.1 Hz, 1H), 7.98-7.92 (m, 1H), 7.86 (s, 1H), 7.62 (d, J = 6.7 Hz, 1H), 7.50 (br. s., 1H), 6.51 (t, J = 7.1 Hz, 1H), 6.35 (s, 1H), 3.27-3.19 (m, 2H), 2.87 (d, J = 3.7 Hz, 3H), 1.87-1.76 (m, 1H), 0.90 (d, J = 6.4 Hz, 6H) |
| 113 | ¹H NMR (400 MHz, DMSO-d₆) δ 9.04 (d, J = 1.3 Hz, 1H), 8.71-8.64 (m, 2H), 8.63 (d, J = 0.6 Hz, 1H), 8.08 (dd, J = 7.4, 1.7 Hz, 1H), 7.88 (s, 1H), 7.55-7.45 (m, 2H), 6.57 (t, J = 7.2 Hz, 1H), 6.40 (s, 1H), 4.57 (br. s., 1H), 3.47 (d, J = 6.1 Hz, 2H), 3.32 (d, J = 3.7 Hz, 2H), 2.88 (d, J = 4.8 Hz, 3H), 2.61 (s, 3H), 0.49-0.42 (m, 2H), 0.42-0.36 (m, 2H) |
| 114 | ¹H NMR (400 MHz, DMSO-d₆) δ 9.20 (d, J = 0.9 Hz, 1H), 8.79-8.73 (m, 2H), 8.71-8.62 (m, 2H), 8.08 (dd, J = 7.3, 1.6 Hz, 1H), 7.87 (s, 1H), 7.56 (dd, J = 7.0, 1.7 Hz, 1H), 7.49 (q, J = 4.8 Hz, 1H), 6.58 (t, J = 7.3 Hz, 1H), 6.40 (s, 1H), 4.57 (t, J = 5.7 Hz, 1H), 3.47 (d, J = 6.1 Hz, 2H), 3.31 (d, J = 3.7 Hz, 2H), 2.87 (d, J = 4.9 Hz, 3H), 0.49-0.42 (m, 2H), 0.42-0.34 (m, 2H) |
| 115 | ¹H NMR (500 MHz, DMSO-d₆) δ 8.48 (s, 1H), 8.07 (br. s., 1H), 7.94 (dd, J = 7.5, 1.7 Hz, 1H), 7.84 (s, 1H), 7.70 (br. s., 1H), 7.39 (q, J = 4.7 Hz, 1H), 7.31 (dd, J = 6.7, 1.7 Hz, 1H), 6.34 (s, 1H), 6.22 (t, J = 7.1 Hz, 1H), 3.54 (s, 3H), 2.87 (d, J = 4.7 Hz, 3H) |
| 116 | ¹H NMR (500 MHz, DMSO-d₆) δ 8.62 (d, J = 4.2 Hz, 1H), 8.49 (s, 1H), 7.89 (s, 1H), 7.86 (dd, J = 7.5, 1.7 Hz, 1H), 7.44 (q, J = 4.8 Hz, 1H), 7.33 (dd, J = 6.8, 1.8 Hz, 1H), 6.36 (s, 1H), 6.24 (t, J = 7.1 Hz, 1H), 4.96-4.75 (m, 1H), 3.55 (s, 3H), 3.02-2.94 (m, 1H), 2.87 (d, J = 5.0 Hz, 3H), 1.29-1.18 (m, 1H), 0.99-0.89 (m, 1H) |
| 117 | ¹H NMR (500 MHz, DMSO-d₆) δ 8.70 (t, J = 6.7 Hz, 1H), 8.47 (s, 1H), 7.87 (d, J = 1.7 Hz, 1H), 7.86 (s, 1H), 7.44 (d, J = 5.0 Hz, 1H), 7.35-7.30 (m, 1H), 6.35 (s, 1H), 6.31 (t, J = 7.2 Hz, 1H), 4.55 (t, J = 6.0 Hz, 1H), 3.54 (s, 3H), 3.10 (d, J = 5.8 Hz, 2H), 2.87 (d, J = 5.0 Hz, 3H), 0.78 (s, 6H) |
| 118 | ¹H NMR (500 MHz, DMSO-d₆) δ 8.73 (s, 1H), 8.40 (d, J = 3.9 Hz, 1H), 8.13 (dd, J = 10.0, 3.1 Hz, 1H), 7.86 (s, 1H), 7.53-7.36 (m, 2H), 6.42 (s, 1H), 4.15 (t, J = 5.3 Hz, 2H), 3.66 (t, J = 5.4 Hz, 2H), 3.27 (s, 3H), 2.90-2.87 (m, 1H), 2.86 (d, J = 4.7 Hz, 3H), 0.79-0.69 (m, 2H), 0.59-0.50 (m, 2H) |
| 119 | ¹H NMR (500 MHz, DMSO-d₆) δ 8.59 (d, J = 4.2 Hz, 1H), 8.58 (s, 1H), 7.98 (dd, J = 7.5, 1.7 Hz, 1H), 7.86 (s, 1H), 7.59-7.53 (m, 2H), 7.51-7.41 (m, 4H), 7.31 (dd, J = 6.9, 1.7 Hz, 1H), 6.39 (t, J = 7.2 Hz, 1H), 6.36 (s, 1H), 2.92 (td, J = 7.3, 3.7 Hz, 1H), 2.88-2.83 (m, 3H), 0.83-0.79 (m, 2H), 0.61-0.56 (m, 2H) |
| 120 | ¹H NMR (500 MHz, DMSO-d₆) δ 9.22 (s, 1H), 8.62 (s, 1H), 8.21-8.04 (m, 1H), 7.94 (s, 1H), 7.60-7.52 (m, 2H), 7.52-7.43 (m, 4H), 7.31 (dd, J = 6.9, 1.7 Hz, 1H), 6.46-6.40 (m, 1H), 6.37 (s, 1H), 2.86 (d, J = 5.0 Hz, 3H), 1.68-1.61 (m, 2H), 1.40-1.33 (m, 2H) |
| 121 | ¹H NMR (500 MHz, DMSO-d₆) δ 8.75 (s, 1H), 8.42 (d, J = 4.0 Hz, 1H), 8.18-8.14 (m, 1H), 7.86 (s, 1H), 7.49 (s, 1H), 7.35 (dd, J = 4.7, 3.2 Hz, 1H), 6.44 (s, 1H), 4.84 (s, 1H), 3.99 (s, 2H), 2.91-2.86 (m, 1H), 2.84 (d, J = 4.5 Hz, 3H), 1.12 (s, 6H), 0.74 (dd, J = 6.9, 2.0 Hz, 2H), 0.57 (dd, J = 4.0, 2.0 Hz, 2H) |
| 122 | ¹H NMR (500 MHz, METHANOL-d₄) δ ppm 7.98-8.03 (1 H, m), 7.92-7.97 (1 H, m), 7.58-7.64 (2 H, m), 7.39-7.49 (2 H, m), 7.20-7.29 (2 H, m), 7.14 (1 H, dd, J = 6.69, 1.73 Hz), 6.44-6.54 (1 H, m), 5.96-6.03 (1 H, m), 3.38-3.45 (2 H, m), 3.20-3.27 (2 H, m), 3.02 (3 H, s), 0.89-0.95 (6 H, m) |
| 123 | ¹H NMR (500 MHz, DMSO-d₆) δ 9.09 (s, 1H), 8.80 (s, 1H), 8.35 (dd, J = 10.2, 3.2 Hz, 1H), 7.96 (s, 1H), 7.50 (d, J = 5.0 Hz, 1H), 7.45 (dd, J = 4.7, |

TABLE 2-continued

<sup>1</sup>H NMR data

| Example # | <sup>1</sup>H NMR data |
|---|---|
| | 3.2 Hz, 1H), 6.47 (s, 1H), 4.15 (t, J = 5.2 Hz, 2H), 3.74-3.59 (m, 2H), 3.27 (s, 3H), 2.85 (d, J = 5.0 Hz, 3H), 1.63-1.53 (m, 2H), 1.38-1.26 (m, 2H) |
| 124 | <sup>1</sup>H NMR (500 MHz, DMSO-d<sub>6</sub>) δ 8.72 (t, J = 6.7 Hz, 1H), 8.61 (s, 1H), 8.00 (dd, J = 7.4, 2.0 Hz, 1H), 7.88 (s, 1H), 7.76 (d, J = 8.4 Hz, 2H), 7.64 (d, J = 8.4 Hz, 2H), 7.52 (q, J = 4.8 Hz, 1H), 7.34 (d, J = 2.0 Hz, 1H), 7.02-7.28 (m, 1H), 6.52-6.42 (m, 1H), 6.38 (s, 1H), 4.63 (br. s., 1H), 3.31 (br. s., 2H), 3.13 (br. s., 2H), 2.86 (d, J = 5.0 Hz, 3H), 0.81 (s, 6H) |
| 125 | <sup>1</sup>H NMR (500 MHz, DMSO-d<sub>6</sub>) δ 8.68 (t, J = 6.5 Hz, 1H), 8.58 (s, 1H), 8.07 (t, J = 1.7 Hz, 1H), 8.00 (dd, J = 7.5, 1.7 Hz, 1H), 7.96 (dt, J = 7.8, 1.2 Hz, 1H), 7.88 (s, 1H), 7.86 (dd, J = 1.9, 1.1 Hz, 1H), 7.78-7.74 (m, 1H), 7.48 (d, J = 4.7 Hz, 1H), 7.36 (dd, J = 6.9, 1.7 Hz, 1H), 6.47 (t, J = 7.2 Hz, 1H), 6.37 (s, 1H), 4.59 (t, J = 5.8 Hz, 1H), 3.32 (d, J = 6.7 Hz, 2H), 3.14 (d, J = 5.8 Hz, 2H), 2.87 (d, J = 4.7 Hz, 3H), 0.82 (s, 6H) |
| 126 | <sup>1</sup>H NMR (500 MHz, DMSO-d<sub>6</sub>) δ 8.61 (s, 1H), 8.58 (d, J = 3.9 Hz, 1H), 8.10 (t, J = 1.7 Hz, 1H), 8.01 (dd, J = 7.5, 1.7 Hz, 1H), 7.97 (dt, J = 7.7, 1.3 Hz, 1H), 7.90 (ddd, J = 8.0, 2.2, 1.1 Hz, 1H), 7.86 (s, 1H), 7.80-7.74 (m, 1H), 7.45 (q, J = 4.9 Hz, 1H), 7.38 (dd, J = 6.8, 1.8 Hz, 1H), 6.42 (t, J = 7.2 Hz, 1H), 6.37 (s, 1H), 2.92 (dt, J = 7.2, 3.6 Hz, 1H), 2.86 (d, J = 5.0 Hz, 3H), 0.83-0.78 (m, 2H), 0.61-0.56 (m, 2H) |
| 127 | <sup>1</sup>H NMR (500 MHz, DMSO-d<sub>6</sub>) δ 8.72 (t, J = 6.7 Hz, 1H), 8.55 (s, 1H), 7.97 (dd, J = 7.5, 1.7 Hz, 1H), 7.88 (s, 1H), 7.60-7.42 (m, 6H), 7.29 (dd, J = 6.9, 1.7 Hz, 1H), 6.48-6.40 (m, 1H), 6.36 (s, 1H), 4.59 (t, J = 5.8 Hz, 1H), 3.32 (d, J = 6.7 Hz, 2H), 3.13 (d, J = 5.8 Hz, 2H), 2.87 (d, J = 4.7 Hz, 3H), 0.82 (s, 6H) |
| 128 | <sup>1</sup>H NMR (500 MHz, DMSO-d<sub>6</sub>) δ 8.81-8.73 (m, 2H), 8.64 (s, 1H), 8.57 (d, J = 3.9 Hz, 1H), 8.01 (dd, J = 7.2, 1.7 Hz, 1H), 7.86 (s, 1H), 7.66-7.59 (m, 2H), 7.45 (q, J = 4.5 Hz, 1H), 7.38 (dd, J = 7.1, 1.8 Hz, 1H), 6.45 (t, J = 7.2 Hz, 1H), 6.37 (s, 1H), 2.92 (dt, J = 7.2, 3.6 Hz, 1H), 2.86 (d, J = 5.0 Hz, 3H), 0.83-0.78 (m, 2H), 0.60-0.56 (m, 2H) |
| 129 | <sup>1</sup>H NMR (500 MHz, DMSO-d<sub>6</sub>) δ 8.94 (d, J = 7.4 Hz, 1H), 8.56 (s, 1H), 8.06 (dd, J = 7.4, 1.5 Hz, 1H), 7.94 (s, 1H), 7.49 (q, J = 4.8 Hz, 1H), 7.34 (dd, J = 6.9, 2.0 Hz, 1H), 6.39 (s, 1H), 6.28 (t, J = 7.2 Hz, 1H), 5.10 (quin, J = 7.3 Hz, 1H), 3.55 (s, 3H), 2.86 (d, J = 5.0 Hz, 3H), 1.55 (d, J = 6.9 Hz, 3H) |
| 130 | <sup>1</sup>H NMR (500 MHz, DMSO-d<sub>6</sub>) δ 8.64 (s, 1H), 8.52 (s, 1H), 7.97 (dd, J = 7.2, 1.7 Hz, 1H), 7.93 (s, 1H), 7.50 (q, J = 4.5 Hz, 1H), 7.33 (dd, J = 6.7, 1.7 Hz, 1H), 6.38 (s, 1H), 6.26 (t, J = 7.2 Hz, 1H), 3.54 (s, 3H), 2.86 (d, J = 5.0 Hz, 3H), 1.72 (s, 6H) |
| 131 | <sup>1</sup>H NMR (500 MHz, DMSO-d<sub>6</sub>) δ 8.69 (t, J = 6.1 Hz, 1H), 8.54 (s, 1H), 8.01 (dd, J = 7.2, 1.7 Hz, 1H), 7.87 (s, 1H), 7.59-7.52 (m, 2H), 7.51-7.42 (m, 4H), 7.29 (dd, J = 6.9, 1.9 Hz, 1H), 6.47 (t, J = 7.2 Hz, 1H), 6.36 (s, 1H), 4.56 (t, J = 5.7 Hz, 1H), 3.47 (d, J = 6.1 Hz, 2H), 3.32 (d, J = 5.5 Hz, 2H), 2.87 (d, J = 4.7 Hz, 3H), 0.48-0.44 (m, 2H), 0.41-0.37 (m, 2H) |
| 132 | <sup>1</sup>H NMR (500 MHz, DMSO-d<sub>6</sub>) δ 8.71 (t, J = 6.7 Hz, 1H), 8.61 (s, 1H), 8.03 (dd, J = 7.4, 2.0 Hz, 1H), 7.97-7.92 (m, 2H), 7.89 (s, 1H), 7.75 (d, J = 8.4 Hz, 2H), 7.52 (q, J = 4.8 Hz, 1H), 7.36 (dd, J = 6.9, 1.5 Hz, 1H), 6.48 (t, J = 7.2 Hz, 1H), 6.39 (s, 1H), 4.53 (t, J = 5.2 Hz, 2H), 3.40-3.29 (m, 2H), 3.24 (d, J = 3.5 Hz, 4H), 2.86 (d, J = 4.5 Hz, 3H), 0.78 (s, 3H) |
| 133 | <sup>1</sup>H NMR (500 MHz, DMSO-d<sub>6</sub>) δ 8.69 (t, J = 6.2 Hz, 1H), 8.61 (s, 1H), 8.09-8.01 (m, 1H), 7.95 (s, 2H), 7.90-7.82 (m, 1H), 7.76 (d, J = 8.4 Hz, 2H), 7.51 (d, J = 5.0 Hz, 1H), 7.36 (dd, J = 6.9, 1.5 Hz, 1H), 6.58-6.47 (m, 1H), 6.38 (s, 1H), 4.60 (t, J = 5.7 Hz, 1H), 3.47 (d, J = 5.9 Hz, 2H), 3.31 (br. s., 2H), 2.86 (d, J = 4.5 Hz, 3H), 0.47-0.44 (m, 2H), 0.40-0.37 (m, 2H) |
| 134 | <sup>1</sup>H NMR (500 MHz, DMSO-d<sub>6</sub>) δ 8.70 (s, 1H), 8.57 (d, J = 4.0 Hz, 1H), 8.44 (d, J = 5.4 Hz, 1H), 8.03 (dd, J = 7.4, 1.5 Hz, 1H), 7.89-7.83 (m, 1H), 7.64 (d, J = 5.4 Hz, 1H), 7.56 (s, 1H), 7.50 (q, J = 4.5 Hz, 1H), 7.42 (dd, J = 6.9, 1.5 Hz, 1H), 6.46 (t, J = 7.2 Hz, 1H), 6.39 (s, 1H), 2.94-2.89 (m, 1H), 2.85 (d, J = 5.0 Hz, 3H), 0.83-0.77 (m, 2H), 0.60-0.54 (m, 2H) |
| 135 | <sup>1</sup>H NMR (500 MHz, DMSO-d<sub>6</sub>) δ 8.61 (d, J = 4.0 Hz, 1H), 8.59 (s, 1H), 7.98 (dd, J = 7.2, 1.7 Hz, 1H), 7.86 (s, 1H), 7.50 (d, J = 8.4 Hz, 2H), 7.48 (br. s., 1H), 7.41 (s, 2H), 7.30 (dd, J = 6.7, 1.7 Hz, 1H), 6.40-6.37 (m, 1H), 6.36 (s, 1H), 5.31 (d, J = 4.5 Hz, 1H), 4.85-4.76 (m, 1H), 2.92 (dd, J = 7.4, 3.5 Hz, 1H), 2.85 (d, J = 5.0 Hz, 3H), 1.38 (d, J = 6.4 Hz, 3H), 0.83-0.78 (m, 2H), 0.60-0.56 (m, 2H) |
| 136 | <sup>1</sup>H NMR (500 MHz, DMSO-d<sub>6</sub>) δ 8.71 (t, J = 6.7 Hz, 1H), 8.62 (s, 1H), 8.00 (dd, J = 7.4, 1.5 Hz, 1H), 7.94 (d, J = 8.4 Hz, 2H), 7.88 (s, 1H), 7.75 (d, J = 8.4 Hz, 2H), 7.52 (d, J = 5.0 Hz, 1H), 7.36 (dd, J = 6.9, 1.5 Hz, 1H), 6.48 (t, J = 7.2 Hz, 1H), 6.38 (s, 1H), 4.62 (t, J = 5.9 Hz, 1H), 3.32 (d, J = 5.9 Hz, 2H), 3.13 (d, J = 5.4 Hz, 2H), 2.86 (d, J = 5.0 Hz, 3H), 0.81 (s, 6H) |
| 137 | <sup>1</sup>H NMR (500 MHz, DMSO-d<sub>6</sub>) δ 9.22 (s, 1H), 8.68 (s, 1H), 8.19 (dd, J = 7.4, 1.5 Hz, 1H), 7.96-7.92 (m, 3H), 7.77 (d, J = 7.9 Hz, 2H), 7.51 (q, J = 5.0 Hz, 1H), 7.38 (dd, J = 6.9, 2.0 Hz, 1H), 6.46 (t, J = 7.2 Hz, 1H), 6.39 (s, 1H), 2.86 (d, J = 4.5 Hz, 3H), 1.67-1.62 (m, 2H), 1.39-1.33 (m, 2H) |
| 138 | <sup>1</sup>H NMR (500 MHz, DMSO-d<sub>6</sub>) δ 8.75-8.61 (m, 2H), 8.44 (d, J = 5.4 Hz, 1H), 8.04-7.99 (m, 1H), 7.88 (s, 1H), 7.69-7.58 (m, 1H), 7.57-7.50 (m, 2H), 7.44-7.37 (m, 1H), 6.51 (s, 1H), 6.39 (s, 1H), 3.33-3.29 (m, 2H), 3.18-3.07 (m, 2H), 2.86 (d, J = 5.0 Hz, 3H), 0.81 (s, 6H) |

TABLE 2-continued

¹H NMR data

| Example # | ¹H NMR data |
|---|---|
| 139 | ¹H NMR (500 MHz, DMSO-$d_6$) δ ppm 8.62 (d, J = 3.96 Hz, 1H), 8.59 (s, 1H), 7.96 (dd, J = 7.43, 1.49 Hz, 1H), 7.86 (s, 1H), 7.49 (d, J = 4.95 Hz, 1H), 7.33 (d, J = 8.92 Hz, 2H), 7.28 (dd, J = 6.94, 1.49 Hz, 1H), 7.08 (d, J = 8.92 Hz, 2H), 6.39-6.33 (m, 2H), 3.80-3.75 (m, 4H), 3.23-3.15 (m, 4H), 2.96-2.91 (m, 1H), 2.86 (d, J = 4.46 Hz, 3H), 0.85-0.77 (m, 2H), 0.62-0.54 (m, 2H) |
| 140 | ¹H NMR (500 MHz, DMSO-$d_6$) δ ppm 9.22 (s, 1H), 8.59 (s, 1H), 8.10 (dd, J = 7.35, 1.80 Hz, 1H), 7.94 (s, 1H), 7.46 (d, J = 4.99 Hz, 1H), 7.34-7.30 (m, 2H), 7.26 (dd, J = 6.94, 1.94 Hz, 1H), 7.06 (d, J = 8.88 Hz, 2H), 6.41-6.38 (m, 1H), 6.37 (s, 1H), 3.79-3.74 (m, 4H), 3.22-3.16 (m, 4H), 2.86 (d, J = 4.72 Hz, 3H), 1.67-1.62 (m, 2H), 1.38-1.33 (m, 2H) |
| 141 | ¹H NMR (500 MHz, DMSO-$d_6$) δ ppm 8.64 (d, J = 4.16 Hz, 1H), 8.56 (s, 1H), 7.96 (dd, J = 7.21, 1.66 Hz, 1H), 7.91 (s, 1H), 7.50 (d, J = 8.32 Hz, 2H), 7.47 (d, J = 4.72 Hz, 1H), 7.44-7.37 (m, 2H), 7.27 (dd, J = 6.94, 1.66 Hz, 1H), 6.38 (s, 1H), 6.35 (t, J = 7.07 Hz, 1H), 5.27 (d, J = 4.16 Hz, 1H), 4.81 (d, J = 4.72 Hz, 2H), 3.05-2.97 (m, 1H), 2.87 (d, J = 4.72 Hz, 3H), 1.38 (d, J = 6.38 Hz, 3H), 1.24 (d, J = 4.44 Hz, 1H), 1.08-0.93 (m, 1H) |
| 142 | ¹H NMR (500 MHz, DMSO-$d_6$) δ ppm 8.72 (d, J = 8.05 Hz, 1H), 8.59 (s, 1H), 8.08 (dd, J = 7.21, 1.66 Hz, 1H), 7.87-7.81 (m, 1H), 7.53-7.48 (m, 2H), 7.47-7.40 (m, 3H), 7.30 (dd, J = 6.94, 1.66 Hz, 1H), 6.41-6.33 (m, 2H), 5.27 (d, J = 4.44 Hz, 1H), 4.85-4.77 (m, 1H), 4.53 (sxt, J = 8.21 Hz, 1H), 2.87 (d, J = 4.99 Hz, 3H), 2.38-2.28 (m, 2H), 2.06-1.94 (m, 2H), 1.79-1.68 (m, 2H), 1.38 (d, J = 6.38 Hz, 3H) |
| 143 | ¹H NMR was not recorded |
| 144 | ¹H NMR (500 MHz, DMSO-$d_6$) δ ppm 8.67 (s, 1H), 8.58 (d, J = 4.16 Hz, 1H), 8.25 (q, J = 8.05 Hz, 1H), 8.01 (dd, J = 7.21, 1.66 Hz, 1H), 7.91-7.87 (m, 1H), 7.84 (dd, J = 7.63, 1.53 Hz, 1H), 7.55 (dd, J = 7.21, 1.66 Hz, 1H), 7.47 (br. s, 1H), 7.35 (dd, J = 8.05, 2.22 Hz, 1H), 6.46 (t, J = 7.21 Hz, 1H), 6.38 (s, 1H), 2.96-2.88 (m, 1H), 2.87 (s, 3H), 0.84-0.75 (m, 2H), 0.61-0.52 (m, 2H) |
| 145 | ¹H NMR (500 MHz, DMSO-$d_6$) δ ppm 8.73-8.55 (m, 2H), 8.25 (q, J = 8.32 Hz, 1H), 7.99 (dd, J = 7.35, 1.53 Hz, 1H), 7.91 (s, 1H), 7.84 (dd, J = 7.63, 1.53 Hz, 1H), 7.59-7.44 (m, 2H), 7.35 (dd, J = 8.05, 2.22 Hz, 1H), 6.56-6.15 (m, 2H), 4.98-4.73 (m, 1H), 3.07-2.94 (m, 1H), 2.87 (d, J = 4.99 Hz, 3H), 1.35-1.17 (m, 1H), 1.08-0.90 (m, 1H) |
| 146 | ¹H NMR (500 MHz, DMSO-$d_6$) δ ppm 8.81-8.68 (m, 1H), 8.65 (d, J = 2.97 Hz, 1H), 8.25 (qd, J = 8.09, 3.47 Hz, 1H), 8.03-7.97 (m, 1H), 7.88 (d, J = 3.47 Hz, 1H), 7.82 (d, J = 7.93 Hz, 1H), 7.57-7.48 (m, 1H), 7.42-7.31 (m, 1H), 6.49 (td, J = 7.18, 2.97 Hz, 1H), 6.37 (d, J = 2.97 Hz, 1H), 4.61 (d, J = 2.48 Hz, 1H), 3.35-3.27 (m, 2H), 3.18-3.07 (m, 2H), 2.96-2.77 (m, 3H), 0.89-0.71 (s, 6H) |
| 147 | ¹H NMR (500 MHz, DMSO-$d_6$) δ ppm 8.64 (d, J = 4.16 Hz, 1H), 8.54 (s, 1H), 7.93 (dd, J = 7.35, 1.53 Hz, 1H), 7.91 (s, 1H), 7.52-7.43 (m, 1H), 7.31 (d, J = 8.88 Hz, 2H), 7.24 (dd, J = 6.94, 1.66 Hz, 1H), 7.06 (d, J = 8.88 Hz, 2H), 6.37 (s, 1H), 6.32 (t, J = 7.21 Hz, 1H), 4.98-4.78 (m, 1H), 3.81-3.72 (m, 4H), 3.22-3.15 (m, 4H), 3.00 (dq, J = 9.09, 4.55 Hz, 1H), 2.87 (d, J = 4.72 Hz, 3H), 1.31-1.19 (m, 1H), 1.06-0.93 (m, 1H) |
| 148 | ¹H NMR (500 MHz, DMSO-$d_6$) δ ppm 9.05 (s, 1H), 8.62 (s, 1H), 8.15 (dd, J = 7.35, 1.80 Hz, 1H), 7.94 (s, 1H), 7.58-7.53 (m, 2H), 7.51-7.45 (m, 4H), 7.28 (dd, J = 6.94, 1.66 Hz, 1H), 6.39 (s, 1H), 6.35 (t, J = 7.21 Hz, 1H), 2.87 (d, J = 4.99 Hz, 3H), 2.79-2.71 (m, 2H), 2.49-2.44 (m, 2H), 2.15-2.06 (m, 2H) |
| 149 | ¹H NMR (500 MHz, DMSO-$d_6$) δ ppm 8.88 (s, 1H), 8.68-8.60 (m, 1H), 8.42 (d, J = 3.88 Hz, 1H), 8.29 (dd, J = 9.99, 3.05 Hz, 1H), 8.10-8.02 (m, 1H), 7.92 (d, J = 8.05 Hz, 1H), 7.90-7.85 (m, 1H), 7.74-7.68 (m, 1H), 7.53 (ddd, J = 7.49, 4.86, 0.97 Hz, 1H), 7.49 (q, J = 4.90 Hz, 1H), 6.46 (s, 1H), 2.94-2.88 (m, 1H), 2.87 (d, J = 4.99 Hz, 3H), 0.80-0.71 (m, 2H), 0.63-0.56 (m, 2H) |
| 150 | ¹H NMR (500 MHz, DMSO-$d_6$) δ ppm 8.90 (s, 1H), 8.67-8.61 (m, 1H), 8.56 (d, J = 7.77 Hz, 1H), 8.32 (dd, J = 9.71, 3.05 Hz, 1H), 8.10-8.02 (m, 1H), 7.92-7.91 (m, 1H), 7.89 (s, 1H), 7.75-7.68 (m, 1H), 7.57-7.45 (m, 2H), 6.47 (s, 1H), 4.56-4.46 (m, 1H), 2.87 (d, J = 4.72 Hz, 3H), 2.34-2.24 (m, 2H), 2.10-1.98 (m, 2H), 1.75-1.65 (m, 2H) |
| 151 | ¹H NMR (500 MHz, DMSO-$d_6$) δ ppm 8.89 (s, 1H), 8.70-8.61 (m, 1H), 8.53 (d, J = 4.16 Hz, 1H), 8.27 (dd, J = 9.71, 3.05 Hz, 1H), 8.05 (td, J = 7.77, 1.94 Hz, 1H), 7.95 (s, 1H), 7.92 (d, J = 8.32 Hz, 1H), 7.77-7.65 (m, 1H), 7.60-7.46 (m, 2H), 6.48 (s, 1H), 4.99-4.61 (m, 1H), 2.97 (dq, J = 9.09, 4.55 Hz, 1H), 2.87 (d, J = 4.72 Hz, 1H), 1.22-1.13 (m, 1H), 1.11-0.97 (m, 1H) |
| 152 | ¹H NMR (500 MHz, DMSO-$d_6$) δ ppm 8.61 (s, 1H), 8.58 (d, J = 3.88 Hz, 1H), 8.01 (dd, J = 7.49, 1.66 Hz, 1H), 7.87-7.82 (m, 1H), 7.62-7.53 (m, 2H), 7.50-7.44 (m, 2H), 7.40 (td, J = 7.70, 1.25 Hz, 1H), 7.31 (d, J = 6.66, 1.66 Hz, 1H), 6.41 (t, J = 7.07 Hz, 1H), 6.36 (s, 1H), 2.92 (tq, J = 7.33, 3.80 Hz, 1H), 2.85 (d, J = 4.99 Hz, 3H), 0.85-0.77 (m, 2H), 0.63-0.54 (m, 2H) |
| 153 | ¹H NMR (500 MHz, DMSO-$d_6$) δ ppm 8.71 (t, J = 6.52 Hz, 1H), 8.58 (s, 1H), 7.99 (dd, J = 7.21, 1.66 Hz, 1H), 7.88 (s, 1H), 7.61-7.51 (m, 2H), 7.50-7.43 (m, 2H), 7.42-7.36 (m, 1H), 7.28 (dd, J = 6.94, 1.66 Hz, 1H), 6.45 (t, J = 7.21 |

TABLE 2-continued

¹H NMR data

| Example # | ¹H NMR data |
|---|---|
| | Hz, 1H), 6.36 (s, 1H), 4.59 (t, J = 5.96 Hz, 1H), 3.32 (d, J = 6.66 Hz, 2H), 3.13 (d, J = 5.83 Hz, 2H), 2.87 (d, J = 4.72 Hz, 3H), 0.80 (s, 6H) |
| 154 | ¹H NMR (500 MHz, DMSO-$d_6$) δ ppm 8.63 (s, 1H), 8.57 (d, J = 4.16 Hz, 1H), 7.93 (dd, J = 7.35, 1.53 Hz, 1H), 7.89-7.84 (m, 1H), 7.61 (dd, J = 7.21, 1.66 Hz, 1H), 7.45 (br. s, 1H), 6.56 (s, 1H), 6.42-6.33 (m, 2H), 3.77 (s, 3H), 2.94-2.88 (m, 1H), 2.87 (br. s, 3H), 2.32 (s, 3H), 0.83-0.76 (m, 2H), 0.59-0.51 (m, 2H) |
| 155 | ¹H NMR (500 MHz, DMSO-$d_6$) δ ppm 8.72 (d, J = 8.05 Hz, 1H), 8.66 (s, 1H), 8.09-7.99 (m, 1H), 7.87 (s, 1H), 7.63 (dd, J = 7.07, 1.80 Hz, 1H), 7.47 (br. s, 1H), 6.58 (d, J = 0.83 Hz, 1H), 6.45-6.32 (m, 2H), 4.52 (dq, J = 16.44, 8.11 Hz, 1H), 3.84-3.71 (m, 3H), 2.94-2.81 (m, 3H), 2.38-2.26 (m, 5H), 2.06-1.88 (m, 2H), 1.80-1.63 (m, 2H) |
| 156 | ¹H NMR (500 MHz, DMSO-$d_6$) δ ppm 9.20 (s, 1H), 8.65 (s, 1H), 8.17 (dd, J = 7.21, 1.66 Hz, 1H), 7.94 (s, 1H), 7.63-7.54 (m, 2H), 7.52-7.44 (m, 2H), 7.40 (t, J = 7.63 Hz, 1H), 7.31 (dd, J = 6.80, 1.53 Hz, 1 H), 6.44 (t, J = 7.07 Hz, 1 H), 6.37 (s, 1H), 2.86 (d, J = 4.99 Hz, 3H), 1.70-1.59 (m, 2H), 1.40-1.31 (m, 2H) |
| 157 | ¹H NMR (500 MHz, DMSO-$d_6$) δ ppm 8.72 (s, 1H), 8.67 (d, J = 8.05 Hz, 1H), 8.10 (dd, J = 7.35, 1.53 Hz, 1H), 7.90-7.79 (m, 1H), 7.56 (dd, J = 7.21, 1.66 Hz, 1H), 7.48 (q, J = 4.62 Hz, 1H), 6.89 (d, J = 0.83 Hz, 1H), 6.46 (t, J = 7.07 Hz, 1H), 6.41-6.33 (m, 1H), 4.50 (sxt, J = 8.16 Hz, 1H), 2.87 (d, J = 4.99 Hz, 3H), 2.52 (s, 3H), 2.38-2.24 (m, 2H), 2.04-1.87 (m, 2H), 1.78-1.63 (m, 2H) |
| 158 | ¹H NMR (500 MHz, DMSO-$d_6$) δ ppm 8.72 (s, 1 H), 8.59 (d, J = 3.88 Hz, 1 H), 8.01-7.91 (m, 2H), 7.83 (d, J = 2.22 Hz, 1H), 7.64 (dd, J = 7.21, 1.66 Hz, 1H), 7.55 (br. s, 1H), 6.75 (d, J = 2.22 Hz, 1H), 6.44 (s, 1H), 6.41 (t, J = 7.21 Hz, 1 H), 3.90 (s, 3H), 2.95-2.88 (m, 1H), 2.87 (s, 3H), 0.96-0.68 (m, 2H), 0.60-0.31 (m, 2H) |
| 159 | ¹H NMR (500 MHz, DMSO-$d_6$) δ ppm 8.71 (d, J = 8.05 Hz, 1H), 8.67 (s, 1 H), 8.04 (dd, J = 7.35, 1.80 Hz, 1H), 7.88-7.80 (m, 2H), 7.65 (dd, J = 7.21, 1.66 Hz, 1H), 7.46 (d, J = 4.72 Hz, 1H), 6.75 (d, J = 2.22 Hz, 1 H), 6.40 (t, J = 7.21 Hz, 1H), 6.38 (s, 1H), 4.51 (dq, J = 16.44, 8.30 Hz, 1H), 3.89 (s, 3H), 2.87 (d, J = 4.72 Hz, 3H), 2.35-2.23 (m, 2H), 2.05-1.89 (m, 2H), 1.79-1.64 (m, 2H) |
| 160 | ¹H NMR (400 MHz, DMSO-$d_6$) δ ppm 8.88-8.74 (m, 2H), 8.11 (s, 1H), 8.09 (d, J = 1.54 Hz, 1H), 7.77 (dd, J = 7.04, 1.54 Hz, 1H), 7.67 (br. s, 1H), 6.74 (s, 1H), 6.58 (s, 1H), 6.53 (t, J = 7.26 Hz, 1H), 5.16-4.93 (m, 1H), 3.95 (s, 3H), 3.17 (d, J = 4.40 Hz, 1H), 3.05 (s, 3H), 2.68 (s, 3H), 1.49-1.35 (m, 1H), 1.22-1.07 (m, 1H) |
| 161 | ¹H NMR (500 MHz, DMSO-$d_6$) δ ppm 8.55 (d, J = 3.88 Hz, 1H), 8.52 (s, 1H), 7.83 (s, 1H), 7.80 (dd, J = 7.35, 1.53 Hz, 1H), 7.42 (q, J = 4.62 Hz, 1H), 7.31 (dd, J = 7.07, 1.80 Hz, 1H), 6.32 (s, 1H), 6.26 (t, J = 7.21 Hz, 1H), 2.93-2.87 (m, 1H), 2.86 (d, J = 4.72 Hz, 3H), 1.47 (s, 3H), 1.02 (s, 2H), 0.97 (s, 2H), 0.82-0.76 (m, 2H), 0.53 (dd, J = 3.88, 1.94 Hz, 2H) |
| 162 | ¹H NMR (500 MHz, DMSO-$d_6$) δ ppm 9.17 (s, 1H), 8.56 (s, 1H), 7.96 (dd, J = 7.35, 1.80 Hz, 1H), 7.92 (s, 1H), 7.45 (q, J = 4.81 Hz, 1H), 7.31 (dd, J = 6.94, 1.66 Hz, 1H), 6.34 (s, 1H), 6.29 (t, J = 7.21 Hz, 1H), 2.86 (d, J = 4.99 Hz, 3H), 1.65-1.60 (m, 2H), 1.47 (s, 3H), 1.34-1.30 (m, 2H), 1.00-1.05 (m, 2H), 1.00-0.94 (m, 2H) |
| 163 | ¹H NMR (500 MHz, DMSO-$d_6$) δ ppm 8.67 (t, J = 6.66 Hz, 1H), 8.48 (s, 1H), 7.90-7.83 (m, 1H), 7.79 (dd, J = 7.35, 1.80 Hz, 1H), 7.44 (q, J = 4.81 Hz, 1H), 7.29 (dd, J = 6.94, 1.66 Hz, 1H), 6.37-6.22 (m, 2H), 4.56 (t, J = 5.83 Hz, 1H), 3.28 (d, J = 6.66 Hz, 2H), 3.10 (d, J = 5.55 Hz, 2H), 2.87 (d, J = 4.72 Hz, 3H), 1.46 (s, 3H), 1.05-0.92 (m, 4H), 0.78 (s, 6H) |
| 164 | ¹H NMR (500 MHz, DMSO-$d_6$) δ ppm 8.70-8.55 (m, 2H), 8.00-7.88 (m, 3H), 7.70-7.58 (m, 1H), 7.52-7.37 (m, 1H), 6.75 (d, J = 2.22 Hz, 1H), 6.46-6.29 (m, 2H), 4.97-4.77 (m, 1H), 3.82-3.74 (m, 1H), 3.04-2.95 (m, 1H), 2.87 (d, J = 4.72 Hz, 3H), 1.28-1.19 (m, 2H), 1.12-1.09 (m, 2H), 1.03-0.97 (m, 2H) |
| 165 | ¹H NMR (500 MHz, DMSO-$d_6$) δ ppm 8.64 (s, 1H), 8.57 (d, J = 3.88 Hz, 1H), 7.94 (dd, J = 7.21, 1.39 Hz, 1H), 7.91 (d, J = 2.22 Hz, 1H), 7.85 (s, 1H), 7.65 (dd, J = 7.07, 1.53 Hz, 1H), 7.47-7.42 (m, 1H), 6.75 (d, J = 2.22 Hz, 1H), 6.40 (s, 1H), 6.36 (s, 1H), 3.81-3.75 (m, 1H), 2.95-2.88 (m, 1H), 2.86 (d, J = 4.99 Hz, 3H), 1.10 (d, J = 3.05 Hz, 2H), 1.00 (d, J = 4.99 Hz, 2H), 0.79 (dd, J = 6.80, 1.80 Hz, 2H), 0.55 (d, J = 3.75, 2.08 Hz, 2H) |
| 166 | ¹H NMR (500 MHz, DMSO-$d_6$) δ ppm 8.71 (d, J = 7.77 Hz, 1H), 8.66 (s, 1H), 8.04 (dd, J = 7.35, 1.80 Hz, 1H), 7.92 (d, J = 2.22 Hz, 1H), 7.87-7.79 (m, 1H), 7.67 (dd, J = 7.07, 1.80 Hz, 1H), 7.45 (q, J = 4.81 Hz, 1H), 6.83-6.70 (m, 1H), 6.48-6.24 (m, 2H), 4.51 (sxt, J = 8.21 Hz, 1H), 3.78 (tt, J = 7.28, 3.81 Hz, 1H), 2.87 (d, J = 4.99 Hz, 3H), 2.39-2.25 (m, 2H), 2.06-1.89 (m, 2H), 1.79-1.63 (m, 2H), 1.13-1.06 (m, 2H), 1.05-0.96 (m, 2H) |
| 167 | ¹H NMR was not recorded |
| 168 | ¹H NMR (400 MHz, DMSO-$d_6$) δ ppm 8.86 (s, 1H), 8.52 (s, 1H), 7.88 (dd, J = 7.37, 1.65 Hz, 1H), 7.81 (s, 1H), 7.42 (q, J = 4.62 Hz, 1H), 7.37 (dd, |

TABLE 2-continued

¹H NMR data

| Example # | ¹H NMR data |
|---|---|
| | J = 6.82, 1.76 Hz, 1H), 6.35 (s, 1H), 6.28 (t, J = 7.04 Hz, 1H), 3.56 (s, 3H), 2.86 (d, J = 4.84 Hz, 3H), 1.41 (s, 3H), 0.78-0.72 (m, 2H), 0.72-0.66 (m, 2H) |
| 169 | ¹H NMR (500 MHz, DMSO-d₆) δ ppm 8.65-8.63 (m, 1H), 8.63-8.60 (m, 1H), 7.93 (dd, J = 7.21, 1.39 Hz, 1H), 7.90 (s, 1H), 7.82 (d, J = 2.22 Hz, 1H), 7.63-7.60 (m, 1H), 7.51-7.44 (m, 1H), 6.75 (s, 1H), 6.39 (s, 1H), 6.38-6.34 (m, 1H), 4.96-4.77 (m, 1H), 3.89 (s, 3H), 3.02-2.95 (m, 1H), 2.87 (d, J = 4.99 Hz, 3H), 1.29-1.19 (m, 1H), 1.03-0.92 (m, 1H) |
| 170 | ¹H NMR (500 MHz, DMSO-d₆) δ ppm 9.04 (d, J = 4.99 Hz, 2H), 8.59 (s, 1H), 8.45 (d, J = 7.49 Hz, 1H), 8.02 (dd, J = 7.21, 1.66 Hz, 1H), 7.85 (s, 1H), 7.72 (t, J = 4.86 Hz, 1H), 7.53-7.38 (m, 2H), 6.38-6.34 (m, 1H), 6.34 (s, 1H), 4.37-4.18 (m, 1H), 2.87 (d, J = 4.99 Hz, 1H), 2.10-1.95 (m, 2H), 1.77-1.64 (m, 2H), 1.62-1.52 (m, 2H), 1.51-1.39 (m, 2H) |
| 171 | ¹H NMR (500 MHz, DMSO-d₆) δ ppm 9.15 (s, 2H), 8.62 (s, 1H), 8.58 (d, J = 3.88 Hz, 1H), 8.02 (dd, J = 7.21, 1.66 Hz, 1H), 7.86 (s, 1H), 7.46 (d, J = 4.99 Hz, 1H), 7.44 (dd, J = 6.94, 1.66 Hz, 1H), 6.43 (t, J = 7.21 Hz, 1H), 6.34 (s, 1H), 2.99-2.88 (m, 1H), 2.86 (d, J = 4.72 Hz, 3H), 0.80 (s, 2H), 0.62-0.52 (m, 2H) |
| 172 | ¹H NMR (500 MHz, DMSO-d₆) δ ppm 9.15 (s, 2H), 8.60 (s, 1H), 8.50-8.41 (m, 1H), 8.07-8.00 (m, 1H), 7.85 (s, 1H), 7.51-7.45 (m, 1H), 7.44-7.39 (m, 1H), 6.40-6.35 (m, 1H), 6.34 (s, 1H), 4.35-4.24 (m, 1H), 2.86 (d, J = 4.99 Hz, 3H), 2.06-1.96 (m, 2H), 1.75-1.64 (m, 2H), 1.62-1.54 (m, 2H), 1.52-1.40 (m, 2H) |
| 173 | ¹H NMR (500 MHz, DMSO-d₆) δ ppm 9.15 (s, 2H), 8.72 (d, J = 8.05 Hz, 1H), 8.64 (s, 1H), 8.11 (dd, J = 7.49, 1.66 Hz, 1H), 7.85 (s, 1H), 7.47 (d, J = 4.72 Hz, 1H), 7.45 (dd, J = 6.94, 1.66 Hz, 1H), 6.43 (t, J = 7.21 Hz, 1H), 6.36 (s, 1H), 4.60-4.42 (m, 1H), 2.87 (d, J = 4.99 Hz, 3H), 2.41-2.25 (m, 2H), 2.08-1.91 (m, 2H), 1.83-1.59 (m, 2H) |
| 174 | ¹H NMR (500 MHz, DMSO-d₆) δ ppm 9.15 (s, 2H), 8.63 (d, J = 4.16 Hz, 1H), 8.61 (s, 1H), 8.01 (dd, J = 7.21, 1.66 Hz, 1H), 7.91 (s, 1H), 7.53-7.46 (m, 1H), 7.41 (dd, J = 6.94, 1.66 Hz, 1H), 6.39 (t, J = 7.21 Hz, 1H), 6.37 (s, 1H), 5.02-4.73 (m, 1H), 3.07-2.95 (m, 1H), 2.87 (d, J = 4.72 Hz, 1H), 1.34-1.17 (m, 1H), 1.09-0.92 (m, 1H) |
| 175 | ¹H NMR (500 MHz, DMSO-d₆) δ ppm 9.56 (s, 2H), 8.67 (s, 1H), 8.58 (d, J = 3.88 Hz, 1H), 8.10-7.98 (m, 1H), 7.86 (s, 1H), 7.53-7.50 (m, 1H), 7.49-7.44 (m, 1H), 6.47 (t, J = 7.07 Hz, 1H), 6.35 (s, 1H), 2.97-2.89 (m, 1H), 2.86 (d, J = 4.72 Hz, 3H), 0.80 (dd, J = 6.94, 1.94 Hz, 2H), 0.57 (dd, J = 3.88, 1.94 Hz, 2H) |
| 176 | ¹H NMR (500 MHz, DMSO-d₆) δ ppm 9.56 (d, J = 0.55 Hz, 2H), 8.72 (d, J = 8.05 Hz, 1H), 8.69 (s, 1H), 8.13 (dd, J = 7.21, 1.66 Hz, 1H), 7.85 (s, 1H), 7.52 (dd, J = 7.07, 1.80 Hz, 1H), 7.49 (d, J = 4.99 Hz, 1H), 6.47 (t, J = 7.21 Hz, 1H), 6.37 (s, 1H), 4.56-4.46 (m, 1H), 2.87 (d, J = 4.99 Hz, 3H), 2.38-2.27 (m, 2H), 1.97 (d, J = 11.65 Hz, 1H), 1.73 (d, J = 3.33 Hz, 1H) |
| 177 | ¹H NMR (400 MHz, DMSO-d₆) δ ppm 8.90 (d, J = 5.50 Hz, 1H), 8.72 (s, 1H), 8.70 (d, J = 7.92 Hz, 1H), 8.12 (dd, J = 7.37, 1.65 Hz, 1H), 7.96 (d, J = 5.50 Hz, 1H), 7.85 (s, 1H), 7.75 (dd, J = 7.26, 1.76 Hz, 1H), 7.48 (q, J = 4.70 Hz, 1H), 6.50 (t, J = 7.26 Hz, 1H), 6.40 (s, 1H), 4.51 (sxt, J = 8.36 Hz, 1H), 2.87 (d, J = 4.84 Hz, 3H), 2.71 (s, 3H), 2.38-2.24 (m, 2H), 2.07-1.88 (m, 2H), 1.82-1.62 (m, 2H) |
| 178 | ¹H NMR (400 MHz, DMSO-d₆) δ ppm 8.89 (d, J = 5.50 Hz, 1H), 8.69 (s, 1H), 8.61 (d, J = 4.18 Hz, 1H), 8.00 (dd, J = 7.26, 1.54 Hz, 1H), 7.95 (d, J = 5.50 Hz, 1H), 7.91 (s, 1H), 7.72 (dd, J = 7.04, 1.54 Hz, 1H), 7.50 (q, J = 4.84 Hz, 1H), 6.46 (t, J = 7.15 Hz, 1H), 6.40 (s, 1H), 5.00-4.68 (m, 1H), 2.99 (d, J = 4.40 Hz, 1H), 2.87 (d, J = 4.62 Hz, 3H), 2.71 (s, 3H), 1.32-1.16 (m, 1H), 1.07-0.88 (m, 1H) |
| 179 | ¹H NMR (500 MHz, DMSO-d₆) δ ppm 9.39 (s, 1H), 8.44 (d, J = 3.88 Hz, 1H), 8.04-7.95 (m, 2H), 7.95-7.88 (m, 1H), 7.68-7.61 (m, 1H), 7.58-7.50 (m, 2H), 7.48-7.39 (m, 1H), 6.55 (s, 1H), 2.93 (tq, J = 7.35, 3.88 Hz, 1H), 2.87 (d, J = 4.99 Hz, 3H), 0.87-0.76 (m, 2H), 0.66-0.52 (m, 2H) |
| 180 | ¹H NMR (500 MHz, DMSO-d₆) δ ppm 9.37 (s, 1H), 8.50 (d, J = 4.16 Hz, 1H), 7.99 (s, 1H), 7.92 (q, J = 4.99 Hz, 1H), 7.66 (q, J = 4.90 Hz, 1H), 7.64-7.61 (m, 2H), 7.57-7.50 (m, 2H), 7.48-7.41 (m, 1H), 6.61-6.54 (m, 1H), 5.03-4.77 (m, 1H), 3.06-2.94 (m, 1H), 2.88 (d, J = 4.99 Hz, 3H), 1.32-1.18 (m, 1H), 1.13-0.99 (m, 1H) |
| 181 | ¹H NMR (500 MHz, DMSO-d₆) δ ppm 8.65 (s, 1H), 8.63 (d, J = 4.16 Hz, 1H), 8.08 (d, J = 8.88 Hz, 1H), 8.04 (dd, J = 7.35, 1.53 Hz, 1H), 7.92 (s, 1H), 7.86 (d, J = 8.88 Hz, 1H), 7.59 (dd, J = 6.94, 1.66 Hz, 1H), 7.49 (d, J = 4.72 Hz, 1H), 6.46 (t, J = 7.07 Hz, 1H), 6.40 (s, 1H), 5.04-4.71 (m, 1H), 3.12-2.95 (m, 3H), 2.87 (d, J = 4.16 Hz, 3H), 1.35 (t, J = 7.63 Hz, 3H), 1.30-1.16 (m, 1H), 1.07-0.91 (m, 1H) |
| 182 | ¹H NMR (500 MHz, DMSO-d₆) δ ppm 9.43 (t, J = 6.06 Hz, 1H), 8.62 (s, 1H), 8.18-7.98 (m, 1H), 7.94 (s, 1H), 7.77 (d, J = 2.69 Hz, 1H), 7.67 (d, J = 3.03 Hz, 1H), 7.62-7.34 (m, 6H), 7.21 (d, J = 6.73 Hz, 1H), 6.38 (s, 1H), 6.11 (t, J = 7.07 Hz, 1H), 4.92 (d, J = 6.06 Hz, 2H), 2.87 (d, J = 4.71 Hz, 3H) |
| 183 | ¹H NMR (500 MHz, DMSO-d₆) δ ppm 8.83 (t, J = 5.83 Hz, 1H), 8.59 (s, 1H), 8.02 (dd, J = 7.49, 1.66 Hz, 1H), 7.93-7.83 (m, 1H), 7.63-7.52 (m, 2H), |

TABLE 2-continued

| Example # | ¹H NMR data |
|---|---|
| | 7.51-7.43 (m, 4H), 7.28 (dd, J = 6.94, 1.66 Hz, 1H), 6.46-6.31 (m, 2H), 4.71-4.51 (m, 2H), 3.84-3.65 (m, 2H), 2.87 (d, J = 4.99 Hz, 3H) |
| 184 | ¹H NMR (500 MHz, DMSO-$d_6$) δ ppm 9.03 (t, J = 6.52 Hz, 1H), 8.61 (s, 1H), 8.04 (dd, J = 7.21, 1.66 Hz, 1H), 7.97 (s, 1H), 7.63-7.43 (m, 6H), 7.29 (dd, J = 6.94, 1.66 Hz, 1H), 6.41 (s, 1H), 6.37 (t, J = 7.21 Hz, 1H), 4.49-4.11 (m, 2H), 2.87 (d, J = 4.99 Hz, 3H) |
| 185 | ¹H NMR (500 MHz, DMSO-$d_6$) δ ppm 8.74 (t, J = 5.55 Hz, 1H), 8.57 (s, 1H), 8.06 (d, J = 7.07 Hz, 1H), 7.87 (s, 1H), 7.61-7.51 (m, 2H), 7.50-7.41 (m, 4H), 7.28 (d, J = 6.73 Hz, 1H), 6.46 (t, J = 7.07 Hz, 1H), 6.36 (s, 1H), 3.58 (m, 1H), 2.88 (s, 2H), 2.86 (d, J = 4.71 Hz, 3H), 2.72 (s, 2H) |
| 186 | ¹H NMR (500 MHz, DMSO-$d_6$) δ ppm 8.79 (br. s, 1H), 8.60 (s, 1H), 8.02 (d, J = 7.07 Hz, 1H), 7.89 (s, 1H), 7.61-7.53 (m, 2H), 7.52-7.43 (m, 4H), 7.30 (d, J = 6.73 Hz, 1H), 6.43 (t, J = 7.07 Hz, 1H), 6.38 (s, 1H), 3.62-3.55 (m, 2H), 3.53-3.48 (m, 2H), 3.26 (s, 3H), 2.87 (d, J = 4.04 Hz, 3H) |
| 187 | ¹H NMR (500 MHz, DMSO-$d_6$) δ ppm 8.64 (t, J = 5.72 Hz, 1H), 8.58 (s, 1H), 7.95 (d, J = 7.07 Hz, 1H), 7.85 (s, 1H), 7.59-7.52 (m, 2H), 7.51-7.42 (m, 4H), 7.31 (d, J = 6.40 Hz, 1H), 6.37 (t, J = 7.07 Hz, 1H), 6.33 (s, 1H), 3.34 (t, J = 6.20 Hz, 2H), 2.86 (d, J = 4.71 Hz, 3H), 1.46 (quin, J = 6.23 Hz, 1H), 1.36-1.24 (m, 1H), 0.85 (t, J = 7.40 Hz, 6H) |
| 188 | ¹H NMR (500 MHz, DMSO-$d_6$) δ ppm 8.58-8.43 (m, 2H), 8.17 (d, J = 7.07 Hz, 1H), 7.88 (s, 1H), 7.59-7.51 (m, 2H), 7.51-7.39 (m, 4H), 7.28 (d, J = 6.73 Hz, 1H), 6.48 (t, J = 7.24 Hz, 1H), 6.40 (s, 1H), 4.98 (d, J = 3.37 Hz, 1H), 4.00 (br. s, 1H), 3.89 (br. s, 1H), 2.93-2.80 (m, 3H), 1.85-1.26 (m, 8H) |
| 189 | ¹H NMR (500 MHz, DMSO-$d_6$) δ ppm 8.57 (s, 1H), 8.47 (d, J = 6.73 Hz, 1H), 8.00 (d, J = 7.07 Hz, 1H), 7.87 (s, 1H), 7.61-7.52 (m, 2H), 7.47 (d, J = 7.07 Hz, 4H), 7.30 (d, J = 6.73 Hz, 1H), 6.44-6.28 (m, 2H), 5.02 (br. s, 1H), 4.12-4.02 (m, 1H), 3.98-3.90 (m, 1H), 2.86 (d, J = 3.37 Hz, 3H), 2.11 (d, J = 7.40 Hz. 1H), 1.93-1.81 (m, 1H), 1.77-1.58 (m, 2H), 1.57-1.39 (m, 2H) |
| 190 | ¹H NMR (500 MHz, DMSO-$d_6$) δ ppm 9.42 (t, J = 6.06 Hz, 1H), 8.66 (s, 1H), 8.62 (d, J = 4.04 Hz, 1H), 8.07-7.99 (m, 2H), 7.94 (s, 1H), 7.80 (d, J = 8.08 Hz, 1H), 7.76 (d, J = 3.03 Hz, 1H), 7.66 (d, J = 3.03 Hz, 1H), 7.52 (dd, J = 7.40, 4.38 Hz, 2H), 7.44 (d, J = 6.73 Hz, 1H), 6.38 (s, 1H), 6.16 (t, J = 7.24 Hz, 1H), 4.91 (d, J = 6.06 Hz, 2H), 2.87 (d, J = 4.71 Hz, 3H) |
| 191 | ¹H NMR (500 MHz, DMSO-$d_6$) δ ppm 8.64 (d, J = 4.16 Hz, 1H), 8.57 (s, 1H), 7.97 (dd, J = 7.21, 1.66 Hz, 1H), 7.91 (s, 1H), 7.58-7.53 (m, 2H), 7.50-7.45 (m, 4H), 7.29 (dd, J = 6.94, 1.66 Hz, 1H), 6.38 (s, 1H), 6.36 (t, J = 7.07 Hz, 1H), 4.97-4.79 (m, 1H), 3.04-2.97 (m, 1H), 2.87 (d, J = 4.99 Hz, 3H), 1.30-1.21 (m, 1H), 1.05-0.95 (m, 1H) |
| 192 | ¹H NMR (500 MHz, DMSO-$d_6$) δ ppm 9.40 (t, J = 6.06 Hz, 1H), 8.68 (s, 1H), 8.23 (q, J = 8.08 Hz, 1H), 8.05 (d, J = 7.07 Hz, 1H), 7.94 (s, 1H), 7.79 (d, J = 7.40 Hz, 1H), 7.76 (d, J = 3.03 Hz, 1H), 7.66 (d, J = 3.37 Hz, 1H), 7.52 (d, J = 4.71 Hz, 1H), 7.43 (d, J = 6.73 Hz, 1H), 7.34 (d, J = 8.08 Hz, 1H), 6.38 (s, 1H), 6.18 (t, J = 7.24 Hz, 1H), 4.90 (d, J = 6.06 Hz, 2H), 2.92-2.83 (m, 3H) |
| 193 | ¹H NMR (500 MHz, DMSO-$d_6$) δ ppm 9.29 (t, J = 5.89 Hz, 1H), 8.65 (s, 1H), 8.50 (d, J = 4.38 Hz, 1H), 8.22 (q, J = 8.08 Hz, 1H), 8.02 (d, J = 7.07 Hz, 1H), 7.97-7.88 (m, 1H), 7.85-7.73 (m, 2H), 7.51 (d, J = 4.71 Hz, 1H), 7.43 (d, J = 7.74 Hz, 1H), 7.37 (d, J = 6.73 Hz, 1H), 7.33 (d, J = 6.39 Hz, 1H), 7.31-7.26 (m, 1H), 6.37 (s, 1H), 5.96 (t, J = 7.24 Hz, 1H), 4.72 (d, J = 5.72 Hz, 2H), 2.87 (d, J = 4.71 Hz, 3H) |
| 194 | ¹H NMR (500 MHz, DMSO-$d_6$) δ ppm 8.73 (t, J = 5.72 Hz, 1H), 8.57 (s, 1H), 8.02 (d, J = 7.07 Hz, 1H), 7.86 (s, 1H), 7.61-7.51 (m, 2H), 7.50-7.40 (m, 4H), 7.33-7.23 (m, 1H), 6.40 (t, J = 7.07 Hz, 1H), 6.32 (s, 1H), 4.59 (t, J = 5.72 Hz, 1H), 4.49 (t, J = 5.72 Hz, 1H), 3.44 (m, 2H), 2.92-2.78 (m, 3H), 2.06-1.83 (m, 2H) |
| 195 | ¹H NMR (500 MHz, DMSO-$d_6$) δ ppm 8.95 (s, 1H), 8.62 (br. s, 1H), 8.38 (d, J = 7.07 Hz, 1H), 8.10 (d, J = 7.07 Hz, 1H), 7.93 (s, 1H), 7.54 (br. s, 1H), 6.65 (t, J = 7.91 Hz, 1H), 6.41 (s, 1H), 5.00-4.70 (m, 1H), 3.01-2.93 (m, 1H), 2.88 (d, J = 4.71 Hz, 3H), 2.82-2.68 (m, 3H), 1.23 (br. s, 1H), 1.03-0.85 (m, 1H) |
| 196 | ¹H NMR (400 MHz, DMSO-$d_6$) δ ppm 8.67-8.56 (m, 2H), 8.09 (t, J = 1.65 Hz, 1H), 8.03-7.94 (m, 2H), 7.91 (s, 1H), 7.89 (ddd, J = 8.16, 2.05, 1.04 Hz, 1H), 7.82-7.72 (m, 1H), 7.49 (d, J = 4.89 Hz, 1H), 7.36 (dd, J = 6.91, 1.65 Hz, 1H), 6.45-6.31 (m, 2H), 4.81 (td, J = 5.59, 3.12 Hz, 1H), 3.04-2.96 (m, 1H), 2.86 (d, J = 4.89 Hz, 3H), 1.24 (br. s, 1H), 1.09-0.92 (m, 1H) |
| 197 | ¹H NMR (400 MHz, DMSO-$d_6$) δ ppm 8.70 (t, J = 6.71 Hz, 1H), 8.63 (dd, J = 4.84, 1.10 Hz, 1H), 8.60 (s, 1H), 8.03 (td, J = 7.76, 1.87 Hz, 1H), 7.98 (dd, J = 7.37, 1.65 Hz, 1H), 7.87 (s, 1H), 7.82 (d, J = 8.14 Hz, 1H), 7.58-7.40 (m, 3H), 6.47 (t, J = 7.15 Hz, 1H), 6.36 (s, 1H), 4.58 (t, J = 5.83 Hz, 1H), 3.31 (d, J = 5.94 Hz, 2H), 3.12 (d, J = 5.94 Hz, 2H), 2.87 (d, J = 4.84 Hz, 3H), 0.80 (s, 6H) |

TABLE 2-continued

¹H NMR data

| Example # | ¹H NMR data |
|---|---|
| 298 | ¹H NMR (400 MHz, DMSO-d₆) δ ppm 8.77-8.66 (m, 1H), 8.62 (s, 1H), 7.98-7.81 (m, 3H), 7.66-7.57 (m, 1H), 7.53-7.38 (m, 1H), 6.73 (d, J = 2.42 Hz, 1H), 6.43 (s, 1H), 6.36 (s, 1H), 4.57 (s, 1H), 3.84-3.69 (m, 1H), 3.28 (d, J = 5.94 Hz, 2H), 3.10 (d, J = 5.94 Hz, 2H), 2.86 (d, J = 4.84 Hz, 3H), 1.13-1.06 (m, 1H), 1.04-0.93 (m, 1H), 0.79 (s, 6H) |
| 299 | ¹H NMR (400 MHz, DMSO-d₆) δ ppm 8.74-8.64 (m, 2H), 8.06 (d, J = 1.54 Hz, 1H), 8.05-8.02 (m, 1H), 7.94 (s, 1H), 7.81 (d, J = 8.80 Hz, 1H), 7.57 (m, 1H), 7.55-7.49 (m, 1H), 6.52 (t, J = 7.15 Hz, 1H), 6.41 (s, 1H), 3.31 (d, J = 6.60 Hz, 2H), 3.12 (s, 2H), 2.87 (s, 3H), 2.71 (s, 3H), 0.81 (s, 6H) |
| 200 | ¹H NMR (400 MHz, DMSO-d₆) δ ppm 8.66 (s, 2H), 8.08-7.99 (m, 2H), 7.85 (s, 1H), 7.80 (s, 1H), 7.61-7.54 (m, 1H), 7.52-7.42 (m, 1H), 6.48 (t, J = 7.15 Hz, 1H), 6.37 (s, 1H), 3.23 (t, J = 6.49 Hz, 2H), 2.86 (d, J = 4.84 Hz, 3H), 2.71 (s, 3H), 1.88-1.75 (m, 1H), 0.90 (d, J = 6.60 Hz, 6H) |
| 201 | ¹H NMR (400 MHz, DMSO-d₆) δ ppm 8.77-8.59 (m, 2H), 8.11-7.99 (m, 2H), 7.93-7.85 (m, 1H), 7.81 (d, J = 8.80 Hz, 1H), 7.57 (dd, J = 6.93, 1.65 Hz, 1H), 7.49 (q, J = 4.77 Hz, 1H), 6.52 (t, J = 7.15 Hz, 1H), 6.37 (s, 1H), 3.33 (d, J = 6.16 Hz, 2H), 2.87 (d, J = 4.84 Hz, 3H), 2.71 (s, 3H), 1.04 (s, 3H), 0.48-0.41 (m, 2H), 0.27-0.21 (m, 2H) |
| 202 | ¹H NMR (400 MHz, DMSO-d₆) δ ppm = 8.65-8.62 (m, 1H), 8.59 (d, J = 3.5 Hz, 1H), 8.13-8.09 (m, 2H), 8.02 (dd, J = 7.4, 1.4 Hz, 1H), 7.87-7.80 (m, 3H), 7.47 (d, J = 4.8 Hz, 1H), 7.38 (dd, J = 6.9, 1.6 Hz, 1H), 6.44 (t, J = 7.2 Hz, 1H), 6.38 (s, 1H), 3.32 (s, 3H), 2.96-2.89 (m, 1H), 2.86 (d, J = 4.8 Hz, 3H), 0.84-0.78 (m, 2H), 0.61-0.56 (m, 2H). |
| 203 | ¹H NMR (400 MHz, DMSO-d₆) δ ppm = 8.64 (s, 1H), 8.57 (d, J = 4.0 Hz, 1H), 8.30 (s, 1H), 7.93 (dd, J = 7.4, 1.6 Hz, 1H), 7.89 (d, J = 0.8 Hz, 1H), 7.85-7.84 (m, 1H), 7.51 (dd, J = 7.0, 1.5 Hz, 1H), 7.46 (q, J = 5.0 Hz, 1H), 6.40 (t, J = 7.2 Hz, 1H), 6.37 (s, 1 H), 3.91 (s, 3H), 2.91-2.87 (m, 1H), 2.86 (d, J = 4.8 Hz, 3 H), 0.82-0.76 (m, 2H), 0.58-0.53 (m, 2H) |
| 204 | ¹H NMR (400 MHz, DMSO-d₆) δ ppm = 8.61 (s, 1H), 8.59 (d, J = 4.0 Hz, 1H), 8.32-8.31 (m, 1H), 8.30 (d, J = 0.8 Hz, 1H), 8.01-7.98 (m, 1H), 7.89 (dd, J = 8.8, 2.8 Hz, 1H), 7.46 (q, J = 4.3 Hz, 1H), 7.34 (dd, J = 6.8, 1.8 Hz, 1H), 7.01-6.97 (m, 1H), 6.40 (t, J = 7.2 Hz, 1H), 6.37 (s, 1H), 3.93 (s, 3H), 2.95-2.88 (m, 1H), 2.85 (d, J = 5.0 Hz, 3H), 0.84-0.78 (m, 2H), 0.60-0.56 (m, 2H) |
| 205 | ¹H NMR (400 MHz, DMSO-d₆) δ ppm = 8.61-8.57 (m, 2H), 8.16-8.15 (m, 1H), 7.96 (dd, J = 7.4, 1.6 Hz, 1H), 7.85 (s, 1H), 7.65-7.61 (m, 1H), 7.45 (q, J = 4.4 Hz, 1H), 7.29 (dd, J = 6.9, 1.6 Hz, 1H), 6.75 (d, J = 9.0 Hz, 1H), 6.37 (t, J = 7.2 Hz, 2H), 3.09-3.08 (2s, 6H), 2.95-2.88 (m, 1H), 2.85(d, J = 5.0 Hz, 3H), 0.84-0.78 (m, 2H), 0.60-0.55 (m, 2H) |
| 206 | ¹H NMR (400 MHz, DMSO-d₆) δ ppm = 8.60-8.57 (m, 2H), 8.10 (d, J = 1.8 Hz, 1H), 7.99 (s, 1H), 7.97 (dd, J = 7.7, 1.6 Hz, 1H), . 7.86 (s, 1H), 7.45 (d, J = 4.9 Hz, 1H), 7.29 (dd, J = 6.9, 1.7 Hz, 1H), 6.69-657 (br. s, 1H), 6.40-6.35 (m, 2H), 2.94-2.88 (m, 1H), 2.86 (s, 6H), 0.84-0.78 (m, 2H), 0.60-0.55 (m, 2H) |
| 207 | ¹H NMR (400 MHz, DMSO-d₆) δ ppm = 8.72 (t, J = 6.6 Hz, 1H), 8.49 (s, 1H), 7.86-7.83 (m, 2H), 7.46 (q, J = 4.6 Hz, 1H), 7.33 (dd, J = 6.8, 1.8 Hz, 1H), 6.36-6.33 (m, 1H), 6.31 (d, J = 7.2 Hz, 1H), 3.54 (s, 3H), 3.25 (d, J = 6.6 Hz, 2H), 2.87 (d, J = 4.9 Hz, 3H), 0.83 (s, 9H). |
| 208 | ¹H NMR (400 MHz, DMSO-d₆) δ ppm = 8.48 (s, 1H), 8.42 (d, J = 7.5 Hz, 1H), 7.90 (dd, J = 7.3, 1.8 Hz, 1H), 7.83 (s, 1H), 7.43 (q, J = 4.9 Hz, 1H), 7.34 (dd, J = 6.8, 1.7 Hz, 1H), 6.35 (s, 1H), 6.21 (t, J = 7.1 Hz, 1H), 4.33-4.22 (m, 1H), 3.55 (s, 3H), 2.86 (d, J = 4.8 Hz, 3H), 2.04-1.95 (m, 2H), 1.71-1.62 (m, 2H), 1.62-1.52 (m, 2H), 1.46-1.36 (m, 2H). |
| 209 | ¹H NMR (400 MHz, DMSO-d₆) δ ppm = 8.52-8.49 (m, 1H), 8.36 (d, J = 7.8 Hz, 1H), 7.90 (dd, J = 7.3, 1.8 Hz, 1H), 7.83 (s, 1H), 7.43 (q, J = 4.8 Hz, 1H), 7.35 (dd, J = 6.8, 1.8 Hz, 1H), 6.36 (s, 1H), 6.25 (t, J = 7.1 Hz, 1H), 4.22-4.12 (m, 1H), 3.55 (s, 3H), 2.86 (d, J = 4.8 Hz, 3H), 1.20 (d, J = 6.6 Hz, 6H) |
| 210 | ¹H NMR (400 MHz, DMSO-d₆) δ ppm = 8.57 (t, J = 5.6 Hz, 1H), 8.51 (s, 1H), 7.93 (dd, J = 7.4, 1.8 Hz, 1H), 7.83 (s, 1H), 7.43 (q, J = 4.7 Hz, 1H), 7.34 (dd, J = 6.8, 1.8 Hz, 1H), 6.35 (s, 1H), 6.28 (t, J = 7.1 Hz, 1H), 3.55 (s, 3H), 3.39 (dq, J = 7.1, 5.9 Hz, 2H), 2.86 (d, J = 4.9 Hz, 3H), 1.17 (t, J = 7.2 Hz, 3H). |
| 211 | ¹H NMR (400 MHz, DMSO-d₆) δ ppm = 8.45 (s, 1H), 8.15 (s, 1H), 7.90 (dd, J = 7.3, 1.8 Hz, 1H), 7.80 (s, 1H), 7.42 (q, J = 4.8 Hz, 1H), 7.32 (dd, J = 6.8, 1.7, Hz, 1H), 6.34 (s, 1H), 6.23 (t, J = 7.1 Hz, 1H), 3.54 (s, 3H), 2.86 (d, J = 4.9 Hz, 3H), 1.40 (s, 9 H). |
| 212 | ¹H NMR (400 MHz, DMSO-d₆) δ ppm = 10.52-10.50 (m, 1H), 8.59 (s, 1H), 8.05 (dd, J = 7.3, 1.8 Hz, 1H), 7.99 (s, 1H), 7.65-7.60 (m, 2H), 7.50 (q, J = 4.8 Hz, 1H), 7.40-7.33 (m, 3H), 7.16-7.11 (m, 1H), 6.38 (s, 1H), 6.07 (t, J = 7.1 Hz, 1H), 3.54 (s, 3 H), 2.89 (d, J = 4.8 Hz, 3H) |
| 213 | ¹H NMR (400 MHz, DMSO-d₆) δ ppm = 8.57 (d, J = 4.0 Hz, 1H), 8.51 (s, 1H), 7.86 (d, J = 1.6 Hz, 1H), 7.84 (s, 1H), 7.45-7.38 (m, 2H), 6.37-6.31 (m, 1H), 5.19-5.16 (m, 1H), 2.93-2.87 (m, 1H), 2.86 (d, J = 4.8 Hz, 3H), 1.35 (d, J = 6.8 Hz, 6H), 0.82-0.76 (m, 2H), 0.56-0.52 (m, 2H). |

TABLE 2-continued

<sup>1</sup>H NMR data

| Example # | <sup>1</sup>H NMR data |
|---|---|
| 214 | <sup>1</sup>H NMR (400 MHz, DMSO-d$_6$) δ ppm = 8.65-8.58 (m, 1H), 8.50 (s, 1H), 7.87 (dd, J = 7.3, 1.8 Hz, 1H), 7.83 (s, 1H), 7.43-7.43 (m, 1H), 7.47-7.41 (m, 1H), 6.36-6.28 (m, 2H), 3.58-3.53 (m, 3H), 3.44-3.39 (m, 2H), 2.86 (d, J = 4.9 Hz, 3H), 2.60 (m, 1H), 2.01-1.90 (m, 2H), 1.86-1.76 (m, J = 2.0 Hz, 2H), 1.71-1.60 (m, 2H). |
| 215 | <sup>1</sup>H NMR (300 MHz, DMSO-d$_6$) δ ppm = 8.51 (s, 0.24H), 8.40 (s, 1H), 8.31 (d, J = 8.2 Hz, 1H), 7.85 (s, 1H), 7.84-7.80 (m, 1H), 7.47 (d, J = 4.9 Hz, 1H), 7.40-7.32 (m, J = 6.7, 1.8 Hz, 1H), 6.36 (s, 0.2H), 6.32 (s, 1H), 6.26-6.18 (m, 1.1H), 4.15-4.13 (br. s, 1H), 3.56-3.53 (m, 4H), 2.86 (d, J = 4.9 Hz, 4H), 2.01 (br. s, 1.2H), 1.75(m, 1.25H), 1.48-1.42 (br. s, 3H), 1.23-1.11 (m, 8H), 0.87 (d, J = 6.3 Hz, 1H), 0.80 (d, J = 7.1 Hz, 3H). |
| 216 | <sup>1</sup>H NMR (400 MHz, DMSO-d$_6$) δ ppm = 9.20 (s, 1H), 8.55 (s, 1H), 8.01 (dd, J = 7.3, 1.7 Hz, 1H), 7.93 (s, 1H), 7.45 (d, J = 4.5 Hz, 1H), 7.41 (dd, J = 7.1, 1.7 Hz, 1H), 6.40-6.34 (m, 2H), 5.18 (quin, J = 6.8 Hz, 1H), 2.86 (d, J = 4.9 Hz, 3H), 1.66-1.61 (m, J = 5.5 Hz, 3H), 1.38-1.31 (m, J = 6.8 Hz, 7H) |
| 217 | <sup>1</sup>H NMR (400 MHz, DMSO-d$_6$) δ ppm = 8.71 (t, J = 6.6 Hz, 1H), 8.48 (s, 1H), 7.86 (s, 1H), 7.84 (dd, J = 7.3, 1.7 Hz, 1H), 7.45 (q, J = 4.7 Hz, 1H), 7.37 (dd, J = 7.1, 1.7 Hz, 1H), 6.38 (t, J = 7.2 Hz, 1H), 6.34 (s, 1H), 5.16 (quin, J = 6.8 Hz, 1H), 4.57 (t, J = 5.9 Hz, 1H), 3.29-3.25 (m, 2H), 3.10 (d, J = 5.8 Hz, 1H), 2.87 (d, J = 4.9 Hz, 3H), 1.34 (d, J = 6.8 Hz, 6H), 0.78 (s, 6H) |
| 218 | <sup>1</sup>H NMR (400 MHz, DMSO-d$_6$) δ ppm = 8.58 (d, J = 4.0 Hz, 1H), 8.55 (s, 1H), 7.85 (d, J = 1.4 Hz, 1H), 7.84-7.83 (m, 1H), 7.45-7.40 (m, 2H), 6.35 (s, 1H), 6.26 (t, J = 7.3 Hz, 1H), 2.94-2.87 (m, 1H), 2.85 (d, J = 4.9 Hz, 3H), 1.68 (s, 9H), 0.83-0.77 (m, 2H), 0.57-0.53 (m, 2H) |
| 219 | <sup>1</sup>H NMR (400 MHz, DMSO-d$_6$) δ ppm = 9.19 (s, 1H), 8.58 (s, 1H), 8.00 (dd, J = 7.2, 1.4 Hz, 1H), 7.92 (s, 1H), 7.46-7.40 (m, 2 H), 6.36 (s, 1H), 6.29 (t, J = 7.3 Hz, 1H), 2.85 (d, J = 4.9 Hz, 3H), 1.68 (s, 9H), 1.65-1.61 (m, 2H), 1.36-1.31 (m, 2H). |
| 220 | <sup>1</sup>H NMR (400 MHz, DMSO-d$_6$) δ ppm = 8.64 (d, J = 4.1 Hz, 2H), 7.86-7.84 (m, 1H), 7.83 (s, 1H), 7.40-7.28 (m, 1H), 7.26 (dd, J = 7.2, 1.6, Hz, 1H), 6.40 (t, J = 7.2 Hz, 2H), 5.48-5.43 (m, 1 H), 4.06 (dt, J = 8.2, 6.1 Hz, 1H), 3.92-3.85 (m, 2H), 3.81 (dt, J = 8.2, 6.1 Hz, 1H), 2.90-2.85 (m, 5H), 2.10-2.05 (m, 1H), 0.83-0.76 (m, 2H), 0.52-0.47 (m, 2H) |
| 221 | <sup>1</sup>H NMR (400 MHz, DMSO-d$_6$) δ ppm = 8.69 (d, J = 8.0 Hz, 1H), 8.56 (s, 1H), 7.99 (dd, J = 7.3, 1.6 Hz, 1H), 7.83 (s, 1H), 7.44 (d, J = 4.8 Hz, 1H), 7.28 (dd, J = 7.1, 1.7 Hz, 1H), 6.39-6.33 (m, 2H), 5.54-5.47 (m, 1H), 4.50 (q, J = 7.7 Hz, 1H), 4.08 (dt, J = 8.3, 6.2 Hz, 1H), 3.92-3.89 (m, J = 2.7 Hz, 2H), 3.78 (dt, J = 8.6, 6.5 Hz, 1H), 2.86 (d, J = 4.8 Hz, 4H), 2.33-2.29 (m, 2H), 1.98-1.89 (m, 3H), 1.77-1.67 (m, 2H) |
| 222 | <sup>1</sup>H NMR (400 MHz, DMSO-d$_6$) δ ppm = 8.51 (s, 1H), 8.40 (d, J = 7.3 Hz, 1H), 7.91 (dd, J = 7.3, 1.6 Hz, 1H), 7.83 (s, 1H), 7.46-7.41 (m, 1H), 7.26 (dd, J = 7.1, 1.7 Hz, 1H), 6.36 (s, 1H), 6.29 (t, J = 7.2 Hz, 1H), 5.53-5.46 (m, 1H), 4.28 (q, J = 7.4 Hz, 1 H), 4.08 (dt, J = 8.4, 6.0 Hz, 1H), 3.94-3.85 (m, J = 5.7 Hz, 2 H), 3.78 (dt, J = 8.6, 6.3 Hz, 1H), 2.86 (d, J = 4.9 Hz, 3H), 2.48-2.43 (m, 1H), 2.06-1.95 (m, 3H), 1.71-1.62 (m, 2H), 1.62-1.53 (m, 2H), 1.47-1.38 (m, 2H) |
| 223 | <sup>1</sup>H NMR (400 MHz, DMSO-d$_6$) δ ppm = 8.70 (br. m, 1H), 8.578 (br. m, 1H), 8.05 (br. m, 1H), 7.86 (br. m, 1H), 7.74 (br. s, 2H), 7.49 (br. m, 1H), 7.24 (br. m, 2H), 6.55 (br. m, 1H), 6.37 (br. s, 1 H), 2.89-2.88 (br. m, 4H), 0.82-0.76 (m, 2H), 0.58-0.53 (m, 2H) |
| 224 | <sup>1</sup>H NMR (400 MHz, DMSO-d$_6$) δ ppm = 8.57 (d, J = 4.0 Hz, 1H), 8.49 (s, 1H), 7.86 (d, J = 1.6 Hz, 1H), 7.85 (s, 1H), 7.44 (d, J = 4.8 Hz, 1H), 7.38 (dd, J = 7.1, 1.6 Hz, 1H), 6.52 (d, J = 14.4 Hz, 2H), 4.80-4.76 (m, 1H), 3.62-3.56 (m, 4H), 2.89 (s, 3 H), 2.88-2.86 (m, 1H), 2.52-2.34 (m, 4H), 2.36-2.31 (m, 1H), 2.10-2.0 (m, 2H), 1.93-1.75 (m, 4H), 1.50-1.41 (m, 2H), 0.83-0.76 (m, 2H), 0.56-0.52 (m, 2H) |
| 225 | <sup>1</sup>H NMR (400 MHz, DMSO-d$_6$) δ ppm = 8.70 (d, J = 8.0 Hz, 1H), 8.52 (s, 1H), 8.00 (d, J = 7.3 Hz, 1H), 7.85 (s, 1H), 7.47 (d, J = 4.9 Hz, 1H), 7.37 (dd, J = 7.1, 1.6 Hz, 1H), 6.37 (d, J = 14.4 Hz, 2H), 4.86-4.77 (m, 1H), 4.52 (q, J = 8.4 Hz, 1H), 4.04 (d, J = 11.0 Hz, 1H), 3.77-3.65 (m, 2H), 3.46 (d, J = 12.7 Hz, 2H), 3.25-3.13 (m, 4H), 2.88 (s, 3H), 2.37-2.18 (m, 4H), 2.03-1.67 (m, 10H) |
| 226 | <sup>1</sup>H NMR (400 MHz, DMSO-d$_6$) δ ppm = 8.56 (d, J = 3.8 Hz, 1H), 8.48 (s, 1H), 7.86-7.81 (m, 2H), 7.45-7.39 (m, 2H), 6.34-6.29 (m, 2H), 4.83-4.75 (m, 1H), 2.89 (d, J = 4.0 Hz, 1H), 2.86 (d, J = 4.8 Hz, 3H), 1.89-1.76 (m, 5H), 1.68 (dd, J = 12.0, 3.3 Hz, 2H), 1.43 (d, J = 12.8 Hz, 2H), 1.29-1.20 (m, 1H), 0.79 (dd, J = 1.9, 6.9 Hz, 2H), 0.53 (dd, J = 2.0, 4.0 Hz, 2H) |
| 227 | <sup>1</sup>H NMR (400 MHz, DMSO-d$_6$) δ ppm = 8.56 (d, J = 4.0 Hz, 1H), 8.48 (s, 1H), 7.86-7.82 (m, 2H), 7.46-7.40 (m, 1H), 7.38 (dd, J = 7.1, 1.5 Hz, 1H), 6.34-6.28 (m, 2H), 4.81-4.71 (m, 1H), 4.68 (br. s., 1H), 4.14 (dd, J = 5.6, 3.6, Hz, 1H), 2.93-2.87 (m, 1H), 2.86 (d, J = 5.0 Hz, 3H), 1.96 (d, J = 9.5 Hz, 2H), 1.85-1.72 (m, 2H), 1.65-1.60 (m, 1H), 1.44-1.21 (m, 4H), 0.82-0.75 (m, 2H), 0.55-0.50 (m, 2H) |

TABLE 2-continued

¹H NMR data

| Example # | ¹H NMR data |
|---|---|
| 228 | ¹H NMR (400 MHz, DMSO-$d_6$) δ ppm = 8.57 (d, J = 4.0 Hz, 1H), 8.51 (s, 1H), 7.86 (dd, J = 7.3, 1.7 Hz, 1H), 7.83 (s, 1H), 7.46 (dd, J = 7.0, 1.7 Hz, 1H), 7.42 (q, J = 4.9 Hz, 1H), 6.36-6.31 (t, J = 7.6 Hz, 2H), 5.16-5.06 (m, 1H), 2.94-2.87 (m, 1H), 2.85 (d, J = 4.9 Hz, 3H), 2.42-2.25 (m, 4H), 1.85-1.76 (m, 2 H), 0.82-0.76 (m, 2H), 0.56-0.51 (m, 2H) |
| 229 | ¹H NMR (400 MHz, DMSO-$d_6$) δ ppm = 9.19 (s, 1H), 8.55 (s, 1H), 8.02 (dd, J = 7.3, 1.6 Hz, 1H), 7.92 (s, 1H), 7.49-7.42 (m, J = 1.6 Hz, 2H), 6.39-6.36 (m, 1H), 6.35 (s, 1H), 5.17-5.07 (m, 1 H), 2.85 (d, J = 4.8 Hz, 3H), 2.43-2.26 (m, 4H), 1.86-1.76 (m, 2H), 1.65-1.60 (m, 2H), 1.35-1.29 (m, 2H) |
| 230 | ¹H NMR (400 MHz, DMSO-$d_6$) δ ppm = 8.73-8.67 (t, J = 6.8 Hz, 1 H), 8.48 (s, 1H), 7.86 (s, 1H), 7.84 (d, J = 1.6 Hz, 1H), 7.48-7.42 (m, 2H), 6.38 (t, J = 7.1 Hz, 1H), 6.34 (s, 1H), 5.11 (t, J = 9.3 Hz, 1H), 4.59-4.55 (t, J = 6 Hz, 1H), 3.29 (s, 2H), 3.10 (d, J = 5.8 Hz, 2H), 2.86 (d, J = 4.9 Hz, 3H), 2.39-2.26 (m, J = 3.3 Hz, 4H), 1.85-1.76 (m, 2H), 0.78 (s, 6H) |
| 231 | ¹H NMR (400 MHz, DMSO-$d_6$) δ ppm = 8.98 (d, J = 1.4 Hz, 1H), 8.73 (d, J = 8.0 Hz, 1H), 8.64 (s, 1H), 8.11 (dd, J = 7.3, 1.7 Hz, 1H), 7.85 (s, 1H), 7.49 (q, J = 4.5 Hz, 1H), 7.42 (dd, J = 6.9, 1.7 Hz, 1H), 6.42 (t, J = 7.2 Hz, 1H), 6.35 (s, 1H), 4.54-4.48 (m, 1H), 2.87 (d, J = 4.9 Hz, 3H), 2.58 (d, J = 2.6 Hz, 3H), 2.37-2.28 (m, 2H), 2.04-1.93 (m, 2H), 1.78-1.68 (m, 2H) |
| 232 | ¹H NMR (400 MHz, DMSO-$d_6$) δ ppm = 8.72 (d, J = 8.0 Hz, 1H), 8.55 (s, 1H), 7.99 (dd, J = 7.3, 1.8 Hz, 1H), 7.84 (s, 1H), 7.43-7.34 (m, 2H), 6.46 (s, 1H), 6.29 (t, J = 7.1 Hz, 1H), 4.53-4.49 (m, 1H), 3.57 (s, 3H), 3.31-3.25 (m, 2H), 2.38-2.25 (m, 2H), 2.01-1.88 (m, 2H), 1.78-1.67 (m, 2H), 1.24 (t, J = 7.2 Hz, 3H) |
| 233 | ¹H NMR (400 MHz, DMSO-$d_6$) δ ppm 0.90 (t, J = 7.37 Hz, 6 H) 1.39-1.51 (m, 2 H) 1.58-1.70 (m, 2 H) 2.72 (s, 3 H) 2.87 (d, J = 4.83 Hz, 3 H) 3.88-3.98 (m, 1 H) 6.42-6.44 (m, 2 H) 7.49 (q, J = 4.68 Hz, 1 H) 7.59 (dd, J = 7.03, 1.69 Hz, 1 H) 7.82 (d, J = 8.97 Hz, 1 H) 7.98 (dd, J = 7.31, 1.73 Hz, 1 H) 8.05 (s, 1 H) 8.07 (s, 1 H) 8.24 (d, J = 9.10 Hz, 1 H) 8.66 (s, 1 H). |
| 234 | ¹H NMR (400 MHz, DMSO-$d_6$) δ ppm 1.24 (d, J = 6.78 Hz, 3 H) 2.71-2.73 (m, 3 H) 2.87 (d, J = 4.89 Hz, 3 H) 3.26(s, 3 H)3.42 (qd, J = 9.76, 4.99 Hz, 3 H) 4.28-4.36 (m, 1 H) 6.42 (s, 1 H) 6.48 (t, J = 7.18 Hz, 1 H) 7.49 (q, J = 5.10 Hz, 1 H) 7.59 (dd, J = 7.00, 1.73 Hz, 1 H) 7.82 (d, J = 8.91 Hz, 1 H) 8.04-8.05 (m, 1 H) 8.06-8.07 (m, 2 H) 8.47 (d, J = 8.47 Hz, 1 H) 8.66 (s, 1 H). |
| 235 | ¹H NMR (400 MHz, DMSO-$d_6$) δ ppm 0.87 (dd, J = 17.60, 6.56 Hz, 6 H) 1.21 (d, J = 6.53 Hz, 3 H) 1.30-1.38 (m, 1 H) 1.41-1.50 (m, 1 H) 1.57-1.66 (m, 1 H) 2.72 (s, 3 H) 2.87 (d, J = 4.89 Hz, 3 H) 4.21 (t, J = 6.53 Hz, 1 H) 6.38 (s, 1 H) 6.46 (t, J = 7.22 Hz, 1 H) 7.46-7.51 (m, 1 H) 7.61 (dd, J = 7.03, 1.69 Hz, 1 H) 7.82 (d, J = 8.97 Hz, 2 H) 8.03 (m, J = 8.85 Hz, 2 H) 8.35 (d, J = 8.60 Hz, 1 H) 8.67 (s, 1 H). |
| 236 | ¹H NMR (400 MHz, DMSO-$d_6$) δ ppm 8.67-8.64 (m, 1 H), 8.57 (s, 1 H), 8.34 (d, J = 9.7 Hz, 1 H), 8.05 (dt, J = 1.9, 7.8 Hz, 1 H), 7.96 (dd, J = 1.7, 7.3 Hz, 1 H), 7.88 (s, 2 H), 7.59-7.52 (m, 3 H), 6.43-6.36 (m, 2 H), 4.69 (d, J = 4.8 Hz, 1 H), 4.25-4.18 (m, 1 H), 3.68-3.62 (m, 1 H), 2.89 (d, J = 4.8 Hz, 3H), 2.07-1.98 (m, 2 H), 1.61-1.50 (m, 3 H), 0.90 (s, 3 H), 0.67 (s, 3 H). |
| 237 | ¹H NMR (400 MHz, DMSO-$d_6$) δ ppm 8.51 (s, 1H), 8.10 (d, J = 2.4 Hz, 1H), 7.93 (d, J = 2.4 Hz, 1H), 7.91 (s, 1H), 7.57-7.40 (m, 6H), 7.30 (d, J = 4.4 Hz, 1H), 6.33-6.29 (m, 2H), 4.61 (d, J = 4.4 Hz, 1H), 4.48-4.45 (m, 1H), 3.58 (d, J = 6.4 Hz, 1H), 2.86 (d, J = 4.8 Hz, 3H), 2.13-2.01 (m, 2H), 1.51-1.39 (m, 2H), 0.86 (s, 3H), 0.69 (s, 3H). |
| 238 | ¹H NMR (400 MHz, DMSO-$d_6$) δ ppm 8.96 (s, 1 H), 8.71-8.64 (m, 3 H), 8.03 (dd, J = 1.7, 7.3 Hz, 1 H), 7.88 (s, 1 H), 7.54 (dd, J = 1.7, 7.1 Hz, 1 H), 7.50 (q, J = 4.4 Hz, 1 H), 6.53 (t, J = 7.2 Hz, 1 H), 6.39 (s, 1 H), 4.59 (t, J = 5.8 Hz, 1 H), 3.51 (s, 1 H), 3.32 (br s., 2 H), 3.17 (d, J = 5.2 Hz, 1 H), 2.87 (d, J = 4.8 Hz, 3 H), 2.59 (s, 3 H), 0.81 (s, 6 H). |

Example 239

N-Cyclobutyl-6-((2-oxo-2H-[1,2'-bipyridin]-3-yl)amino)-9,10-dihydro-8H-imidazo[1',2':1,6]pyridazino[4,5-b][1,4]oxazine-3-carboxamide

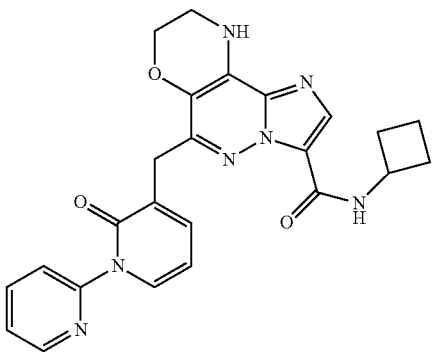 [SMILES: O=C(NC1CCC1)c1cnc2c3c(c(Cc4cccn(-c5ccccn5)c4=O)nn12)OCCN3]

Step 1: Ethyl 6-chloro-8-((2-hydroxyethyl)(4-methoxybenzyl)amino)imidazo[1,2-b]pyridazine-3-carboxylate

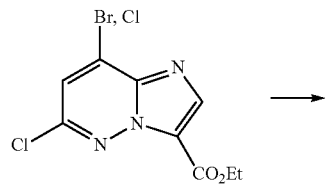

A homogeneous, light orange solution of ethyl 8-bromo-6-chloroimidazo[1,2-b]pyridazine-3-carboxylate (5.27 g, 17.29 mmol), 2-((4-methoxybenzyl)amino)ethanol (3.7600 g, 20.75 mmol) and DIPEA (6.04 ml, 34.6 mmol) in tetrahydrofuran (43.2 ml) in a sealed tube was heated to 100° C. and stirred overnight. After cooling to room temperature, this was combined with another similarly run reaction and concentrated in vacuo to give a residue which was purified by flash chromatography using an ISCO 330 g column (solid loading) eluting with 50-100% EtOAc/hexane. Appropriate fractions were collected and concentrated in vacuo to give ethyl 6-chloro-8-((2-hydroxyethyl)(4-methoxybenzyl)amino)imidazo[1,2-b]pyridazine-3-carboxylate (11.10 g, 88.2%).

Step 2: Ethyl 7-bromo-6-chloro-8-((2-hydroxyethyl)(4-methoxybenzyl)amino)imidazo[1,2-b]pyridazine-3-carboxylate

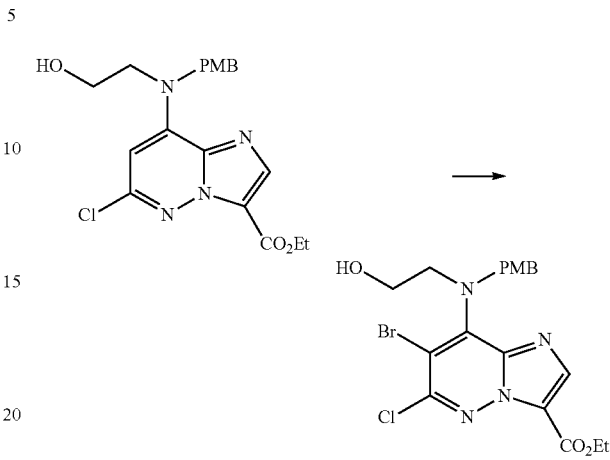

To a homogeneous, yellow solution of ethyl 6-chloro-8-((2-hydroxyethyl)(4-methoxybenzyl)amino)imidazo[1,2-b]pyridazine-3-carboxylate (4.2056 g, 10.39 mmol) in DMF (29.7 ml) under nitrogen was added 1-bromopyrrolidine-2,5-dione (2.0428 g, 11.48 mmol). After 1 h, the reaction was diluted with EA (250 mL), washed with sat aq NaHCO$_3$ (3×75 mL) and brine (75 mL), dried over Na$_2$SO$_4$, filtered and concentrated in vacuo to give a residue which was purified by flash chromatography using an ISCO 330 g column (solid loading) eluting with 20-80% EtOAc/hexane. Appropriate fractions were collected and concentrated in vacuo to give ethyl 7-bromo-6-chloro-8-((2-hydroxyethyl)(4-methoxybenzyl)amino)imidazo[1,2-b]pyridazine-3-carboxylate (4.27 g, 7.86 mmol, 76% yield) as an off-white solid.

Step 3: Ethyl 6-chloro-10-(4-methoxybenzyl)-9,10-dihydro-8H-imidazo[1',2':1,6]pyridazino[4,5-b][1,4]oxazine-3-carboxylate

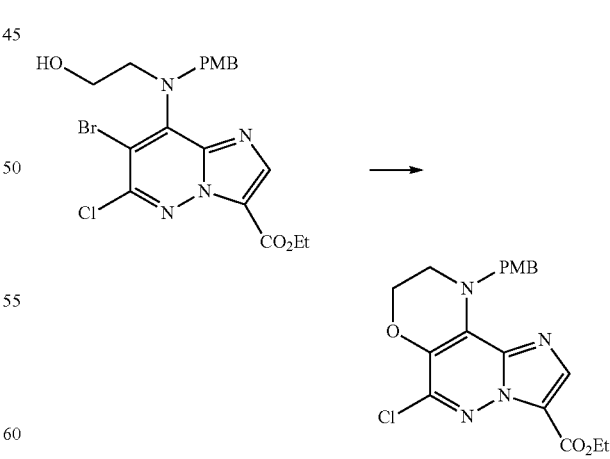

A solution of ethyl 7-bromo-6-chloro-8-((2-hydroxyethyl)(4-methoxybenzyl)amino)imidazo[1,2-b]pyridazine-3-carboxylate (2.0159 g, 4.17 mmol), [1,1'-binaphthalen]-2-yldi-tert-butylphosphine (0.664 g, 1.667 mmol), cesium carbonate (2.444 g, 7.50 mmol), and palladium(II) acetate (0.187 g, 0.833 mmol) in Toluene (41.7 ml) in a sealed pressure tube was stirred to 100° C. After stirring overnight, the reaction was cooled to room temperature, diluted with EtOAc (50 mL) and filtered through Celite. The filtrate was diluted with EtOAc (100 mL) and washed with sat aq NaHCO$_3$ (2×30 mL), dried over Na$_2$SO$_4$, filtered and concentrated in vacuo to give a residue which was purified by flash chromatography using an ISCO 120 g column (solid loading) eluting with 0-60% EtOAc/hexane. Appropriate fractions were collected and concentrated in vacuo to give ethyl 6-chloro-10-(4-methoxybenzyl)-9,10-dihydro-8H-imidazo[1',2':1,6]pyridazino[4,5-b][1,4]oxazine-3-carboxylate (0.2075 g, 0.515 mmol, 12.36% yield) as a light yellow foam.

Step 4: Ethyl 10-(4-methoxybenzyl)-6-((2-oxo-2H-[1,2'-bipyridin]-3-yl)amino)-9,10-dihydro-8H-imidazo[1',2':1,6]pyridazino[4,5-b][1,4]oxazine-3-carboxylate Step 5: 10-(4-Methoxybenzyl)-6-((2-oxo-2H-[1,2'-bipyridin]-3-yl)amino)-9,10-dihydro-8H-imidazo[1',2':1,6]pyridazino[4,5-b][1,4]oxazine-3-carboxylic acid

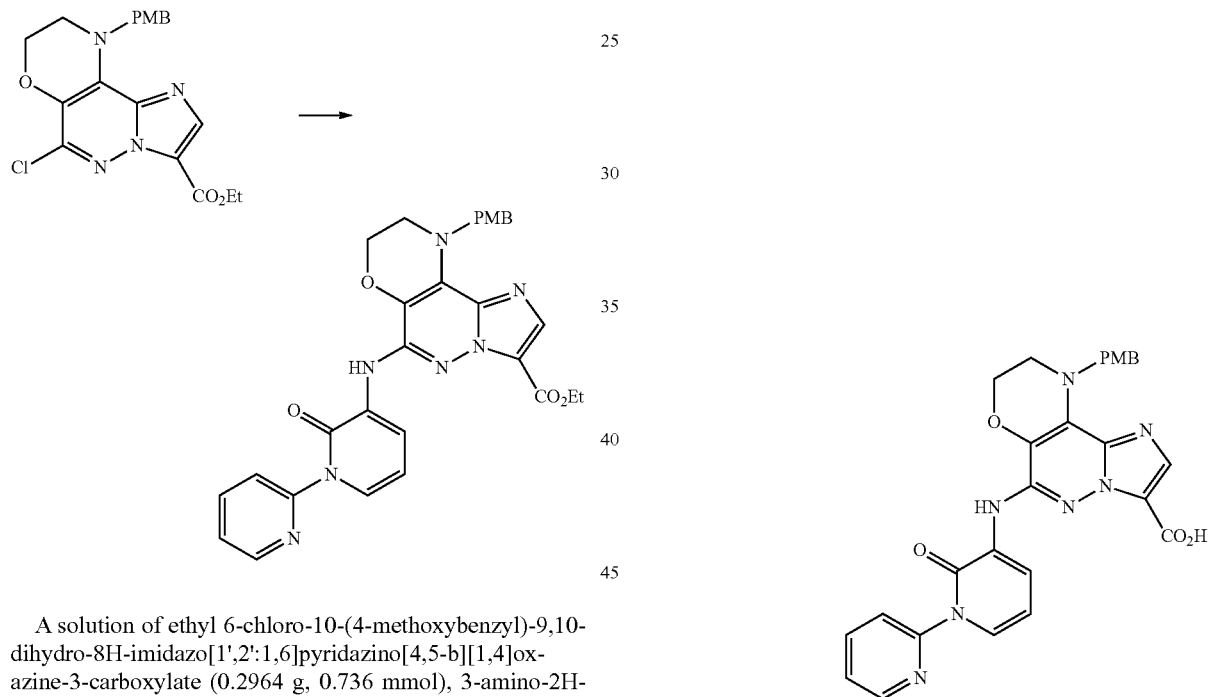

A solution of ethyl 6-chloro-10-(4-methoxybenzyl)-9,10-dihydro-8H-imidazo[1',2':1,6]pyridazino[4,5-b][1,4]oxazine-3-carboxylate (0.2964 g, 0.736 mmol), 3-amino-2H-[1,2'-bipyridin]-2-one (0.172 g, 0.920 mmol), brettphos (0.079 g, 0.147 mmol), potassium carbonate (0.153 g, 1.104 mmol) and palladium(II) acetate (0.033 g, 0.147 mmol) in Dioxane (7.36 ml) in a pressure tube was stirred to 100° C. After 2.5 h, the reaction was cooled to room temperature, diluted with EtOAc (100 mL) and filtered through Celite. The filtrate was washed with water (2×30 mL) and brine (30 mL); dried over Na$_2$SO$_4$, filtered and concentrated in vacuo to give a residue which was purified by flash chromatography using an ISCO 24 g column (solid loading) eluting with 10-100% EA/hexane. Appropriate fractions were collected and concentrated in vacuo to give desired as a slightly green solid. This was triturated with Et$_2$O to give ethyl 10-(4-methoxybenzyl)-6-((2-oxo-2H-[1,2'-bipyridin]-3-yl)amino)-9,10-dihydro-8H-imidazo[1',2':1,6]pyridazino[4,5-b][1,4]oxazine-3-carboxylate (0.2262 g, 0.409 mmol, 55.5% yield) as an off-white solid.

To a heterogeneous solution of ethyl 10-(4-methoxybenzyl)-6-((2-oxo-2H-[1,2'-bipyridin]-3-yl)amino)-9,10-dihydro-8H-imidazo[1',2':1,6]pyridazino[4,5-b][1,4]oxazine-3-carboxylate (0.225 g, 0.406 mmol) in tetrahydrofuran (6 ml) and methanol (3.00 ml) was added lithium hydroxide, H$_2$O (0.0926 g, 2.207 mmol) in water (3 mL). The reaction was stirred overnight. A solution of LiOH hydrate (0.0485 g, 1.16 mmol) in water (1.5 mL) was added. After 3.5 h, the solution was concentrated in vacuo not to dryness. 1 N aq HCl was added until pH 5 by litmus paper. The precipitate was filtered, washed with water and dried at 50° C. to give 10-(4-methoxybenzyl)-6-((2-oxo-2H-[1,2'-bipyridin]-3-yl) amino)-9, 10-dihydro-8H-imidazo[1',2':1,6]pyridazino[4,5-b][1,4]oxazine-3-carboxylic acid (0.2088 g, 0.377 mmol, 93% yield) as a white solid.

Step 6: 6-((2-Oxo-2H-[1,2'-bipyridin]-3-yl)amino)-9,10-dihydro-8H-imidazo[1',2':1,6]pyridazino[4,5-b][1,4]oxazine-3-carboxylic acid, 3 HCl

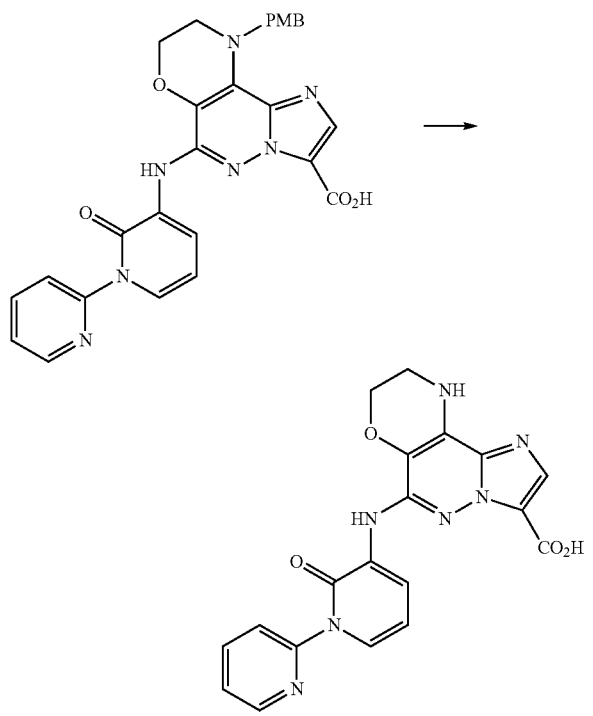

To a heterogeneous, colorless solution of 10-(4-methoxybenzyl)-6-((2-oxo-2H-[1,2'-bipyridin]-3-yl)amino)-9,10-dihydro-8H-imidazo[1',2':1,6]pyridazino[4,5-b][1,4]oxazine-3-carboxylic acid (0.2076 g, 0.395 mmol) in Dichloromethane (8 ml) under nitrogen was added 4N hydrogen chloride/dioxane (6, 24.00 mmol). The reaction was stirred overnight and concentrated in vacuo. The residue was triturated with EtOAc, filtered and rinsed with EtOAc to give 6-((2-oxo-2H-[1,2'-bipyridin]-3-yl)amino)-9,10-dihydro-8H-imidazo[1',2':1,6]pyridazino[4,5-b][1,4]oxazine-3-carboxylic acid, 3 HCl (0.182 g, 0.336 mmol, 85% yield) as a light tan solid.

Step 7: N-Cyclobutyl-6-((2-oxo-2H-[1,2'-bipyridin]-3-yl)amino)-9,10-dihydro-8H-imidazo[1',2':1,6]pyridazino[4,5-b][1,4]oxazine-3-carboxamide To a somewhat homogeneous, colorless solution of 6-((2-oxo-2H-[1,2'-bipyridin]-3-yl)amino)-9,10-dihydro-8H-imidazo[1',2':1,6]pyridazino[4,5-b][1,4]oxazine-3-carboxylic acid, 3 HCl (0.0346 g, 0.064 mmol) and cyclobutanamine (9.08 mg, 0.128 mmol) in DMF (1.5 mL) were added BOP (0.056 g, 0.128 mmol) and DIPEA (0.067 mL, 0.383 mmol). The reaction was sealed and heated to 50° C. After 1 h, the reaction was cooled to room temperature. Water (10 mL) was added, and the solution was stirred for 15 min, filtered and washed with water to give a residue. This was triturated with $CH_2Cl_2$, filtered and dried overnight at 50° C. to give N-cyclobutyl-6-((2-oxo-2H-[1,2'-bipyridin]-3-yl)amino)-9,10-dihydro-8H-imidazo[1',2':1,6]pyridazino[4,5-b][1,4]oxazine-3-carboxamide as a white solid. LCMS (M+H)$^+$ =459.1. $^1$H NMR (400 MHz, DMSO-$d_6$) δ ppm 8.64 (1 H, dt, J=3.91, 1.02 Hz), 8.53 (1 H, d, J=7.92 Hz), 8.23 (1 H, s), 8.17 (1 H, dd, J=7.26, 1.76 Hz), 8.05 (1 H, td, J=7.81, 1.98 Hz), 7.89 (1 H, s), 7.87 (1 H, s), 7.60 (1 H, dd, J=7.15, 1.65 Hz), 7.51-7.58 (2 H, m), 6.48 (1 H, t, J=7.15 Hz), 4.47-4.61 (1H, m), 4.35 (2 H, t, J=3.96 Hz), 3.56 (2 H, d, J=2.64 Hz), 2.26-2.43 (2H, m), 1.96-2.09 (2 H, m), 1.71-1.81 (2 H, m)

The following examples (Ex 240-242) were prepared according to the procedure described for the preparation of example 235. The analytical data for the compounds is shown in Table 3.

Example 240

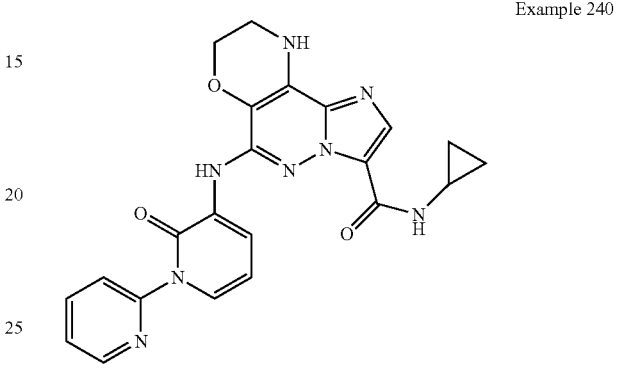

Example 241

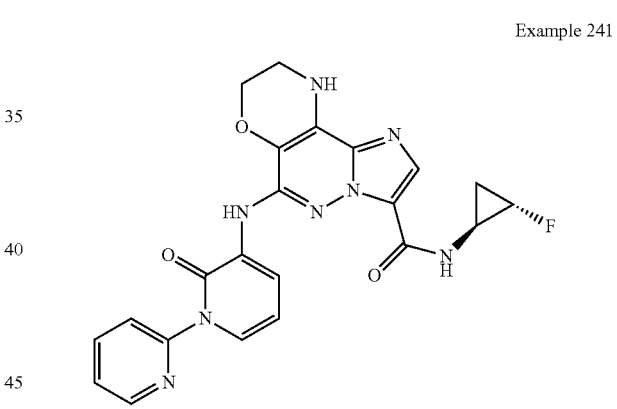

Example 242

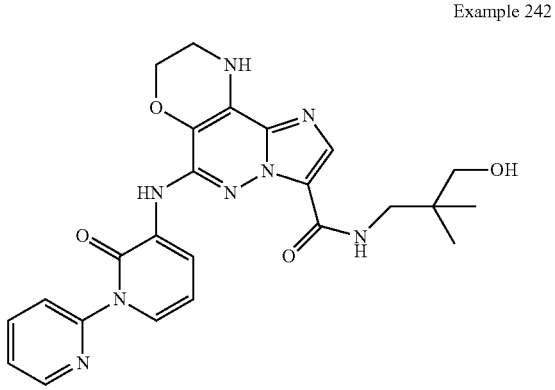

TABLE 3

| Ex | Analytical data |
|---|---|
| 240 | LCMS (M + H)+ = 445.0. $^1$H NMR (400 MHz, DMSO-$d_6$) δ ppm 8.64 (1 H, dt, J = 4.84, 0.88 Hz), 8.40 (1 H, d, J = 3.74 Hz), 8.20 (1 H, s), 8.06 (2 H, ddd, J = 15.79, 7.54, 1.76 Hz), 7.84-7.90 (2 H, m), 7.60 (1 H, dd, J = 7.15, 1.65 Hz), 7.54 (2 H, ddd, J = 6.82, 5.50, 0.88 Hz), 6.49 (1 H, t, J = 7.15 Hz), 4.34 (2 H, t, J = 4.07 Hz), 3.55 (2 H, d, J = 2.64 Hz), 2.90-2.98 (1 H, m), 0.83 (2 H, dd, J = 6.93, 1.87 Hz), 0.60 (2 H, dd, J = 3.85, 2.09 Hz) |
| 241 | LCMS (M + H)+ = 463.2. $^1$H NMR (400 MHz, DMSO-$d_6$) δ ppm 8.67-8.61 (m, 1H), 8.43 (d, J = 4.18 Hz, 1H), 8.27-8.20 (m, 1H), 8.09-7.99 (m, 2H), 7.93 (s, 1H), 7.87 (d, J = 7.92 Hz, 1H), 7.61-7.56 (m, 2H), 7.54 (ddd, J = 7.48, 4.84, 0.88 Hz, 1H), 6.46 (t, J = 7.26 Hz, 1H), 5.04-4.78 (m, 1H), 4.35 (t, J = 4.07 Hz, 2H), 3.56 (d, J = 2.86 Hz, 2H), 3.08-2.97 (m, 1H), 1.34-1.19 (m, 1H), 1.10-0.95 (m, 1H) |
| 242 | LCMS (M + H)+ = 491.3. $^1$H NMR (400 MHz, DMSO-$d_6$) δ ppm 8.60-8.71 (1 H, m), 8.47 (1 H, t, J = 6.49 Hz), 8.25 (1 H, s), 8.00-8.10 (2 H, m), 7.90 (1 H, s), 7.81-7.89 (1 H, m), 7.45-7.65 (3 H, m), 6.54 (1 H, t, J = 7.26 Hz), 4.35 (2 H, t, J = 4.18 Hz), 3.56 (2 H, br. s.), 3.36 (4 H, br d, J = 6.60 Hz), 0.85 (6 H, s) |

Example 243

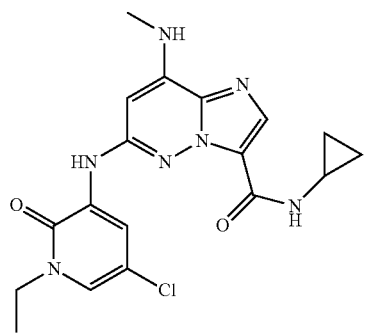 [SMILES: CCn1cc(Cl)cc(Nc2cc(NC)c3ncc(C(=O)NC4CC4)n3n2)c1=O]

Step 1:
5-chloro-1-ethyl-3-nitro-1,2-dihydropyridin-2-ol

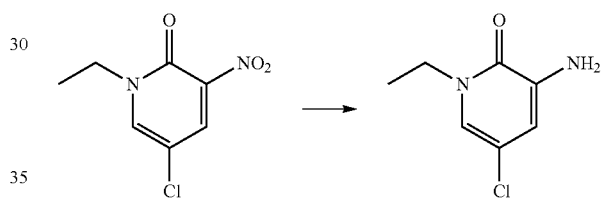

A stirred mixture of 5-chloro-3-nitropyridin-2-ol (0.200 g, 1.146 mmol), iodoethane (0.137 mL, 1.719 mmol) and Potassium carbonate (0.348 g, 2.52 mmol) in DMF (5 mL) was stirred at room temperature for 4 hours. LC-MS showed complete conversion to the desired product mass. The reaction mixture was concentrated under vacuum, diluted with ethyl acetate and washed with brine. The ethyl acetate extract was dried over sodium sulfate, filtered and concentrated. The concentrate was chromatographed on Silica Gel eluting with 30% Ethyl acetate:70% hexane to give 5-chloro-1-ethyl-3-nitro-1,2-dihydropyridin-2-ol(0.144 g, 0.704 mmol, 61% yield) as a yellow solid.LC-MS m+1 203.2; 205.2

Step 2: 3-amino-5-chloro-1-ethylpyridin-2(1H)-one

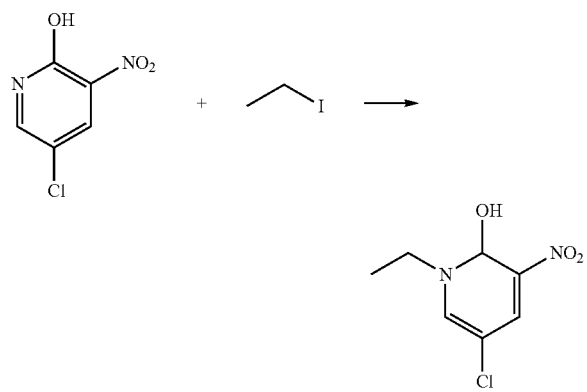

Zinc dust (0.587 g, 8.98 mmol) was quickly added to a stirred mixture of 5-chloro-1-ethyl-3-nitropyridin-2(1H)-one (0.130 g, 0.642 mmol) and Ammonium chloride (0.481 g, 8.98 mmol) in MeOH (6 mL) and THF (2.000 mL) at room temperature. The reaction mixture was stirred at room temperature for one (1) hour. LC-MS showed complete conversion to the desired product mass. The reaction mixture was diluted with ethyl acetate and filtered. The filtrate was concentrated under vacuum. The concentrate was diluted with 50 ml dichloromethane, washed with water, dried over sodium sulfate and filtered. The filtrate was concentrated to give 3-amino-5-chloro-1-ethylpyridin-2 (1H)-one (0.108 g, 0.625 mmol, 98%) as a white solid.

Step 3: Ethyl 6-((5-chloro-1-ethyl-2-oxo-1,2-dihydropyridin-3-yl)amino)-8-((4-methoxybenzyl)(methyl)amino)imidazo[1,2-b]pyridazine-3-carboxylate

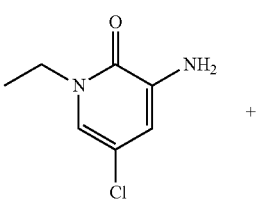

177

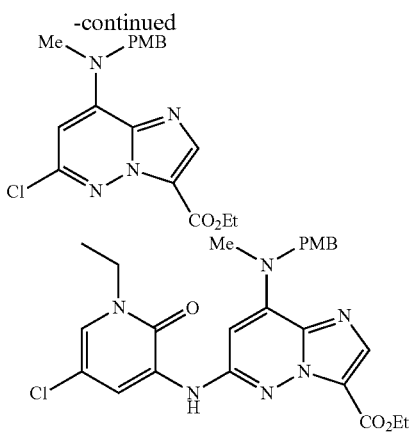

A stirred mixture of ethyl 6-chloro-8-((4-methoxybenzyl)(methyl)amino)imidazo[1,2-b]pyridazine-3-carboxylate (0.235 g, 0.627 mmol), 3-amino-5-chloro-1-ethylpyridin-2(1H)-one (0.130 g, 0.753 mmol), Tris(dibenzylideneacetone)dipalladium (0) (0.069 g, 0.075 mmol), 9,9-Dimethyl-4,5-bis(diphenylphosphino)xanthene[Xantphos](0.044 g, 0.075 mmol) and Cesium carbonate (0.613 g, 1.881 mmol) in NMP (15 mL) was degassed with nitrogen and heated at 125° C. for two hours. LC-MS showed complete conversion to the desired product mass. The reaction mixture was cooled to room temperature, diluted with ethyl acetate[25 m] and filtered. The filtrate was diluted with an additional 75 ml ethyl acetate and washed with water, sat'd ammonium chloride solution, brine, dried over sodium sulfate and concentrated to give 0.554 g crude product mixture. The crude product mixture was chromatographed on Silica Gel eluting with first with 15% Ethyl Acetate: 85% Hexane, then with 15% MeOH:40% EtOAc:45% Hexane to elute the product. The product obtained was triturated with methanol, allowed to stand and filtered to give ethyl 6-((5-chloro-1-ethyl-2-oxo-1,2-dihydropyridin-3-yl)amino)-8-((4-methoxybenzyl)(methyl)amino)imidazo[1,2-b]pyridazine-3-carboxylate (0.101 g, 0.198 mmol, 32%) as a greenish solid.

Step 4: 6-((5-chloro-1-ethyl-2-oxo-1,2-dihydropyridin-3-yl)amino)-8-((4-methoxybenzyl)(methyl)amino)imidazo[1,2-b]pyridazine-3-carboxylic acid

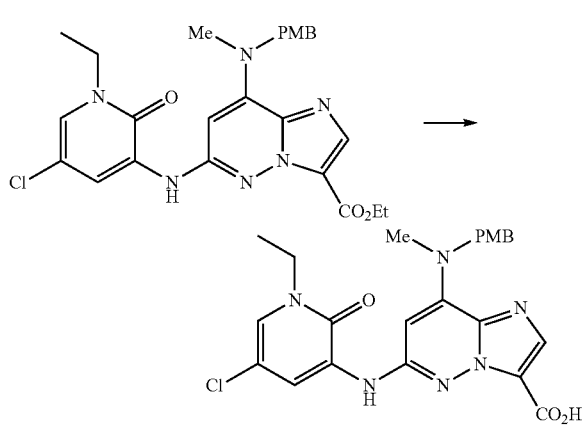

178

A stirred mixture of ethyl 6-((5-chloro-1-ethyl-2-oxo-1,2-dihydropyridin-3-yl)amino)-8-((4-methoxybenzyl)(methyl)amino)imidazo[1,2-b]pyridazine-3-carboxylate (0.100 g, 0.196 mmol) and Lithium hydroxide (0.023 g, 0.979 mmol) [dissolved in Water (2.500 mL)] in Tetrahydrofuran (5 mL) and MeOH (2.273 mL) was stirred at room temperature for 4 hours. LC-MS showed complete conversion to the desired product mass. The reaction mixture was concentrated under vacuum to approx 5 ml solution, then acidified with 1N HCl solution to pH 3-4, and filtered. The solid residue was dried overnight under vacuum to give 6-((5-chloro-1-ethyl-2-oxo-1,2-dihydropyridin-3-yl)amino)-8-((4-methoxybenzyl)(methyl)amino)imidazo[1,2-b]pyridazine-3-carboxylic acid (0.045 g, 0.093 mmol, 48%) as an offwhite solid.

Step 5: 6-((5-chloro-1-ethyl-2-oxo-1,2-dihydropyridin-3-yl)amino)-N-cyclopropyl-8-(methylamino)imidazo[1,2-b]pyridazine-3-carboxamide

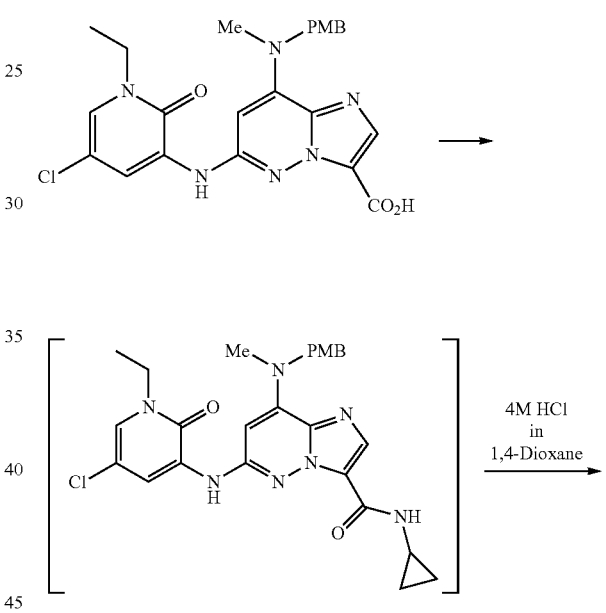

A stirred mixture of 6-((5-chloro-1-ethyl-2-oxo-1,2-dihydropyridin-3-yl)amino)-8-((4-methoxybenzyl)(methyl)amino)imidazo[1,2-b]pyridazine-3-carboxylic acid (0.040 g, 0.083 mmol), Cyclopropylamine (5.91 mg, 0.104 mmol), BOP (0.048 g, 0.108 mmol) and N,N-Di-iso-propylethylamine (0.043 g, 0.331 mmol) in DMF (2.5 mL) was heated at 50° C. for 2 hours. LC-MS showed complete conversion to the desired intermediate product mass. The reaction mixture was concentrated under vacuum. The residue was partitioned between ethyl acetate and water. The ethyl acetate extract was dried over sodium sulfate and concentrated. The concentrated intermediate was dissolved in 2 ml dichloromethane. 0.5 ml 4M HCl in Dioxane was added and the reaction mixture stirred at room temperature for thirty minutes. The reaction mixture was concentrated to give 65 mg crude product mixture which was triturated with 2 ml methanol, and filtered to give 6-((5-chloro-1-ethyl-2-oxo-1,2-dihydropyridin-3-yl)amino)-N-cyclopropyl-8-(methylamino)imidazo[1,2-b]pyridazine-3-carboxamide (0.024 g, 0.727 mmol, 73%) as a white solid.

The following example (Ex 244) was prepared according to the procedure described for the preparation of example 243. The analytical data for the compound is shown in Table 4.

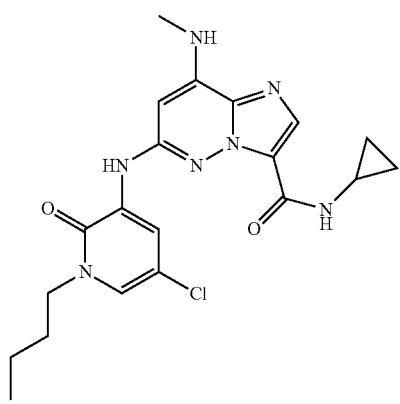 [SMILES: CCCCn1cc(Cl)cc(Nc2cc(NC)c3ncc(C(=O)NC4CC4)n3n2)c1=O]

Example 244

Example 245

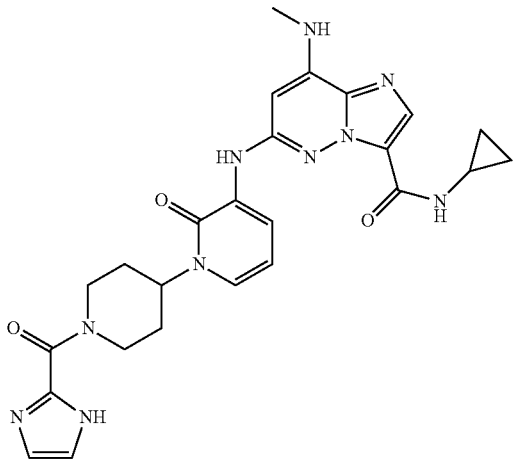 [SMILES: CNc1cc(Nc2cccn(C3CCN(C(=O)c4ncc[nH]4)CC3)c2=O)nn2c(C(=O)NC3CC3)cnc12]

Step 1: methyl 1-(1-((benzyloxy)carbonyl)piperidin-4-yl)-2-oxo-1,2-dihydropyridine-3-carboxylate

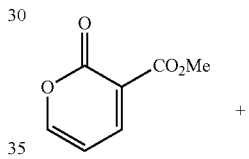

+

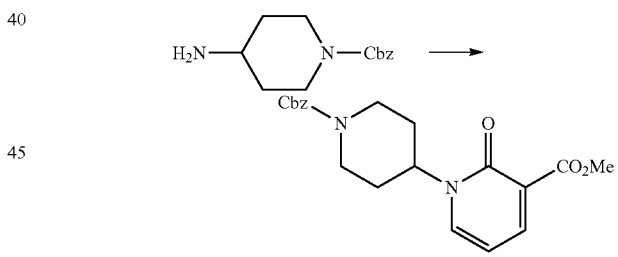

Benzyl 4-aminopiperidine-1-carboxylate (3.04 g, 12.98 mmol) was added to a stirred mixture of methyl 2-oxo-2H-pyran-3-carboxylate (2.00, 12.98 mmol) in DMF (50 mL) at 0° C. The reaction mixture was stirred at 0° C. A solid precipitated out of the solution. The heterogeneous mixture was stirred at 0° C. for five hours then allowed to warm to room temperature. EDC (3.23 g, 16.87 mmol) was added followed by 4-Dimethylaminopyridine (0.396 g, 3.24 mmol) and the reaction mixture stirred at room temperature overnight. The reaction mixture was partitioned between ethyl acetate and water. The ethyl acetate extract was dried over sodium sulfate, filtered and concentrated to give g crude product mixture. Chromatography over Silica Gel gave methyl 1-(1-((benzyloxy)carbonyl)piperidin-4-yl)-2-oxo-1,2-dihydropyridine-3-carboxylate (3.397 g, 9.2 mmol, 71% yield) as a tan viscous glue.

TABLE 4

| Ex | Analytical data x |
|---|---|
| 243 | LCMS (M + H)+ = 402.3; 404.3. $^1$H NMR (400 MHz, DMSO-$d_6$) δ ppm 8.70 (s, 1H), 8.44 (d, J = 3.5 Hz, 1H), 8.05 (d, J = 2.4 Hz, 1H), 7.86 (s, 1H), 7.59 (d, J = 2.6 Hz, 1H), 6.40 (s, 1H), 5.74 (s, 1H), 4.20-3.88 (m, 2H), 2.85 (d, J = 3.5 Hz, 3H), 1.34-1.23 (m, 3H), 1.17 (t, J = 7.0 Hz, 1H), 0.75 (dd, J = 7.0, 2.0 Hz, 2H), 0.62-0.34 (m, 2H) |
| 244 | LCMS (M + H)+ = 430.2; 432.2. $^1$H NMR (500 MHz, DMSO-$d_6$) δ ppm 8.72 (s, 1H), 8.46 (d, J = 3.5 Hz, 1H), 8.07 (d, J = 2.5 Hz, 1H), 7.86 (s, 1H), 7.59 (d, J = 2.5 Hz, 1H), 7.54-7.46 (m, 1H), 6.40 (s, 1H), 4.19-3.68 (m, 2H), 2.93-2.66 (m, 3H), 1.69 (t, J = 7.4 Hz, 2H), 1.41-1.03 (m, 2H), 0.93 (t, J = 7.2 Hz, 3H), 0.85-0.69 (m, 2H), 0.59-0.30 (m, 2H) |

Step 2: 1-(1-((benzyloxy)carbonyl)piperidin-4-yl)-2-oxo-1,2-dihydropyridine-3-carboxylic acid

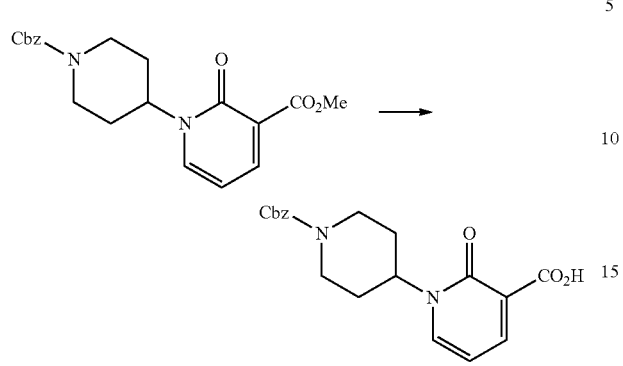

A stirred mixture of methyl 1-(1-((benzyloxy)carbonyl)piperidin-4-yl)-2-oxo-1,2-dihydropyridine-3-carboxylate (3.397 g, 9.17 mmol) and Lithium hydroxide (1.098 g, 45.9 mmol) [dissolved in Water (25.00 mL)] in Tetrahydrofuran (50 mL) and MeOH (22.73 mL) was stirred at room temperature for 4 hours. LC-MS showed complete conversion to the desired product mass. The reaction mixture was concentrated under vacuum to approx 5 ml solution, then acidified with 1N HCl solution to pH 3-4, filtered and the solid residue was dried under vacuum to give 1-(1-((benzyloxy)carbonyl)piperidin-4-yl)-2-oxo-1,2-dihydropyridine-3-carboxylic acid (3.10 g, 8.70 mmol, 95%) as a white solid.

Step 3: Benzyl 4-(3-((tert-butoxycarbonyl)amino)-2-oxopyridin-1(2H)-yl)piperidine-1-carboxylate

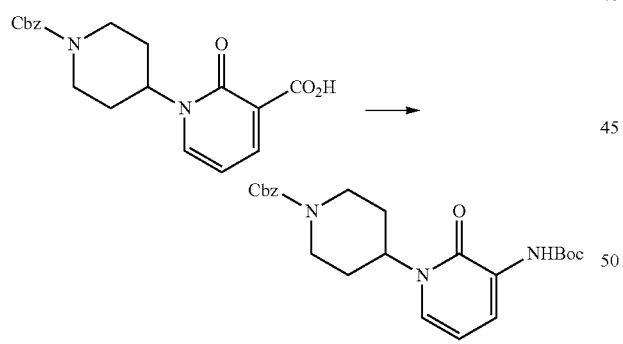

A stirred mixture of 1-(1-((benzyloxy)carbonyl)piperidin-4-yl)-2-oxo-1,2-dihydropyridine-3-carboxylic acid (2.60 g, 7.30 mmol), Diphenylphosphoryl azide (2.170 mL, 10.07 mmol) and Triethyl amine (1.410 mL, 10.12 mmol) in t-Butanol (21 mL) was heated at 75° C. for three hours then overnight. The reaction mixture was then cooled and concentrated under vcacuum. The concentrate was dissolved in 100 ml ethyl acetate and washed with water, brine, dried over sodium sulfate and concentrated. Chromatography on Silica Gel gave benzyl 4-(3-((tert-butoxycarbonyl)amino)-2-oxopyridin-1(2H)-yl)piperidine-1-carboxylate (0.467 g, 1.092 mmol, 15% yield) as a viscous tan glue/film.

Step 4: Benzyl 4-(3-amino-2-oxopyridin-1 (2H)-yl)piperidine-1-carboxylate

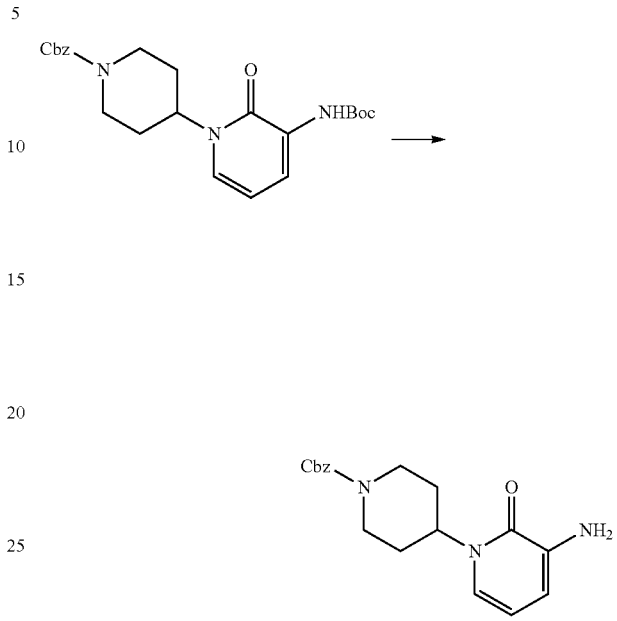

A mixture of benzyl 4-(3-((tert-butoxycarbonyl)amino)-2-oxopyridin-1(2H)-yl)piperidine-1-carboxylate (0.467 g, 1.092 mmol) and Hydrochloric acid[6M in dioxane](0.182 mL, 1.092 mmol) inDioxane (10 mL) was stirred at room temperature for 4 hours then overnight at 50° C. overnight. The reaction mixture was concentrated under vacuum to give benzyl 4-(3-amino-2-oxopyridin-1 (2H)-yl)piperidine-1-carboxylate (0.350 g, 1.069 mmol, 98% yield) as a tan solid.

Step 5: Benzyl 4-(3-((3-(cyclopropylcarbamoyl)-8-((4-methoxybenzyl)(methyl)amino)imidazo[1,2-b]pyridazin-6-yl)amino)-2-oxopyridin-1 (2H)-yl)piperidine-1-carboxylate

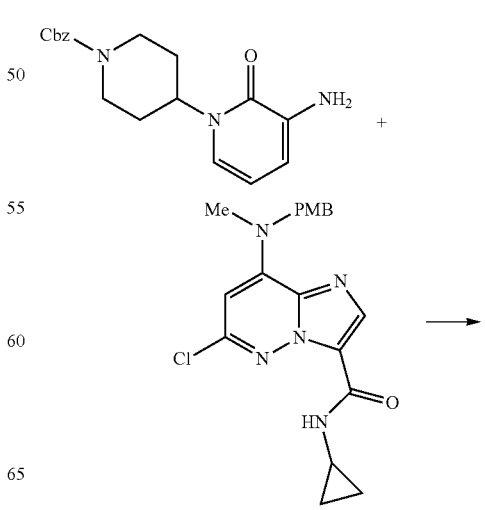

-continued

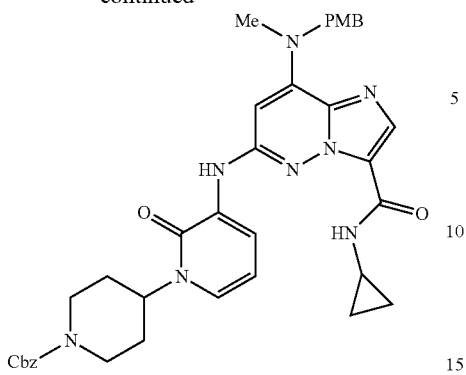

A stirred mixture of 6-chloro-N-cyclopropyl-8-((4-methoxybenzyl)(methyl)amino) imidazo[1,2-b]pyridazine-3-carboxamide (0.806 g, 2.089 mmol), benzyl 4-(3-amino-2-oxopyridin-1(2H)-yl)piperidine-1-carboxylate (0.570 g, 1.741 mmol), 9,9-Dimethyl-4,5-bis(diphenylphosphino)xanthene[Xantphos](0.121 g, 0.209 mmol), Tris(dibenzylideneacetone) dipalladium (0) (0.191 g, 0.209 mmol) and Cesium carbonate (1.702 g, 5.22 mmol) was degassed with nitrogen for a few minutes, then the reaction mixture was heated at 125° C. overnight. The reaction mixture was cooled to room temperature and partitioned between ethyl acetate and water. The ethyl acetate extract was filtered, dried over sodium sulfate and concentrated. The crude product was chromatographed on Silica Gel to give benzyl 4-(3-((3-(cyclopropylcarbamoyl)-8-((4-methoxybenzyl)(methyl)amino)imidazo[1,2-b]pyridazin-6-yl)amino)-2-oxopyridin-1(2H)-yl)piperidine-1-carboxylate (0.890 g, 1.315 mmol, 76% yield) as a greenish viscous liquid.

Step 6: N-cyclopropyl-8-((4-methoxybenzyl)(methyl)amino)-6-((2-oxo-1-(piperidin-4-yl)-1,2-dihydropyridin-3-yl)amino)imidazo[1,2-b]pyridazine-3-carboxamide A stirred mixture of benzyl 4-(3-((3-(cyclopropylcarbamoyl)-8-((4-methoxybenzyl)(methyl)amino)imidazo[1,2-b]pyridazin-6-yl)amino)-2-oxopyridin-1(2H)-yl)piperidine-1-carboxylate (0.890 g, 1.315 mmol) and 10% Pd/Carbon (0.200 g, 0.132 mmol) in Ethanol (20 mL) and THF (10.00 mL) was subjected to hydrogenation conditions using a Parr Shaker Apparatus for ½ hour. The reaction mixture was filtered through a celite plug washing eith ethyl acetate. The ethyl acetate filtrate was concentrated to give N-cyclopropyl-8-((4-methoxybenzyl)(methyl)amino)-6-((2-oxo-1-(piperidin-4-yl)-1,2-dihydropyridin-3-yl)amino)imidazo[1,2-b]pyridazine-3-carboxamide (0.412 g, 0.759 mmol, 58% yield) as a tan solid.

Step 7: N-cyclopropyl-6-((1-(1-(4-methyl-1H-imidazole-2-carbonyl)piperidin-4-yl)-2-oxo-1,2-dihydropyridin-3-yl)amino)-8-(methylamino)imidazo[1,2-b]pyridazine-3-carboxamide

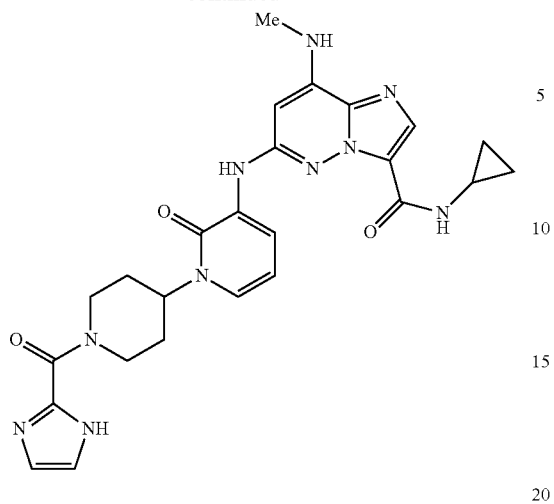

Ex. 247

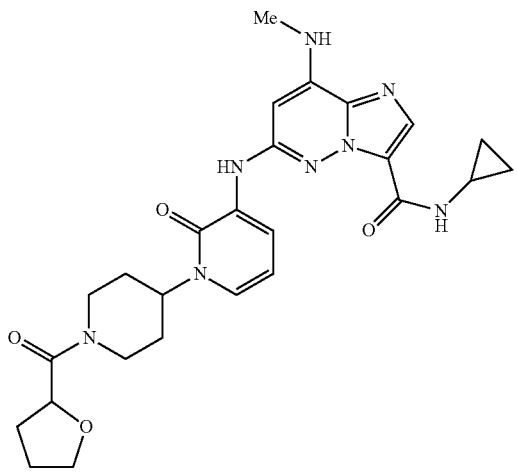

A mixture of N-cyclopropyl-8-((4-methoxybenzyl)(methyl)amino)-6-((2-oxo-1-(piperidin-4-yl)-1,2-dihydropyridin-3-yl)amino)imidazo[1,2-b]pyridazine-3-carboxamide (0.015 g, 0.028 mmol), 4-methyl-1H-imidazole-2-carboxylic acid (6.97 mg, 0.055 mmol), BOP (0.024 g, 0.055 mmol) and N,N-Di-iso-propylethylamine (0.018 g, 0.138 mmol) in DMF (1.0 mL) was stirred at room temperature overnight. The reaction mixture was concentrated. The residue was dissolved in 2 ml dichloromethane. 0.2 ml TFA was added and the reaction mixture stirred at room temperature overnight. The crude product mixture was chromatographed using Reverse-Phase PREP LC to give N-cyclopropyl-6-((1-(1-(4-methyl-1H-imidazole-2-carbonyl)piperidin-4-yl)-2-oxo-1,2-dihydropyridin-3-yl)amino)-8-(methylamino)imidazo[1,2-b]pyridazine-3-carboxamide (0.007 g, 0.014 mmol, 50% yield) as a white solid.

The following examples (Ex 246-251) were prepared according to the procedures described for the preparation of Example 245. Ex. 250 was prepared by alkylation of the intermediate obtained from step 7 of example 245, followed by deprotection of the PMB-ester protecting group.

Ex. 248

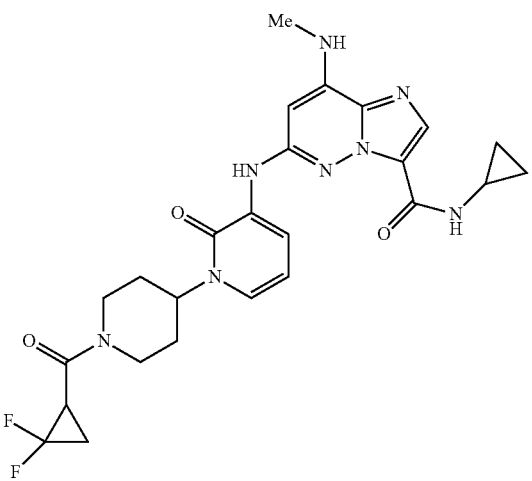

Ex. 246

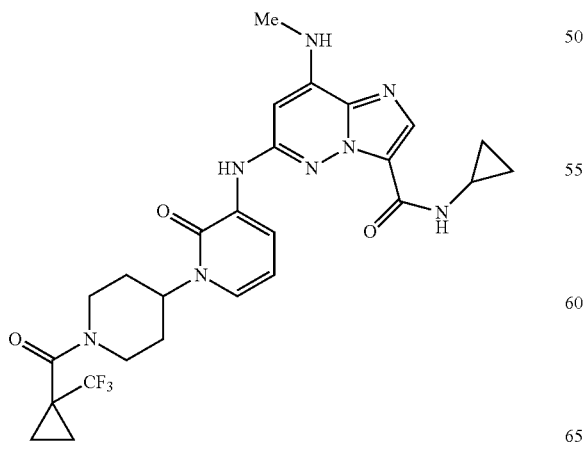

Ex. 249

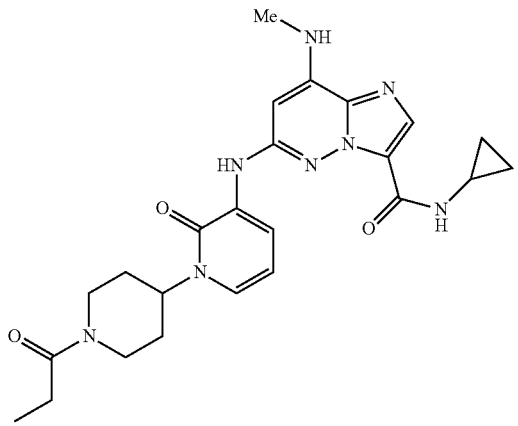

Ex. 250
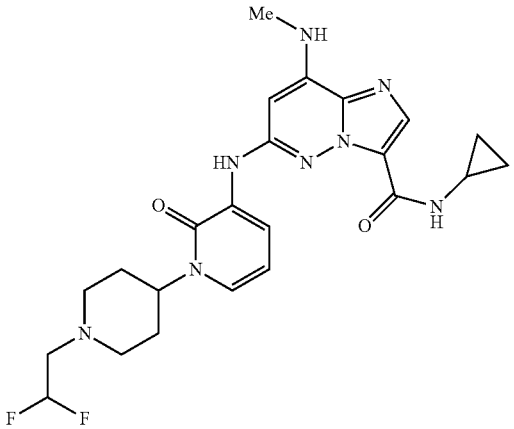

Ex. 251
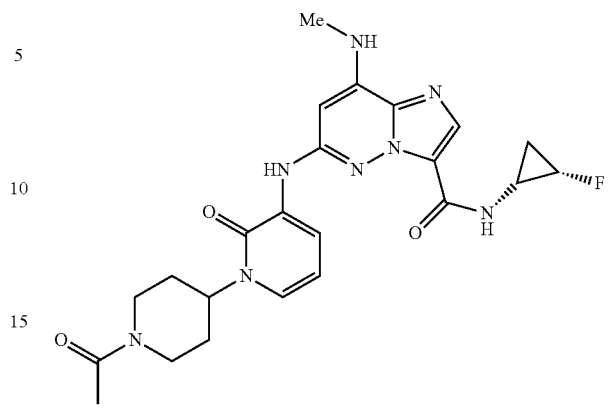

TABLE 5

| Ex | Analytical data x |
|---|---|
| 245 | LCMS (M + H)$^+$ = 517.1. $^1$H NMR (500 MHz, DMSO-d$_6$) δ ppm 12.95 (br. s., 1H), 8.78-8.29 (m, 1H), 7.92-7.75 (m, 1H), 7.61-7.39 (m, 1H), 7.28 (s, 1H), 7.10 (s, 1H), 6.46-6.17 (m, 1H), 6.06 (d, J = 12.9 Hz, 1H), 5.27-5.03 (m, 1H), 4.74 (d, J = 11.9 Hz, 1H), 3.30-3.19 (m, 4H), 3.02-2.91 (m, 1H), 2.91-2.81 (m, 3H), 2.17-1.64 (m, 4H), 0.90-0.63 (m, 2H), 0.64-0.34 (m, 2H) |
| 246 | LCMS (M + H)$^+$ = 559.1. $^1$H NMR (500 MHz, METHANOL-d$_4$) δ ppm 7.99 (s, 1H), 7.87 (dd, J = 7.4, 1.5 Hz, 1H), 7.62 (s, 1H), 7.20 (dd, J = 6.9, 1.5 Hz, 1H), 6.47 (t, J = 7.4 Hz, 1H), 5.39-5.00 (m, 1H), 3.13-2.95 (m, 4H), 3.02 (s, 3H), 3.00-2.76 (m, 1H), 2.08 (d, J = 11.4 Hz, 2H), 1.98-1.78 (m, 2H), 1.51-1.30 (m, 2H), 1.26 (br. s., 2H), 1.03-0.74 (m, 2H), 0.71-0.42 (m, 2H) |
| 247 | LCMS (M + H)$^+$ = 521.1. $^1$H NMR (500 MHz, METHANOL-d$_4$) δ ppm 7.99 (s, 1H), 7.86 (dd, J = 7.2, 1.2 Hz, 1H), 7.62 (s, 1H), 7.19 (d, J = 7.4 Hz, 1H), 6.47 (td, J = 7.2, 2.5 Hz, 1H), 5.36-5.03 (m, 1H), 4.80-4.73 (m, 1H), 4.42-4.22 (m, 1H), 3.99 (t, J = 8.2 Hz, 1H), 3.91-3.78 (m, 1H), 3.30 (m, 1H), 3.04 (s, 3H), 3.02-2.75 (m, 2H), 2.25-2.09 (m, 2H), 2.04-1.94 (m, 6H), 1.96-1.77 (m, 1H), 1.07-0.82 (m, 2H), 0.74-0.49 (m, 2H) |
| 248 | LCMS (M + H)$^+$ = 527.1. $^1$H NMR (500 MHz, METHANOL-d$_4$) δ ppm 7.99 (s, 1H), 7.87 (d, J = 7.4 Hz, 1H), 7.62 (s, 1H), 7.27-6.97 (m, 1H), 6.47 (td, J = 7.2, 2.0 Hz, 1H), 5.32-5.10 (m, 1H), 4.44-4.22 (m, 1H), 3.49-3.39 (m, 2H), 3.04 (s, 3H), 2.98-2.91 (m, 1H), 2.85 (m, 2H), 2.25-1.91 (m, 4H), 1.93-1.59 (m, 2H), 1.07-0.81 (m, 2H), 0.71-0.49 (m, 2H) |
| 249 | LCMS (M + H)$^+$ = 479.2. $^1$H NMR (500 MHz, METHANOL-d$_4$) δ ppm 7.99 (s, 1H), 7.86 (dd, J = 7.4, 1.5 Hz, 1H), 7.61 (s, 1H), 7.18 (dd, J = 6.9, 1.5 Hz, 1H), 6.46 (t, J = 7.4 Hz, 1H), 5.32-4.98 (m, 1H), 3.25-3.20 (m, 4H), 3.04 (s, 3H), 3.00-2.86 (m, 1H), 2.56-2.35 (m, 2H), 2.47 (q, J = 7.4 Hz, 2H), 2.12-1.93 (m, 2H), 1.85 (td, J = 12.6, 4.0 Hz, 2H), 1.18 (t, J = 7.4 Hz, 3H), 1.00-0.83 (m, 2H), 0.71-0.37 (m, 2H) |
| 250 | LCMS (M + H)$^+$ = 487.2. $^1$H NMR (500 MHz, DMSO-d$_6$) δ ppm 8.32 (d, J = 3.9 Hz, 1H), 8.26 (s, 1H), 7.68-7.47 (m, 1H), 7.32-7.05 (m, 1H), 6.22-6.03 (m, 1H), 6.09-5.67 (m, 1H), 4.72-4.32 (m, 1H), 2.83 (d, J = 11.4 Hz, 2H), 2.72-2.36 (m, 6H), 2.16 (t, J = 11.8 Hz, 2H), 1.83-1.60 (m, 2H), 1.53 (d, J = 9.4 Hz, 2H), 0.60-0.41 (m, 2H), 0.39-0.07 (m, 2H) |
| 251 | LCMS (M + H)$^+$ = 483.1. $^1$H NMR (500 MHz, DMSO-d$_6$) δ ppm 8.62 (d, J = 3.7 Hz, 1H), 8.51 (s, 1H), 7.90 (s, 1H), 7.86 (d, J = 7.1 Hz, 1H), 7.50 (d, J = 5.0 Hz, 1H), 7.40 (d, J = 6.7 Hz, 1H), 6.38 (s, 1H), 6.29 (t, J = 7.2 Hz, 1H), 5.04 (t, J = 11.8 Hz, 1H), 3.48-3.13 (m, 2H), 2.97 (m, 1H), 2.94 (s, 3H), 2.78-2.58 (m, 2H), 2.06 (s, 3H), 1.97-1.58 (m, 6H), 1.40-1.17 (m, 2H), 1.06-0.79 (m, 2H) |

Example 252

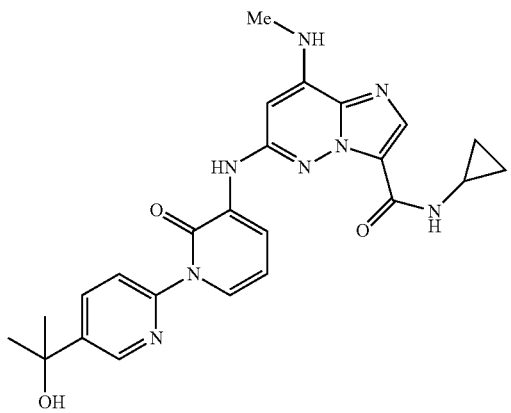 [SMILES: CNc1cc(Nc2cccn(-c3ccc(C(C)(C)O)cn3)c2=O)nn2c(C(=O)NC3CC3)cnc12]

Step 1: 3-amino-5'-(2-hydroxypropan-2-yl)-2H-[1,2'-bipyridin]-2-one

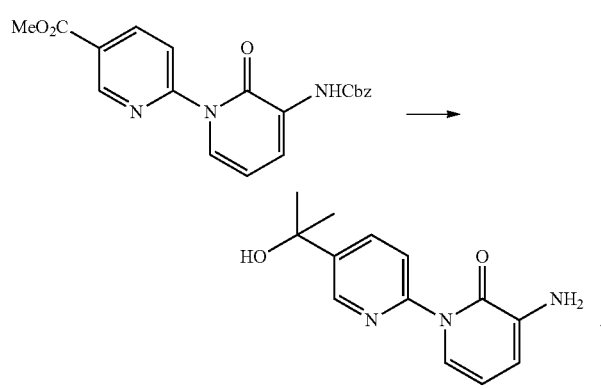

A stirred mixture of methyl 3-(((benzyloxy)carbonyl) amino)-2-oxo-2H-[1,2'-bipyridine]-5'-carboxylate (0.100 g, 0.264 mmol) in THF (10 mL) was cooled to −78° C. Methyl Lithium-1.6M in Diethyl Ether (0.494 mL, 0.791 mmol) was added quickly and the resulting reaction mixture stirred at −78° C. for 2 hours. LC-MS showed complete conversion to the desired product mass. The reaction mixture was quenched with sat'd ammonium chloride solution at −78° C., the allowed to warm to room temperature. The organic layer was separated; the aqueous layer washed with ethyl acetate. The organic layers were combined, dried and concentrated to give benzyl (5'-(2-hydroxypropan-2-yl)-2-oxo-2H-[1,2'-bipyridin]-3-yl)carbamate (0.105 g, 0.264 mmol, 100%) as a yellowish solid. A mixture of benzyl (5'-(2-hydroxypropan-2-yl)-2-oxo-2H-[1,2'-bipyridin]-3-yl)carbamate (0.109 g, 0.287 mmol) in Ethanol (15 mL) and THF (7.50 mL) was run in a Parr Apparatus with 10% Palladium on Carbon (0.031 g, 0.287 mmol) in an hydrogen atmosphere for 4 hours. The reaction mixture was filtered through celite and the filtrate concentrated to give 3-amino-5'-(2-hydroxypropan-2-yl)-2H-[1,2'-bipyridin]-2-one, (0.067 g, 0.273 mmol, 97% yield) as a tan viscous glue.

Step 2: N-cyclopropyl-6-((5'-(2-hydroxypropan-2-yl)-2-oxo-2H-[1,2'-bipyridin]-3-yl)amino)-8-(methylamino)imidazo[1,2-b]pyridazine-3-carboxamide

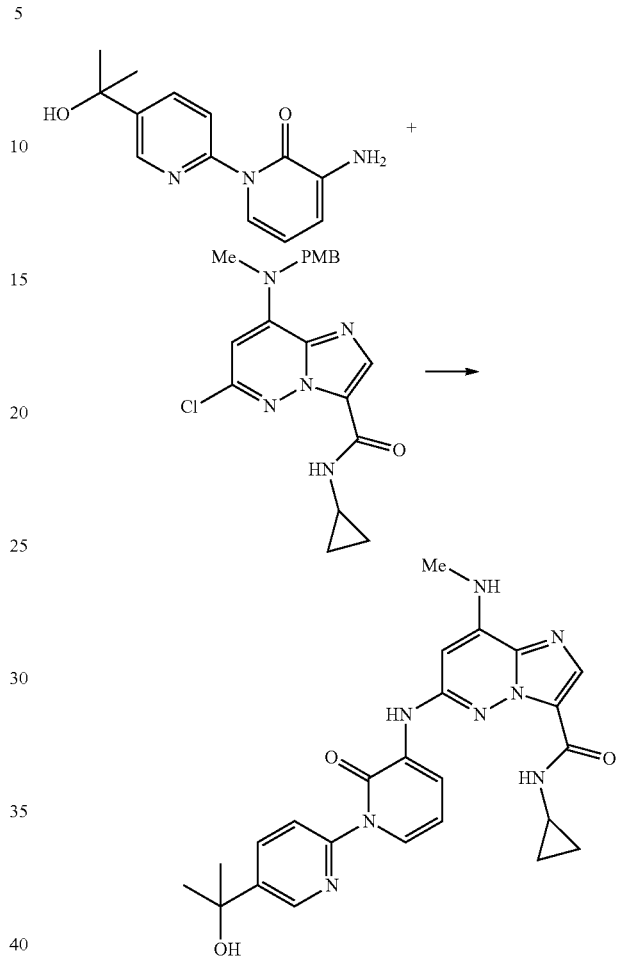

A stirred mixture of 3-amino-5'-(2-hydroxypropan-2-yl)-2H-[1,2'-bipyridin]-2-one (0.084 g, 0.342 mmol), 3-amino-5'-(2-hydroxypropan-2-yl)-2H-[1,2'-bipyridin]-2-one (0.084 g, 0.342 mmol), Tris(dibenzylideneacetone)dipalladium (0) (3.13 mg, 3.42 µmol), 9,9-Dimethyl-4,5-bis(diphenylphosphino)xanthene[Xantphos](1.979 mg, 3.42 µmol) and Cesium carbonate (0.279 g, 0.855 mmol) in NMP (15 mL) was heated at 125° C. for two hours. LC-MS showed complete conversion to the desired product mass. The reaction mixture was diluted with ethyl acetate(100 ml), and filtered. The filtrate was washed with water, dried and concentrated under vacuum. A mixture of N-cyclopropyl-6-((5'-(2-hydroxypropan-2-yl)-2-oxo-2H-[1,2'-bipyridin]-3-yl)amino)-8-((4-methoxybenzyl)(methyl) amino)imidazo[1,2-b]pyridazine-3-carboxamide (0.100 g, 0.168 mmol) and hydrogen chloride solution [4.0M in dioxane](0.084 ml, 0.336 mmol) was stirred at room temperature for approx. one hour. The reaction mixture was concentrated and chromatographed using PREP LC to give N-cyclopropyl-6-((5'-(2-hydroxypropan-2-yl)-2-oxo-2H-[1,2'-bipyridin]-3-yl) amino)-8-(methylamino)imidazo[1,2-b]pyridazine-3-carboxamide (0.025 g, 0.052 mmol, 31% yield) as a white solid.

The following examples (Ex 253-254) were prepared according to procedures previously described. The analytical data for the compounds is shown in Table 6.

Ex. 253

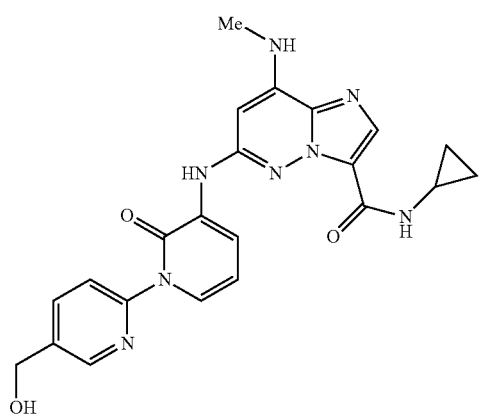

Ex. 254

TABLE 6

| | |
|---|---|
| 252 | LCMS (M + H)⁺ = 475.3. ¹H NMR (500 MHz, DMSO-d₆) δ ppm 8.78 (s, 1H), 8.72 (d, J = 2.0 Hz, 1H), 8.69-8.41 (m, 1H), 8.08 (dd, J = 8.2, 2.2 Hz, 1H), 7.99 (s, 1H), 7.87 (s, 1H), 7.77 (d, J = 8.4 Hz, 1H), 7.55 (dd, J = 7.1, 1.3 Hz, 1H), 7.48 (d, J = 5.0 Hz, 1H), 6.44 (t, J = 7.2 Hz, 1H), 6.37 (s, 1H), 3.02-2.79 (m, 4H), 1.53 (s, 6H), 0.93-0.69 (m, 2H), 0.67-0.37 (m, 2H) |
| 253 | LCMS (M + H)⁺ = 447.1. ¹H NMR (500 MHz, DMSO-d₆) δ ppm 8.70 (s, 1H), 8.62 (d, J = 3.7 Hz, 1H), 8.58 (s, NH), 8.06-7.97 (m, 1H), 7.95 (d, J = 1.7 Hz, 1H), 7.80 (d, J = 8.4 Hz, 1H), 7.54 (d, J = 5.7 Hz, 1H), 7.49 (d, J = 4.7 Hz, 1H), 6.45 (t, J = 7.1 Hz, 1H), 6.37 (s, 1H), 4.64 (d, J = 5.7 Hz, 2H), 3.03-2.80 (m, 4H), 0.94-0.71 (m, 2H), 0.68-0.29 (m, 2H) |
| 254 | LCMS (M + H)⁺ = 461.1 ¹H NMR (500 MHz, DMSO-d₆) δ ppm 8.65 (s, 1H), 8.64-8.50 (m, 1H), 8.07-7.95 (m, 1H), 7.87 (s, 1H), 7.80 (d, J = 8.4 Hz, 1H), 7.62-7.52 (m, 1H), 7.49 (d, J = 4.7 Hz, 1H), 6.44 (t, J = 7.2 Hz, 1H), 6.38 (s, 1H), 5.05-4.77 (m, 1H), 3.00-2.79 (m, 4H), 1.43 (d, J = 6.7 Hz, 3H), 0.93-0.75 (m, 2H), 0.61-0.50 (m, 2H) |

Example 255

N-((1R,2S)-2-Fluorocyclopropyl)-6-((1-(5-(2-hydroxypropan-2-yl)pyrazin-2-yl)-2-oxo-1,2-dihydropyridin-3-yl)amino)-8-(methylamino)imidazo[1,2-b]pyridazine-3-carboxamide

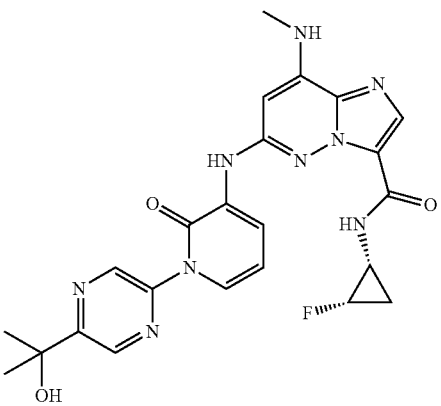 [SMILES: CNc1cc(Nc2cccn(-c3cnc(C(C)(C)O)cn3)c2=O)nn2c(C(=O)N[C@@H]3C[C@@H]3F)cnc12]

Step 1: 2-(5-Chloropyrazin-2-yl)propan-2-ol

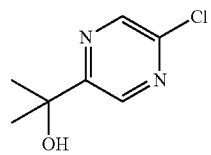

To a suspension of 2-bromo-5-chloropyrazine (2.02 g, 10.44 mmol) in diethyl ether (30 mL) at −78° C. was added n-butyllithium (4.26 mL, 10.65 mmol) over 10 min. The resulting mixture was stirred at −78° C. for 15 min before propan-2-one (1.917 mL, 26.1 mmol) was introduced over 2 min. The mixture was stirred at −78° C. for 15 min and then at rt for 30 min. The reaction was quenched with saturated NH4Cl solution (30 mL), and the solution was extracted with ethyl acetate (4×40 mL). The combined extract was dried over anhydrous Na2SO4. The desired product, 2-(5-chloropyrazin-2-yl)propan-2-ol (0.507 g, 2.94 mmol, 28.1% yield), was isolated by ISCO (120 g silica gel, solid loading, 10-40% ethyl acetate/hexane).

Step 2: Benzyl (1-(5-(2-hydroxypropan-2-yl)pyrazin-2-yl)-2-oxo-1,2-dihydropyridin-3-yl)carbamate

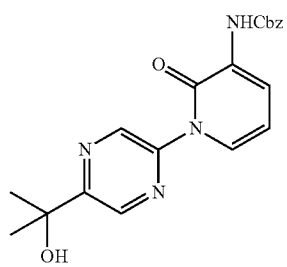 [SMILES: CC(C)(O)c1cnc(-n2cccc(NC(=O)OCc3ccccc3)c2=O)cn1]

A mixture of benzyl (2-hydroxypyridin-3-yl)carbamate (A29 step 1, 1.00 g, 4.09 mmol), 2-(5-chloropyrazin-2-yl)propan-2-ol (1.046 g, 6.06 mmol), N1,N2-dimethylethane-1,2-diamine (0.174 mL, 1.638 mmol), copper(I) iodide (0.234 g, 1.228 mmol), and potassium carbonate (1.415 g, 10.24 mmol) in 1,4-Dioxane (18 mL) in a pressure tube was heated at 110° C. for 20 h. Upon cooling to rt, the mixture was diluted with ethyl acetate (20 mL) and filtered through Celite. The filtrate was further diluted with ethyl acetate (130 mL), washed with water (2×30 mL) and brine (30 mL). The organic solution was dried over anhydrous MgSO4. The desired product, benzyl (1-(5-(2-hydroxypropan-2-yl)pyrazin-2-yl)-2-oxo-1,2-dihydropyridin-3-yl)carbamate (1.077 g, 2.83 mmol, 69.2% yield) was isolated as a white solid by ISCO (80 g silica gel, solid loading, 30-60% ethyl acetate/hexane).

Step 3: 3-Amino-1-(5-(2-hydroxypropan-2-yl)pyrazin-2-yl)pyridin-2(1H)-one

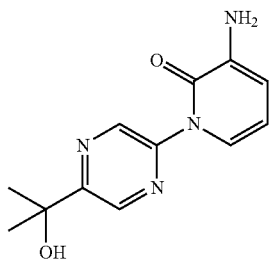 [SMILES: CC(C)(O)c1cnc(-n2cccc(N)c2=O)cn1]

A mixture of benzyl (1-(5-(2-hydroxypropan-2-yl)pyrazin-2-yl)-2-oxo-1,2-dihydropyridin-3-yl)carbamate (1.077 g, 2.83 mmol) and 10% Pd/C (0.300 g, 0.282 mmol) in MeOH (30 mL) and THF (10 mL) was stirred at rt under H2, provided with a H2 Balloon, for 1 h. The reaction was complete and clean. The solid phase was removed by suction filtration through Celite. The filtrate was concentrated under vacuum to dryness to provide the desired product, 3-amino-1-(5-(2-hydroxypropan-2-yl)pyrazin-2-yl)pyridin-2(1H)-one (0.697 g, 2.83 mmol, 100% yield) as a tan solid.

Step 4: N-((1R,2S)-2-Fluorocyclopropyl)-6-((1-(5-(2-hydroxypropan-2-yl)pyrazin-2-yl)-2-oxo-1,2-dihydropyridin-3-yl)amino)-8-(methylamino)imidazo[1,2-b]pyridazine-3-carboxamide A mixture of 6-chloro-N-((1R,2S)-2-fluorocyclopropyl)-8-((4-methoxybenzyl)(methyl)amino)imidazo[1,2-b]pyridazine-3-carboxamide (4u, 60 mg, 0.149 mmol), 3-amino-1-(5-(2-hydroxypropan-2-yl)pyrazin-2-yl)pyridin-2(1H)-one (45.7 mg, 0.186 mmol), palladium(II) acetate (6.67 mg, 0.030 mmol), BrettPhose (15.95 mg, 0.030 mmol), and potassium carbonate (30.8 mg, 0.223 mmol) in 1,4-Dioxane (1.5 mL) was heated at 80° C. for 2.5 h. The reaction mixture was diluted with ethyl acetate (5 mL) and filtered through Celite. The filtrate was diluted with ethyl acetate (80 mL), washed with water (2×25 mL) and brine (25 mL), and dried over anhydrous MgSO4. The solvent was removed under vacuum. The residue was dissolved in Dichloromethane (8 mL). To this solution at rt was added hydrochloric acid in 1,4-dioxane (8.0 mL, 32.00 mmol). The mixture was stirred at rt for 30 min, and then concentrated under vacuum. The residue was diluted with DMSO (1.5 mL) and MeOH (4.5 mL), divided into 3 portions, and injected to prep. HPLC. The correct fractions were combined, concentrated under vacuum, basified with 1.5 M K2HPO4 solution to pH 9 and extracted with dichloromethane (4×40 mL). The combined extract was dried over anhydrous Na2SO4. Removal of solvent under vacuum provided the desired product, N-((1R,2S)-2-fluorocyclopropyl)-6-((1-(5-(2-hydroxypropan-2-yl)pyrazin-2-yl)-2-oxo-1,2-dihydropyridin-3-yl)amino)-8-(methylamino)imidazo[1,2-b]pyridazine-3-carboxamide (28.2 mg, 0.056 mmol, 37.7% yield), as white solid. LCMS (M+H)+=494.2. $^1$H NMR (400 MHz, DMSO-d$_6$) δ 9.08 (d, J=1.5 Hz, 1H), 8.93 (d, J=1.5 Hz, 1H), 8.69 (s, 1H), 8.64 (d, J=4.0 Hz, 1H), 8.04 (dd, J=7.4, 1.7 Hz, 1H), 7.92 (s, 1H), 7.58 (dd, J=7.1, 1.7 Hz, 1H), 7.52 (q, J=4.6 Hz, 1H), 6.47 (t, J=7.2 Hz, 1H), 6.42 (s, 1H), 5.62 (s, 1H), 5.04-4.75 (m, 1H), 3.07-2.95 (m, 1H), 2.88 (d, J=4.8 Hz, 3H), 1.55 (s, 6H), 1.34-1.18 (m, 1H), 1.07-0.92 (m, 1H).

Example 256

6-((1-(5-(Dimethylcarbamoyl)pyrazin-2-yl)-2-oxo-1,2-dihydropyridin-3-yl)amino)-N-((1R,2S)-2-fluorocyclopropyl)-8-(methylamino)imidazo[1,2-b]pyridazine-3-carboxamide

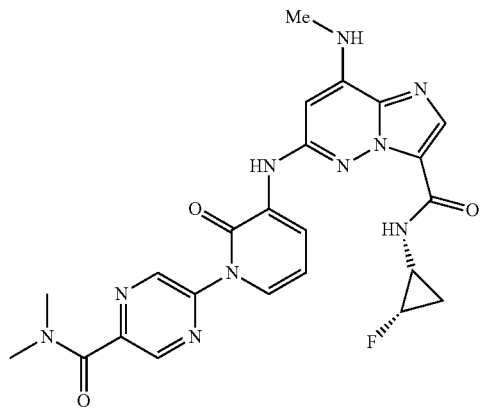

Step 1:
5-Chloro-N,N-dimethylpyrazine-2-carboxamide

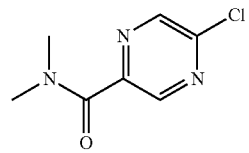

To a suspension of 5-chloropyrazine-2-carboxylic acid (3.00 g, 18.92 mmol) in Dichloromethane (35 mL) and DMF (0.15 mL) at rt was added oxalyl chloride (2.411 mL, 21.76 mmol) dropwise over 10 min. The mixture was stirred at rt for 2 h before it was concentrated under vacuum to dryness. The residue was dissolved in dichloromethan (35 mL). dimethylamine in THF (11.83 mL, 23.65 mmol) was added at rt over 10 min, followed by the addition of triethylamine (5.80 mL, 41.6 mmol). The mixture was stirred at rt for 3 h. The mixture was diluted with ethyl acetate (50 mL) and filtered through Celite. The filtrate was concentrated under vacuum to dryness, and the residue was applied to ISCO (220 g silica gel, solid loading, 70-100% ethyl acetate) to provide the desired product, 5-chloro-N,N-dimethylpyrazine-2-carboxamide (3.18 g, 17.13 mmol, 91% yield), as a white solid.

Step 2: Benzyl (1-(5-(dimethylcarbamoyl)pyrazin-2-yl)-2-oxo-1,2-dihydropyridin-3-yl)carbamate

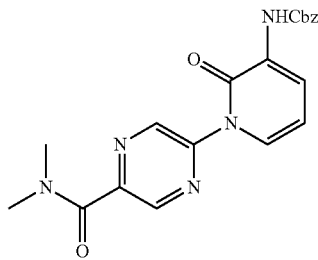 [SMILES: CN(C)C(=O)c1cnc(-n2cccc(NC(=O)OCc3ccccc3)c2=O)cn1]

A mixture of benzyl (2-hydroxypyridin-3-yl)carbamate (A29 step 1, 0.393 g, 1.609 mmol), 5-chloro-N,N-dimethylpyrazine-2-carboxamide (0.373 g, 2.011 mmol), N1,N2-dimethylethane-1,2-diamine (0.069 mL, 0.644 mmol), copper(I) iodide (0.092 g, 0.483 mmol), and potassium carbonate (0.556 g, 4.02 mmol) in 1,4-Dioxane (7 mL) in a pressure tube was heated at 110° C. for 20 h. Upon cooling to rt, the mixture was diluted with ethyl acetate (20 mL) and filtered through Celite. The filtrate was further diluted with ethyl acetate (130 mL), washed with water (2×30 mL) and brine (30 mL). The organic solution was dried over anhydrous MgSO4. The desired product, benzyl (1-(5-(dimethylcarbamoyl)pyrazin-2-yl)-2-oxo-1,2-dihydropyridin-3-yl) carbamate (0.134 g, 0.341 mmol, 21.17% yield), was isolated as a white solid by ISCO (80 g silica gel, solid loading, 50-90% ethyl acetate/hexane).

Step 3: 5-(3-Amino-2-oxopyridin-1 (2H)-yl)-N,N-dimethylpyrazine-2-carboxamide

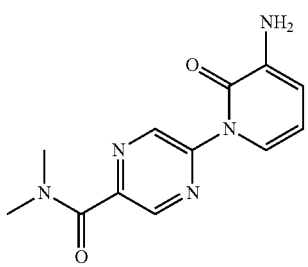 [SMILES: CN(C)C(=O)c1cnc(-n2cccc(N)c2=O)cn1]

A mixture of benzyl (1-(5-(dimethylcarbamoyl)pyrazin-2-yl)-2-oxo-1,2-dihydropyridin-3-yl)carbamate (0.134 g, 0.341 mmol) and 10% Pd/C (0.035 g, 0.033 mmol) in MeOH (6 mL) and THF (2 mL) was stirred at rt under H2, provided with a H2 Balloon, for 1 h. The reaction was complete and clean. The solid phase was removed by suction filtration through Celite. The filtrate was concentrated under vacuum to dryness to provide the desired product, 5-(3-amino-2-oxopyridin-1 (2H)-yl)-N,N-dimethylpyrazine-2-carboxamide (84 mg, 0.324 mmol, 95% yield) as a tan solid.

Step 4: 6-((1-(5-(Dimethylcarbamoyl)pyrazin-2-yl)-2-oxo-1,2-dihydropyridin-3-yl)amino)-N-((1R,2S)-2-fluorocyclopropyl)-8-(methylamino)imidazo[1,2-b]pyridazine-3-carboxamide A mixture of 6-chloro-N-((1R,2S)-2-fluorocyclopropyl)-8-((4-methoxybenzyl)(methyl)amino)imidazo[1,2-b] pyridazine-3-carboxamide (4u, 50 mg, 0.124 mmol), 5-(3-amino-2-oxopyridin-1 (2H)-yl)-N,N-dimethylpyrazine-2-carboxamide (40.1 mg, 0.155 mmol), palladium(II) acetate (5.56 mg, 0.025 mmol), BrettPhose (13.29 mg, 0.025 mmol), and potassium carbonate (25.7 mg, 0.186 mmol) in 1,4-Dioxane (1.5 mL) was heated at 80° C. for 2.5 h. The reaction mixture was diluted with ethyl acetate (5 mL) and filtered through Celite. The filtrate was diluted with ethyl acetate (80 mL), washed with water (2×25 mL) and brine (25 mL), and dried over anhydrous MgSO4. The solvent was removed under vacuum. The residue was dissolved in Dichloromethane (8 mL). To this solution at rt was added hydrochloric acid in 1,4-dioxane (8.0 mL, 32.00 mmol). The mixture was stirred at rt for 30 min, and then concentrated under vacuum. The residue was diluted with DMSO (1.5 mL) and MeOH (4.5 mL), divided into 3 portions, and injected to prep. HPLC. The correct fractions were combined, concentrated under vacuum, basified with 1.5 M K₂HPO₄ solution to pH 9 and extracted with dichloromethane (4×40 mL). The combined extract was dried over anhydrous Na2SO4. Removal of solvent under vacuum provided the desired product, 6-((1-(5-(dimethylcarbamoyl) pyrazin-2-yl)-2-oxo-1,2-dihydropyridin-3-yl)amino)-N-((1R,2S)-2-fluorocyclopropyl)-8-(methylamino)imidazo[1,2-b]pyridazine-3-carboxamide (17.9 mg, 0.035 mmol, 28.3% yield), as a yellow solid. LCMS (M+1)=507.1. ¹H NMR (400 MHz, DMSO-d₆) δ 9.23 (d, J=1.3 Hz, 1H), 8.92 (d, J=1.5 Hz, 1H), 8.73 (s, 1H), 8.63 (d, J=4.2 Hz, 1H), 8.05 (dd, J=7.3, 1.6 Hz, 1H), 7.93 (s, 1H), 7.62 (dd, J=7.1, 1.7 Hz, 1H), 7.52 (q, J=4.6 Hz, 1H), 6.50 (t, J=7.2 Hz, 1H), 6.42 (s, 1H), 5.02-4.75 (m, 1H), 3.08 (s, 3H), 3.06 (s, 3H), 3.04-2.95 (m, 1H), 2.88 (d, J=4.8 Hz, 3H), 1.33-1.18 (m, 1H), 1.09-0.90 (m, 1H).

Example 257

6-((5'-(Dimethylcarbamoyl)-2-oxo-2H-[1,2'-bipyridin]-3-yl)amino)-N-((1R,2S)-2-fluorocyclopropyl)-8-(methylamino)imidazo[1,2-b]pyridazine-3-carboxamide

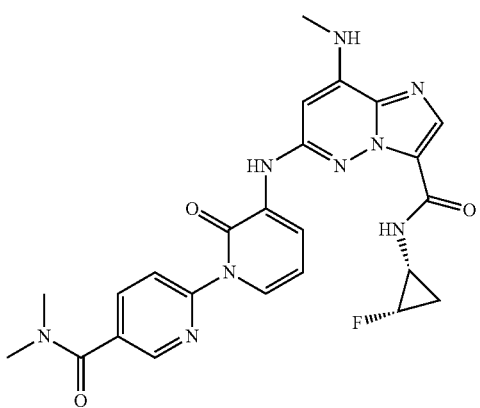 [SMILES: CNc1cc(Nc2cccn(-c3ccc(C(=O)N(C)C)cn3)c2=O)nn2c(C(=O)N[C@@H]3C[C@@H]3F)cnc12]

Step 1: Ethyl 3-(((benzyloxy)carbonyl)amino)-2-oxo-2H-[1,2'-bipyridine]-5'-carboxylate

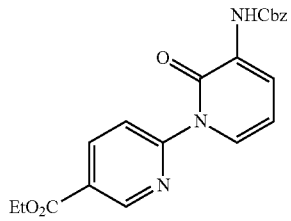 [SMILES: CCOC(=O)c1ccc(-n2cccc(NC(=O)OCc3ccccc3)c2=O)nc1]

A mixture of benzyl (2-hydroxypyridin-3-yl)carbamate (A29 step 1, 1.20 g, 4.91 mmol), ethyl 6-chloronicotinate (1.459 g, 7.86 mmol), N1,N2-dimethylethane-1,2-diamine (0.209 mL, 1.965 mmol), copper(I) iodide (0.281 g, 1.474 mmol), and potassium carbonate (1.698 g, 12.28 mmol) in 1,4-Dioxane (25 mL) in a pressure tube was heated at 110° C. for 60 h (weekend). Upon cooling to rt, the mixture was diluted with ethyl acetate (50 mL) and filtered through Celite. The filtrate was further diluted with ethyl acetate (150 mL), washed with water (2×35 mL) and brine (35 mL). The organic solution was dried over anhydrous MgSO4. The desired product, ethyl 3-(((benzyloxy)carbonyl)amino)-2-oxo-2H-[1,2'-bipyridine]-5'-carboxylate (0.857 g, 2.178 mmol, 44.3% yield), was isolated as a white solid by ISCO (120 g silica gel, solid loading, 15-50% ethyl acetate/hexane).

Step 2: Ethyl 3-amino-2-oxo-2H-[1,2'-bipyridine]-5'-carboxylate

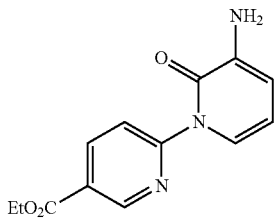 [SMILES: CCOC(=O)c1ccc(-n2cccc(N)c2=O)nc1]

A mixture of ethyl 3-(((benzyloxy)carbonyl)amino)-2-oxo-2H-[1,2'-bipyridine]-5'-carboxylate (0.857 g, 2.178 mmol) and 10% Pd/C (0.220 g, 0.207 mmol) in MeOH (18 mL) and THF (6 mL) was stirred at rt under H2, provided with a H2 Balloon, for 1 h. The reaction was complete and clean. The solid phase was removed by suction filtration through Celite. The filtrate was concentrated under vacuum to dryness to provide the desired product, ethyl 3-amino-2-oxo-2H-[1,2'-bipyridine]-5'-carboxylate (0.524 g, 2.021 mmol, 93% yield) as a tan solid.

Step 3: Ethyl 3-((3-(((1R,2S)-2-fluorocyclopropyl)carbamoyl)-8-((4-methoxybenzyl)(methyl)amino)imidazo[1,2-b]pyridazin-6-yl)amino)-2-oxo-2H-[1,2'-bipyridine]-5'-carboxylate

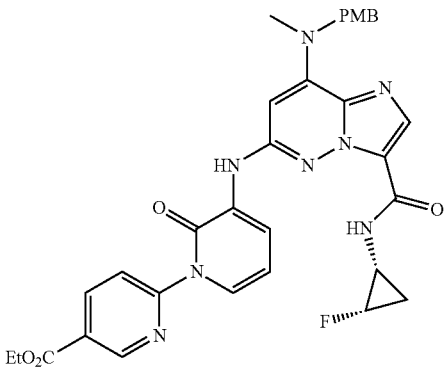

A mixture of 6-chloro-N-((1R,2S)-2-fluorocyclopropyl)-8-((4-methoxybenzyl)(methyl)amino)imidazo[1,2-b]pyridazine-3-carboxamide (0.400 g, 0.990 mmol), ethyl 3-amino-2-oxo-2H-[1,2'-bipyridine]-5'-carboxylate (0.321 g, 1.238 mmol), palladium(II) acetate (0.044 g, 0.198 mmol), BrettPhose (0.106 g, 0.198 mmol), and potassium carbonate (0.205 g, 1.486 mmol) in 1,4-Dioxane (8 mL) was heated at 80° C. for 2.5 h. The reaction mixture was diluted with ethyl acetate (30 mL) and filtered through Celite. The filtrate was diluted with ethyl acetate (120 mL), washed with water (2×25 mL) and brine (25 mL), and dried over anhydrous MgSO4. The desired product, ethyl 3-((3-(((1R,2S)-2-fluorocyclopropyl)carbamoyl)-8-((4-methoxybenzyl)(methyl)amino)imidazo[1,2-b]pyridazin-6-yl)amino)-2-oxo-2H-[1,2'-bipyridine]-5'-carboxylate (0.402 g, 0.642 mmol, 64.8% yield), was isolated as a beige solid by ISCO (80 g silica gel, solid loading, 30-60% ethyl acetate/hexane).

Step 4: 3-((3-(((1R,2S)-2-Fluorocyclopropyl)carbamoyl)-8-((4-methoxybenzyl) (methyl)amino)imidazo[1,2-b]pyridazin-6-yl)amino)-2-oxo-2H-[1,2'-bipyridine]-5'-carboxylic acid

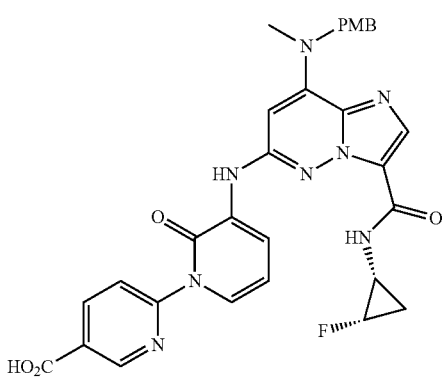

To a solution of ethyl 3-((3-(((1R,2S)-2-fluorocyclopropyl)carbamoyl)-8-((4-methoxybenzyl)(methyl)amino)imidazo[1,2-b]pyridazin-6-yl)amino)-2-oxo-2H-[1,2'-bipyridine]-5'-carboxylate (402 mg, 0.642 mmol) in Methanol (1.5 mL) and Tetrahydrofuran (4.5 mL) at rt was added a solution of lithium hydroxide hydrate (108 mg, 2.57 mmol) in Water (1.5 mL) over 1 min. The resulting solution was stirred at rt for 1.5 h before it was concentrated under vacuum to a volume of approximately 1.5 mL. The reside was diluted with water (3 mL), acidified with 1 N HCl solution to pH 6. The precipitating product (crop 1) was collected by suction filtration. The filtration was extracted with ethyl acetate (3×20 mL). The combined extract was dried over anhydrous MgSO4. Removal of solvent under vacuum gave the second crop of product. The two crops were combined to gave the desired product, 3-((3-(((1R,2S)-2-fluorocyclopropyl)carbamoyl)-8-((4-methoxybenzyl)(methyl)amino)imidazo[1,2-b]pyridazin-6-yl)amino)-2-oxo-2H-[1,2'-bipyridine]-5'-carboxylic acid (337 mg, 0.563 mmol, 88% yield), as a beige solid.

Step 5: 3-((3-(((1R,2S)-2-Fluorocyclopropyl)carbamoyl)-8-(methylamino)imidazo[1,2-b]pyridazin-6-yl)amino)-2-oxo-2H-[1,2'-bipyridine]-5'-carboxylic acid

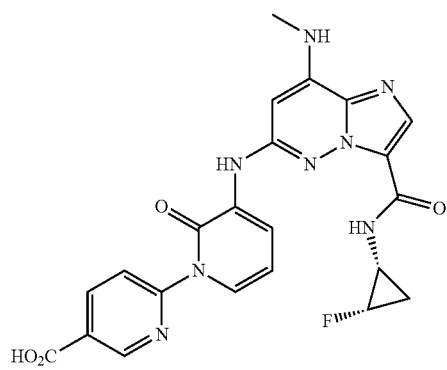 [SMILES: CNc1cc(Nc2cccn(-c3ccc(C(=O)O)cn3)c2=O)nn2c(C(=O)N[C@@H]3C[C@@H]3F)cnc12]

To a suspension of 3-((3-(((1R,2S)-2-fluorocyclopropyl) carbamoyl)-8-((4-methoxybenzyl)(methyl)amino)imidazo [1,2-b]pyridazin-6-yl)amino)-2-oxo-2H-[1,2'-bipyridine]-5'-carboxylic acid (0.337 g, 0.563 mmol) in Dichloromethane (15 mL) at rt was added hydrogen chloride in 1,4-dioxane (10 mL, 40.0 mmol) over 3 min. The mixture was stirred at rt for 2 h. Removal of volatiles under vacuum provided the desired product,3-((3-(((1R,2S)-2-fluorocyclopropyl)carbamoyl)-8-(methylamino)imidazo[1,2-b] pyridazin-6-yl)amino)-2-oxo-2H-[1,2'-bipyridine]-5'-carboxylic acid, 2 HCl (0.302 g, 0.548 mmol, 97% yield), as a beige solid.

Step 6: 6-((5'-(Dimethylcarbamoyl)-2-oxo-2H-[1,2'-bipyridin]-3-yl)amino)-N-((1R,2S)-2-fluorocyclopropyl)-8-(methylamino)imidazo[1,2-b]pyridazine-3-carboxamide A mixture of 3-((3-(((1R,2S)-2-fluorocyclopropyl)carbamoyl)-8-(methylamino)imidazo[1,2-b]pyridazin-6-yl) amino)-2-oxo-2H-[1,2'-bipyridine]-5'-carboxylic acid, 2 HCl (40 mg, 0.073 mmol), dimethylamine in THF (0.073 mL, 0.145 mmol), BOP (40.1 mg, 0.091 mmol), and N,N-diisopropylethylamine (0.063 mL, 0.363 mmol) in DMF (0.5 mL) was heated at 50° C. for 2 h. Reaction was cleanly complete. The mixture was diluted with DMF (1.5 mL) and submitted to SCP group for purification to give the desired product, 6-((5'-(dimethylcarbamoyl)-2-oxo-2H-[1,2'-bipyridin]-3-yl)amino)-N-((1R,2S)-2-fluorocyclopropyl)-8-(methylamino)imidazo[1,2-b]pyridazine-3-carboxamide, 2 HCl (27.8 mg, 0.048 mmol, 65.6% yield). LCMS (M+H)$^+$ =506.1. $^1$H NMR (500 MHz, DMSO-d$_6$) δ 8.71-8.65 (m, 3H), 8.10 (dd, J=8.3, 2.0 Hz, 1H), 8.00 (d, J=6.8 Hz, 1H), 7.94 (d, J=8.3 Hz, 1H), 7.92 (s, 1H), 7.59 (d, J=6.1 Hz, 1H), 7.51 (d, J=4.7 Hz, 1H), 6.44 (t, J=7.2 Hz, 1H), 6.38 (s, 1H), 4.98-4.78 (m, 1H), 3.05 (s, 3H), 3.02-2.98 (m, 4H), 2.88 (d, J=4.7 Hz, 3H), 1.31-1.19 (m, 1H), 1.05-0.92 (m, 1H).

The following examples were prepared according to the procedures described for the representative examples.

Ex. 258

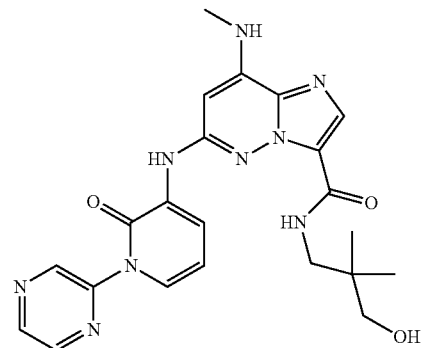

Ex. 259

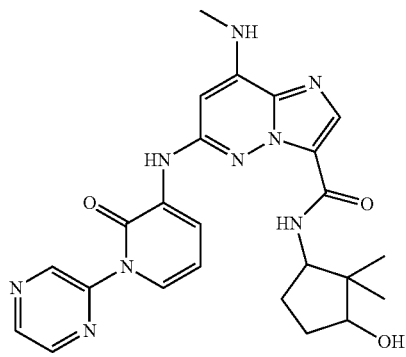

Ex. 260

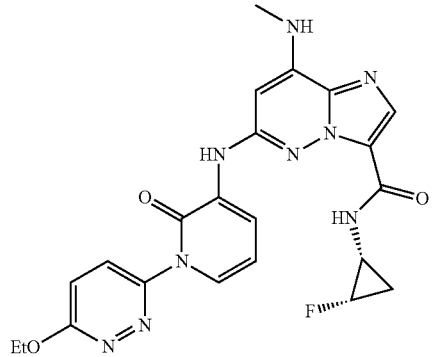

Ex. 261
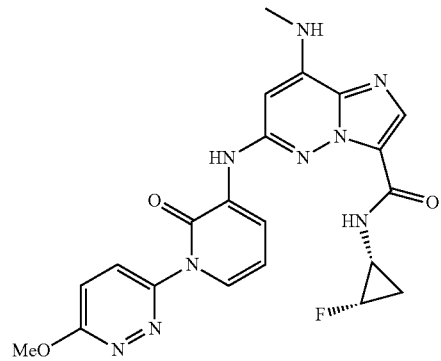
Ex. 262
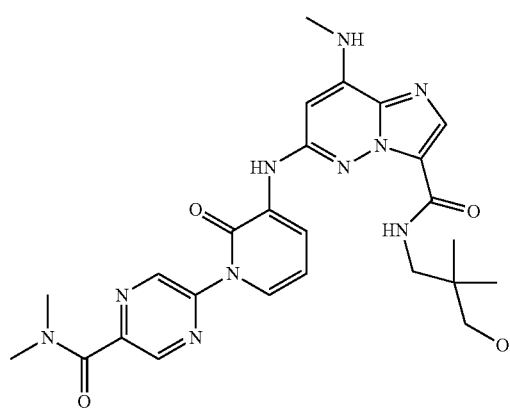
Ex. 263
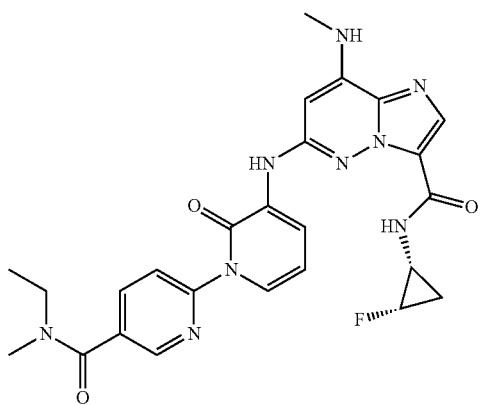
Ex. 264
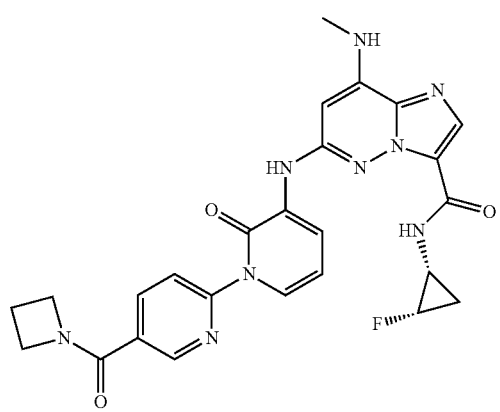
Ex. 265
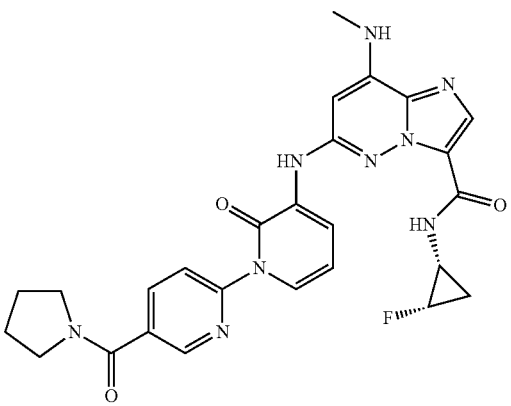
Ex. 266
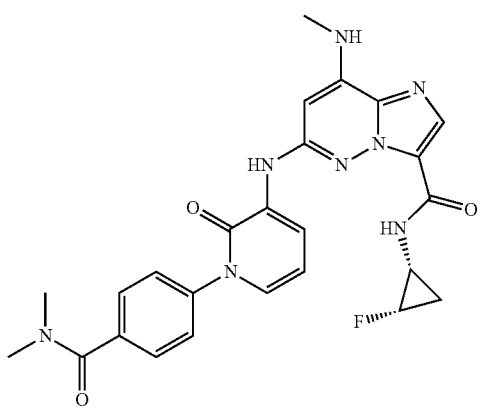
Ex. 267
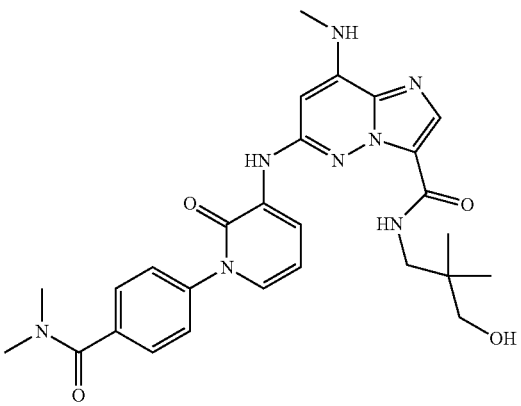

TABLE 7

| Ex # | Analytical data |
|---|---|
| 258 | LCMS (M + 1)$^+$ = 489.2. $^1$H NMR (400 MHz, DMSO-$d_6$) δ ppm 9.53 (s, 1 H) 9.32 (s, 1 H) 8.75 (s, 1 H) 8.67 (t, J = 6.78 Hz, 1 H) 8.08 (dd, J = 7.28, 1.76 Hz, 1 H) 7.90 (s, 1 H) 7.56-7.63 (m, 1 H) 7.52 (d, J = 5.02 Hz, 1 H) 6.60 (t, J = 7.28 Hz, 2 H) 6.42 (s, 1 H) 4.60 (s, 1 H) 3.14 (d, J = 5.52 Hz, 2 H) 2.88 (d, J = 5.02 Hz, 3 H) 0.82 (s, 6 H). |
| 259 | LCMS (M + H)$^+$ = 490.2. $^1$H NMR (400 MHz, DMSO-$d_6$) δ 9.20-9.18 (m, 1 H), 8.78-8.74 (m, 2 H), 8.66-8.63 (m, 1 H), 8.33-8.24 (m, 1 H), 8.01-7.96 (m, 1 H), 7.87 (s, 1 H), 7.62-7.57 (m, 1 H), 7.53-7.47 (m, 1 H), 6.49-6.36 (m, 2 H), 4.68 (d, J = 4.6 Hz, 1 H), 4.24-4.16 (m, 1 H), 3.67-3.60 (m, 1 H), 2.87 (d, J = 4.8 Hz, 3 H), 2.17-1.96 (m, 2 H), 1.60-1.49 (m, 2 H), 0.89 (s, 3 H), 0.69-0.65 (m, 3 H) |
| 260 | LCMS (M + H)$^+$ = 480.0. $^1$H NMR (400 MHz, DMSO-$d_6$) δ 8.63-8.64 (d, 2 H) 8.02-8.05 (m, 2 H) 7.92 (s, 1 H) 7.43-7.55 (m, 3 H) 6.40-6.46 (m, 2 H) 4.75-5.05 (m, 1 H) 4.53-4.59 (m, 2 H) 2.95-3.09 (m, 1 H) 2.81-2.93 (m, 3 H) 1.44 (s, 3 H) 1.16-1.34 (m, 1 H) 0.90-1.08 (m, 1 H). |
| 261 | LCMS (M + H)$^+$ = 466.2. $^1$H NMR (400 MHz, DMSO-$d_6$) δ 8.66 (s, 1H), 8.63 (d, J = 4.2 Hz, 1H), 8.07-8.01 (m, 2H), 7.91 (s, 1H), 7.55-7.44 (m, 3H), 6.44 (t, J = 7.2 Hz, 1H), 6.40 (s, 1H), 5.02-4.75 (m, 1H), 4.11 (s, 3H), 3.06-2.93 (m, 1H), 2.87 (d, J = 4.8 Hz, 3H), 1.25 (dtd, J = 15.1, 8.5, 6.1 Hz, 1H), 1.09-0.89 (m, 1H) |
| 262 | LCMS (M + H)$^+$ = 535.1. $^1$H NMR (400 MHz, DMSO-$d_6$) δ 9.21 (d, J = 1.3 Hz, 1H), 8.91 (d, J = 1.5 Hz, 1H), 8.78-8.53 (m, 2H), 8.05 (dd, J = 7.4, 1.7 Hz, 1H), 7.89 (s, 1H), 7.61 (dd, J = 7.1, 1.7 Hz, 1H), 7.51 (q, J = 4.8 Hz, 1H), 6.57 (t, J = 7.2 Hz, 1H), 6.40 (s, 1H), 4.59 (t, J = 5.8 Hz, 1H), 3.33-3.27 (m, 2H), 3.13 (d, J = 6.0 Hz, 2H), 3.07 (s, 3H), 3.05 (s, 3H), 2.88 (d, J = 4.8 Hz, 3H), 0.81 (s, 6H) |
| 263 | LCMS (M + H)$^+$ = 520.1. $^1$H NMR (500 MHz, DMSO-$d_6$) δ 8.71-8.62 (m, 2H), 8.07 (d, J = 12.6 Hz, 1H), 8.00 (d, J = 7.2 Hz, 1H), 7.96-7.90 (m, 2H), 7.60 (d, J = 6.9 Hz, 1H), 7.52 (d, J = 4.8 Hz, 1H), 6.44 (t, J = 7.1 Hz, 1H), 6.39 (s, 1H), 5.01-4.78 (m, 1H), 3.04-2.94 (m, 6H), 2.88 (d, J = 4.6 Hz, 3H), 1.30-1.21 (m, 1H), 1.21-1.08 (m, 3H), 1.05-0.93 (m, 1H) |
| 264 | LCMS (M + H)$^+$ = 518.1. $^1$H NMR (500 MHz, DMSO-$d_6$) δ 8.84 (s, 1H), 8.66 (br. s., 2H), 8.24 (d, J = 7.1 Hz, 1H), 7.98 (dd, J = 12.2, 7.8 Hz, 2H), 7.91 (s, 1H), 7.59 (d, J = 6.8 Hz, 1H), 7.52 (d, J = 4.4 Hz, 1H), 6.43 (t, J = 7.2 Hz, 1H), 6.38 (s, 1H), 5.01-4.74 (m, 1H), 4.41 (t, J = 7.3 Hz, 2H), 4.10 (t, J = 7.4 Hz, 2H), 2.98 (br. s., 1H), 2.86 (d, J = 4.4 Hz, 3H), 2.36-2.22 (m, 2H), 1.24 (dd, J = 15.3, 7.1 Hz, 1H), 1.07-0.89 (m, 1H) |
| 265 | LCMS (M + H)$^+$ = 532.1. $^1$H NMR (500 MHz, DMSO-$d_6$) δ 8.78 (s, 1H), 8.69-8.62 (m, 2H), 8.22-8.15 (m, 1H), 8.00 (d, J = 7.0 Hz, 1H), 7.94 (d, J = 8.3 Hz, 1H), 7.91 (s, 1H), 7.59 (d, J = 6.9 Hz, 1H), 7.52 (d, J = 4.6 Hz, 1H), 6.43 (t, J = 7.2 Hz, 1H), 6.39 (s, 1H), 5.00-4.75 (m, 1H), 3.57-3.43 (m, 2H), 2.99 (s, 1H), 2.87 (d, J = 4.7 Hz, 3H), 1.98-1.76 (m, 6H), 1.32-1.16 (m, 1H), 1.07-0.91 (m, 1H) |
| 266 | LCMS (M + H)$^+$ = 505.0. $^1$H NMR (400 MHz, DMSO-$d_6$) δ 8.64 (d, J = 4.2 Hz, 1H), 8.60 (s, 1H), 7.98 (dd, J = 7.5, 1.6 Hz, 1H), 7.91 (s, 1H), 7.61-7.52 (m, 4H), 7.49 (d, J = 5.0 Hz, 1H), 7.33 (dd, J = 7.0, 1.7 Hz, 1H), 6.42-6.33 (m, 2H), 5.00-4.77 (m, 1H), 3.05-2.94 (m, 7H), 2.87 (d, J = 4.6 Hz, 3H), 1.32-1.19 (m, 1H), 1.08-0.93 (m, 1H) |
| 267 | LCMS (M + H)$^+$ = 533.1. $^1$H NMR (400 MHz, DMSO-$d_6$) δ 8.72 (t, J = 6.6 Hz, 1H), 8.57 (s, 1H), 7.98 (dd, J = 7.4, 1.7 Hz, 1H), 7.88 (s, 1H), 7.60-7.52 (m, 4H), 7.49 (q, J = 4.6 Hz, 1H), 7.33 (dd, J = 6.9, 1.7 Hz, 1H), 6.46 (t, J = 7.2 Hz, 1H), 6.36 (s, 1H), 4.60 (br. s., 1H), 3.33 (br. s., 2H), 3.13 (br. s., 2H), 3.02 (br. s., 3H), 2.97 (br. s., 3H), 2.87 (d, J = 4.8 Hz, 3H), 0.82 (s, 6H) |

What is claimed is:

1. A compound of the formula

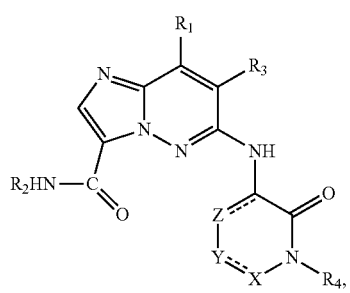

or a pharmaceutically acceptable salt, tautomer or stereoisomer thereof, wherein $R_1$ is H or —$NHR_5$;

$R_2$ is

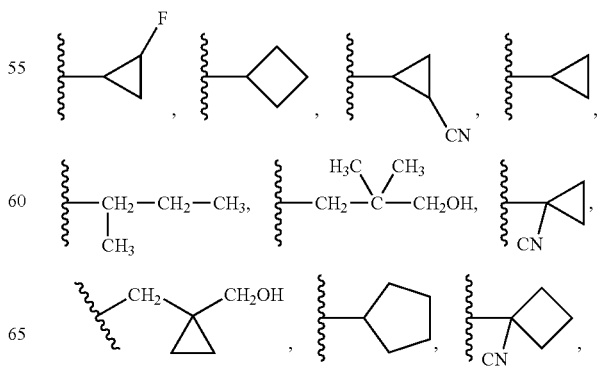

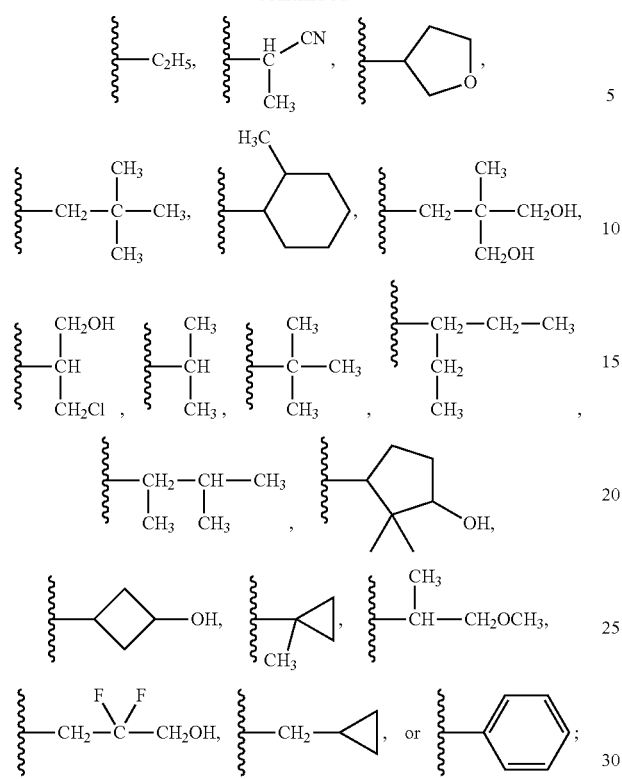
$R_3$ is H, halo or $C_1$-$C_6$ alkyl;
$R_4$ is H; or
$R_4$ is
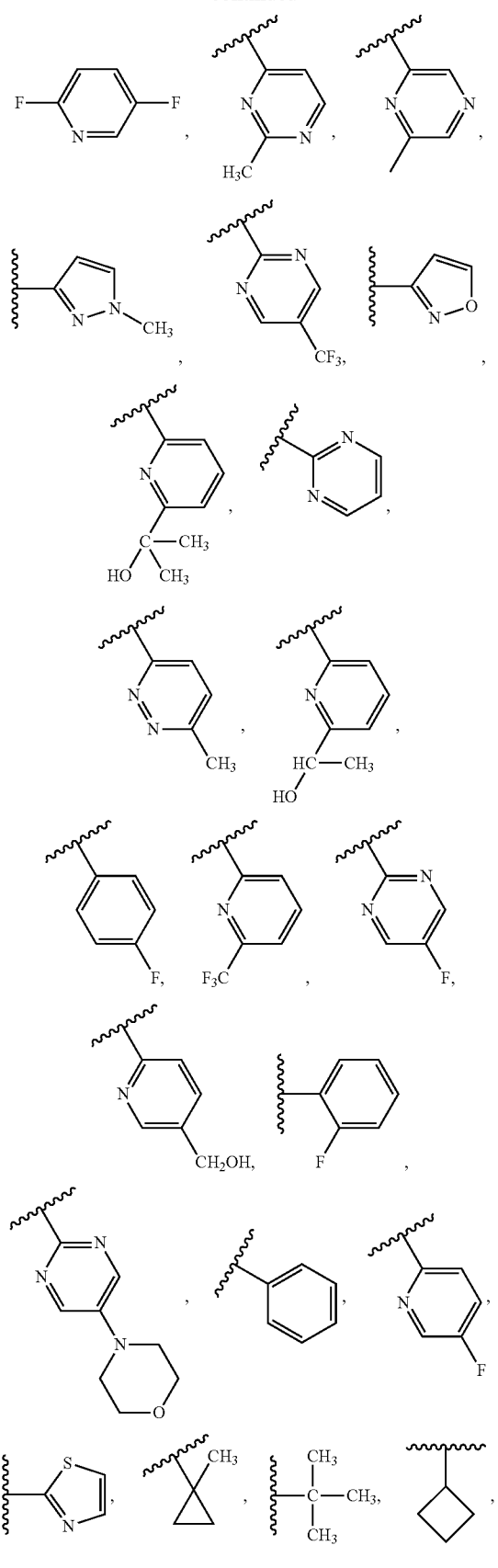

-continued
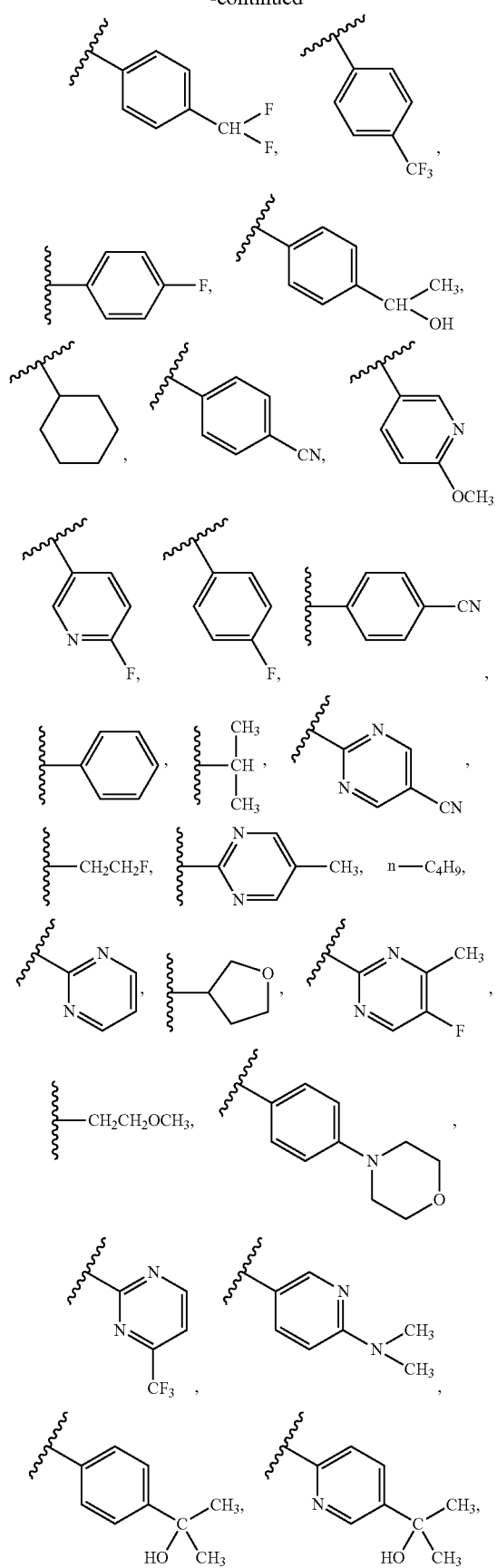
-continued
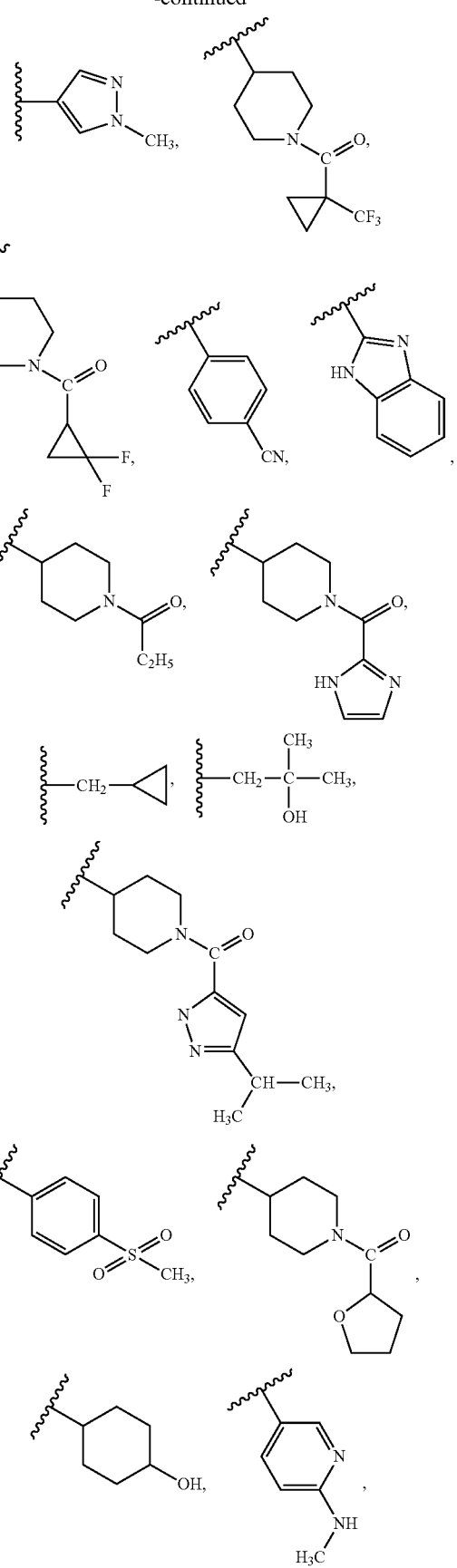

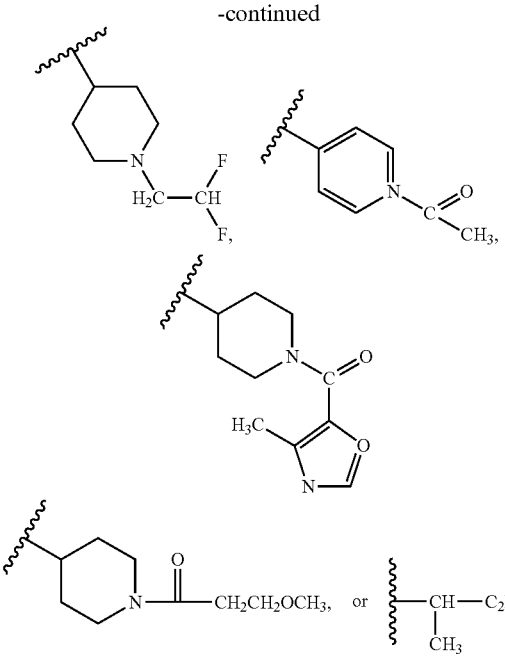
$R_5$ is $C_1$-$C_4$ alkyl;
X is CH or N;
Y is
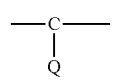
or N, where Q is H or halogen; and
Z is CH or N.
2. A pharmaceutical composition comprising one or more compounds according to claim 1 and a pharmaceutically acceptable carrier or diluent.
* * * * *